United States Patent
Palczewski et al.

(10) Patent No.: US 10,426,773 B2
(45) Date of Patent: *Oct. 1, 2019

(54) SYSTEMS PHARMACOLOGY FOR TREATING OCULAR DISORDERS

(71) Applicant: Case Western Reserve Univeristy, Cleveland, OH (US)

(72) Inventors: Krzysztof Palczewski, Cleveland, OH (US); Yu Chen, Cleveland, OH (US); Akiko Maeda, Cleveland, OH (US)

(73) Assignee: CASE WESTERN UNIVERSITY, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/181,161

(22) Filed: Nov. 5, 2018

(65) Prior Publication Data

US 2019/0099420 A1    Apr. 4, 2019

Related U.S. Application Data

(63) Continuation-in-part of application No. 15/487,963, filed on Apr. 14, 2017, now Pat. No. 10,117,868, which is a continuation-in-part of application No. 15/316,412, filed as application No. PCT/US2015/034189 on Jun. 4, 2015, now Pat. No. 10,272,106, said application No. 15/487,963 is a continuation-in-part of application No. 14/262,141, filed on Apr. 25, 2014, which is a continuation-in-part of application No. PCT/US2012/061931, filed on Oct. 25, 2012.

(60) Provisional application No. 62/322,538, filed on Apr. 14, 2016, provisional application No. 62/007,710, filed on Jun. 4, 2014, provisional application No. 61/551,148, filed on Oct. 25, 2011.

(51) Int. Cl.

| | |
|---|---|
| *A61K 31/4985* | (2006.01) |
| *A61K 31/517* | (2006.01) |
| *A61K 31/185* | (2006.01) |
| *A61K 31/138* | (2006.01) |
| *A61K 45/06* | (2006.01) |
| *A61K 31/18* | (2006.01) |
| *A61K 31/48* | (2006.01) |

(52) U.S. Cl.
CPC ........ *A61K 31/4985* (2013.01); *A61K 31/138* (2013.01); *A61K 31/18* (2013.01); *A61K 31/185* (2013.01); *A61K 31/48* (2013.01); *A61K 31/517* (2013.01); *A61K 45/06* (2013.01)

(58) Field of Classification Search
None
See application file for complete search history.

(56) References Cited

U.S. PATENT DOCUMENTS

| 10,117,868 B2* | 11/2018 | Palczewski ............ A61K 45/06 |
| 2005/0059744 A1 | 3/2005 | Donello et al. |
| 2009/0197967 A1 | 8/2009 | Kubota et al. |
| 2011/0104155 A1 | 5/2011 | Rekik |

FOREIGN PATENT DOCUMENTS

| WO | 2008/147528 A1 | 12/2008 |
| WO | 2013/063269 A2 | 5/2013 |

OTHER PUBLICATIONS

Bromocriptine. https://en.wikipedia.org/wiki/Bromocriptine#cite_ref-19 accessed on Jul. 31, 2018 (Year: 2018).
Wentzel al. Molecular mechanisms of light-induced photoreceptor apoptosis and neuroprotection for retinal degeneration. Progress in Retinal and Eye Research 24 (2005) 275-306.
Shen et al. Effect of Guanabenz on Rat AMO Models and Rabbit Choroidal Blood Flow. The Open Ophthalmology Journal, 2011, 5, 27-31.
Maeda, et al., "Primary amines protect against retinal degeneration in mouse models of retinopathies", Nature Chemical Biology, vol. 8.2012, pp. 170-178.
Du, et al., "Contribution of GPCRs and NADPH oxidase to increased generation of superoxide by retinal photoreceptor cells in elevated glucose", Investigative Ophthalmology & Visual Science Jun. 2013, vol. 54. (ARVO Annual Meeting Abstract).
Extended European Search Report for Application No. 15802805. 0-1109/3151818.
Supplementary European Search Report for Application No. 15802805. 5-1109/3151818.

* cited by examiner

*Primary Examiner* — Brian J Davis
(74) *Attorney, Agent, or Firm* — Tarolli, Sundheim, Covell & Tummino LLP

(57) ABSTRACT

A method of treating an ocular disorder in a subject includes administering to the subject subtherapeutic amounts of two or more agents that inhibit and/or blocks the activation of Gs- or Gq-protein coupled receptors or Gs- or Gq-signaling cascade in ocular cells of the subject, and/or activates Gi-protein coupled receptors, which is induced or triggered by light induced all-trans-retinal generation.

17 Claims, 52 Drawing Sheets

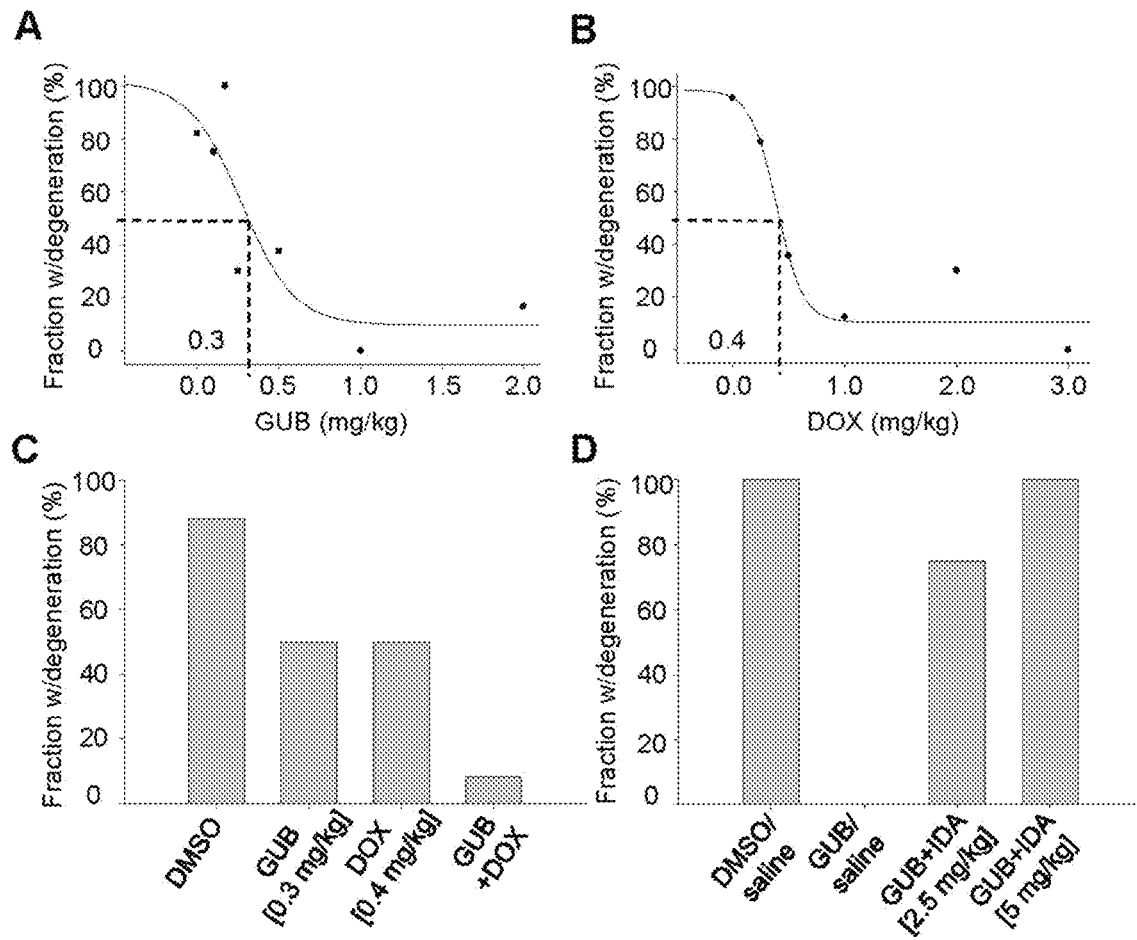
Figs. 25A-D

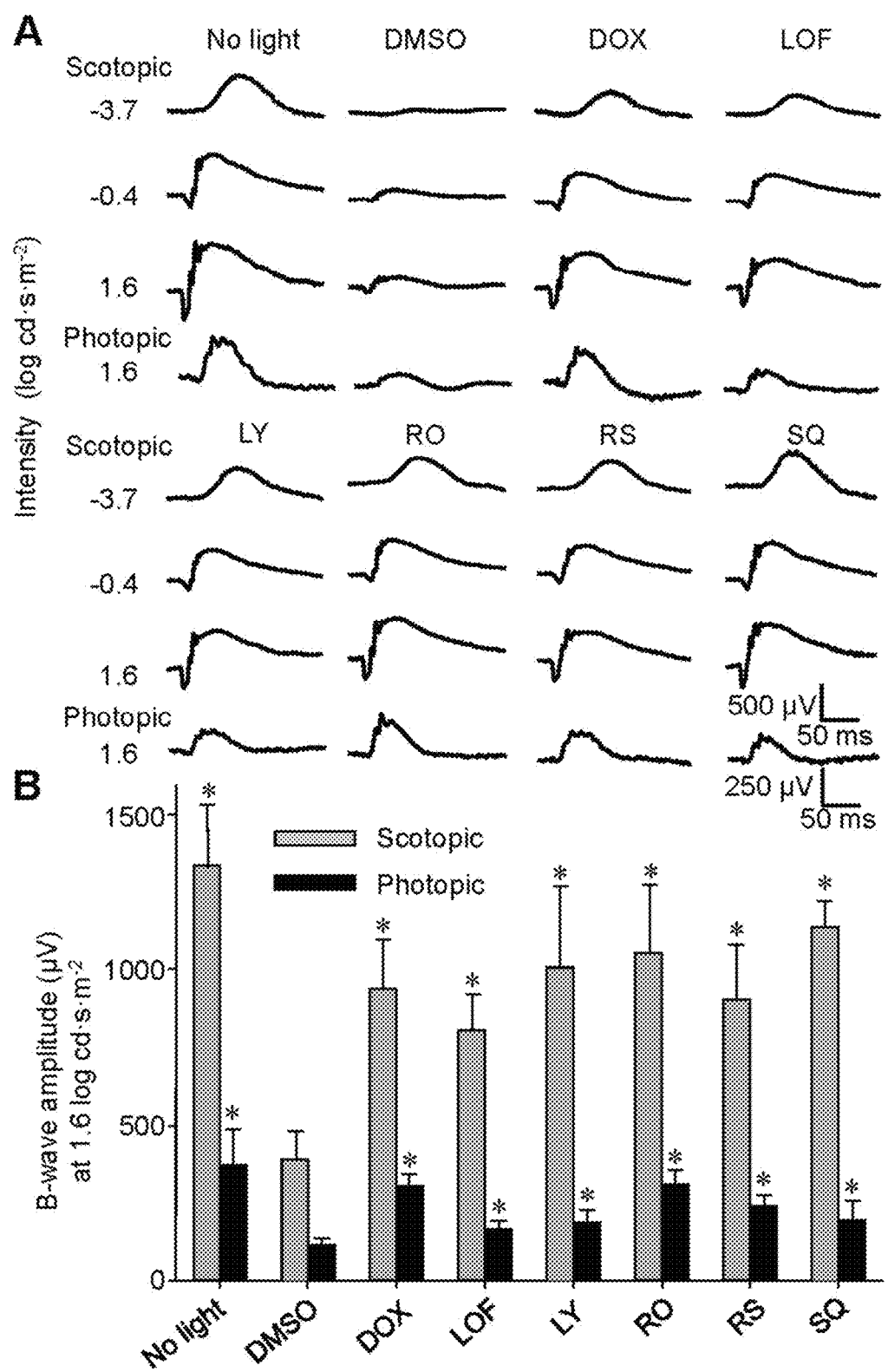
Figs. 26A-B

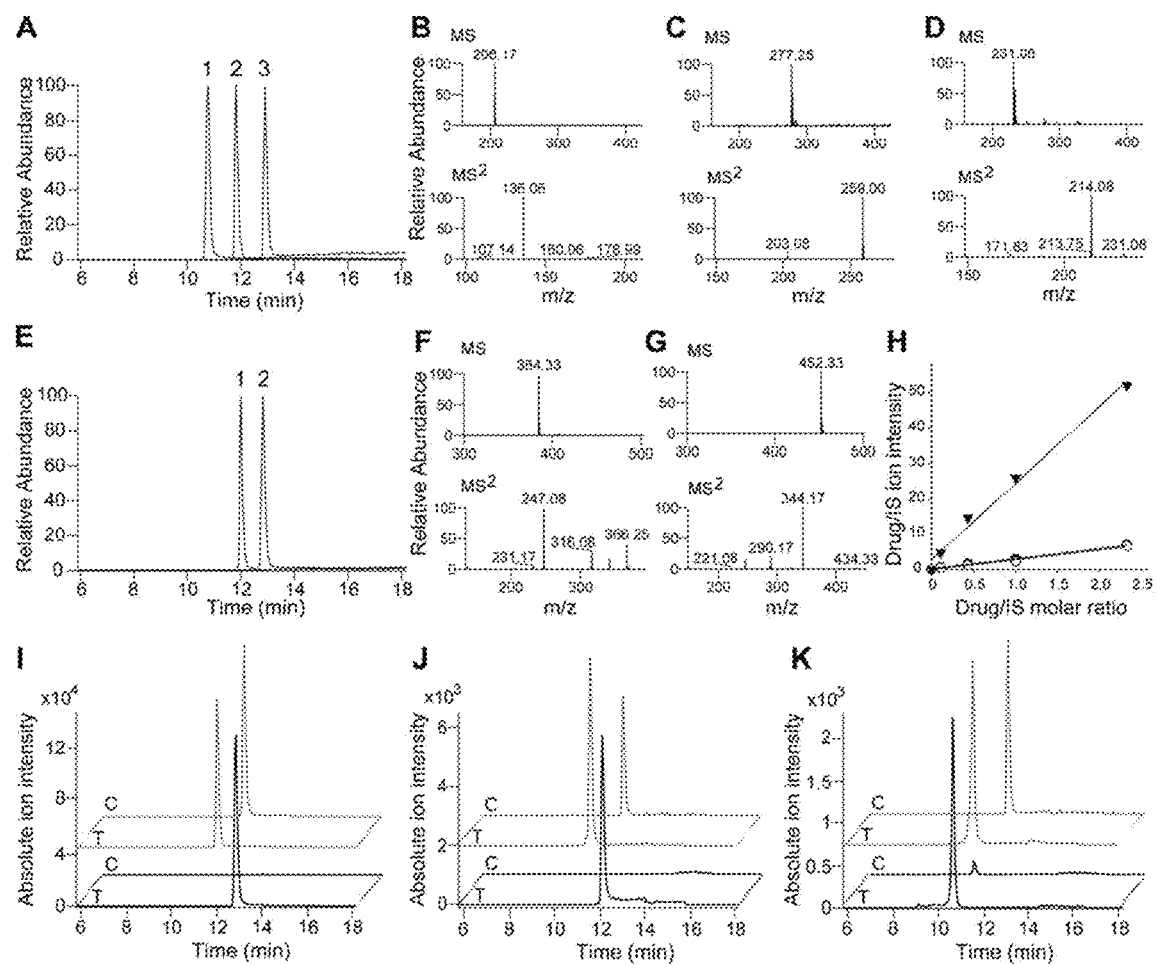
Figs. 29A-K

A
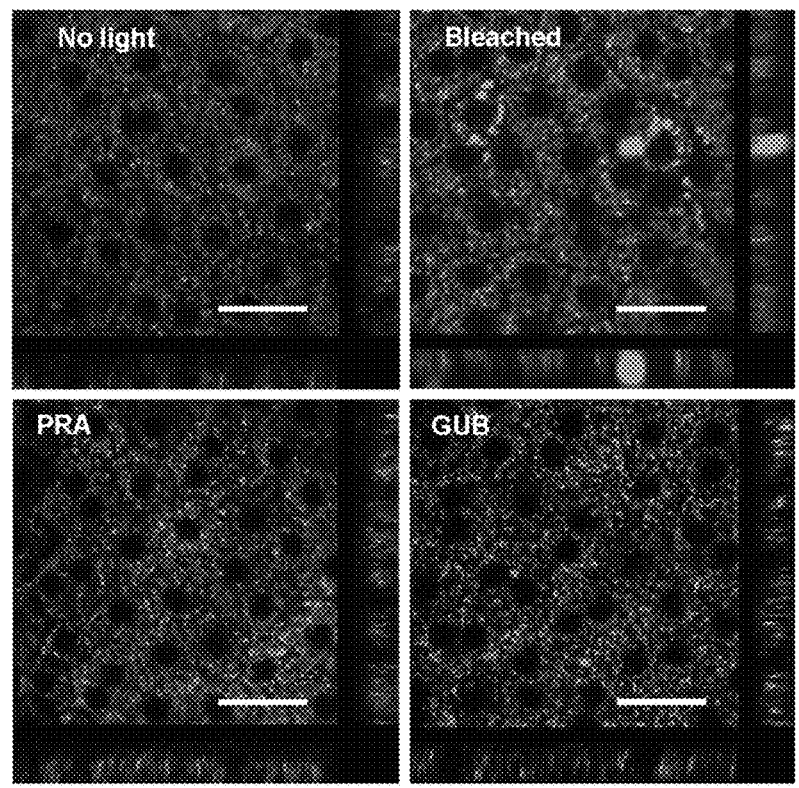
B
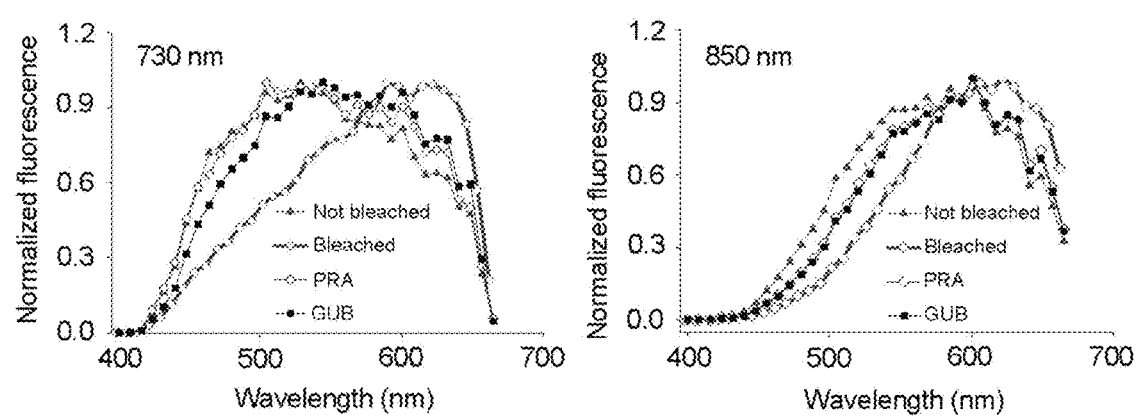
Figs. 30A-B

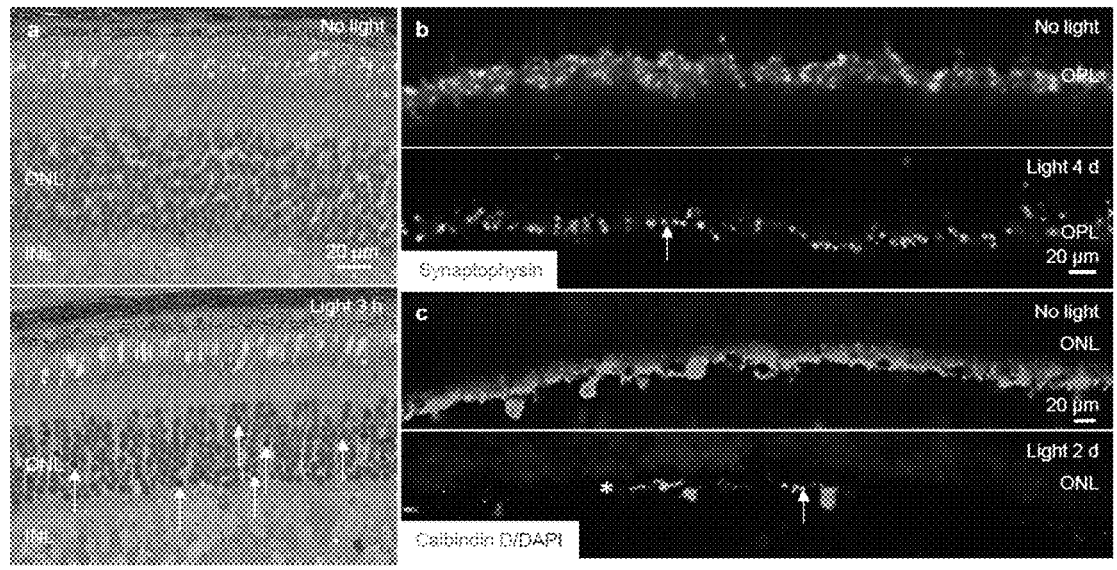
Figs. 40A-C
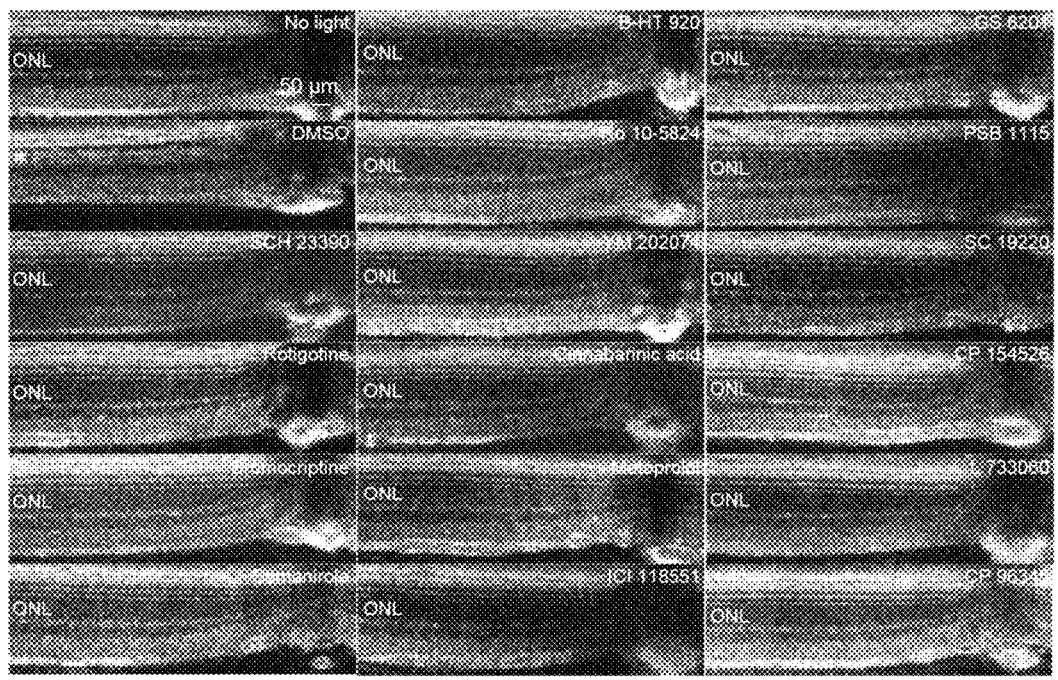
Fig. 41 b
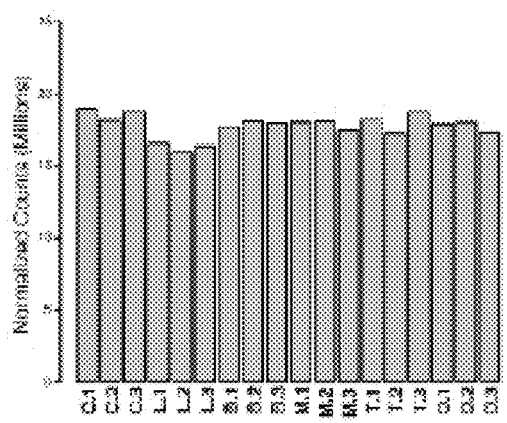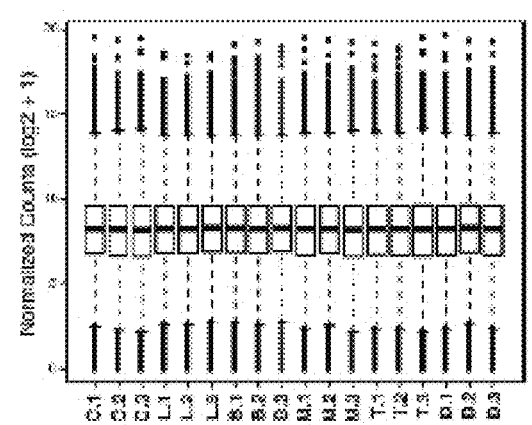
c
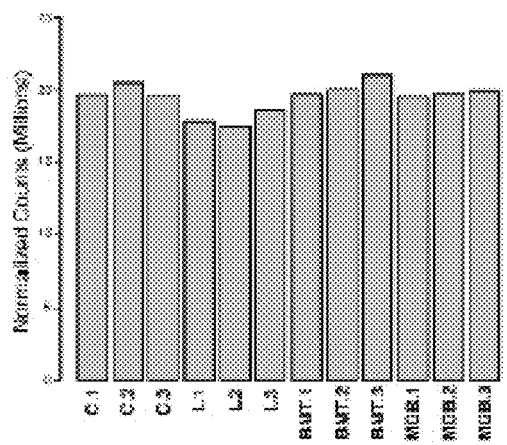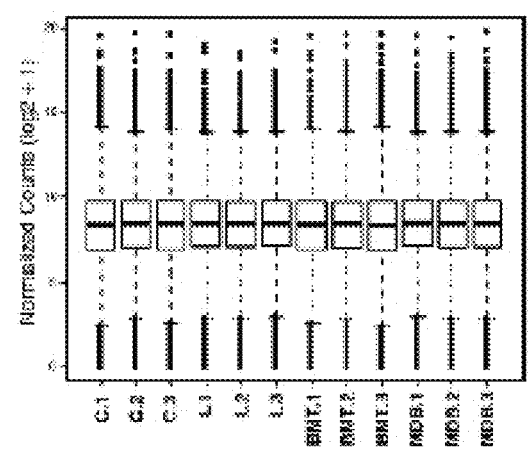
Figs. 45B-C

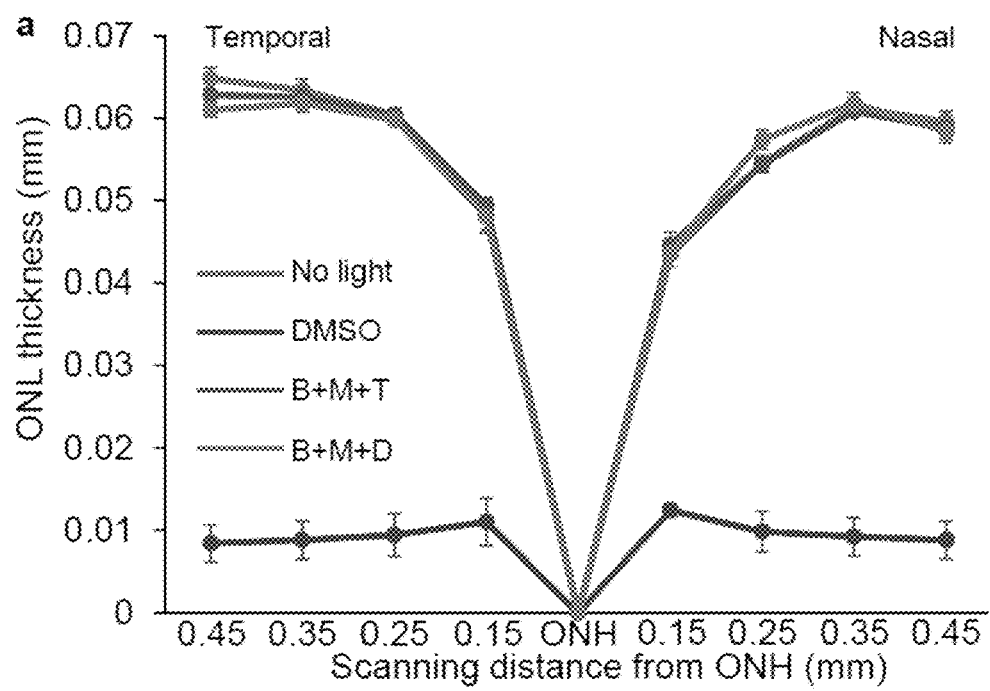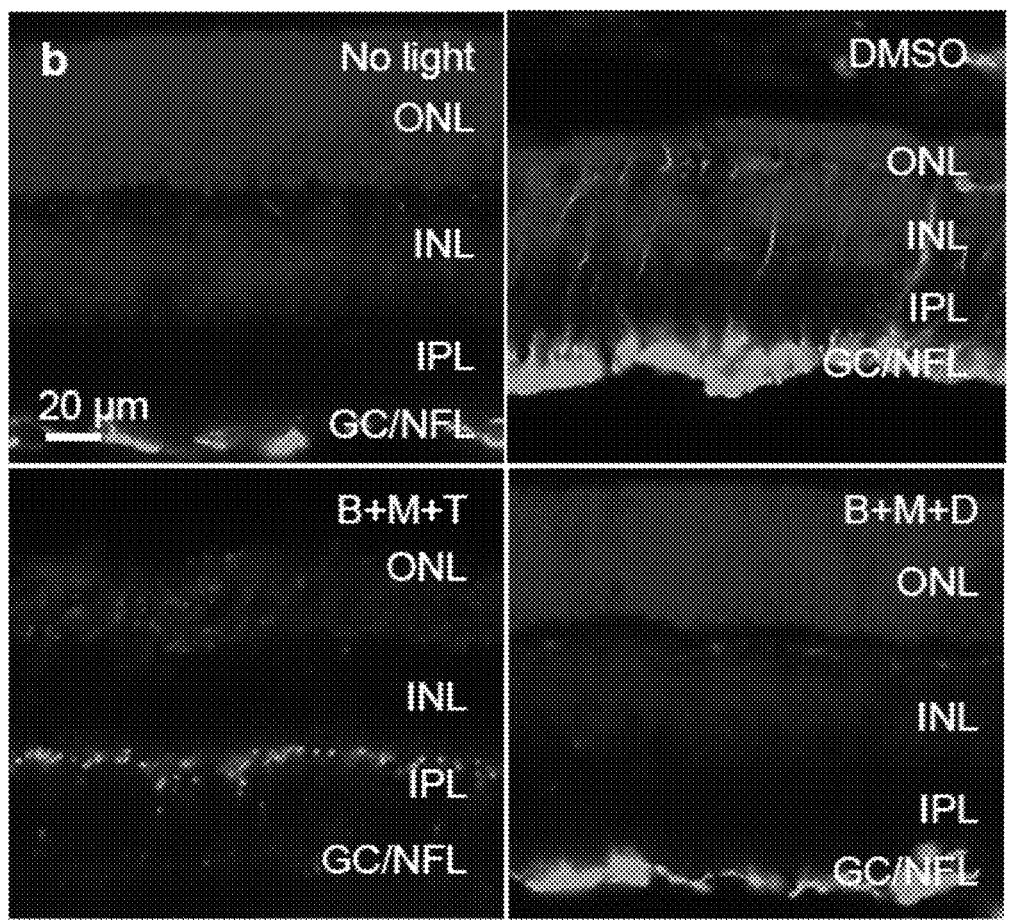
Figs. 49A-B

SYSTEMS PHARMACOLOGY FOR TREATING OCULAR DISORDERS

RELATED APPLICATION

This application claims priority to U.S. Provisional Application Ser. No. 62/322,538, filed Apr. 14, 2016, this application is also a Continuation-in-Part of Ser. No. 15/316,412, filed Dec. 5, 2016, and is also a Continuation-in-Part of PCT Application No. PCT/US2012/061931, filed Oct. 25, 2012, which claims the benefit of U.S. Provisional Application Nos. 61/551,148, filed Oct. 25, 2011 and claims priority from U.S. Provisional Application Ser. No. 61/904,218 filed Nov. 14, 2013, the subject matter of which are incorporated herein by reference in their entirety.

TECHNICAL FIELD

This application relates to use of systems pharmacology for treating ocular and/or retinal disorders that are associated with light induced retinal degeneration, aberrant all-trans-retinal clearance in the retina, and/or the generation of reactive oxygen species.

BACKGROUND

To sustain vision, atRAL released from light-activated visual pigments, including rhodopsin, must be continuously isomerized back to its 11-cis isomer. This process occurs by a sequence of reactions catalyzed by membrane-bound enzymes of the retinoid cycle located in rod and cone photoreceptor outer segments and the retinal pigmented epithelium (RPE). Regeneration of rhodopsin requires 11-cis-retinal (11-cis-RAL) supplied from the RPE, but cone pigments are also regenerated in cone-dominant species by a separate "cone visual cycle". A high flux of retinoids through the retinoid cycle, as occurs during intense light exposure, can cause elevated levels of toxic intermediates, especially atRAL, that can induce photoreceptor degeneration. Toxic effects of atRAL include caspase activation and mitochondrial-associated cell death, but the precise sequence of molecular events that leads to photoreceptor degeneration remains to be clarified.

Oxidative stress is one major mechanism contributing to photoreceptor cell death in animal models of retinal degeneration, including light-induced retinopathy. Tightly regulated low levels of reactive oxygen species (ROS) are needed to mediate physiological functions including cell survival, growth, differentiation and metabolism. NADPH oxidase is the primary enzymatic source of $O_2^-$ and $H_2O_2$ involved in retinal degeneration. atRAL stimulates the production of reactive oxygen species superoxide via NADPH oxidase, however such stimulation does not result from a direct interaction between atRAL and this enzyme. Effective compositions and methods to reduce and minimize the production and release of ROSs in patients suffering from a variety of disparate ocular disorders would be a great boon to medicine and serve to reduce and eliminate a substantial amount of human suffering.

SUMMARY

Embodiments described herein relate to a systems pharmacology approach to treating an ocular disorder in a subject associated with light induced retinal degeneration, aberrant all-trans-retinal clearance and/or reactive oxygen species (ROS) generation in the retina. The ocular disorder can include, for example, retinal disorders, such as retinal degeneration, geographic atrophy (GA), macular degeneration, including age-related macular degeneration, Stargardt disease, retinitis pigmentosa, and diabetic retinopathy.

The systems pharmacology approach can include administering to a subject with an ocular disorder associated with light induced retinal degeneration, aberrant all-trans-RAL clearance and/or ROS production subtherapeutic or subeffective amounts of two more agents that can inhibit and/or antagonize Gs- or Gq-protein coupled receptor activation, inhibit and/or antagonize the Gq signaling cascade (e.g., agents that inhibit or antagonize PLC activation, $IP_3$ binding to its receptor), inhibit or antagonize the Gs signaling cascade (e.g., agents that inhibit and/or antagonize andenylyl cyclase activation) and/or agents that activate Gi signaling cascade in a retina cell. These agents can be used in combination with each other as well as with other agents to modify several pathways that culminate in a common response, whether mediated by an enzyme, second messengers or channels, and treat retinal disorders associated with light induced retinal degeneration, all-trans-retinal accumulation and/or reactive oxygen species generation.

The systems pharmacology therapies described herein can preserve photoreceptor cells as well as the structure, function and transcriptional integrity of the retina. By way of example, combined therapies for treating light induced photoreceptor death were tested for 2-Bromo-α-ergocryptine methanesulfonate salt (BRM), an agonist of Gi-coupled dopamine D2 receptors, metoprolol tartrate (MTP), an antagonist of Gs-coupled β1 adrenergic receptors and two additional Gq-coupled α1 adrenergic receptor antagonists, tamsulosin (TAM) and doxazosin (DOX). The results demonstrate that administration of combined treatments consisting of BRM, MTP and TAM, or BRM, MTP and DOX with each component dosed at an individual sub-effective level caused significant morphological and functional protection of photoreceptor cells. In addition, protection of bipolar and horizontal cells also was achieved by these combined treatments.

BRIEF DESCRIPTION OF THE DRAWINGS

FIGS. 25(A-D) illustrate contributions of Gi and Gq pathways to light-induced retinal pathogenesis. (A) Guanabenz (GUB), a Gi pathway activator, protected $Abca4^{-/-}Rdh8^{-/-}$ mouse retinas from bright light-induced degeneration in a dose-dependent fashion with a half maximal effective dose determined as 0.3 mg/kg. n≥for each data point. (B) The Gq pathway inhibitor, doxazosin (DOX), also protected mouse retinas from bright light-induced degeneration in a dose-dependent fashion with a half maximal effective dose of 0.4 mg/kg. n≥5 for each data point. (C) The combination of GUB at 0.3 mg/kg BW and DOX at 0.4 mg/kg BW, protected the retina in at least an additive manner, n≥5. (D) Idazoxan (IDA) at 2.5 mg/kg BW and 5 mg/kg BW, counteracted the protective action of GUB at 2 mg/kg BW, on bright light-induced retinal degeneration, n≥5.

FIGS. 26(A-B) illustrate therapeutics targeting Gq-, Gs-, Gi-coupled GPCRs and AC preserve retinal function in $Abca4^{-/-}Rdh8^{-/-}$ mice. $Abca4^{-/-}Rdh8^{-/-}$ mice at 4- to 5-weeks of age were exposed to 10,000 lux light for 30 min after pre-treatment with the pharmacological agents at indicated doses, DOX (10 mg/kg BW), LOF (2 mg/kg BW), LY (10 mg/kg BW), RO (30 mg/kg BW), RS (20 mg/kg BW) and SQ (0.5 mg/kg BW). ERGs were recorded to evaluate the effects of these agents on retinal function 2 weeks after light exposure. (A) ERG responses were compared between mice unexposed to intense light (no light), vehicle only (DMSO) and tested agents under both scotopic and photopic conditions. Amplitudes of b-waves at 1.6 log $cd \cdot s \cdot m^{-2}$ under scotopic and photopic conditions are shown (B). Tested compounds showed significant protective effects compared to DMSO-treated mice which displayed significantly impaired retinal function indicated by decreased ERG amplitudes, *($p<0.05$). Bars indicate SDs. n=4-6 eyes per group.

FIGS. 29(A-K) illustrate detection and quantification of doxazosin (DOX), guanabenz (GUB), and SQ 22536 (SQ) in mouse eye. (A) HPLC separation of SQ (peak 1), clenbuterol (internal standard, IS) (peak 2), and GUB (peak 3). (B) (C) (D) MS and $MS^2$ patterns for SQ, clenbuterol, and GUB, respectively. Characteristic fragmentation profiles were used to design the selected reaction monitoring-based detection and quantification method. (E) Elution profile of parazosin (IS) (peak 1) and DOX (peak 2). (F) (G) MS and $MS^2$ fragmentation pattern for parazosin and DOX. (H) Relationships between ion intensities and molar ratio for drug/internal standard pairs (DOX/parazosin (filled triangles), GUB/clenbuterol (filled circles), and SQ/clenbuterol (open circles)) which were used for IS-based drug quantification. (I) (J) (K) Representative chromatograms of the eye extract indicating the presence of DOX, GUB, and SQ, respectively. Black chromatograms correspond to ion intensities of SRM transitions characteristic for the tested drugs. Gray lines represent ion intensities for the internal standards. Letters "T" and "C" discriminate between samples obtained from drug-treated mice (T) and control, non-treated animals (C).

FIGS. 30(A-B) illustrate GPCR-targeted therapeutics prevent formation of large fluorescent granules in the RPE of $Abca4^{-/-}Rdh8^{-/-}$ mice (6-7 weeks of age) after exposure to bright light. (A) Representative TPM images of the RPE 10 days after exposure to bright light. Upper left panel, unexposed to light (No light) control; upper right panel, exposed to bright light (Bleached) and DMSO treated control; lower left panel, pre-treated with prazosin (PRA); lower right panel, pre-treated with guanabenz (GUB). Cross-sections shown at the right edge and at the bottom of each en-face RPE image reveal that fluorescent granules, most pronounced in the bleached DMSO treated control, extend across the whole thickness of the RPE and into the outer retina-photoreceptor space. Scale bars indicate 25 µm. (B) Emission spectra after excitation with 730 nm light (left panel) and after excitation with 850 nm light (right panel). The spectra from exposed to light, DMSO-treated control are notably red-shifted for both excitation wavelengths.

FIG. 40(A-C) illustrate Abca4-/-Rdh8-/- mice exposed to bright light exhibit pyknosis of photoreceptor cells, diminished expression of synaptophysin in the OPL and altered horizontal cell morphology. A Retinal thick sections from Abac4$^{-/-}$Rdh8$_{-/-}$ mice unexposed to bright light (No light) and 3 h after light exposure (Light 3 h) were stained with toluidine blue and examined by light microscopy. White arrows indicate pyknotic photoreceptor cells. Scale bar: 20 µm. B and C Albino Abca4$^{-/-}$Rdh8$^{-/-}$ mice were exposed to bright light at 10,000 lux for 1 h. Retinal cryosections were prepared from mice unexposed to bright light and at indicated times after light exposure, i.e., 2 d (Light 2d) and 4 d (Light 4d). IHC was performed to assess the expression of synaptophysin (b) and calbindin D (C). ONL: outer nuclear layer; OPL: outer plexiform layer. White arrows in b and c indicate representative areas in the OPL with diminished expression of synaptophysin and calbindin D, respectively. Asterisks in c identify areas where calbindin D immunoreactivity was not readily detected. Scale bar: 20 µm.

FIG. 41 illustrates pharmacological pretreatments targeting different GPCRs preserve retinal structure in bright light-exposed Abca4$^{-/-}$Rdh8$^{-/-}$ mice. OCT imaging was performed to examine retinal structures in Abca4$^{-/-}$Rdh8$^{-/-}$ mice either unexposed to bright light, or with light exposure after pretreatment with either DMSO or the compounds indicated in Table 7 that modulate the activity of GPCRs. ONL: outer nuclear layer. Asterisk marks severely attenuated ONL. OCT was performed 7 days after bright light.

DETAILED DESCRIPTION

Figure 1:
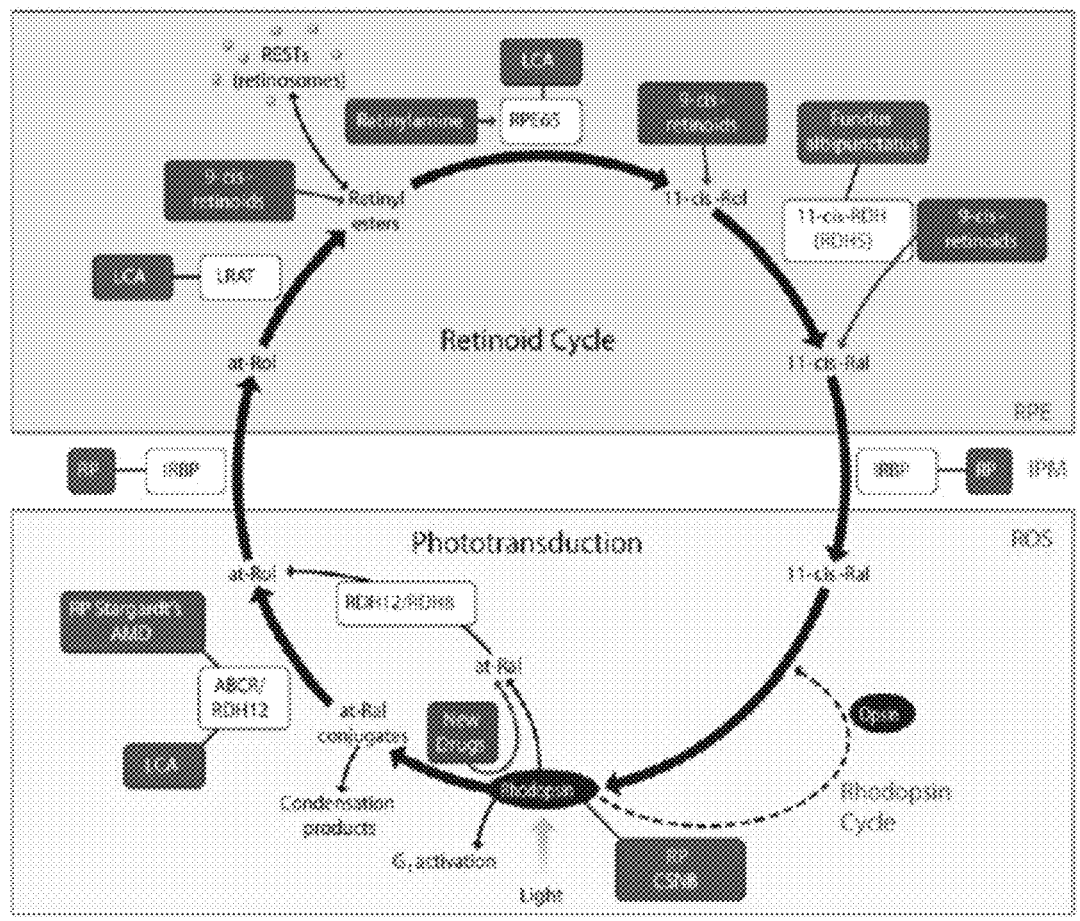
FIG. 1 is a schematic illustration of the visual cycle.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n–1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intraocular, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulfadryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like (e.g., Bundegaard, H. "Design of Prodrugs" p 1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, $2^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenylmethyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated, such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as retinal degeneration or other forms of retinal disease whose etiology involves light induced retinal degeneration or aberrant clearance of all trans-retinal. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species, such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The term "RAL" means retinaldehyde. "Free RAL" is defined as RAL that is not bound to a visual cycle protein. The terms "trans-RAL" and "all-trans-RAL" are used interchangeably and mean all-trans-retinaldehyde.

Embodiments described herein relate to a systems pharmacology approach to treating an ocular disorder in a subject associated with light induced retinal degeneration, aberrant all-trans-retinal clearance and/or reactive oxygen species (ROS) generation in the retina. The ocular disorder can include, for example, retinal disorders, such as retinal degeneration, geographic atrophy (GA), macular degeneration, including age-related macular degeneration, Stargardt disease, retinitis pigmentosa, and diabetic retinopathy.

Complex diseases are not easily managed and typically are confounded by aging. For example, multiple distinct cellular pathways have been associated with age-related macular degeneration and should be targeted for successful treatment. Monotherapies typically have partial effects, even at high doses. Poly-pharmacology that takes advantage of diverse and unrelated targets can effectively deal with the initial problem but at the risk of multiple unwanted side effects. This risk could be acceptable for treating terminal diseases or chronic infections, e.g., HIV, but for other diseases such as blindness, poly-pharmacology is not the best solution. Systems pharmacology differs from poly-pharmacology in that it modifies several pathways that culminate in a common response, whether mediated by an enzyme, second messengers or channels. Most advantageous is the modulation of pharmacologically accessible GPCRs, because their overlapping pathways can elicit synergistic effects. Thus, suboptimal doses of different GPCR modulators can be employed in concert to achieve an enhanced desired effect. Low doses of combined GPCR-targeted drugs can also prevent massive internalization of their receptors and enable prolonged therapy. For chronic diseases, where prophylaxis would be most beneficial, systems pharmacology can play a major role. As examples of neuronal diseases, rod and cone retinopathies, such as Stargardt disease, AMD, retinitis pigmentosa, or diabetic retinopathy can benefit greatly from systems pharmacology approaches focused on long-term preservation of cone function.

Figure 2:
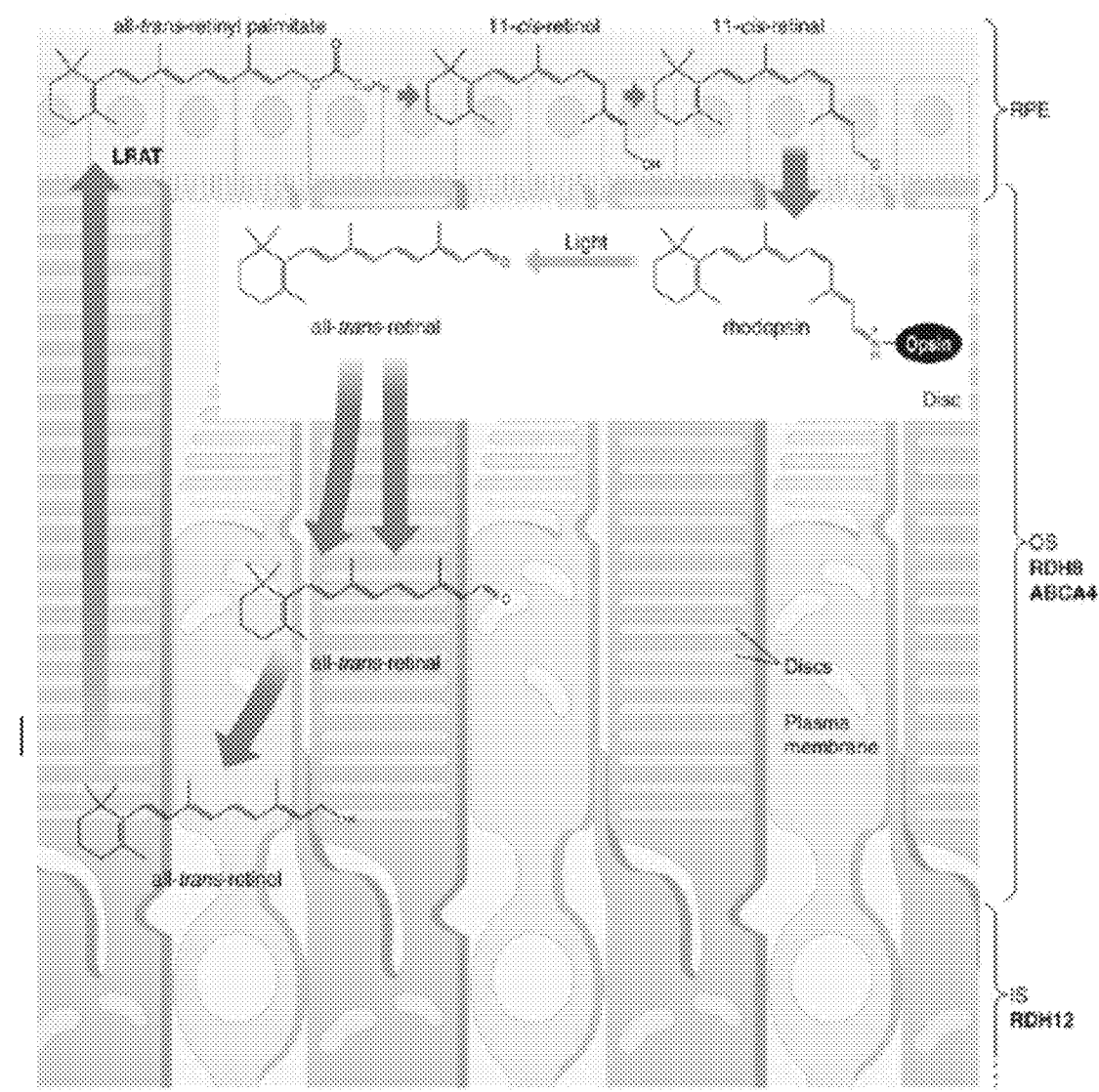
FIG. 2 is a schematic illustration of retinoid flow and all-trans-retinal clearance in the visual cycle.

FIGS. 1 and 2 show the retinoid flow in the visual cycle including condensation of all-trans-RAL, and all-trans-RAL clearance. After 11-cis-retinal binds to opsin from rhodopsin, the resulting visual chromophore 11-cis-retinylidene is photoisomerized to all-trans-retinylidene, the precursor or all-trans-RAL that is later released. Most of the all-trans-RAL dissociates from opsin into the cytoplasm before it is reduced to all-trans-retinol by RDHs including RDH8. The fraction of all-trans-RAL that dissociates into disc lumens is transported by ABCA4 before it is reduced. Thus, condensation products can be generated both within the disc lumens and the cytoplasm before it is reduced.

Figure 3:
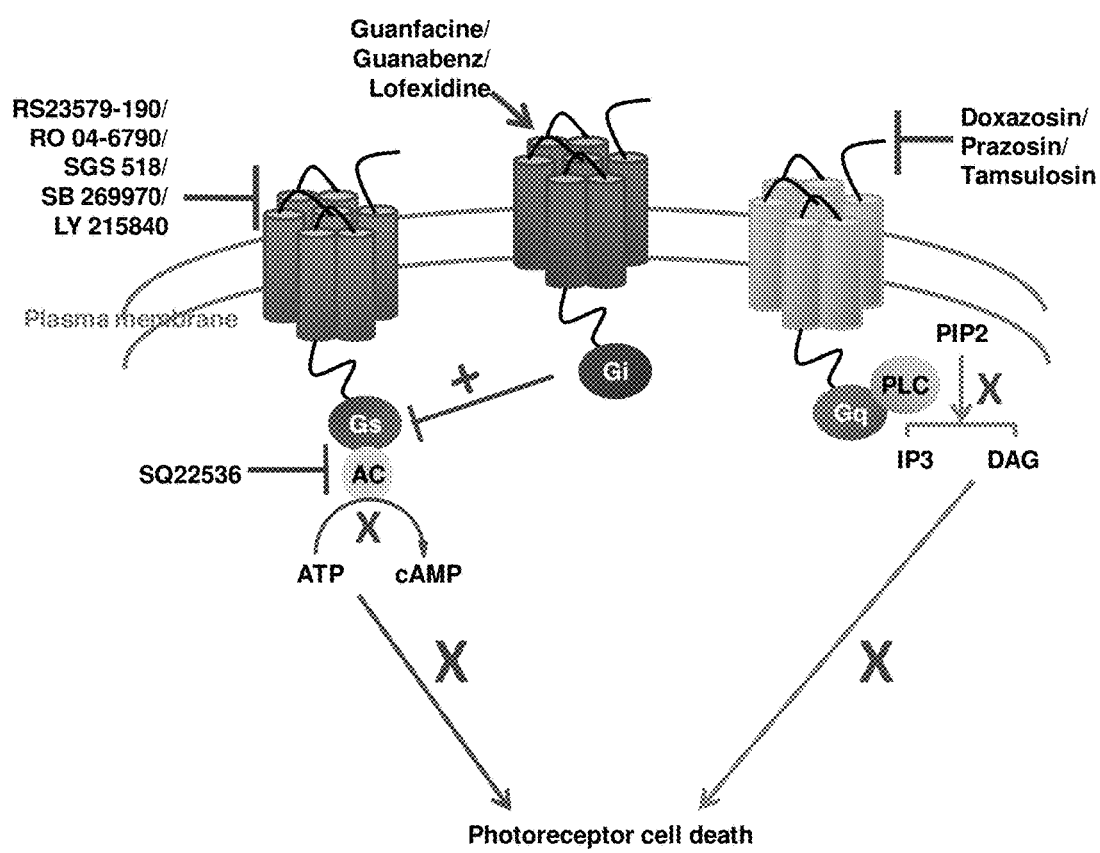
FIG. 3 is a schematic illustration of strategies targeting multiple GPCRs for therapeutic treating of photoreceptor degeneration.
Figure 4:
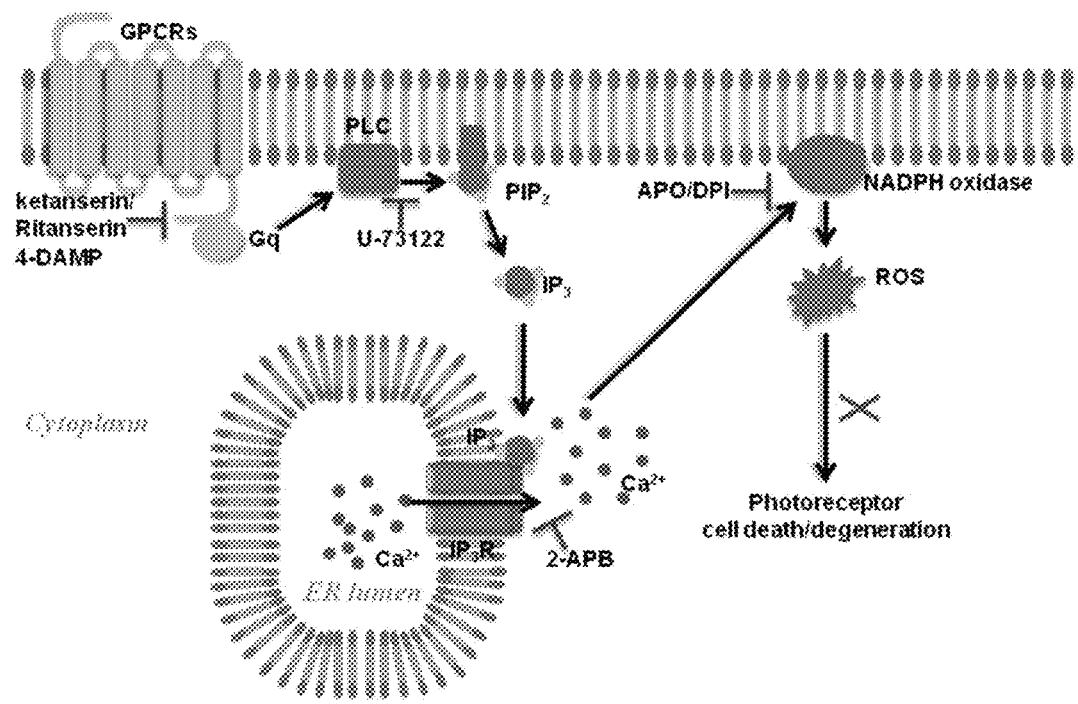
FIG. 4 is a schematic illustration of the phospholipase signaling pathway and targets for agents.

It was found that all-trans-RAL that has escaped sequestering by opsins in photoreceptor outer segments of the retina is toxic to retina cells and that aberrant all-trans-RAL clearance from the inner disc membrane to the outer disc membrane can cause retinal degeneration. As illustrated in FIGS. 3 and 4, aberrant all-trans-retinal clearance from the retina can trigger the activation of the Gs and Gq protein-coupled receptors, such as serotonin receptors (e.g., 5-HT$_{2a}$ receptor, 5-HT$_{2b}$ receptor, 5-HT$_{2c}$ receptor, 5-HT$_{2a/c}$ receptor, 5-HT$_4$ receptor, 5-HT$_6$ receptor, and 5-HT$_7$ receptor), alpha-1 adrenergic receptors, H1 histamine receptor, or M3 muscarinic receptor (M3R), and pathways associated with Gs and Gq activation.

Increase$_d$ functionality or activity of Gs-coupled GPCRs and subsequent activati$_o$n of adenylyl cyclase ($_4$C) was found to cause photoreceptor cell death. On the other hand, Gi-coupled GPCRs functionally lead to suppression of AC activity. Agonists activating α2 adrenergic receptor, a Gi-coupled GPCR, prevented photoreceptor death. Therefore, AC as the central player mediating Gs-coupled and Gi-coupled GPCR signaling, can serve as therapeutic target to preserve photoreceptors during degeneration, which could be achieved by inhibition of AC activity by an AC inhibitor.

In addition, activation of Gq-coupled GPCRs leads to the activation of phospholipase C (PLC), which in turn cleaves phosphatidylinositol 4,5-bisphosphate (PIP$_2$), into diglyceride (DAG) and inositol triphosphate (IP$_3$). Subsequently, IP$_3$ binds to its receptor, inositol triphosphate receptor (IP$_3$R) located on the endoplasmic reticulum (ER). This binding triggers the release of Ca$^{2+}$ from the ER and leads to the increased production of ROS by NADPH oxidase. The ROS generated via this signaling cascade is a major cause of retinal degeneration and ocular disorders.

The systems pharmacology approach used to treat an ocular disorder in a subject associated with light induced retinal degeneration, aberrant all-trans-retinal clearance and/or reactive oxygen species (ROS) generation in the retina can include administering to the subject subtherapeutic or subeffective amounts of two more agents that inhibit and/or antagonize activation of the Gs- or Gq-protein coupled receptors or the Gs- or Gq-signaling cascade, which is induced or triggered by light induced all-trans-retinal generation. In embodiments described herein, agents used to treat an ocular disorder associated with light induced retinal degeneration, aberrant all-trans-RAL clearance and/or ROS production can include those agents that can inhibit and/or antagonize Gs- or Gq-protein coupled receptor activation, inhibit and/or antagonize the Gq signaling cascade (e.g., agents that inhibit or antagonize PLC activation, IP$_3$ binding to its receptor), inhibit or antagonize the Gs signaling cascade (e.g., agents that inhibit and/or antagonize adenylyl cyclase activation) and/or agents that activate Gi signaling cascade in a retinal cell. These agents can be used in combination with each other as well as with other agents to modify several pathways that culminate in a common response, whether mediated by an enzyme, second messengers or channels, and treat retinal disorders associated with light induced retinal degeneration, all-trans-retinal accumulation and/or reactive oxygen species generation.

By way of example, combined therapies were tested for 2-Bromo-α-ergocryptine methanesulfonate salt (BRM), an agonist of Gi-coupled dopamine D2 receptors, metoprolol tartrate (MTP), an antagonist of Gs-coupled β1 adrenergic receptors and two additional Gq-coupled α1 adrenergic receptor antagonists, tamsulosin (TAM) and doxazosin (DOX). The results demonstrate that administration of combined treatments consisting of BRM, MTP and TAM, or BRM, MTP and DOX with each component dosed at an individual sub-effective level caused significant morphological and functional protection of photoreceptor cells. In addition, protection of bipolar and horizontal cells also was achieved by these combined treatments. In some embodiments, agents used to treat an ocular disorder associated with light induced retinal degeneration, aberrant all-trans-RAL clearance and/or ROS production can include Gs or Gq coupled serotonin receptor antagonists, such as 5-HT$_{2a}$ receptor antagonists, 5-HT$_{2b}$ receptor antagonists, 5-HT$_{2c}$ receptor antagonists, 5-HT$_{2a/c}$ receptor antagonists, 5-HT$_4$ receptor antagonists, 5-HT$_6$ receptor antagonists, and 5-HT$_7$ receptor antagonists, Dopamine receptor D1 antagonists, Dopamine receptor D5 antagonists, β1 adrenergic receptor antagonists, β2 adrenergic receptor antagonists, Adenosine A$_{2B}$ receptor antagonists, corticotropin releasing hormone receptor 1 antagonists, metabotropic glutamate receptor 1 antagonists, tachykinin receptor 1 antagonist, and prostaglandin E receptor 1 antagonists. Examples of include Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine A$_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists are described in Tables 1 and 5-10.

Examples of serotonin receptor antagonists are citalopram, escitalopram, fluoxetine, R-fluoxetine, sertraline, paroxetine, fluvoxamine, venlafaxine, duloxetine, dapoxetine, nefazodone, imipramine, imipramine N-oxide, desipramine, pirandamine, dazepinil, nefopam, befuraline, fezolamine, femoxetine, clomipramine, cianoimipramine, litoxetine, cericlamine, seproxetine, WY 27587, WY 27866, imeldine, ifoxetine, tiflucarbine, viqualine, milnacipran, bazinaprine, YM 922, S 33005, F 98214-TA, OPC 14523, alaproclate, cyanodothepine, trimipramine, quinupramine, dothiepin, amoxapine, nitroxazepine, McN 5652, McN 5707, O1 77, Org 6582, Org 6997, Org 6906, amitriptyline, amitriptyline N-oxide, nortriptyline, CL 255.663, pirlindole, indatraline, LY 113.821, LY 214.281, CGP 6085 A, RU 25.591, napamezole, diclofensine, trazodone, EMD 68.843, BMY 42.569, NS 2389, sercloremine, nitroquipazine, ademethionine, sibutramine, clovoxamine, desmethylsubitramine, didesmethylsubitramine, clovoxamine vilazodone, N-[(1-[(6-Fluoro-2-napthalenyl)methyl]-4-piperidinyl]amino]carbonyl]-3-pyridine carboxamide, [trans-6-(2-chlorophenyl)-1,2,3,5,6,10b-hexahydropyrrolo-(2,1-a)isoquinol-ine] (McN 5707), (dl-4-exo-amino-8-chloro-benzo-(b)-bicyclo [3.3.1] nona-2-6 alpha (10 alpha)-diene hydrochloride) (Org 6997), (dl)-(5 alpha,8 alpha,9 alpha)-5,8,9,10-Tetrahydro-5,9-methanobenzocycloocten-8-amine hydrochloride (Org 6906), -[2-[4[(6-fluoro-1H-indol-3-yl)-3,6-dihydro-1(2H)-pyridinyl]ethyl]-3-isopropyl-6-(methylsulphonyl)-3,4-dihydro-1H-2,1,3-benzothiadiazine-2,2-dioxide (LY393558), [4-(5,6-dimethyl-2-benzofuranyl)-piperidine] (CGP 6085), dimethyl-[5-(4-nitro-phenoxy)-6,7,8,9-tetrahydro-5H-benzocyclohepten-7-yl-]amine (RU 25.591), or a pharmaceutically acceptable salt of any of these compounds.

In one embodiment, the serotonin receptor antagonist is selected from agomelatine, pizotifen, RS 23579-190, Ro 04-6790 (4-Amino-N-[2,6-bis(methylamino)-4-pyrimidinyl]benzenesulfonamidev), SGS 518 oxalate (1-methyl-3-(1-methyl-4-piperidyl)indol-5-yl] 2,6-difluorobenzenesulfonate; oxalic acid), SB 269970 (3-({(2R)-2-[2-(4-Methyl-1-piperidinyl)ethyl]-1-pyrrolidinyl}sulfonyl)phenol hydrochloride (1:1)), LY 215840 ((8β)-N-[(1S,2R)-2-Hydroxycyclopentyl]-1-isopropyl-6-methylergoline-8-carboxamide), citalopram, escitalopram, fluoxetine, sertraline, paroxetine, fluvoxamine, venlafaxine, duloxetine, dapoxetine, nefazodone, imipramine, femoxetine and clomipramine or a pharmaceutically acceptable salt of any of these compounds.

In other embodiments, the agent can include a 5-HT$_{2a}$ receptor antagonist. Examples of 5-HT$_{2a}$ receptor antagonists are described in U.S. Pat. No. 4,444,778 and can include nefazodone, pizotifen, ketanserin, desipramine, imipramine, chlorimipramine, protriptylene, dibenzepine, amitryptyline, doxepin, prothiadene, pirandamine, spirobenzofuran, ciclazindol, nefopam, deximafen, daledalin, amedalin, quipazine, trazodone, zimelidine, tofenacine, fenetazole and fenflurame. Additional compounds which have 5-HT$_{2a}$ antagonist activity and can be used are 11-amino-1,5-methano-1,2,5,6-tetrahydrobenzocine; 1-methylamino-4-phenyl-1,2,3,4-tetrahydronaphthylene; 6-cyano-1,3-dihydro-3-dimethylaminopropyl-3-(p-fluorophenyl)-isobenzofuran; 4-benzyl-1-(2-benzofurancarbonyl)-piperidide, 1,4-ethano-4-phenyl-cyclohexylamine, α-(p-chlorophenyl)-2-methylaminomethylbenzyl alcohol; α-(2-methylaminoethyl)-2-methoxy or 4-trifluoromethylphenylbenzyl ether or p-anisyl-(1-methyl-4-phenyl-3-pipecolinyl)-ether. Still other examples of 5-HT$_{2a}$ receptor antagonists include piperidinylamino-thieno[2,3-d]pyrimidine compounds described in U.S. Pat. No. 7,030,240 and 1,4-substituted cyclic amine derivatives described in U.S. Pat. No. 7,541,371

In other embodiments, agents used to treat an ocular disorder associated with light induced retinal degeneration, aberrant all-trans-RAL clearance and/or ROS production can include alpha 1 adrenergic antagonists. Examples of alpha 1 adrenergic receptor antagonists that can be used to treat ocular disorders described herein include phentolamine family antagonists, known as imidazolines, alkylating agents such as phenoxybenzamine, or piperazinyl quinazolines.

In specific embodiments, the alpha 1 adrenergic receptor antagonist can include, for example, doxazosin, prazosin, tamsulosin, terazosin and 5-methylurapadil. The syntheses of these compounds are described in U.S. Pat. Nos. 3,511,836, 3,957,786, 4,026,894, 5,798,362, 5,792,767, 5,891,882, 5,959,108, and 6,046,207. Additionally, other alpha 1 adrenergic receptor antagonist are well known in the art. See, for example, Lagu, "Identification of alpha 1A-adrenoceptor selective antagonists for the treatment of benign prostatic hyperplasia", Drugs of the Future 2001, 25(8), 757-765 and Forray et al., 8 Exp. Opin. Invest. Drugs 2073 (1999), hereby incorporated by reference in its entirety, which provide examples of numerous alpha 1 adrenergic receptor antagonists.

In other embodiments, agents used to treat an ocular disorder associated with light induced retinal degeneration, aberrant all-trans-RAL clearance and/or ROS production can include agents that activate the Gi signaling cascade and/or inhibit andenylyl cyclase activity. Agents that activate the Gi signaling cascade and/or inhibit andenylyl cyclase activity can include dopamine receptor D2 agonists, dopamine receptor D3 agonists, dopamine receptor D4 agonists, alpha-2 adrenergic receptor agonists, and metabotropic glutamate receptor 4 agonists. Examples of dopamine receptor D2 agonists, dopamine receptor D3 agonists, dopamine receptor D4 agonists, alpha-2 adrenergic receptor agonists, and metabotropic glutamate receptor 4 agonists are described in Tables 1, and 5-10.

Examples of alpha-2 adrenergic receptor agonists include L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, medetomide, moxonidine, mivazerol, rilmenidine, UK 14,304, B-HT 933, B-HT 920, octopamine or a combination thereof.

Other examples of alpha-2 adrenergic receptor agonists include, but are not limited to amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

In still other embodiments, agents used to treat an ocular disorder associated with light induced retinal degeneration, aberrant all-trans-RAL clearance and/or ROS production can include an adenylyl cyclase inhibitor. Examples of adenylyl cyclase inhibitors are 9-tetrahydrofuryl adenine, such as THFA or SQ 22536, 2',5'-dideoxyadenosine, or 9-(cyclopentyl)-adenine.

In another embodiment of the application, the agent can include a M3 receptor antagonist, such as 4-DAMP or tolterodine. Other examples of M3 receptor antagonists are described in U.S. Pat. Nos. 7,723,356, 7,361,648, and 7,947,730.

In another embodiment of the application, the agent can include a phospholipase C (PLC) inhibitor. Examples of PLC inhibitors are described in U.S. Pat. No. 6,235,729 and can include U73122 (1-(6-((17β-3-methoxyestra-1,3,5(10)-trien-17-yl)amino)hexyl)-1H-pyrrole-2,5-dione), ET-18-OCH$_3$ (1-O-octadecyl-2-O-methyl-sn-glycero-3-phosphorylcholine), and RHC-80267 (1,6-bis-(cyclohexyloximinocarbonylamino)-hexane). Still other examples of PLC inhibitors can include o-hydroxyphosphonate compounds described in U.S. Pat. No. 5,519,163.

The agents used in methods described herein can be administered to the subject to treat the ocular disorder (e.g., macular degeneration, geographic atrophy, or Stargardt disease) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the primary amine compound can be administered after induction of macular degeneration has occurred.

The treatment methods can include administering to the subject a therapeutically effective amount of the agents alone or in combination. Determination of a therapeutically effective amount is within the capability of those skilled in the art. The exact formulation, route of administration, and dosage can be chosen by the individual physician in view of the subject's condition.

In some embodiments, a combination of agents described herein can be administered to a subject as a combination therapy to treat the ocular disorder. The phrase "combinatorial therapy" or "combination therapy" embraces the administration of one or more agents described herein, and/or potentially one or more other therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, a therapeutically effective amount at least two or more, three or more, or four or more of a Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists, dopamine receptor D2 agonists, dopamine receptor D3 agonists, dopamine receptor D4 agonists, and metabotropic glutamate receptor 4 agonists, an alpha-2 adrenergic receptor agonist, an adenylyl cyclase inhibitor, an M3 receptor antagonist, and/or a PLC inhibitor can be administered to a subject to treat the ocular disorder.

The dose, amount, and/or quantity of the agents described herein which are administered to the subject, can depend on the specific Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists, dopamine receptor D2 agonists, dopamine receptor D3 agonists, dopamine receptor D4 agonists, and metabotropic glutamate receptor 4 agonists, an alpha-2 adrenergic receptor agonist, an adenylyl cyclase inhibitor, an M3 receptor antagonist, or a PLC inhibitor selected. It will be appreciated that the dosage amounts used will depend on the potency of the specific Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists, dopamine receptor D2 agonists, dopamine receptor D3 agonists, dopamine receptor D4 agonists, and metabotropic glutamate receptor 4 agonists, an alpha-2 adrenergic receptor agonist, an adenylyl cyclase inhibitor, an M3 receptor antagonist, or a PLC inhibitor and the therapeutic regimen employed.

In another aspect, the specific Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists, dopamine receptor D2 agonists, dopamine receptor D3 agonists, dopamine receptor D4 agonists, and metabotropic glutamate receptor 4 agonists, an alpha-2 adrenergic receptor agonist, an adenylyl cyclase inhibitor, an M3 receptor antagonist, and/or a PLC inhibitor when administered in combination to subject can be administered at an amount or dosage to achieve a therapeutic effect that is substantially less (i.e., subtherapeutic or subeffective dose or amount) than the amount or dose that would be required to achieve a therapeutic effect if each compound was administered alone. In some embodiments, the subtherapeutic or subeffective dose or amount can be a dose or amount of a compound when administered alone provides protection or less than 20% complete protection. Co-administration of a Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists, dopamine receptor D2 agonists, dopamine receptor D3 agonists, dopamine receptor D4 agonists, and metabotropic glutamate receptor 4 agonists, an alpha-2 adrenergic receptor agonist, an adenylyl cyclase inhibitor, an M3 receptor antagonist, and/or a PLC inhibitor to the subject can also mitigate resistance to one single agent. Such resistance results either in the requirement for higher dosages of the drug and/or the renewed symptoms.

Moreover, co-administration of a Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, and tachykinin receptor 1 antagonist, and prostaglandin E receptor 1 antagonists, dopamine receptor D2 agonists, dopamine receptor D3 agonists, dopamine receptor D4 agonists, and metabotropic glutamate receptor 4 agonists, an alpha-2 adrenergic receptor agonist, an adenylyl cyclase inhibitor, an M3 receptor antagonist, and/or a PLC inhibitor to the subject can mitigate toxicity and side effects associated with potentially administering a single agent at an amount effective to achieve a therapeutic effect. If two or more agents are used in concert, the dosage of any single drug can be lowered. This is beneficial to the patient since using lower levels of therapeutic agents is generally safer for the patient. Additionally, cells are less likely to generate resistance to the combination of drugs as they are to a single drug. Thus in some aspects, the agents described herein can be administered to a subject at a subtherapeutic level.

Formulation of pharmaceutical compositions using agents described herein for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, one or more of the agents can be provided in an ophthalmic preparation that can be administered to the subject's eye. The ophthalmic preparation can contain the agent in a pharmaceutically acceptable solution, suspension or ointment. Some variations in concentration will necessarily occur, depending on the particular agent employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The agents can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the agent in a pharmaceutical acceptable carrier. The formulation of the agent for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of macular degeneration, which are not readily accessible or suitable for ophthalmic (e.g. eye-drops) and/or topical administration, can be treated by a systemic approach, such as intravenous infusion. For example, the agent can be administered at a low dosage by continuous intravenous infusion. In another example, in which a patient requires longer-term care, the agent can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the agent to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the agent.

As discussed above, the agent may be administered to a subject in order to treat or prevent macular degeneration and other forms of retinal disease whose etiology involves light induced retinal degeneration, aberrant all-trans-RAL clearance, and/or ROS generation, such as molecular degeneration, geographic atrophy, Stargardt disease, and retinitis pigmentosa. Other diseases, disorders, or conditions characterized by light induced degeneration, aberrant all-trans-RAL and ROS generation may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves aberrant all-trans-RAL clearance, such as geographic atrophy (GA), and then the compound is administered. In another embodiment, a subject may be identified as being at risk for developing other forms of retinal disease whose etiology involves all-trans-RAL clearance, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves light induced retard degeneration aberrant all-trans-RAL clearance, and/or ROS generation, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In still other embodiments, the agents can be administered alone or as part of a combinatorial therapy with additional therapeutic agents that can inhibit and/or antagonize the Gs or Gq signaling cascade and inhibit ROS production and/or inhibit and/or antagonize all-trans-retinal accumulation. In some embodiments, the additional therapeutic agents can include NADPH oxidase inhibitors, such as apocynin (1-(4-hydroxy-3-methoxyphenylethanone) or diacylglycerols) and agents that selectively target aberrant all-trans-retinal accumulation in the retina.

Examples of agents that selectively target all-trans-retinal accumulation are described in PCT/US 2011/071995 and can include primary amines (i.e., primary amine compounds) that form reversible Schiff-bases with free all-trans-RAL, which has escaped sequestering in photoreceptor outer segments of the retina without adversely affecting normal retinoid cycle.

In an embodiment of the application, the primary amine compounds that can form stable Schiff-bases with all-trans-RAL under physiological conditions of the retina and that can inhibit retinal degeneration upon administration to a subject can be selected using an in vitro assay that measures the ability of a primary amine compound to form a Schiff base with retinal under physiological condition of the retina and in vivo assays that measure, respectively, 11-cis-retinal formation and the optical coherence tomography score of retinas of Rdh8$^{-/-}$Abca4$^{-/-}$ mice. Primary amine compounds that form a Schiff-base with all-trans-RAL or its metabolite under physiologic conditions of the retina and that when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal are effective in treating retinal degeneration in a subject associated with aberrant all-trans-RAL clearance. Primary amines compounds that do not form a form a Schiff-base with all-trans-RAL or its metabolite under physiologic conditions of the retina or which when administered to a Rdh8$^{-/-}$ Abca4$^{-/-}$ mouse do not increase the optical coherence tomography score of the mouse to at least about 2.5 and increase 11-cis-retinal amount at least about 30% in comparison to untreated control animal, were found to be ineffective in treating retinal degeneration in a subject associated with aberrant all-trans-RAL clearance. Additionally, therapeutic efficacy of the primary amine compounds of the application can be determined using an in vitro assay that measures the ability of a primary amine compound to improve viability of RPE cells treated with retinal.

In some embodiments, the primary amine compound is a compound having the following structural formula:

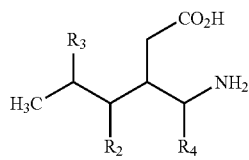

wherein $R_2$ is hydrogen or $(C_1$-$C_6)$ straight chain or branched unsubstituted or substituted alkyl;

$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;

$R_4$ is hydrogen or $(C_1$-$C_6)$ straight chain or branched unsubstituted or substituted alkyl, or carboxyl;

as well as pharmaceutically acceptable salts thereof.

In other embodiments, the primary amine compound is a compound having the following structural formula:

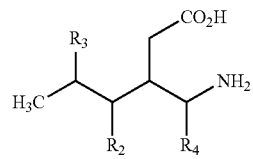

wherein $R_2$ is hydrogen, straight or branched alkyl of from 1 to 6 carbon atoms or phenyl;

$R_3$ is straight or branched alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl OH-alkylphenyl, -alkylphenoxy, -phenyl or substituted phenyl; and $R_4$ is hydrogen, and $R_2$ is straight or branched alkyl of from 1 to 6 carbon atoms or phenyl when $R_3$ is methyl, or a pharmaceutically acceptable salt thereof.

In other embodiments, the primary amine compound can have the following structural formula:

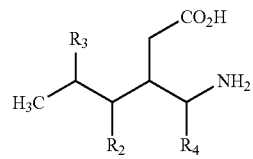

wherein $R_2$ is methyl, $R_3$ is an alkyl, and $R_4$ is a hydrogen, or a pharmaceutically acceptable salt thereof.

Specific examples of compounds of above noted formulas are selected from: 3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-

(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoic acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptanoic acid; (3S,5S)-3-Aminomethyl-5-methyl-7-(3-trifluoromethyl-phenoxy)-heptanoic acid; (3S,5S)-3-Aminomethyl-5-methyl-7-(2-trifluoromethyl-phenoxy)-heptanoic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6- trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; (3S,5R)-3-Aminomethyl-5-methyl-7-phenyl-heptanoic acid; and pharmaceutically acceptable salts thereof. Methods of synthesizing the above noted compounds are described in PCT Patent Application No. WO 00/76958, which is incorporated herein by reference in its entirety.

In other embodiments, the primary amine compound can comprise at least one of (S)-3-(Aminomethyl)-5-methylhexanoic acid or (R)-3-(Aminomethyl)-5-methylhexanoic acid. In still other embodiments, the primary amine compound can include a mixture of (S)-3-(Aminomethyl)-5-methylhexanoic acid and (R)-3-(Aminomethyl)-5-methylhexanoic acid. For example, the primary amine compound can comprise a racemic mixture of (S)-3-(Aminomethyl)-5-methylhexanoic acid and (R)-3-(Aminomethyl)-5-methylhexanoic acid. In other examples, the primary amine compound can comprise a mixture of: less than about 50% by weight (S)-3-(Aminomethyl)-5-methylhexanoic acid and greater than about 50% by weight (R)-3-(Aminomethyl)-5-methylhexanoic acid, less than about 25% by weight (S)-3-(Aminomethyl)-5-methylhexanoic acid and greater than about 75% by weight (R)-3-(Aminomethyl)-5-methylhexanoic acid, less than about 10% by weight (S)-3-(Aminomethyl)-5-methylhexanoic acid and greater than about 90% by weight (R)-3-(Aminomethyl)-5-methylhexanoic acid, less than about 1% by weight (S)-3-(Aminomethyl)-5-methylhexanoic acid and greater than about 99% by weight (R)-3-(Aminomethyl)-5-methylhexanoic acid, greater than about 50% by weight (S)-3-(Aminomethyl)-5-methylhexanoic acid and less than about 50% by weight (R)-3-(Aminomethyl)-5-methylhexanoic acid, greater than about 75% by weight (S)-3-(Aminomethyl)-5-methylhexanoic acid and less than about 25% by weight (R)-3-(Aminomethyl)-5-methylhexanoic acid, greater than about 90% by weight (S)-3-(Aminomethyl)-5-methylhexanoic acid and less than about 10% by weight (R)-3-(Aminomethyl)-5-methylhexanoic acid, or greater than about 99% by weight (S)-3-(Aminomethyl)-5-methylhexanoic acid and less than about 1% by weight (R)-3-(Aminomethyl)-5-methylhexanoic acid.

In a still further embodiment, the primary amine compound can consist essentially of or consist of (S)-3-(Aminomethyl)-5-methylhexanoic acid. In yet another embodiment, the primary amine compound can consist essentially of or consist of (R)-3-(Aminomethyl)-5-methylhexanoic acid.

Other examples of primary amine compounds that can be administered in combination with the agent are selected from the group consisting of: 5-amino-2,3-dihydrophthalazine-1,4-dione, 3,4-diethoxyaniline, 1-isopropyl-2-methyl-benzimidazol-5-amine, N2-(4-dimethylaminophenyl)-1,3-benzothiazole-2,6-diamine, N-[(3-aminophenyl)methyl]-6-methoxy-chroman-4-amine, 1-[[4-(aminomethyl)phenyl]methyl]hexahydropyrimidin-2-one, 1-(2,4-diphenylpyrimidin-5-yl)ethanamine, 3-(5-aminopentyl)-1-[(E)-(5-nitro-2-furyl)methyleneamino]imidazolidine-2,4-dione, 2-amino-N-[1-[[1-[(2-amino-1-benzyl-2-oxo-ethyl)carbamoyl]-2-methyl-propyl]carbamoyl]-3-methyl-butyl]-4-methyl-pentanamide, 2-(2-furyl)bicyclo[2.2.1]hept-5-en-3-amine, 5-(3-aminophenyl)furan-2-carboxamidine, 3-(3-aminopropanoyl)-1-[(E)-[5-(4-methoxyphenyl)-2-furyl]methyleneamino]imidazolidine-2,4-dione, 4-amino-N-(2-amino-2-oxo-ethyl)benzamide, 4-amino-N-[2-oxo-2-[(2-oxooxazolidin-3-yl)amino]ethyl]benzamide, (1S,2S,4R)-2-amino-4-isopropenyl-1-methyl-cyclohexanol, 2-amino-4-benzyl-phenol, (3S,5R,8R,9S,10S,13R,14S)-14-amino-3-hydroxy-10,13-dimethyl-1,2,3,4,5,6,7,8,9,11,12,15,16,17-tetradecahydrocyclopenta[a]phenanthrene-17-carboxylic acid, methyl (3S,5R,8R,9S,10S,13R,14S)-14-amino-3-[(2S,5R)-5-hydroxy-6-methyl-tetrahydropyran-2-yl]oxy-10,13-dimethyl-1,2,3,4,5,6,7,8,9,11,12,15,16,17-tetradecahydro-cyclopenta[a]phenanthrene-17-carboxylate, 1-[(E)-[5-(4-aminophenyl)-2-furyl]methyleneamino]-3-[4-(4-methylpiperazin-1-yl)butyl]imidazolidine-2,4-dione, 4-amino-2-hydroxy-benzoic acid, fluoranthen-3-amine, phenazine-2,3-diamine, 3-chloro-4-(4-chlorophenoxy)aniline, 4-(6-methyl-1,3-benzothiazol-2-yl)aniline, 3-[5-(1H-benzimidazol-2-yl)-2-furyl]aniline, N-(2-aminoethyl)-7-tert-butyl-3,3-dimethyl-2H-benzofuran-5-carboxamide, N'-benzylpropane-1,3-diamine, 5,6-dihydro-2-methyl-4H-pyrrolo[3,2,1-ij]quinoline-1-propanamine, 5-(4-aminophenyl)-2-(o-tolyl)pyrazol-3-amine, (2,3-dimethyl-1H-indol-5-yl)methanamine, 2,4-dimethyl-6-nitro-aniline, methyl 2-amino-4,5-dimethoxy-benzoate, 2-(5-propyl-1H-indol-3-yl)ethanamine, 2-(7-methoxy-5-nitro-1H-indol-3-yl)ethanamine, 5-amino-2-[(4-carboxyphenyl)carbamoyl]benzoic acid, 5-amino-2-[(3-carboxyphenyl)carbamoyl]benzoic acid, [2-[2-(3-aminobenzoyl)oxyphenyl]phenyl] 3-aminobenzoate, [4-[1-[4-(4-aminobenzoyl)oxyphenyl]-1-methyl-ethyl]phenyl] 4-aminobenzoate, 4-amino-N'-(4-chlorobenzoyl)benzohydrazide, 3-(4-aminophenyl)propanoic acid, 2,1,3-benzothiadiazole-4,5-diamine, 1H-benzimidazol-2-yl-methanamine, 2-amino-1-[16-(2-aminoacetyl)-1,4,10,13-tetraoxa-7,16-diazacyclooctadec-7-yl]ethanone, methyl 6-(2-aminophenyl)-6-oxo-hexanoate, 2-(3-amino-4-ethyl-phenyl)pyridin-3-ol, (5-amino-6,7-dimethoxy-3-methyl-benzofuran-2-yl)-morpholino-methanone, (3,5-diaminophenyl)methyl N-butylcarbamate, (3,5-diaminophenyl)methyl N-(2,4-dimethoxyphenyl)carbamate, 1-(4-aminophenyl)-3-

(3,4-difluorophenyl)-1-phenyl-propan-2-one, N-(2-aminoethyl)-2-[bis(2-hydroxyethyl)amino]acetamide, (Z)—N-(2-aminoethyl)-3-(1-naphthyl)prop-2-enamide, N-(2-aminoethyl)naphthalene-1-carboxamide, (2-amino-5-chloro-phenyl)-phenyl-methanone, 4-(4-bromophenoxy) aniline, 3-aminophenazin-2-ol, 5-amino-N-butyl-2-hydroxy-benzenesulfonamide, ethyl 2-[(2-aminophenyl)carbamothioylamino]acetate, 2-(2-aminophenyl)sulfanyl-4,6-dimethyl-pyridine-3-carbonitrile, 2-amino-1-phenyl-ethanone, 2-(2-methylphenoxy)aniline, (2-amino-5-chloro-phenyl)-(2-chlorophenyl)methanone, (1-phenylcyclopentyl)methanamine, tetralin-5-amine, 2-amino-3-(2-hydroxyphenyl)propanoic acid, 3-aminopropane-1-sulfinic acid, (3R,4R,5R)-2-[(1S,2S)-4,6-diamino-3-[(2R,3R)-3-amino-6-[1-(methylamino)ethyl]tetrahydropyran-2-yl]oxy-2-hydroxy-cyclohexoxy]-5-methyl-4-(methylamino)tetrahydropyran-3,5-diol, 4-ethoxyaniline, N-(4-amino-5-chloro-2-hydroxy-phenyl)benzenesulfonamide, 3-amino-N-(3,5-dichloro-2-hydroxy-4-methyl-phenyl)benzamide, 5,6,7,8-tetrahydrophenanthren-2-amine, 2-amino-N-(2-amino-1-benzyl-2-oxo-ethyl)-3-methyl-pentanamide, 1-benzylpiperidin-4-amine, (2R)-2-amino-3-ethylsulfanyl-propanoic acid, 2-amino-N-[2-(2,5-dioxopiperazin-1-yl)-2-oxo-ethyl]propanamide, 2-amino-3-(1H-imidazol-4-yl)propanamide, 2-amino-N-(2-naphthyl)acetamide, (2-amino-6-methyl-phenyl)-phenyl-methanone, 3-[2-(2-aminoethylamino)ethylamino]propanenitrile, 2-amino-1-(3-bromophenyl)ethanone, (1,1-dioxothiolan-3-yl)methanamine, 2,4,6-tritert-butylaniline, N1,N4-bis(4-amino-2-chloro-phenyl)terephthalamide, 4-[(3,4-diaminophenyl)methyl]benzene-1,2-diamine, 5-methoxy-2-methyl-1,3-benzothiazol-6-amine, 2-(2-methyl-5-nitro-imidazol-1-yl)ethanamine, 1-bromonaphthalen-2-amine, 4-amino-2,6-dibromo-benzenesulfonamide, N'-[(E)-(2-aminophenyl)methyleneamino]-N-(4-chloro-3-nitro-phenyl)oxamide, 2-bromo-4,5-dimethyl-aniline, ethyl 2-[(4-amino-3-nitro-benzoyl)amino]-4,5,6,7-tetrahydrobenzothiophene-3-carboxylate, 4-amino-2-morpholinosulfonyl-phenol, 4-[(4-amino-3,5-diethyl-phenyl)methyl]-2,6-diethyl-aniline, 5-[1-(3-amino-4-methyl-phenyl)-2,2,2-trifluoro-1-(trifluoromethyl)ethyl]-2-methyl-aniline, 4-pyridylmethanamine, 2-phenylbenzotriazole-4,5-diamine, 5-amino-2-hydroxy-N,N-dimethyl-benzenesulfonamide, methyl 2-amino-3-phenyl-propanoate, 4-amino-N-[4-[6-[(4-aminobenzoyl)amino]-7-chloro-1H-benzimidazol-2-yl]phenyl]benzamide, 3-chloro-4-(2-naphthyloxy)aniline, 2-bromo-6-(difluoromethylsulfonyl)-4-nitro-aniline, 5-(4-aminophenoxy)-2-(1-naphthyl)isoindoline-1,3-dione, 5-(3-aminophenoxy)-2-(1-naphthyl)isoindoline-1,3-dione, 7-[3-(aminomethyl)-1-piperidyl]-1-cyclopropyl-8-methoxy-4-oxo-quinoline-3-carboxylic acid, 7-[3-(1-amino-1-methyl-ethyl)-1-piperidyl]-1-cyclopropyl-8-methoxy-4-oxo-quinoline-3-carboxylic acid, N-(3-amino-4-chloro-phenyl)-4,4-dimethyl-3-oxo-pentanamide, (4-aminophenyl)-(4-fluorophenyl)methanone, 2-(5-fluoro-1H-indol-3-yl)ethanamine, N1-(4-methoxyphenyl)benzene-1,4-diamine, 2-nitro-5-piperazin-1-yl-aniline, 5-(4-methylpiperazin-1-yl)-2-nitro-aniline, 2-amino-N—[(Z)-1-(4-chlorophenyl)ethylideneamino]benzamide, 3-amino-N-(2-amino-5-methyl-phenyl)-N-benzyl-benzamide, 1-[(Z)-1-(4-aminophenyl)ethylideneamino]-3-(m-tolyl)thiourea, 2-amino-4-cyclopropyl-6-(4-methoxyphenyl)benzene-1,3-dicarbonitrile, 2-(2-naphthyl)-1,3-benzoxazol-5-amine, N-[(E)-1-(4-aminophenyl)ethylideneamino]furan-2-carboxamide, 4-(4-aminophenyl)thiazol-2-amine, (2R)-2-acetamido-6-[[(2R)-2-aminobutanoyl]amino]-N-[[3-(trifluoromethyl)phenyl]methyl]hexanamide, (4S)-5-[[(5R)-5-acetamido-6-oxo-6-(propylamino)hexyl]amino]-4-amino-5-oxo-pentanoic acid, N-[(1R)-5-[[4-(aminomethyl)cyclohexanecarbonyl]amino]-1-[[(2R)-2-hydroxypropyl]carbamoyl]pentyl]thiophene-2-carboxamide, N-[(1R)-1-(allylcarbamoyl)-5-[(4-aminobenzoyl)amino]pentyl] thiophene-2-carboxamide, (4S)-4-amino-5-oxo-5-[[(5R)-6-oxo-6-[2-(2-thienyl)ethylamino]-5-(thiophene-2-carbonylamino)hexyl]amino]pentanoic acid, 2-[(6-amino-1,3-benzothiazol-2-yl)sulfanyl]-N-(2-fluorophenyl)acetamide, N-(5-amino-2-methoxy-phenyl)-2,4-dichlorobenzamide, N-(6-amino-4-methyl-1,3-benzothiazol-2-yl)acetamide, 3-amino-N'-[2-(2-naphthyloxy)acetyl]-5-nitrobenzohydrazide, 2-(2-aminophenyl)sulfanyl-N-[3,5-bis(trifluoromethyl)phenyl]-2-phenyl-acetamide, ethyl 2-[[2-[2-[[2-amino-3-(4-hydroxyphenyl)propanoyl]amino]propanoylamino]acetyl]amino]acetate, 2-amino-5-chloro-N-(4-pyridylmethyl)benzamide, 8-nitronaphthalen-1-amine, 2-amino-3-cyclopropyl-propanoic acid, 2-(2-isopropyl-5-methyl-phenoxy)ethanamine, 2-amino-N-[(E)-1-(2-hydroxyphenyl)ethylideneamino]benzamide, (2R)-2-amino-3-benzhydrylsulfanyl-propanoic acid, tert-butyl 2-aminopropanoate, 2-[4-(1-ethylpropyl)phenoxy]-5-(trifluoromethyl)aniline, N1-methylbenzene-1,3-diamine, 1-(4-aminophenyl)sulfanyl-3-(diethylamino)propan-2-ol, 2-(4-aminophenyl)-2,2-dimethyl-propanamide, 2-amino-3-(4-nitrophenyl)butanoic acid, 2-(2-amino-5-bromo-phenyl)-4-methyl-benzo[g]quinoxalin-3-one, N-[3-[(2-aminophenyl)methylamino]-1-methyl-3-oxo-propyl]-2-phenyl-quinoline-4-carboxamide, N-[2-[(2-aminophenyl)methylamino]-2-oxo-1-phenyl-ethyl]-2-phenyl-quinoline-4-carboxamide, (5S)-5-(4-aminobutyl)-3-[4-(o-tolyl)phenyl]imidazolidine-2,4-dione, (5S)-5-(4-aminobutyl)-3-[4-(benzothiophen-2-yl)-1-naphthyl]-2-thioxo-imidazolidin-4-one, 2-amino-4,6-ditert-butyl-phenol, 5-(aminomethyl)-2,4-dimethyl-pyridin-3-amine, 3-amino-N-[5-hydroxy-1-(2,4,6-trichlorophenyl)pyrazol-3-yl]benzamide, (2R)-2-amino-3-(4-fluorophenyl)-N-[4-guanidino-1-(1-piperidylmethyl)butyl]propanamide, 3-[[2-[2-(3-aminopropylcarbamoyl)phenyl]benzoyl]-[(2,5-difluorophenyl)methyl]amino]propanoic acid, N-[(4-acetamidophenyl)methyl]-N-(3-amino-2,2-dimethyl-propyl)-2-(4-ethylphenyl)pyridine-4-carboxamide, N-(3-aminopropyl)-2-(4-ethylphenyl)-N-[(3,4,5-trimethoxyphenyl)methyl]pyridine-4-carboxamide, N-(2-aminoethyl)-5-(4-fluorophenyl)-N-(2-pyridylmethyl) pyridine-3-carboxamide, N-[[4-(aminomethyl)phenyl]methyl]-5-(1-naphthyl)-N-(2-pyridylmethyl)pyridine-3-carboxamide, 2-(3-acetylphenyl)-N-(3-aminopropyl)-N-(2,3-dihydro-1,4-benzodioxin-6-ylmethyl)pyridine-4-carboxamide, 2-[(4S,5R)-2-[(1R)-1-amino-2-(4-fluorophenyl)ethyl]-5-(2-naphthyl)tetrahydropyran-4-yl] acetonitrile, (2R)-2-amino-1-[(2S,4R)-4-benzyloxy-2-[2-(1,2,4-triazol-4-yl)ethyl]pyrrolidin-1-yl]-3-(4-fluorophenyl) propan-1-one, (2R)-2-amino-3-phenyl-1-[4-phenyl-4-(1,2,4-triazol-1-ylmethyl)-1-piperidyl]propan-1-one, N'-cyclododecylethane-1,2-diamine, 7-[2-[(2-amino-2-methyl-propyl)amino]pyrimidin-4-yl]-6-(4-fluorophenyl)-2,3-dihydro-1H-pyrazolo[1,2-a]pyrazol-5-one, 2,3,4,5-tetrahydro-1-benzothiepin-5-amine, 5-[(2R,3R,4S)-3-amino-4-(methoxycarbonylamino)tetrahydrothiophen-2-yl] pentanoic acid, 3-(2-aminophenyl)sulfanyl-3-(3,4-dichlorophenyl)-1-phenyl-propan-1-one, and pharmaceutically acceptable salts thereof.

The invention is further illustrated by the following examples, which are not intended to limit the scope of the claims.

Example 1

In this Example, we investigated the in vivo signaling mechanisms that mediate the action of atRAL in causing ROS production and light-induced photoreceptor degeneration. The results indicate that PLC activation and the resulting second messenger $IP_3$ contribute to atRAL-induced NADPH oxidase activation. The toxic action of atRAL was diminished by blocking serotonin 2A ($5-HT_{2A}R$) or $M_3$-muscarinic ($M_3R$) receptors, implicating G protein-coupled receptors GPCR(s) participation in the overall process. These observations show that certain types of retinal degeneration are be prevented by therapies selectively targeting transient sequestration (buffering) of elevated atRAL, antagonizing a subset of GPCRs, or inhibiting PLC, $IP_3R$ or NADPH oxidase, alone or in combination.

Methods

Animals $Abca4^{-/-}Rdh8^{-/-}$ mice, generated and genotyped as previously described were used when they reached 4- to 5-weeks of age. Eight- to 12-week old Balb/c mice were obtained from Jackson Laboratory (Bar Harbor, Me.). All mice were housed in the Animal Resource Center at the School of Medicine, Case Western Reserve University, where they were routinely maintained in a 12 h light (less than 50 lux in the cage)/12 h dark cycle environment. For bright light exposure experiments mice were dark-adapted for 24 h prior to illumination at 10,000 lux (150 W spiral lamp, Commercial Electric) for either 30 min ($Abca4^{-/-}Rdh8^{-/-}$ mice) or 2 h (Balb/c mice). $Abca4^{-/-}Rdh8^{-/-}$ mouse pupils were dilated with 1% tropicamide prior to light exposure whereas Balb/c mice did not require pupil dilation before such exposure. Analyses of retinal structural and functional changes were performed 7 days after bright light exposure. All animal handling procedures and experiments were approved by the Institutional Animal Care and Use Committee at Case Western Reserve University.

Chemicals atRAL was purchased from Toronto Research Chemicals, Inc (Toronto, Canada). all-trans-Retinoic acid (atRA), Apocynin (APO), diphenyliodonium (DPI), 2-aminoethoxydiphenyl borate (2-APB), ketanserin and 8-hydroxy-N,N-dipropyl-2-aminotetralin (8-(OH)-DPAT) were obtained from Sigma (St. Louis, Mo.). R and S enantiomer of pregablin was synthesized by Ricerca Bioscience LLC (Concord, Ohio). A2E (2) and $Ret-NH_2$ (3) were synthesized as previously described (3). U-73122 was purchased from Calbiochem (Gibbstown, N.J.). Ritanserin and 1,1-dimethyl-4-diphenylacetoxypiperidinium iodide (4-DAMP) were purchased from TOCRIS (Ellisville, Mo.).

In Vitro Detection and Quantification of Intracellular Reactive Oxygen Species (ROS)

ARPE19 cells were cultured in Dulbecco's Modified Eagle's Medium (DMEM) (low glucose) supplemented with 10% fetal bovine serum. The ROS probes, 2',7'-dichlorofluorescein diacetate (DCF-DA, Sigma, St. Louis, Mo.) or dihydroethidium (DHE, Invitrogen Corporation, Carlsbad, Calif.) were added after indicated pretreatments and incubated at 37° C. for 10-min before thorough washing in PBS and the ROS signals were subsequently observed at the same exposure setting under an inverted fluorescence microscope (Leica DMI 6000 B). Fluorescence quantification was performed with Metamorph imaging software (Molecular Devices, Downington, Pa.). Thresholds corresponding to fluorescent signals were set from the images and average fluorescence intensities were recorded for statistical analysis.

In Vivo Detection of ROS

The ROS probe, DHE, at a dose of 20 mg/kg body weight was administered to $Abca4^{-/-}Rdh8^{-/-}$ mice via intraperitoneal injection 30 min prior to light exposure. Eye cups obtained after removing the cornea, lens and vitreous body from enucleated eye globes 3 h post light illumination were fixed in 4% paraformaldehyde. Cryosections were prepared from fixed eye cups and cut at 12 am thickness for microscopic assessment of ROS signal fluorescence in the retina.

Mouse Treatments $Ret-NH_2$ and R and S enantiomer of pregablin were administered by gavage to 24-h dark-adapted mice at a dose of 100 mg/kg body weight 2 h before the illumination. All other experimental compounds were given to 24 h dark-adapted mice by intraperitoneal injection through a 28 gauge needle at 24 h and 1 h prior to bright light exposure. Tested compounds and their doses were: APO, 50 mg/kg body weight; DPI, 1 mg/kg body weight; U-73122, 6.25 mg/kg body weight; 2-APB, 2.5 mg/kg body weight; ketanserin, 1.25 mg/kg body weight; ritanserin, 3.75 mg/kg body weight; 8-(OH)-DPAT, 10 mg/kg body weight; and 4-DAMP, 6.25 mg/kg body weight.

Optical Coherence Tomography (OCT)

Ultra-high resolution SD-OCT (Bioptigen, Research Triangle Park, N.C.) was performed for in vivo imaging of mouse retinas. Mice were anesthetized by intraperitoneal injection of an anesthetic cocktail of ketamine (6 mg/ml) and xylazine (0.44 mg/ml) diluted with 10 mM sodium phosphate, pH 7.2, 100 mM NaCl at the dose of 20 µl/g body weight. Pupils were dilated with 1% tropicamide prior to imaging. Four frames of OCT images were acquired in the B-mode and averaged for presentation.

Histology and Immunohistochemistry

Retinal histology and immunohistochemistry (IHC) was performed as previously described. Briefly, eye cups free of cornea, lens and vitreous body were fixed in 2% glutaraldehyde/4% paraformaldehyde and processed for Epon embedding. Sections 1 am thick were cut and stained with toluidine blue for histological examination under a light microscope. IHC analysis was performed on 12 am thick cryosections prepared from 4% paraformaldehyde-fixed eye cups. Collected cryosections were subjected to examination for rhodopsin, PNA and DAPI expression.

ERGs

All ERG procedures were performed by published methods. For single-flash recording, the duration of white light flash stimuli (from 20 s to 1 ms) was adjusted to provide a range of illumination intensities (from −3.7 to 1.6 log cd·s/$m^2$). Three to 5 recordings were made at sufficient intervals between flash stimuli (from 3 s to 1 min) to allow recovery from any photo-bleaching effects.

Retinoid Analyses

Extraction, derivatization, and separation of retinoids were performed and 11-cis-retinoid content was analyzed by HPLC by procedures previously described.

Statistical Analyses

Results were collected from at least three independent experiments. Data were expressed as means±SEM and statistical analyses were performed using the students t-test.

Results atRAL Stimulates Intracellular ROS Production Through NADPH Oxidase

Figure 5:
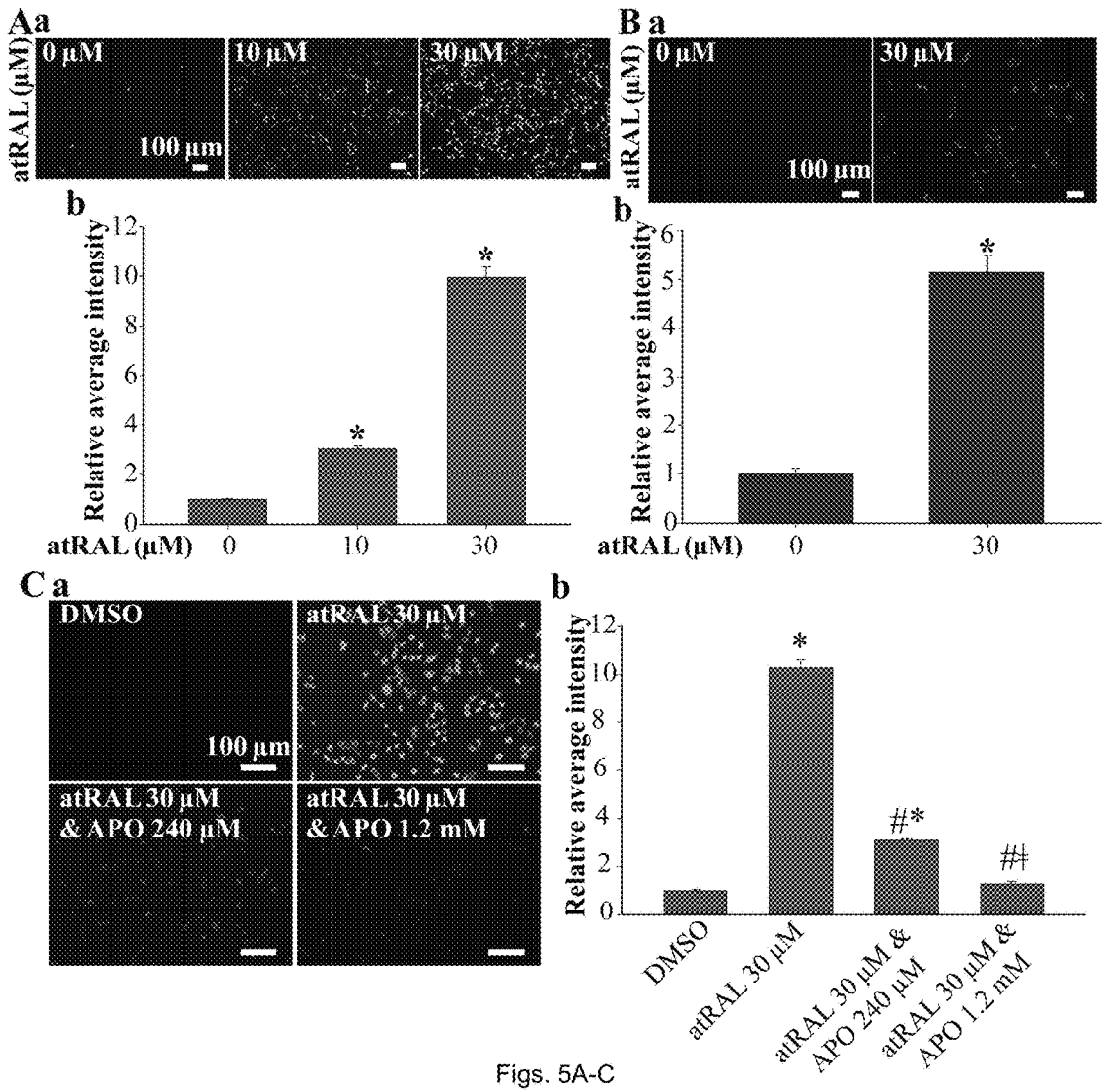
FIGS. 5(A-C)(a-c) illustrate: (A) (a) images of the ROS signal obtained with the same exposure time under a fluorescence microscope, and (b) average fluorescence intensities recorded and compared with Metamorph imaging software for statistical analyses (Means±SEM; * compared to 0 µM, p<0.01); (B) (a) images of the ROS signal detected by DHE were obtained under a fluorescence microscope. (b) Recorded ROS signals were then compared using by the method described above. (C) atRAL and/or the NADPH oxidase inhibitor, Apocynin (APO) was applied to cultured ARPE19 cells at concentrations indicated. ROS generation was monitored 1 h after indicated treatments via DCF-DA detection as noted above. (a) Fluorescence images were recorded with the same exposure times, and (b) statistical analyses were performed as noted above (* compared to control, p<0.01; # compared to atRAL 30 µM, p<0.01; ‡ compared to control, p>0.05).
Figure 12:
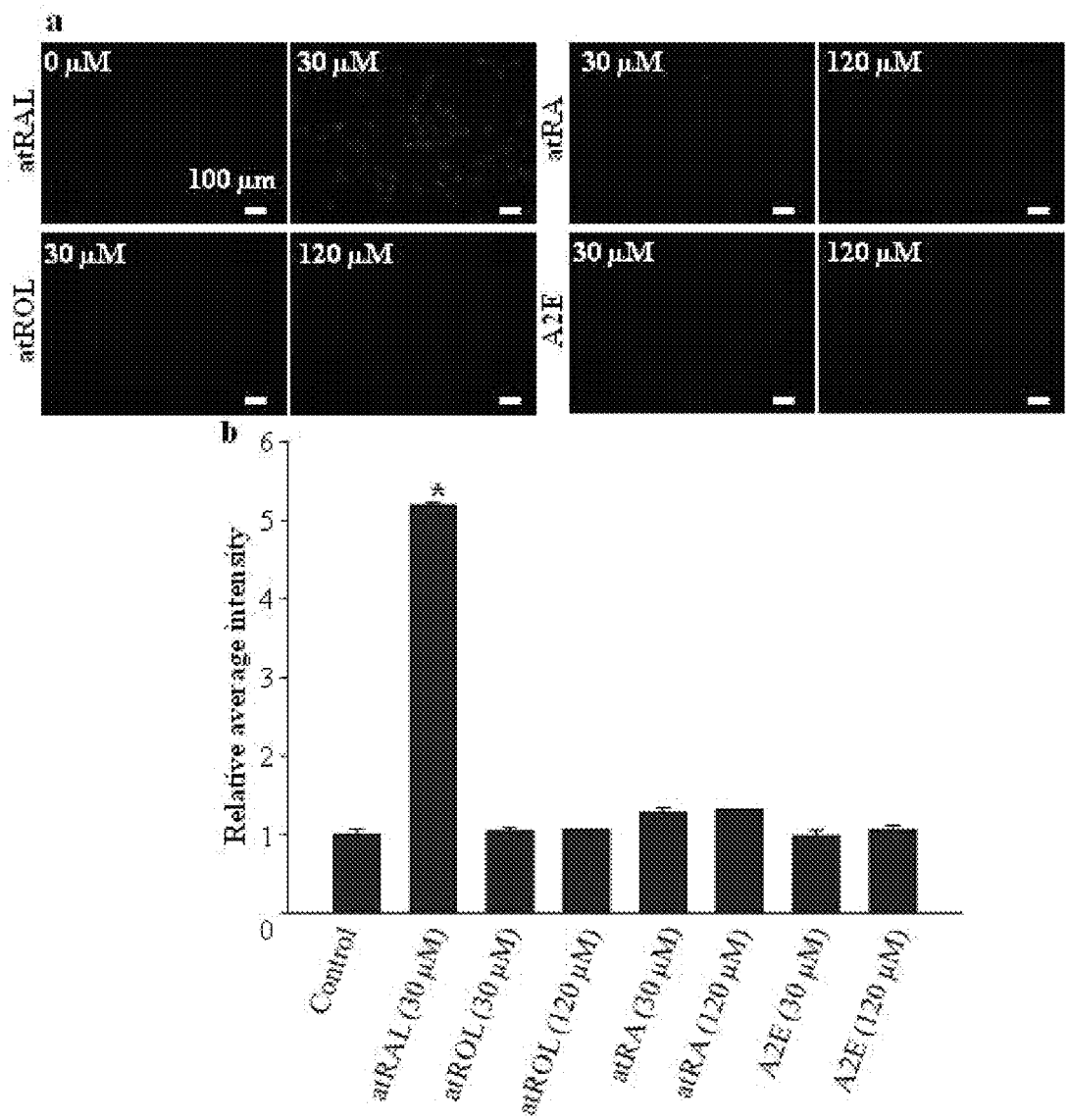
FIGS. 12(A-B) illustrate: (A) Fluorescent images obtained after the same exposure time of either atRAL, all-trans-retinol (atROL), all-trans-retinoic acid (atRA) or di-retinoid-pyridinium-ethanolamine (A2E) applied to cultured ARPE19 cells at indicated concentrations 1 h prior to addition of the ROS probe, DHE. (B) Quantification and comparison of ROS signals as described above.

To determine the effect of atRAL on retinal ROS production, we incubated ARPE19 cells, an immortalized human RPE-like cell line susceptible to atRAL-induced cell death, with atRAL followed by examination with a ROS probe. As shown in FIG. 5A, atRAL application significantly elevated intracellular ROS production prior to massive cell death in a dose dependent manner. Because the probe used, 5-(and -6)-chloromethyl-2',7'-dichlorodihydrofluorescein diacetate (DCF-DA), is not entirely selective for $H_2O_2$ and hydroxyl radicals, intracellular ROS levels were also examined by another commonly used ROS probe, dihydroethidium (DHE), which is especially sensitive to superoxide. Consistently, the intracellular ROS signal examined by the DHE probe was markedly increased in ARPE19 cells treated with atRAL at 30 μM (FIG. 5B), a dose that reproducibly causes excessive ARPE19 cell death as reported previously. This concentration of atRAL would be produced by a ~1% bleach of rhodopsin under physiological conditions. Interestingly, atRAL-related metabolic products such as all-trans-retinol (atROL), all-trans-retinoic acid (atRA) and A2E did not induce overproduction of intracellular ROS (FIG. 12). The differences between atRAL and the other retinoids in triggering intracellular ROS production may explain the difference in their effect on inducing cell death, as neither atROL, atRA nor A2E induced cell death at the doses examined.

It is known that NADPH oxidase is the primary enzymatic source of atRAL-stimulated superoxide generated in neutrophils. To further explore the involvement of NADPH oxidase in atRAL-induced ROS production in retinal cells, APO, a widely used NADPH oxidase inhibitor that interrupts NADPH oxidase complex assembly, was applied to ARPE19 cells together with atRAL. As shown in FIG. 4C, APO treatment inhibited atRAL-induced intracellular ROS generation which was associated with improved ARPE19 cell survival (FIG. 12). Taken together, these results indicate that NADPH oxidase is required for atRAL-induced ROS production in ARPE19 cells, a finding that implies a mechanistic involvement of NADPH oxidase-mediated ROS generation in atRAL-induced retinal cell death.

Figure 6:
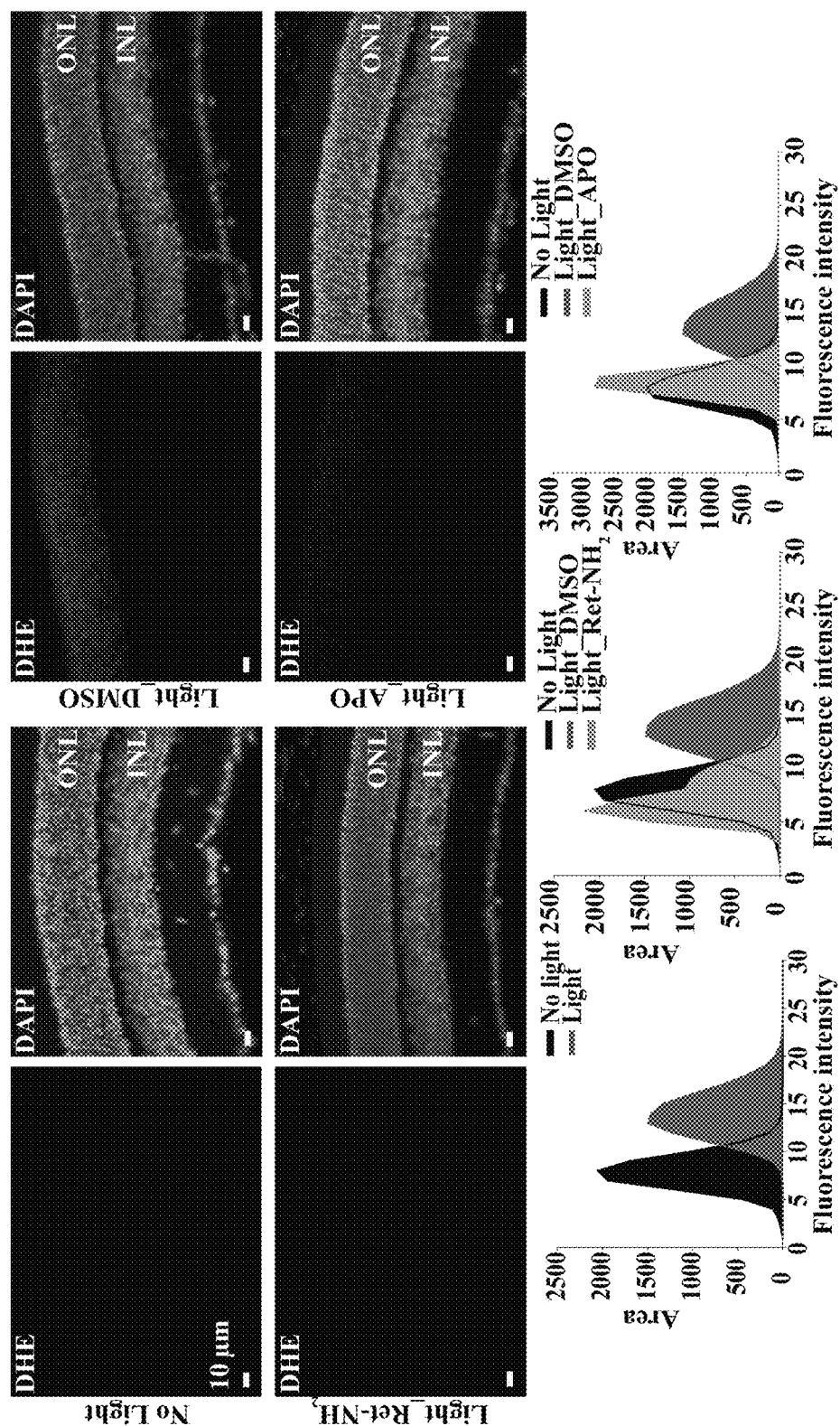
FIG. 6 illustrates atRAL is associated with NADPH oxidase-mediated ROS generation in photoreceptors. Dark-adapted Rdh8$^{-/-}$Abca4$^{-/-}$ mice at age of 4 to 5 weeks were treated with the ROS probe, DHE, prior to light exposure at 10,000 lux for 30 min. DMSO vehicle control (Light_DMSO) and NADPH oxidase inhibitor, APO (Light_APO) were administered by intraperitoneal injection 1 h prior to light exposure. Retinylamine (Ret-NH$_2$) was gavaged 2 h before illumination (Light_Ret-NH$_2$). Dark-adapted Rdh8$^{-/-}$Abca4$^{-/-}$ mice unexposed to experimental light were included for the DHE probe treatment as well (No light). Retinas were harvested 3 h after illumination. ROS signals were obtained with same exposure setup under a fluorescence microscope. DAPI staining was performed simultaneously to visualize cell nuclei and gross retinal structure. Recorded ROS fluorescence intensity averaged from various areas was plotted as a histogram for group comparisons.
Figure 13:
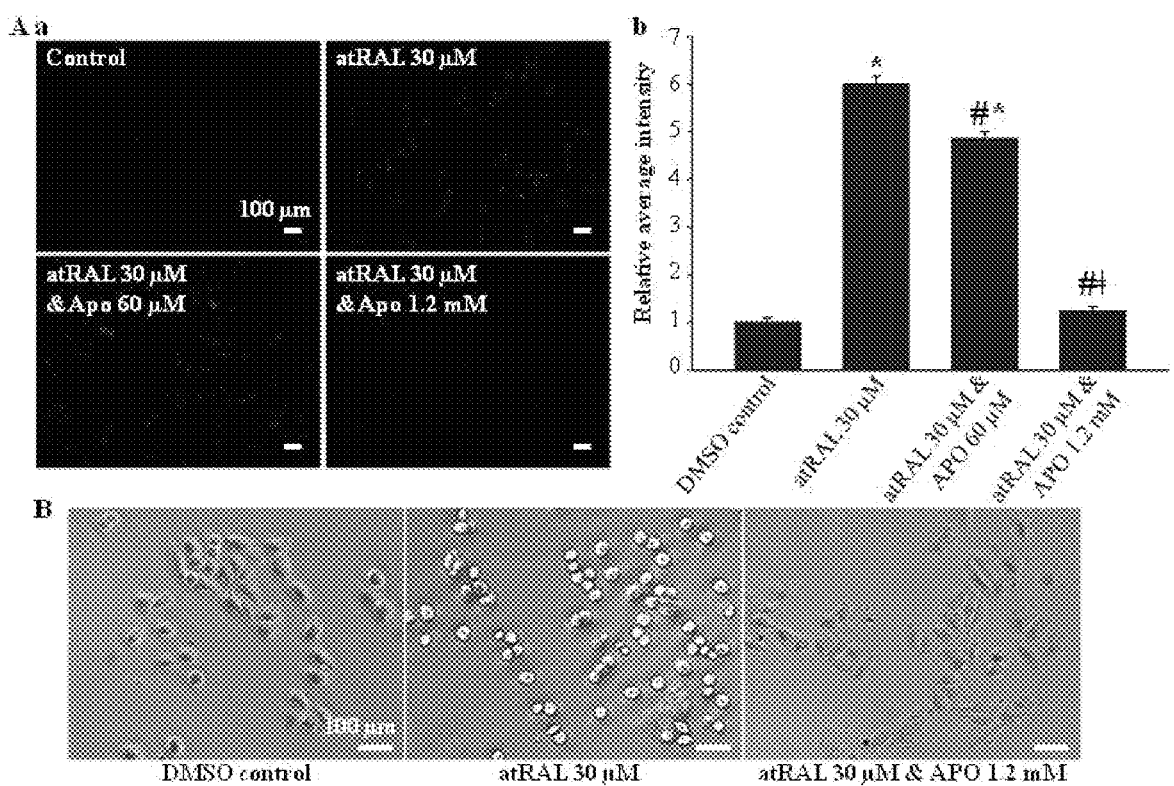
FIGS. 13(A(a-b)-B) illustrate: (A) The inhibitory effect of APO on atRAL-induced ROS production was evaluated with the ROS probe, DHE, in cultured ARPE19 cells 1 h after indicated treatments. (a) Fluorescence images were recorded with the same exposure time and (b) statistical analyses were performed based on average fluorescence intensity generated by Metamorph imaging software (Means±SEM; * compared to DMSO control, $p<0.01$; # compared to atRAL 30 µM, $p<0.01$; ‡ compared to control, $p>0.05$). (B) APO treatment prevents atRAL-induced cell death in cultured APRE19 cells. Indicated treatments were applied to cultured ARPE19 cells for 24 h and the morphology of cells was observed by light microscopy (10×).
Figure 14:
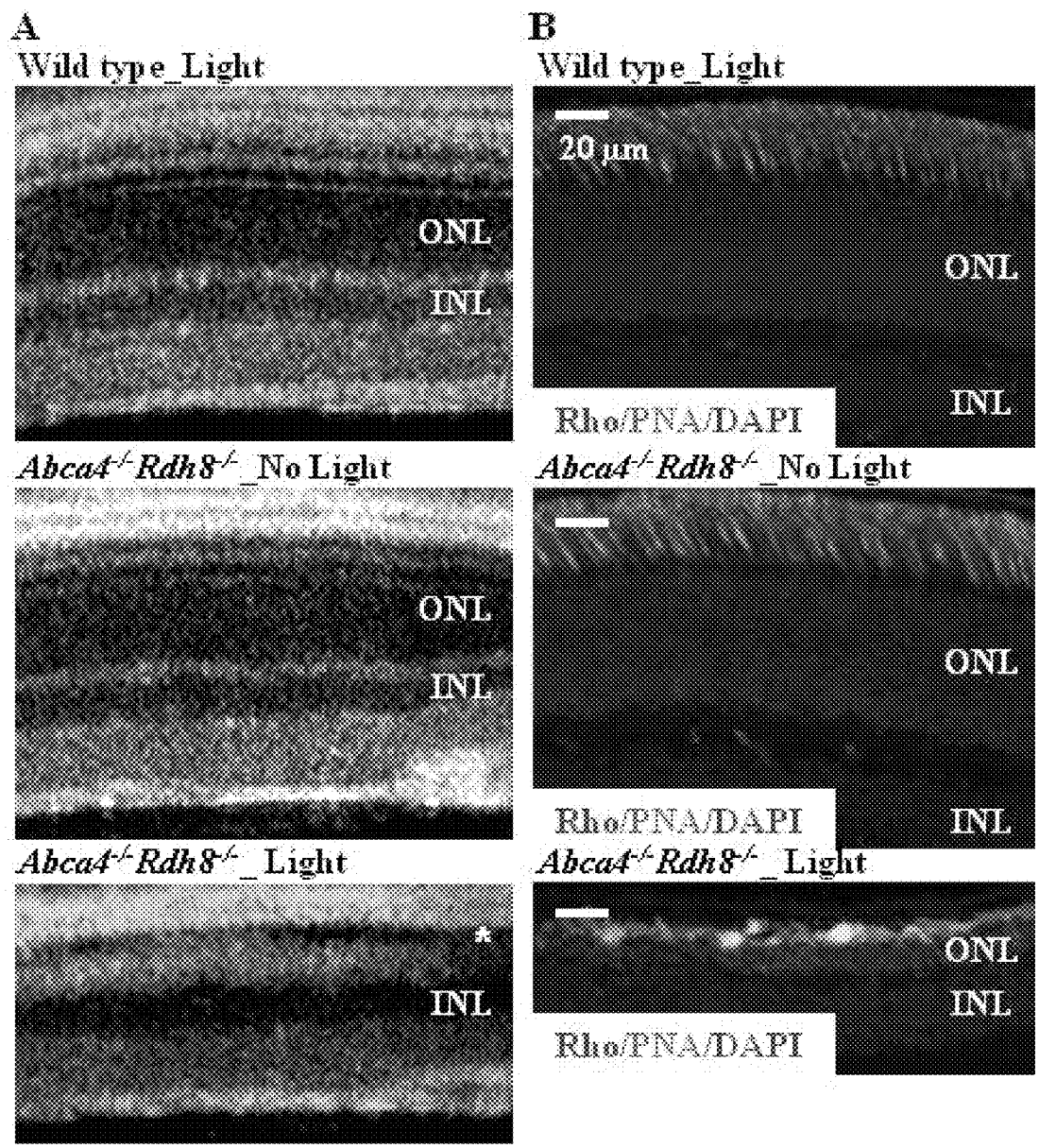
FIGS. 14(A-B) illustrate Rdh8$^{-/-}$Abca4$^{-/-}$ mouse photoreceptors exhibit light-induced degeneration in vivo. 4- to 5-week old Rdh8$^{-/-}$Abca4$^{-/-}$ mice develop severe light-induced photoreceptor degeneration compared to the wild type controls. Dark-adapted wild type and Rdh8$^{-/-}$Abca4$^{-/-}$ mice at 4 to 5 years of age were exposed to white light at 10,000 lux for 30 min. Seven days after this exposure, retinal structure and histology was examined by OCT (A) and immunohistochemistry (IHC) (B). Both OCT (see asterisk) and IHC indicate disrupted photoreceptor structure. Rdh8$^{-/-}$ Abca4$^{-/-}$ mice unexposed to light were also included for these analyses.
Figure 15:
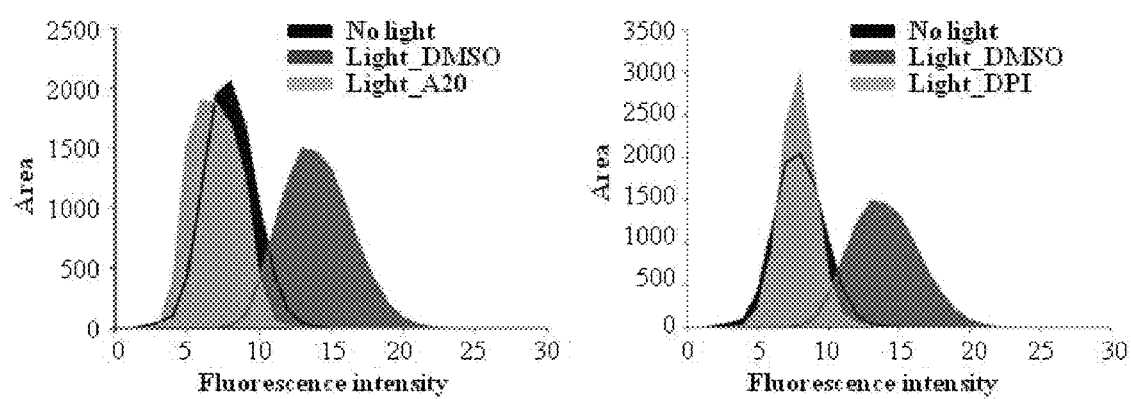
FIG. 15 illustrates 4- to 5-week old Rdh8$^{-/-}$Abca4$^{-/-}$ mice were treated with the ROS probe DHE 30 min prior to white light exposure at 10,000 lux for 30 min. DMSO vehicle control and the NADPH oxidase inhibitor DPI were administered by intraperitoneal injection 1 h prior to light exposure. R and S enantiomer of pregablin was gavaged 2 h before the light exposure. Retinas were harvested 3 h after light exposure. ROS signals (in red) from prepared cryosections were all obtained under a fluorescence microscope with same exposure setup. Recorded ROS signals are plotted as histograms for comparison with Rdh8$^{-/-}$Abca4$^{-/-}$ mice without light exposure (No Light), with light exposure and pretreated with either vehicle control (Light_DMSO), Amine 20 (Light_Amine 20) or the NADPH oxidase inhibitor, DPI (Light_DPI).

NADPH Oxidase Mediates Light-Induced ROS Production in $Rdh8^{-/-}Abca4^{-/-}$ Mouse Retina To further test the observation that atRAL induces ROS overproduction through NADPH oxidase in vivo, the ROS probe DHE was administered to $Abca4^{-/-}Rdh8^{-/-}$ mice 30 min before light exposure at 10,000 lux for 30 min. This regimen was selected because this intensity of illumination causes marked photoreceptor degeneration in $Abca4^{-/-}Rdh8^{-/-}$ mice, whereas wild type controls manifest no obvious morphological changes (FIG. 13). Compared to the ROS signal detected in the outer nuclear layer (ONL) of $Abca4^{-/-}Rdh8^{-/-}$ mice unexposed to light, a strong ROS signal was recorded in the ONL of retinas from light-exposed and vehicle only treated $Abca4^{-/-}Rdh8^{-/-}$ mice (FIG. 6). When APO was administered 1 h prior to illumination, these APO-treated $Abca4^{-/-}Rdh8^{-/-}$ mice displayed substantially decreased ROS production in the ONL with an intensity similar to that observed in retinas from non-light exposed $Abca4^{-/-}Rdh8^{-/-}$ mice (FIG. 6). In addition, diphenyleneiodonium (DPI), another commonly used NADPH oxidase inhibitor structurally different from APO, exhibited a similar effect on ROS production in light-challenged $Abca4^{-/-}Rdh8^{-/-}$ mice (FIG. 15). The association of atRAL with ROS production in vivo was further confirmed by pretreating light-exposed $Abca4^{-/-}Rdh8^{-/-}$ mice with all-trans-retinylamine (Ret-$NH_2$), a retinal scavenger and retinoid cycle inhibitor. Ret-$NH_2$ significantly decreased ROS production as well (FIG. 6). This effect was also consistently observed in mice pretreated with R and S enantiomer of pregabalin, which also reduced free atRAL (FIG. 15). Together, these results demonstrate that atRAL promotes ROS production in photoreceptors upon light exposure. This effect is mediated by NADPH oxidase, suggesting that atRAL-induced NADPH oxidase-mediated ROS generation could be involved in the pathogenesis of acute light-induced photoreceptor degeneration.

Figure 7:
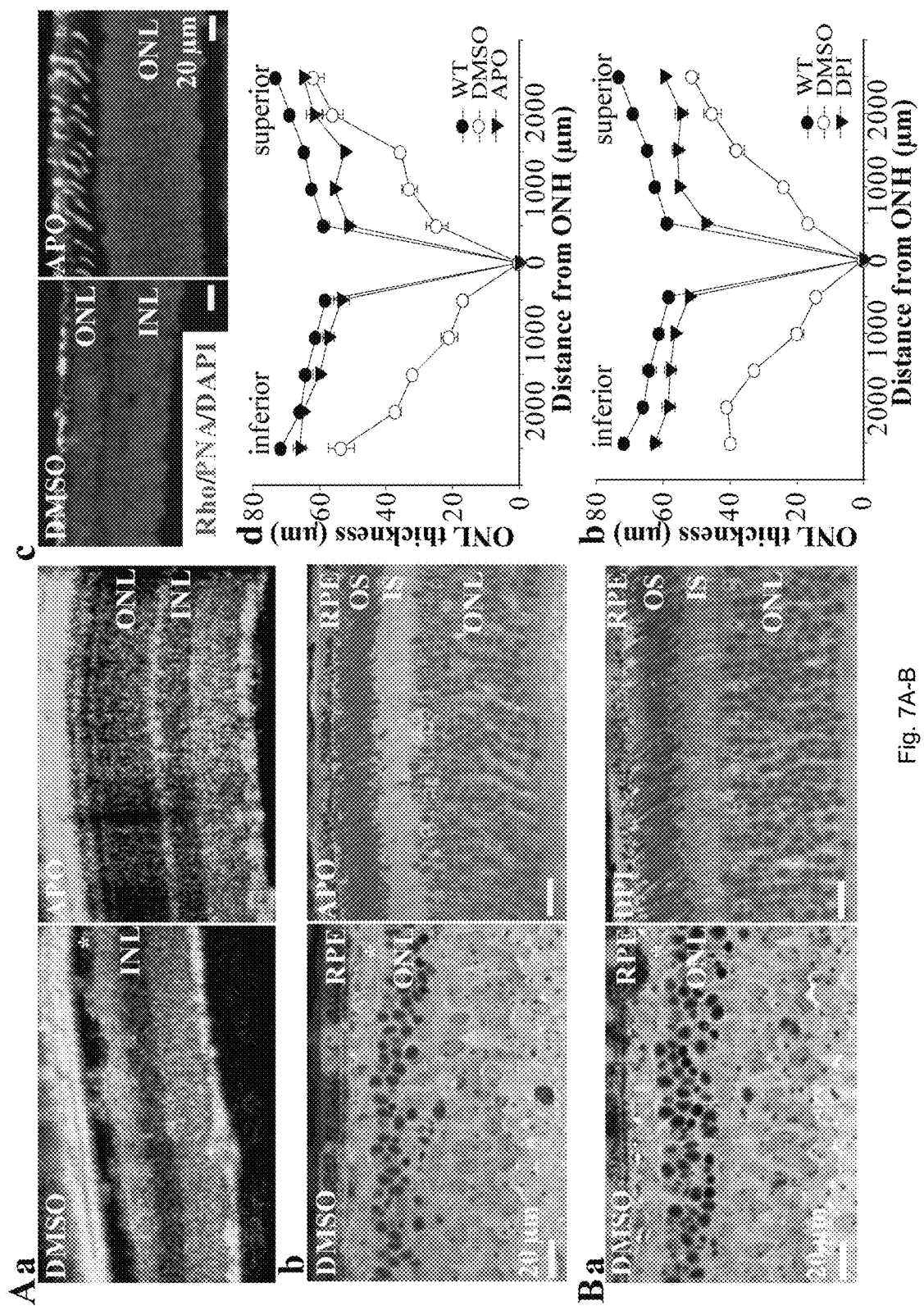
FIGS. 7(A-B)(a-b) illustrate NADPH oxidase inhibitor protects Rdh8$^{-/-}$Abca4$^{-/-}$ mouse photoreceptors from light-induced degeneration. (A) 4- to 5-week old Rdh8$^{-/-}$ Abca4$^{-/-}$ mice were exposed to white light at 10,000 lux for 30 min after pre-treatment with either vehicle control DMSO or APO. (B) Rdh8$^{-/-}$Abca4$^{-/-}$ mice were exposed to white light at 10,000 lux for 30 min after pre-treatment with either vehicle control (DMSO) or the structurally different NADPH oxidase inhibitor, DPI. For both APO and DPI pretreatment, evaluations performed 7 days after illumination included OCT imaging (A, * indicates disrupted photoreceptors in the retinal structure), retinal histological examination (B, * indicates disrupted and decreased length of outer and inner photoreceptor segments; 63×), photoreceptor IHC and measurements of outer nuclear layer thickness after DAPI staining (d, RPE, retinal pigmented epithelium; OS, outer segment; IS, inner segment; ONH, optic nerve head).

Inhibition of NADPH Oxidase Protects Retinal Morphology Against Acute Light-Induced Photoreceptor Degeneration in $Rdh8^{-/-}Abca4^{-/-}$ Mice To examine directly if atRAL-induced NADPH oxidase-mediated ROS production is mechanistically implicated in acute light-induced photoreceptor degeneration, $Abca4^{-/-}Rdh8^{-/-}$ mice were treated with APO, DPI or a vehicle control (DMSO) 1 h prior to light exposure at 10,000 lux for 30 min. The effect of NADPH oxidase inhibitor treatment was assessed 7 days after illumination. Optical coherence tomography (OCT) scans revealed significantly disrupted photoreceptor structure in DMSO-treated mice. OCT of both APO-treated (FIG. 7Aa) and DPI-treated (data not shown) mice exhibited well-preserved retinal morphology compared to that of the vehicle-treated controls. This observation was supported further by retinal histological examination. In agreement with the OCT images, retinas from DMSO-treated mice manifested prominent structural disarrangement with shortened lengths of photoreceptor outer segment/inner segment, markedly decreased cell numbers in the ONL and increased pyknosis of photoreceptor nuclei. This morphology contrasted sharply with the nearly intact retinal morphology manifested by APO-treated (FIG. 7Ab) or DPI-treated mice (FIG. 7Ba). Immunohistochemical examination for rhodopsin in rod photoreceptor outer segments and peanut agglutinin lectin (PNA)-labeling of cone cell matrix sheaths was also performed. These images revealed abundant and organized expression of rhodopsin and PNA in APO-treated (FIG. 7Ac) or DPI-treated (data not shown) mice, in sharp contrast to the residual pattern of rhodopsin and PNA expression detected in DMSO-treated mice. Quantification of ONL thickness after DAPI staining revealed that both APO (FIG. 7Ad) and DPI (FIG. 7Bb) pretreatment greatly preserved photoreceptors compared to DMSO pretreatment. These results support the notion that NADPH oxidase-mediated ROS generation is mechanistically implicated in the action of atRAL during light-induced photoreceptor degeneration.

Involvement of $PLC/IP_3/Ca^{2+}$ Signaling in Light-Induced Photoreceptor atRAL-Mediated Degeneration To test the hypothesis that $PLC/IP_3/Ca^{2+}$ signaling is involved in the cascade of events related to atRAL toxicity, we pretreated $Abca4^{-/-}Rdh8^{-/-}$ mice with the selective PLC inhibitor, U-73122, prior to light exposure. In contrary to $Abca4^{-/-}Rdh8^{-/-}$ mice pretreated with DMSO that reproducibly manifested severe histological photoreceptor degeneration, $Abca4^{-/-}Rdh8^{-/-}$ mice pretreated with U-73122 exhibited markedly less light-induced photoreceptor damage (FIG. 8Aa) and ONL thickness measurements provided further evidence of a protective effect (FIG. 8Ab). These results strongly support the involvement of PLC activation in light-induced atRAL-mediated photoreceptor degeneration.

To further validate the involvement of $PLC/IP_3/Ca^{2+}$ signaling in atRAL-mediated photoreceptor degeneration in vivo, 2-aminoethoxydiphenyl borate or 2-APB, primarily known as an antagonist of $IP_3/IP_3R$ mediated $Ca^{2+}$ release was administered to $Abca4^{-/-}Rdh8^{-/-}$ mice prior to light exposure. Retinal morphological examination revealed that 2-APB pretreatment significantly preserved retinal morphology after illumination compared to DMSO pretreatment (FIG. 8Ba). Further, 2-APB pretreatment reduced ROS production in light-exposed $Abca4^{-/-} Rdh8^{-/-}$ mouse photoreceptors to a level comparable to that observed in photoreceptors of mice without light exposure (FIG. 8Bb). Thus, $IP_3$-mediated $Ca^{2+}$ elevation is mechanistically associated with atRAL-induced ROS production during light-induced photoreceptor degeneration. Taken together, our results demonstrate that the $PLC/IP_3/Ca^{2+}$ pathway acts upstream of light-induced atRAL-mediated ROS generation and consequent photoreceptor degeneration.

Figure 8:
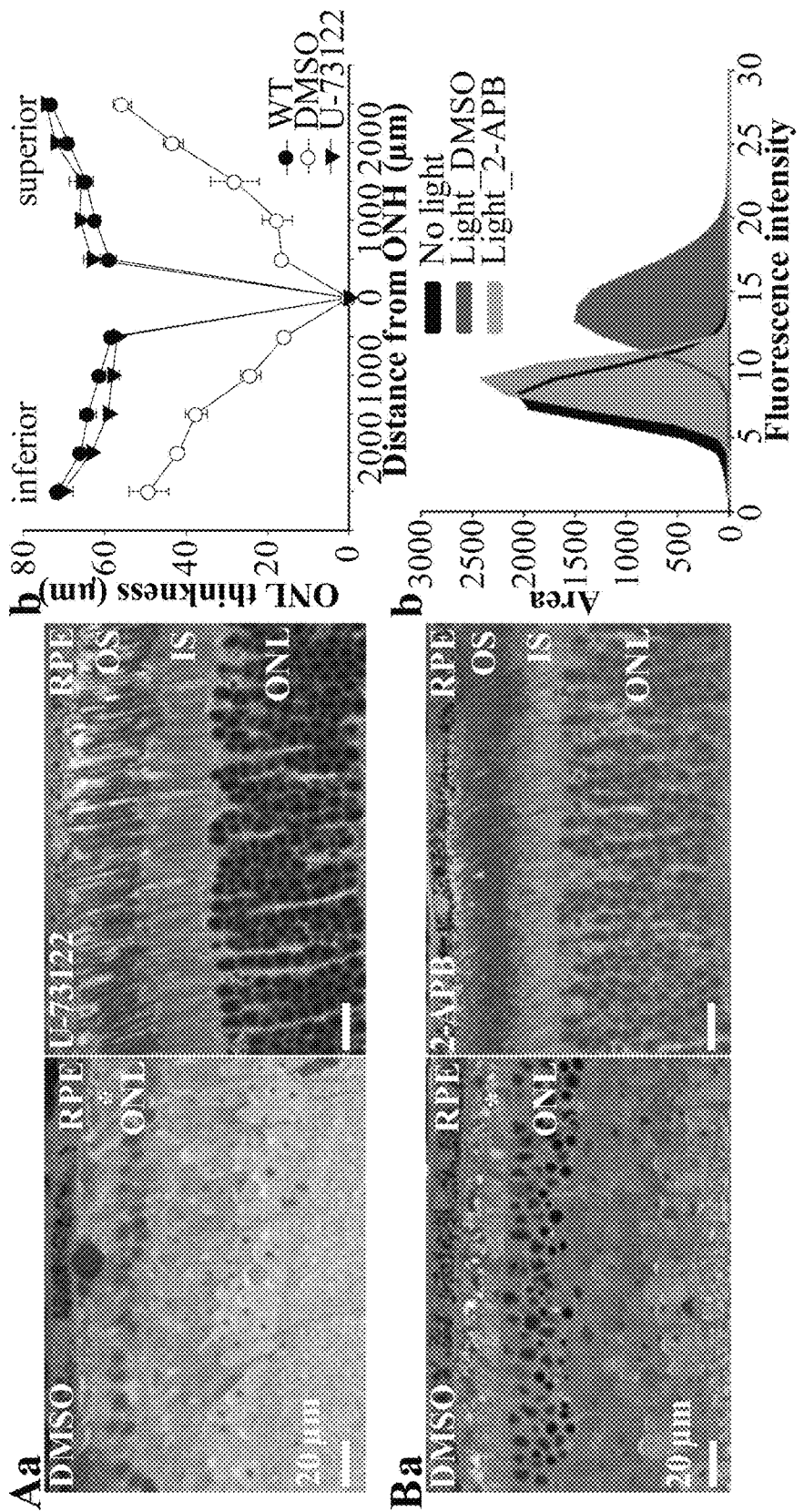
FIGS. 8(A-B)(a-b) illustrate inhibition of PLC/IP$_3$/Ca$^{2+}$ signaling preserves retinal morphology in light-challenged Rdh8$^{-/-}$Abca4$^{-/-}$ mice. (A) 4- to 5-week old Rdh8$^{-/-}$ Abca4$^{-/-}$ mice were exposed to white light at 10,000 lux for 30 min after pre-treatment with either vehicle control (DMSO) or the PLC inhibitor, U-73122. a, retinal histology (63×), with * indicating disorganized and reduced length of outer/inner segments, and b, analysis of ONL thickness were performed 7 days after illumination. (B) Light-challenged Rdh8$^{-/-}$Abca4$^{-/-}$ mice were pre-treated with either vehicle control (DMSO) or 2-APB, an antagonist against IP$_3$ mediated intracellular Ca$^{2+}$ release. a, retinal histology was analyzed 7 days after illumination; and b, In situ ROS production after 2-APB treatment was assessed as described in FIG. 2.
Figure 9:
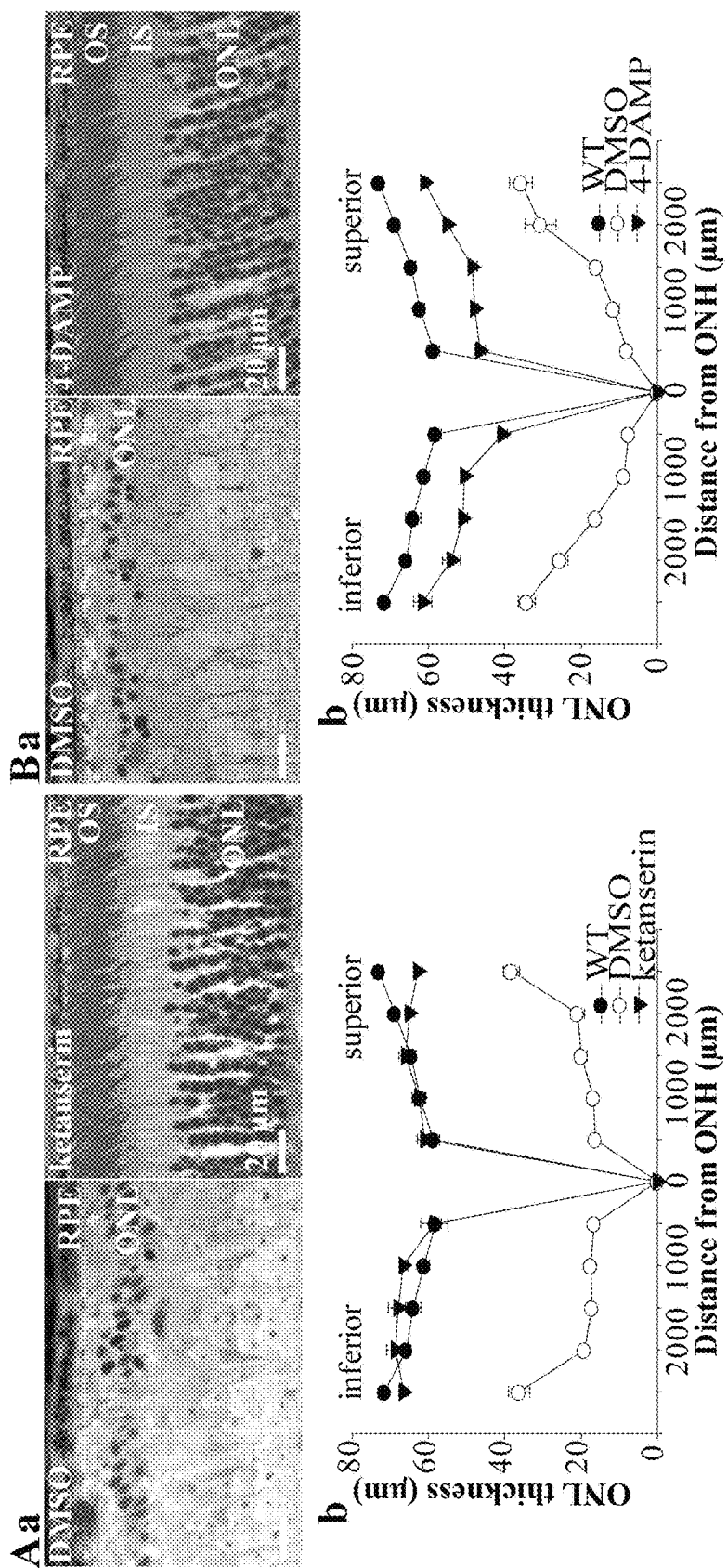
FIGS. 9(A-B)(a-b) illustrate inhibition of either 5-HT$_{2A}$ or M3 protects against light-induced atRAL-mediated photoreceptor degeneration in Rdh8$^{-/-}$Abca4$^{-/-}$ mice. (A) 4- to 5-week old Rdh8$^{-/-}$Abca4$^{-/-}$ mice were exposed to white light at 10,000 lux for 30 min after pre-treatment with either vehicle control (DMSO) or the 5-HT$_{2A}$ receptor antagonist, ketanserin. (B) The M3 antagonist, 4-DAMP, was independently tested and compared with a vehicle control (DMSO) in illuminated Rdh8$^{-/-}$Abca4$^{-/-}$ mice. Seven days later, retinal histological examination (63×) (a, * indicates disrupted and reduced length of outer/inner segments) and measurements of ONL thickness (b) were performed.
Figure 16:
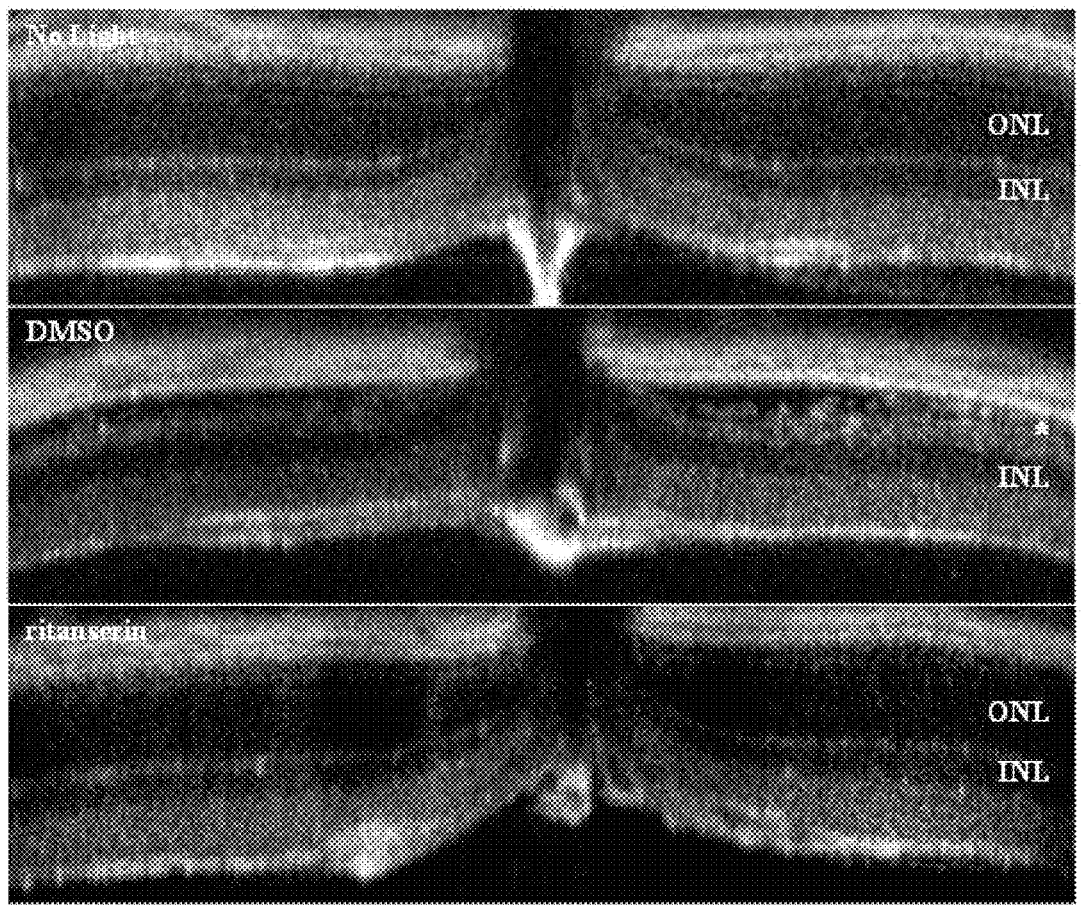
FIG. 16 illustrates pretreatment with a 5-HT$_{2A}$ antagonist protects Rdh8$^{-/-}$Abca4$^{-/-}$ mouse retinas from light-induced degeneration. 4- to 5-week old Rdh8$^{-/-}$Abca4$^{-/-}$ mice were exposed to white light at 10,000 lux for 30 min after pre-treatment with either vehicle control (DMSO) or the 5-HT$_{2A}$ receptor antagonist, ritanserin. Rdh8$^{-/-}$Abca4$^{-/-}$ mice without light exposure (No light) were included as negative controls. OCT images were taken to evaluate retinal structure 7 days after light exposure and revealed that ritanserin treatment substantially protected photoreceptors from light-induced degeneration (* indicates disrupted photoreceptors in the retinal structure in DMSO vehicle treated mice)
Figure 17:
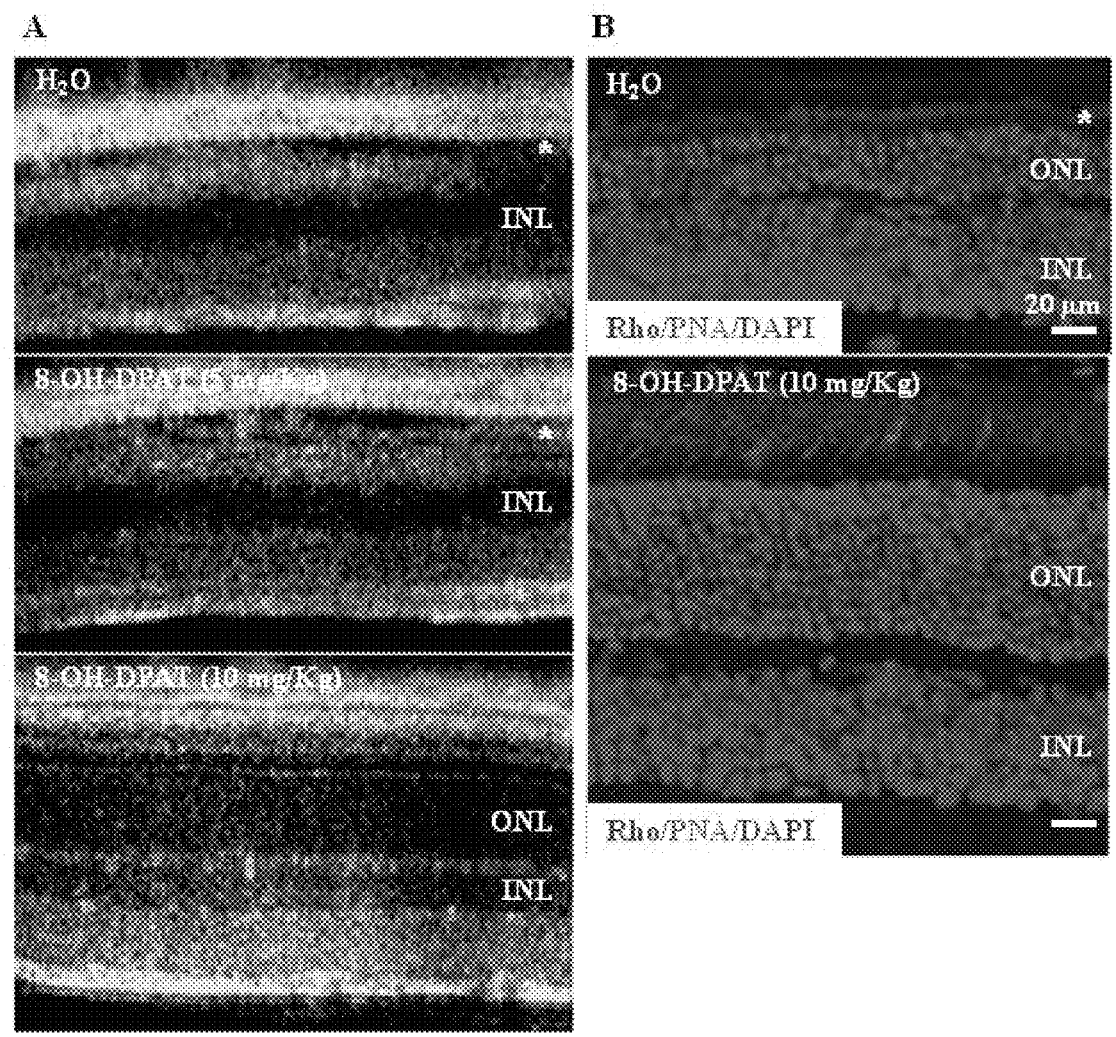
FIGS. 17(A-B) illustrate 5-HT$_{1A}$ agonist pretreatment protects Rdh8$^{-/-}$Abca4$^{-/-}$ mouse retinas from light-induced degeneration. OCT imaging (A) and retinal IHC (B) was performed 7 days after exposing 4- to 5-week old Rdh8$^{-/-}$Abca4$^{-/-}$ mice to light at 10,000 lux for 30 min following pretreatment with the 5-HT$_{1A}$ agonist, 8-OH-DPAT. The protective effect of 8-OH-DPAT was dose-dependent.

Involvement of Gq-Coupled Receptors in Light-Induced atRAL-Mediated Retinal Degeneration $5-HT_{2A}R$ has been suggested to be involved in NADPH oxidase activation. Additionally, chronic or acute activation of $5-HT_{2A}R$ causes considerable reduction in $5-HT_{1A}R$ activity. The $5-HT_{1A}R$ was recently shown to be involved in light-induced photoreceptor degeneration because selective $5-HT_{1A}R$ agonists protected the rat retina against photooxidative stress. Therefore we hypothesized that increased activation of the $5-HT_{2A}R$ could contribute to the pathogenesis of light-induced photoreceptor degeneration in $Abca4^{-/-}Rdh8^{-/-}$ mice, given that it activates PLC and such activation is involved in the in vivo action of atRAL (FIG. 8). To test this hypothesis, $Abca4^{-/-}Rdh8^{-/-}$ mice were treated with the selective $5-HT_{2A}R$ antagonist ketanserin prior to light exposure. A substantial protective effect of ketanserin against light-induced photoreceptor degeneration was observed compared to DMSO pretreatment (FIG. 9Aa, b). A similar observation was made when $Abca4^{-/-}Rdh8^{-/-}$ mice were treated with another selective $5-HT_{2A}R$ antagonist, ritanserin (FIG. 16). A role for 5-HTRs in light-induced atRAL-mediated retinal degeneration in $Abca4^{-/-}Rdh8^{-/-}$ mice is additionally supported by the protective effect of the $5-HT_{1A}R$ agonist, 8-hydroxy-N,N-dipropyl-2-aminotetralin or 8-OH-DPAT (FIG. 17).

Considering that PLC can be activated by multiple Gq-coupled receptors, we address the issue of whether the $5-HT_{2A}R$ is the only GPCR involved in atRAL-induced PLC activation. Interestingly, the $M_3R$ antagonist, 1,1-dimethyl-4-diphenylacetoxypiperidinium iodide or 4-DAMP, also was found to preserve retinal morphology in $Abca4^{-/-}Rdh8^{-/-}$ mice challenged by acute light exposure (FIG. 9Ba, b), supporting the idea that multiple Gq-coupled receptors could be activated to mediate the effect of atRAL on PLC activation.

Figure 10:
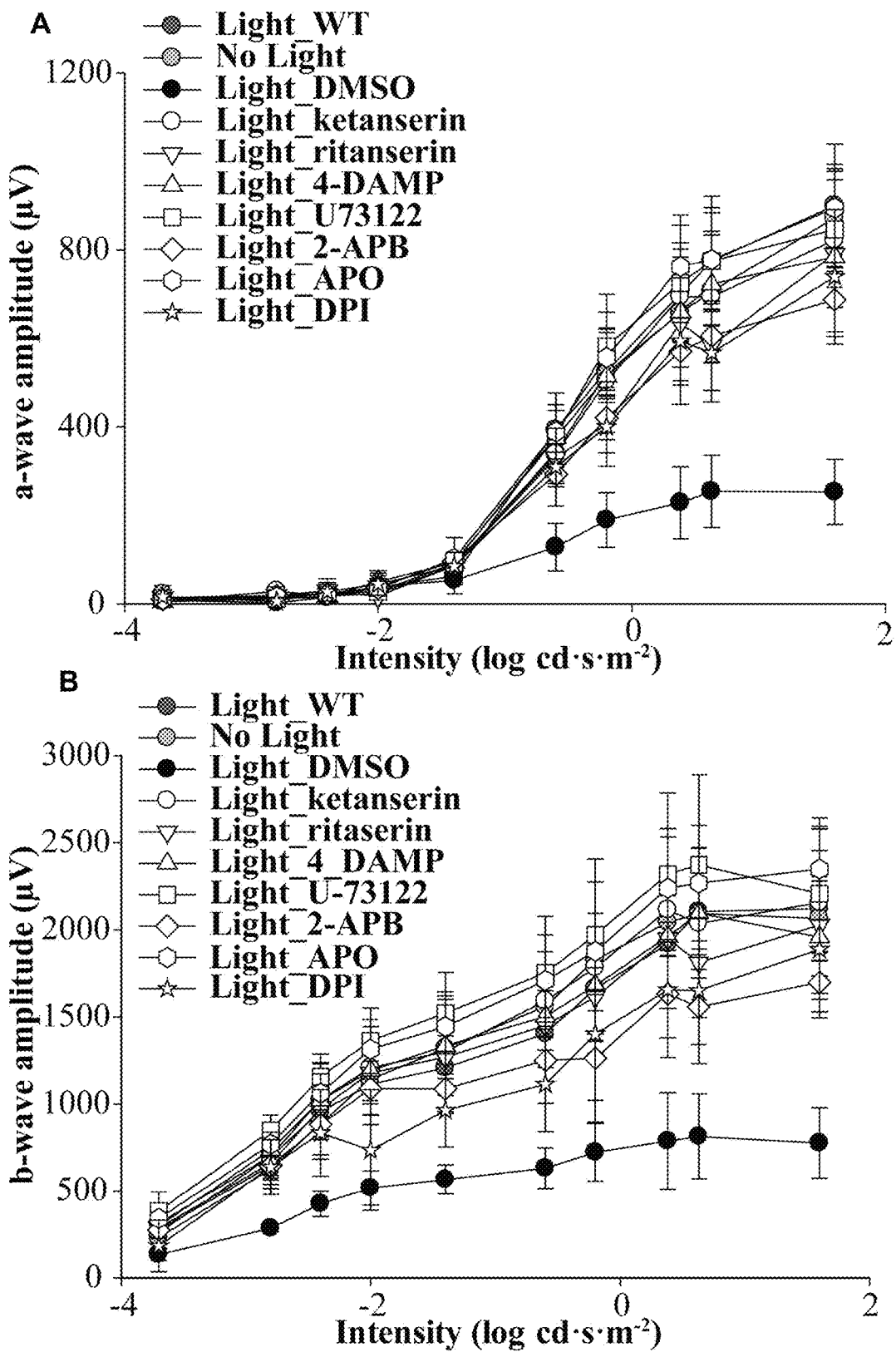
FIGS. 10(A-B) illustrate plots showing retinal function in Rdh8$^{-/-}$Abca4$^{-/-}$ mice is substantially preserved by several different treatments. Scotopic ERGs were recorded and both a-waves and b-waves were plotted to evaluate retinal function in Rdh8$^{-/-}$Abca4$^{-/-}$ mice 7 days after they were pretreated with the indicated compounds. Compared to wild type mice exposed to bright light (Light_WT) and Rdh8$^{-/-}$ Abca4$^{-/-}$ mice without light exposure (No light), light exposure at 10,000 lux for 30 min significantly impaired retinal function as indicated by decreased a-wave and b-wave amplitude in mice treated with DMSO vehicle control (Light_DMSO). Compounds showing a protective effect against this light-induced retinopathy included: ketanserin, ritanserin, 4-DAMP, U-73122, 2-APB, APO and DPI.

Involvement of these mechanisms in light-induced atRAL-mediated photoreceptor degeneration was also shown by improved retinal function of light-challenged $Abca4^{-/-}Rdh8^{-/-}$ mice after pretreatment with several pharmacological agents that protected against histological damage. As indicated in FIG. 10 and compared to light-challenged wild type control and $Abca4^{-/-}Rdh8^{-/-}$ mice without light exposure, light-challenged $Abca4^{-/-}Rdh8^{-/-}$ mice pretreated with DMSO exhibited decreased amplitudes of both a-waves and b-waves indicating marked impairment of their retinal function. The protective effect of these treatments on retinal function was evidenced by increased a-wave and b-wave amplitudes compared to those observed in DMSO-treated $Abca4^{-/-}Rdh8^{-/-}$ mice.

Figure 11:
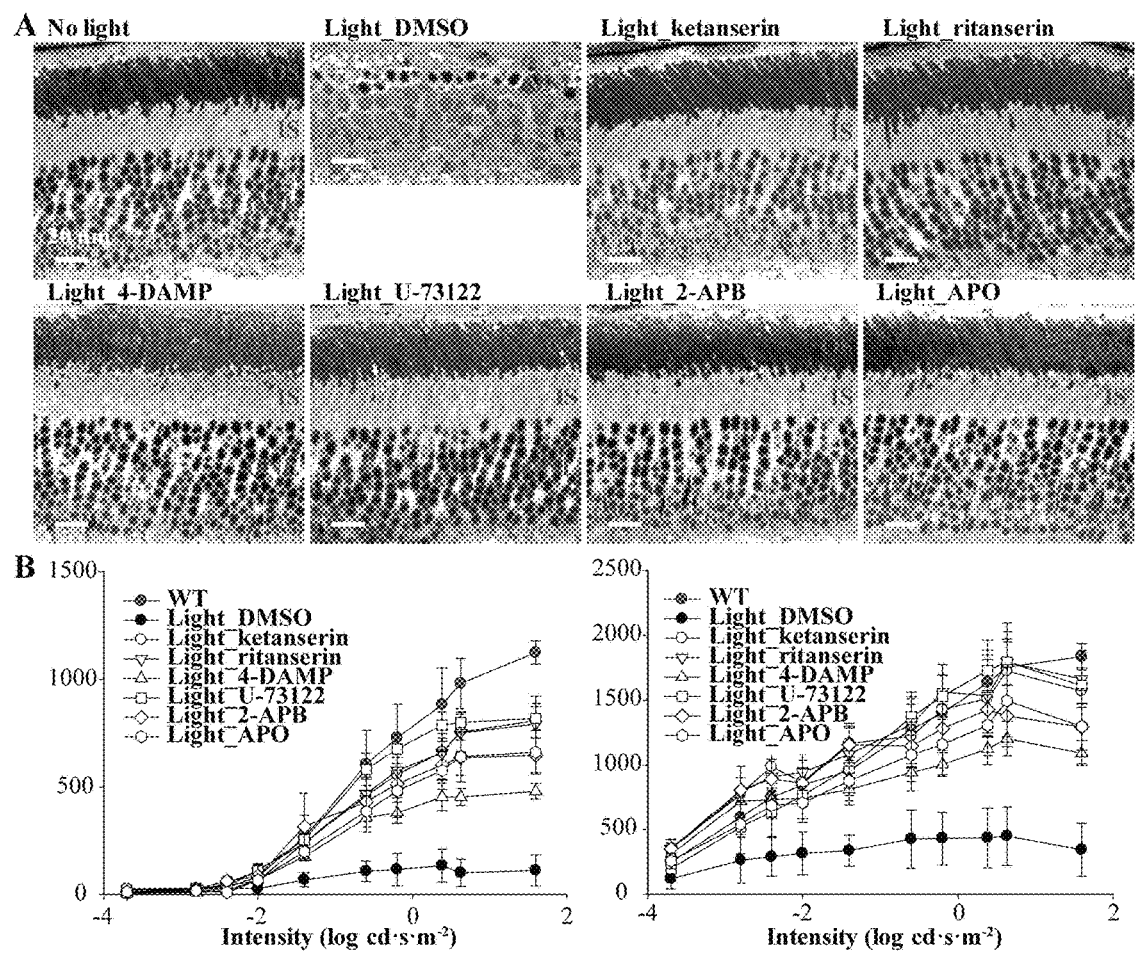
FIGS. 11(A-B) illustrate light-induced retinal degeneration in Balb/c mice. Twelve-week old Balb/c mice were dark-adapted followed by indicated pharmacological treatments via intraperitoneal injection 1 h prior to their exposure to white light at 10,000 lux for 2 h. All experimental evaluations were carried out 7 days later. Controls either without light exposure (No light) or with DMSO vehicle treatment followed by light exposure (Light_DMSO) were included for all analyses. (A) Retinal thin sections examined under light microscopy (63×) after toluidine blue staining. (B) Retinal function assessed by scotopic ERG in Balb/c mice seven days after the indicated pretreatments.
Figure 18:
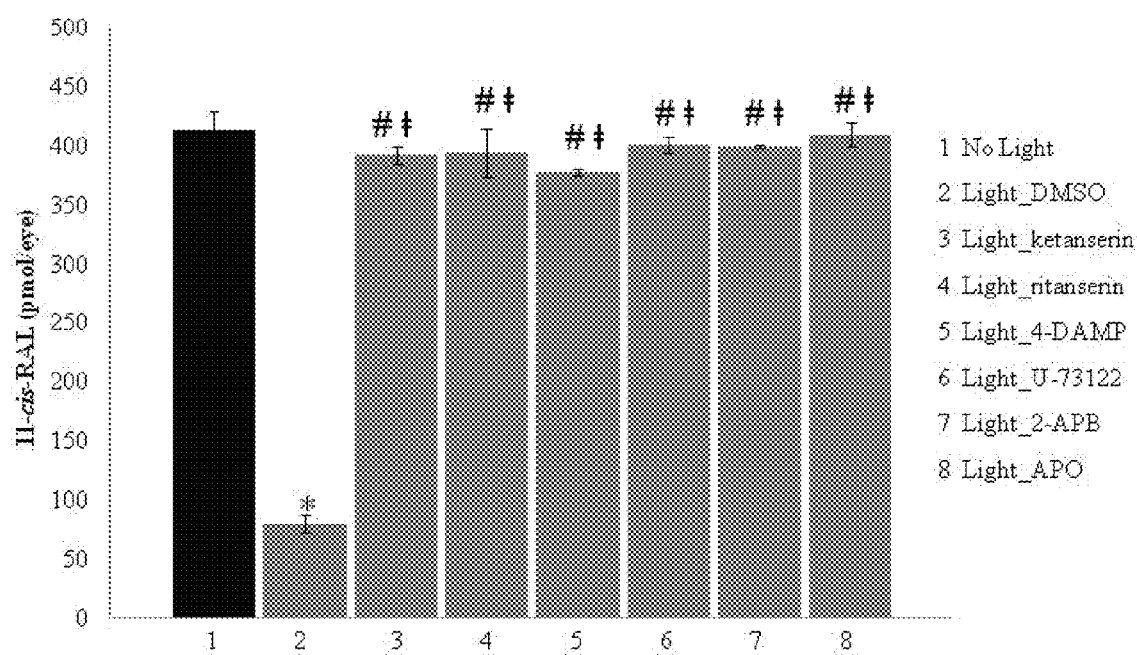
FIG. 18 illustrates 11—compared to No light, p>0.05). All listed pretreatments preserved 11-cis-retinal content. cis-Retinal (11-cis-RAL) content in Balb/c mouse eyes (pmol/eye) after indicated pretreatments was quantified by HPLC (* compared to No light, p<0.01; # compared to Light_DMSO, p<0.01).

Data presented above were derived from studies with $Abca4^{-/-}Rdh8^{-/-}$ mice, a genetically modified animal model with a deficiency in atRAL transport and clearance owing to targeted deletion of the Rdh8 and Abca4 genes. To determine if the mechanisms proposed were merely secondary to genetic modification or arose from some unidentified off-target effects in $Abca4^{-/-}Rdh8^{-/-}$ mice, we tested our hypotheses further in the light-challenged Balb/c mouse, a classical model of light-induced photoreceptor degeneration. Consistently, as compared to unexposed control mice, Balb/c mice acutely exposed to light exhibited severe photoreceptor degeneration evidenced by disrupted retinal histology (FIG. 11A), decreased ocular 11-cis-RAL content (FIG. 18) and impaired retinal function (FIG. 11B). In contrast, pharmacological pretreatment targeting each proposed mechanism displayed significant protection of photoreceptors against acute light-induced degeneration as assessed by morphological (FIG. 11A), biochemical (FIG. 18) and functional tests (FIG. 11B).

Example 2

In this Example, pharmacological compounds targeting multiple GPCRs, which are identified in Table 1 below, were evaluated as potential therapeutic candidates to prevent photoreceptor cells from light-induced degeneration. Various antagonists at multiple Gs-coupled GPCRs prevented photoreceptor cell death, implying that increased functionality of Gs-coupled GPCRs and subsequent activation of adenylyl cyclase (AC) may cause photoreceptor cell death. On the other hand, Gi-coupled GPCRs functionally lead to suppression of AC activity. Agonists activating α2 adrenergic receptor, a Gi-coupled GPCR, prevented photoreceptor death. Therefore, AC as the central player mediating Gs-coupled and Gi-coupled GPCR signaling, could also serve as therapeutic target to preserve photoreceptor during degeneration, which could be achieved by inhibition of AC activity by AC inhibitor.

Methods

Animals $Abca4^{-/-}Rdh8^{-/-}$ mice were generated and genotyped as previously described and were used in the present study when they reached 4- to 5-weeks of age. All mice were routinely maintained in a 12 h light (less than 10 lux)/12 h dark cycle environment in the Animal Resource Center at the School of Medicine, Case Western Reserve University. For bright light exposure experiments, $Abca4^{-/-}Rdh8^{-/-}$ mouse pupils were dilated with 1% tropicamide prior to white light exposure at 10,000 lux (150 W spiral lamp, Commercial Electric) for 30 min. Assessment of retinal structural and functional changes were performed 7 days after light exposure. All mouse handling procedures and protocols were approved by the Institutional Animal Care and Use Committee at Case Western Reserve University.

Chemicals

Doxazosin (DOX) was purchased from Selleckchem (Houston, Tex.). Lofexidine was purchased from Santa Cruz (Santa Cruz, Calif.). Prazosin (PRA), Tamsulosin (TAM), RS 23579-190 (RS), RO 04-6790 (RO), SB 269970 (SB), SGS 518 oxalate (SGS), LY 215840 (LY), Guanabenz (GUB), Guanfacine (GUF) and SQ 22536 (SQ) were ordered from TOCRIS Biosciences (Bristol, United Kingdom).

Mouse Treatments

All the experimental compounds were administered to mice by intraperitoneal injection through a 28 gauge needle at 30 min prior to bright light exposure. Tested compounds and their doses were: DOX, 10 mg/kg body weight (bw); PRA, 2 mg/kg bw; TAM, 2 mg/kg bw; RS, 20 mg/kg bw; RO, 30 mg/kg bw; SB, 30 mg/kg bw; SGS, 30 mg/bw; LY, 10 mg/kg bw; GUB, 2 mg/kg bw; GUF, 2 mg/kg bw; LOF, 2 mg/kg bw; SQ1: 0.083 mg/kg bw; SQ2, 0.125 mg/kg bw; SQ3, 0.25 mg/kg bw; SQ4: 0.5 mg/kg bw.

Optical Coherence Tomography (OCT)

Non-invasive ultra-high resolution SD-OCT (Bioptigen, Research Triangle Park, N.C.) was performed for in vivo imaging of mouse retinas. Mice were anesthetized with by intraperitoneal injection of anesthetic cocktail of ketamine (6 mg/ml) and xylazine (0.44 mg/ml) diluted with 10 mM sodium phosphate, pH 7.2, 100 mM NaCl at the dose of 20 µl/g bw. Pupils were dilated with 1% tropicamide prior to SD-OCT imaging. Five frames of OCT images were acquired in the B-mode and averaged for image presentation.

Scanning Laser Ophthalmoscopy (SLO)

SLO (Heidelberg Engineering, Heidelberg, Germany) was carried out for whole fundus imaging of mouse retinas. Mice were anesthetized by intraperitoneal injection of anesthetic cocktail indicated above, which was followed by pupil dilation using 1% tropicamide prior to SLO imaging under autofluorescence mode.

Immunohistochemistry

Retinal immunohistochemistry (IHC) was carried out as previously described. Briefly, eyes were enucleated and eye cups were made to eliminate cornea, lens and vitreous body and fixed in 4% paraformaldehyde and processed for cryosectioning. 12 am thick cryosections were collected cryosections and subjected to examination for rhodopsin, peanut agglutinin lectin (PNA) and DAPI expression.

ERGs

ERGs were performed as previously described. Briefly, dark-adapted mice were examined under dim red light transmitted through a Kodak No. 1 Safelight filter (transmittance 560 nm). Pupils were dilated with 1% tropicamide under anesthesia induced by method described above. Contact lens electrodes were placed on the eyes, and a reference electrode and ground electrode were positioned on the ear and tail, respectively. ERGs were recorded with the universal testing and electrophysiologic system, UTAS E-3000 (LKC Technologies, Inc. Gaithersburg, Md.).

Statistical Analyses

Results were collected from at least 4 mice per experimental group. Data were expressed as means±SEM and statistical analyses were performed using the Students t-test or ANOVA.

Results

Figure 19:
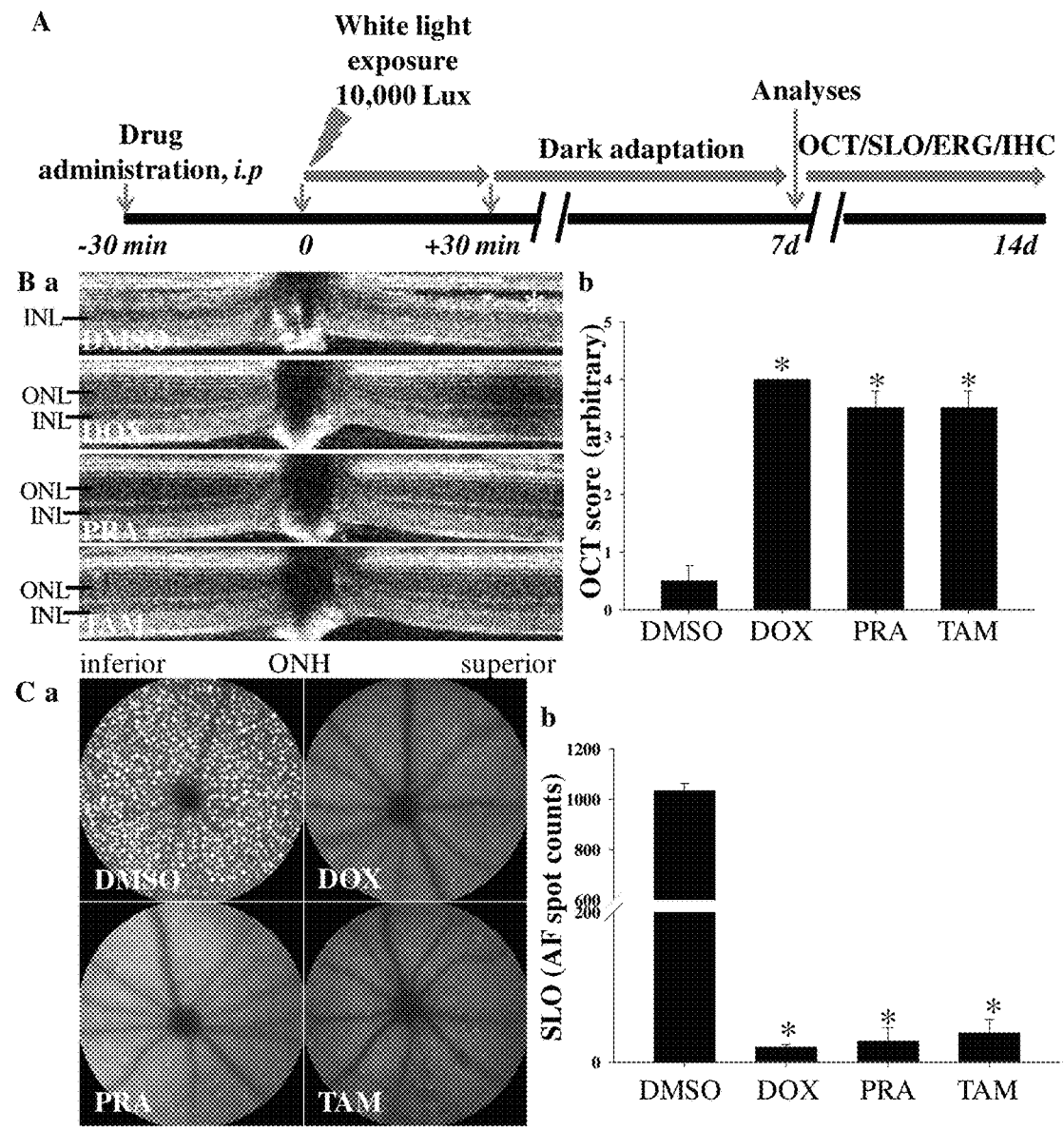
FIGS. 19(A-C) illustrate antagonists at α1-adrenergic receptor, a Gq-couple GPCR, protect retina from light-induced degeneration in Abca4$^{-/-}$Rdh8$^{-/-}$ mouse. (A) Scheme of pharmacological treatment: all the pharmacological compounds tested in the present study was administered via intraperitoneal injection to 4- to 5-week old Abca4$^{-/-}$Rdh8$^{-/-}$ mice 30 min prior to white light exposure at 10,000 Lux at the duration of 30 min. After light exposure, the mice were kept in the darkness for 7 to 14 days before morphological and functional examination by OCT, SLO, IHC and ERG, respectively. (B) α1-adrenergic receptor antagonist, including doxazosin (DOX), prazosin (PRA) and tamsulosin (TAM) or vehicle control (DMSO) was administered to Abca4$^{-/-}$Rdh8$^{-/-}$ mice prior to white light exposure. OCT imaging was performed 7 days later to evaluate retinal morphology. a. Representative OCT images were presented. * indicates severely disrupted photoreceptor structure; ONH, optic nerve head; ONL, outer nuclear layer; INL inner nuclear layer. b. OCT scores were summarized from different treatment groups and subject to statistical analysis (Means±SEM; compared to DMSO control, * p<0.01). (C) SLO imaging was performed 8 days after light exposure. a. Retinal autofluorescence images. b. The number of retinal autofluorescence spots were counted and summarized for statistical analysis (Means±SEM; * compared to DMSO control, p<0.01).

Pharmacological Compounds Targeting α1 Adrenergic Receptor, a Gq-Coupled GPCR Preserves Retinas Against Light-Induced Retinopathy in Abca4$^{-/-}$Rdh8$^{-/-}$ Mice Pharmacological compounds antagonizing α1 adrenergic receptor (α1R), a class of Gq-coupled GPCR, were evaluated for the effect on light-induced retinopathy. α1R antagonists including Doxazosin (DOX), Prazosin (PRA) and Tamsulosin (TAM) were independently tested in Abca4$^{-/-}$Rdh8$^{-/-}$ mice, which displayed severe light-induced retinopathy as previously reported. DOX, PRA or TAM was administered to Abca4$^{-/-}$Rdh8$^{-/-}$ mice at the age of 4- to 5-weeks prior to the exposure to white light at the intensity of 10,000 Lux for 30 min. The effects of each treatment were first evaluated by non-invasive OCT imaging. As shown in FIG. 19A, compared to severely disrupted photoreceptor structure manifested by Abca4$^{-/-}$Rdh8$^{-/-}$ mice treated with DMSO vehicle control and exposed to intense light, substantial protection on photoreceptor morphology was observed when light-exposed Abca4$^{-/-}$Rdh8$^{-/-}$ mice were pre-treated by DOX, PRA or TAM, respectively. SLO imaging on autofluorescence mode was also carried out to assess light-induced photoreceptor damage in DMSO-treated Abca4$^{-/-}$Rdh8$^{-/-}$ mice and those pre-treated by DOX, PRA or TAM. As shown in FIG. 19B, numerous autofluorescence spots were readily observed in Abca4$^{-/-}$Rdh8$^{-/-}$ mice treated by DMSO 8-days after light exposure, which is typical of light-induced photoreceptor damage. In distinct contrast, treatment of DOX, PRA or TAM significantly protected retinas from developing light-induced damage revealed by SLO imaging, which is consistent with the data collected from OCT imaging. These results therefore provide experimental evidence that α1 adrenergic receptor could be viewed as a valid therapeutic target in the intervention of light-induced retinopathy.

Figure 20:
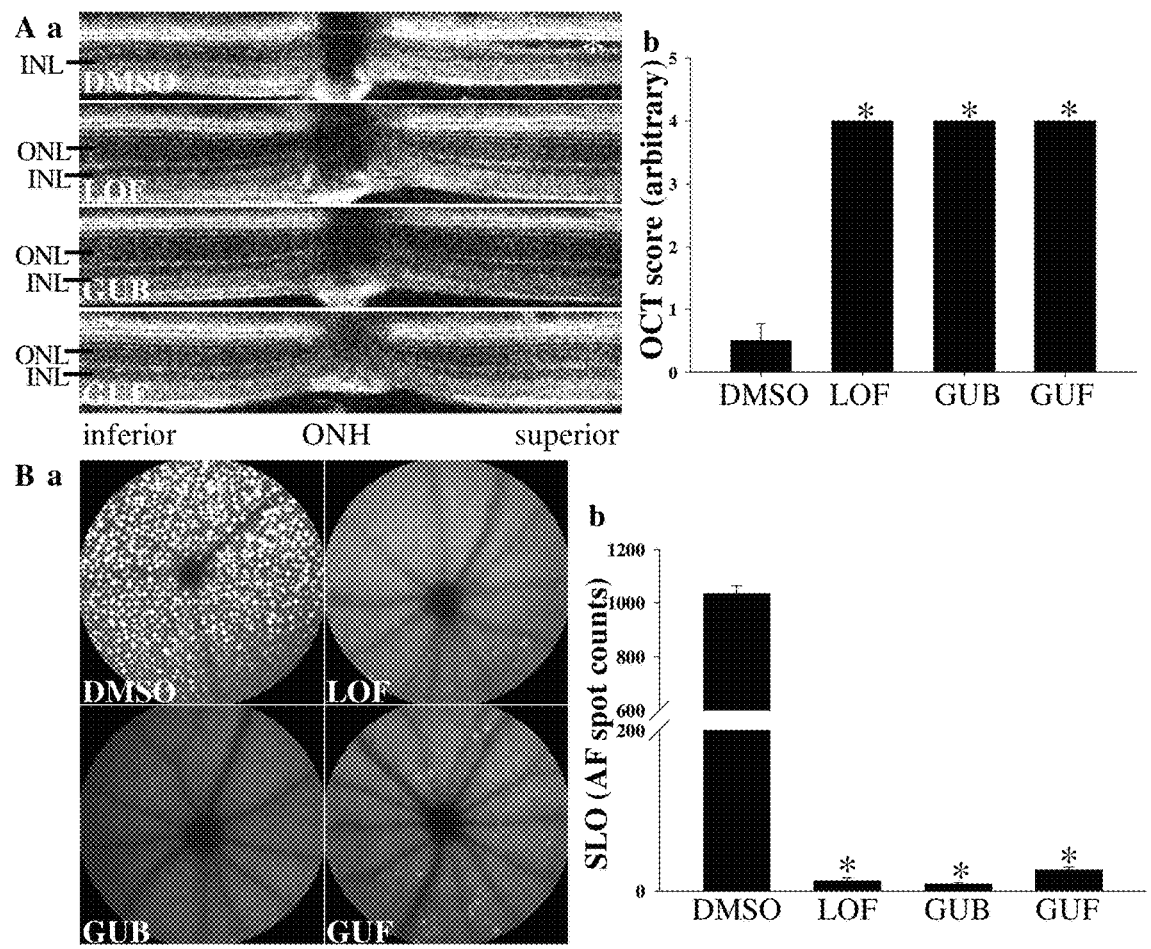
FIGS. 20(A-B)(a-b) illustrate the agonists at α2-adrenergic receptor, a Gi-couple GPCR, protect retina from light-induced degeneration in Abca4$^{-/-}$Rdh8$^{-/-}$ mouse. α2-adrenergic receptor agonist, lofexidine (LOF), guanabenz (GUB) and guanafacine (GUF), was delivered to 4- to 5-week old Abca4$^{-/-}$Rdh8$^{-/-}$ mice through intraperitoneal injection prior to white light exposure at the intensity of 10,000 Lux for 30 min. DMSO was included as a vehicle control. (A) OCT imaging was carried out to evaluate the effect of each treatment 7 days after light exposure. a. OCT images: * indicates markedly damaged photoreceptor structure; ONH, optic nerve head; ONL, outer nuclear layer; INL inner nuclear layer. b. Statistical analysis of OCT scores (Means±SEM; compared to DMSO control, * p<0.01). (B) SLO imaging was performed at autofluorescence mode 8 days after light exposure. a. Representative retinal autofluorescence images with bright spots correlated with retinal damage. b. SLO autofluorescence images were further analyzed for statistical analysis (Means±SEM; compared to DMSO control, * p<0.01).

Pharmacological Compounds Targeting Multiple Gs-Coupled GPCRs Protects Retinas from Light-Induced Retinopathy in Abca4$^{-/-}$Rdh8$^{-/-}$ Mice To further evaluate the therapeutic potential targeting other types of GPCRs, we also examined the effect of multiple antagonists against GPCRs that are coupled to Gs. Antagonists blocking the activation of 5-HT4 receptor, RS 23579-190 (RS), 5-HT6 receptor, RO 04-6790 (RO) and SGS 518 (SGS), 5-HT7 receptor, SB 269970 (SB) and LY 215840 (LY) were individually tested in Abca4$^{-/-}$Rdh8$^{-/-}$ light-induced retinopathy model. Each of the compounds was administered to 4- to 5-week old Abca4$^{-/-}$Rdh8$^{-/-}$ mice 30 min before white light exposure at 10,000 Lux for 30 min. OCT imaging was performed 7 days later to evaluate the retinal structural changes. In contrast to dramatically damaged photoreceptor structure displayed by DMSO-treated, light-exposed Abca4$^{-/-}$Rdh8$^{-/-}$ mice, profound preservation of photoreceptor morphology was observed in Abca4$^{-/-}$Rdh8$^{-/-}$ treated with compounds blocking the activation of Gs-coupled GPCRs such as 5-HT4 receptor, 5-HT6 receptor and 5-HT7 receptor, respectively (FIG. 20A). The protective effects of indicated compounds were further supported by significantly reduced formation of autofluorescence spots in Abca4$^{-/-}$Rdh8$^{-/-}$ mice treated with antagonists against these receptors (FIG. 20B). Our results indicated that Gs-coupled GPCRs could be further explored as plausible therapeutic target in degenerative photoreceptor disorders.

Figure 21:
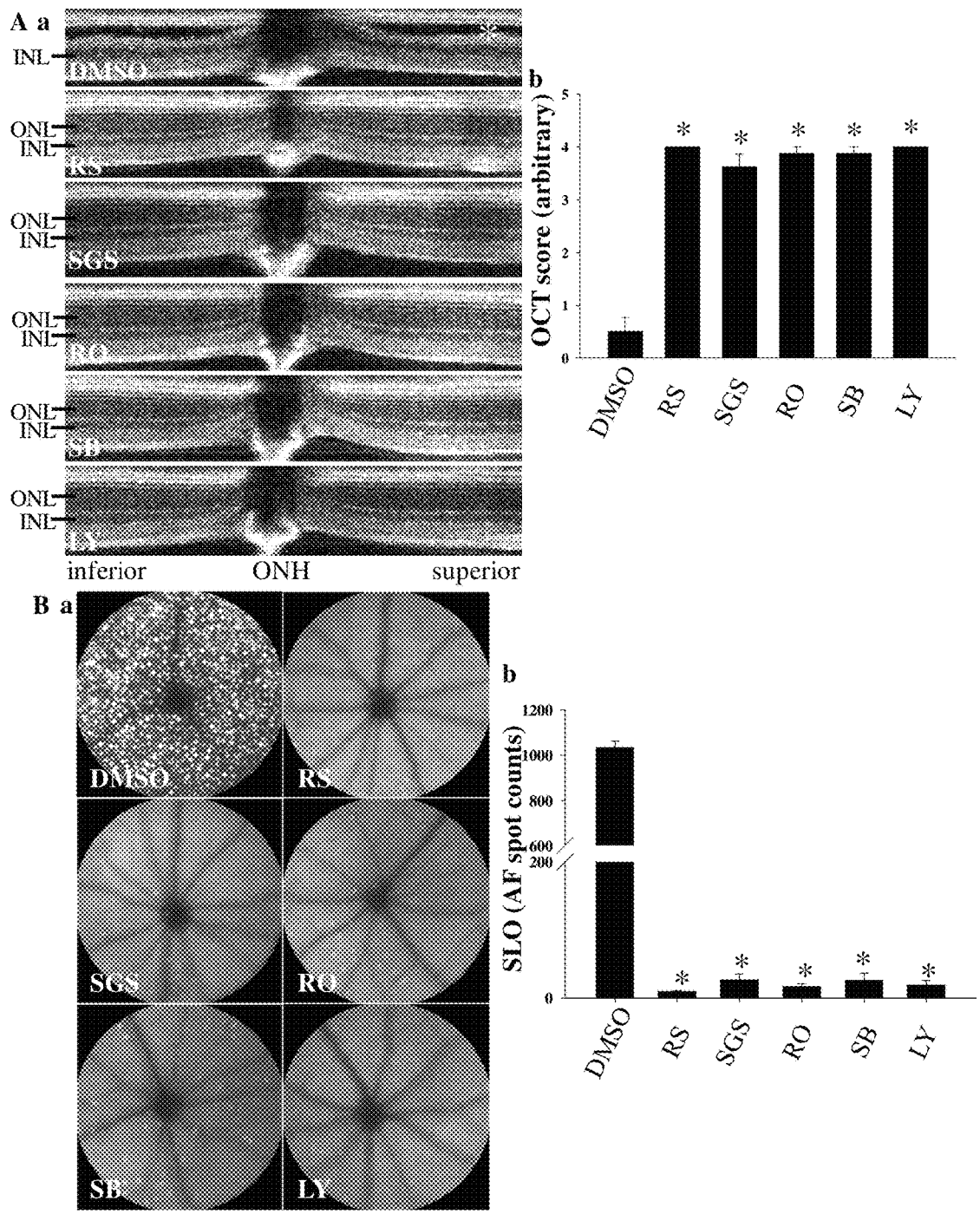
FIGS. 21(A-B)(a-b) illustrate multiple pharmacological compounds antagonizing Gs-couple GPCRs render retinas resistant to light-induced damage. RS 23579-190 (RS), a 5-HT4R antagonist, SGS 518 oxalate (SGS) and RO 04-6790 (RO), selective 5-HT6R antagonists, SB 269970 (SB) and LY-215840 (LY), 5-HT7R antagonists, together with DMSO vehicle control, was each administered to 4- to 5-week old Abca4$^{-/-}$Rdh8$^{-/-}$ mice through intraperitoneal injection prior to white light exposure at the intensity of 10,000 Lux for 30 min. (A) The effect of each treatment aforementioned was examined by OCT imaging 7 days after light exposure. a. Representative OCT images: * indicates disrupted photoreceptor structure; ONH, optic nerve head; ONL, outer nuclear layer; INL inner nuclear layer. b. OCT scores after statistical analysis (Means±SEM; compared to DMSO control, * p<0.01). (B) SLO imaging was performed 8 days after light exposure. a. Representative retinal autofluorescence images. b. The number of retinal autofluorescence spots were counted and followed by statistical analysis (Means±SEM; * compared to DMSO control, p<0.01).

Pharmacological Compounds Activating α2 Adrenergic Receptor, a Gi-Coupled GPCR Provide Significant Protection Against Light-Induced Retinopathy in Abca4$^{-/-}$Rdh8$^{-/-}$ Mice α2 adrenergic receptor (α2R), a Gi-coupled GPCR was evaluated as well to address the possibility of serving as therapeutic candidate treating photoreceptor degeneration. Agonists activating α2R including Guanabenz (GUB), Guanafacine (GUF) and Lofexidine (LOF) was each administered 30 min prior to bright light exposure of Abca4$^{-/-}$Rdh8$^{-/-}$ mice. OCT images were taken 7 days after light exposure. As shown in FIG. 21A, compared to the photoreceptor disruption manifested by DMSO-treated mice, light-induced retinal morphological damage was significantly prevented by treatment of GUB, GUF or LOF. Furthermore, markedly less autofluorescence spots indicative of light-induced photoreceptor damage were observed in mice treated with GUB, GUF or LOF, which is in sharp contrast to large amount of autofluorescence spots presented by DMSO-treated mice (FIG. 21B).

Figure 22:
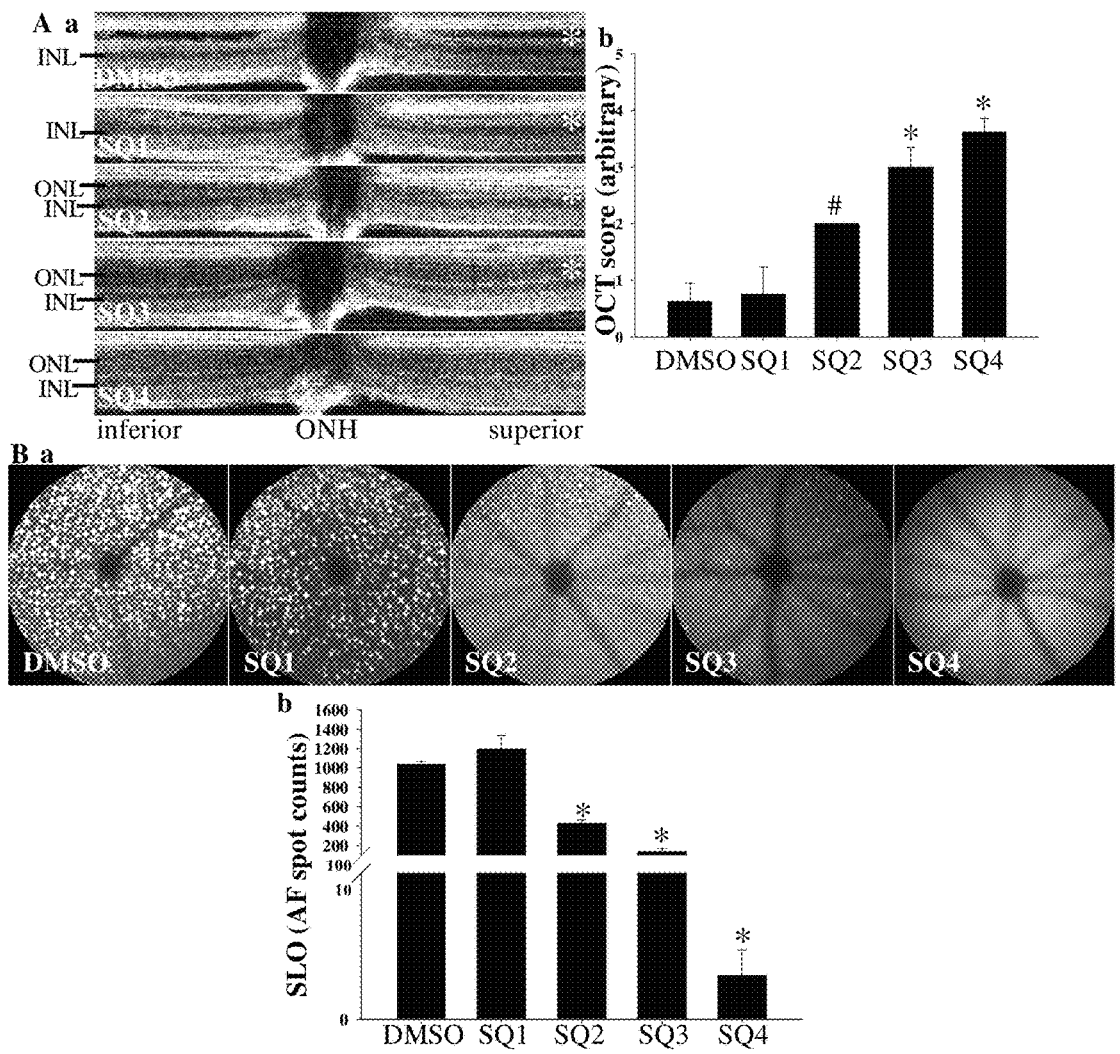
FIGS. 22(A-B)(a-b) illustrate adenylyl cyclase inhibitor dose-dependently protects retina against light-induced damage in Abca4$^{-/-}$Rdh8$^{-/-}$ mouse. Adenylyl cyclase inhibitor SQ 22536 (SQ) was given to 4- to 5-week old Abca4$^{-/-}$Rdh8$^{-/-}$ mice at various doses through intraperitoneal injection prior to white light exposure at the intensity of 10,000 Lux for 30 min. SQ1: 0.083 mg/Kg; SQ2: 0.125 mg/Kg; SQ3: 0.25 mg/Kg; SQ4: 0.5 mg/Kg. (A) The effect of SQ treatment was assessed by OCT imaging 7 days after light exposure. a. OCT images: * indicates damaged photoreceptor structure; ONH, optic nerve head; ONL, outer nuclear layer; INL inner nuclear layer. b. Statistical analysis of OCT scores (Means±SEM; compared to DMSO control, # p<0.05; * p<0.01). (B) Retinal autofluorescence was examined by SLO imaging 8 days after light exposure. A. Representative retinal autofluorescence images with bright spots correlated with retinal damage. B. Statistical analysis of the number of SLO autofluorescence spots (Means±SEM; compared to DMSO control, * p<0.01).
Figure 23:
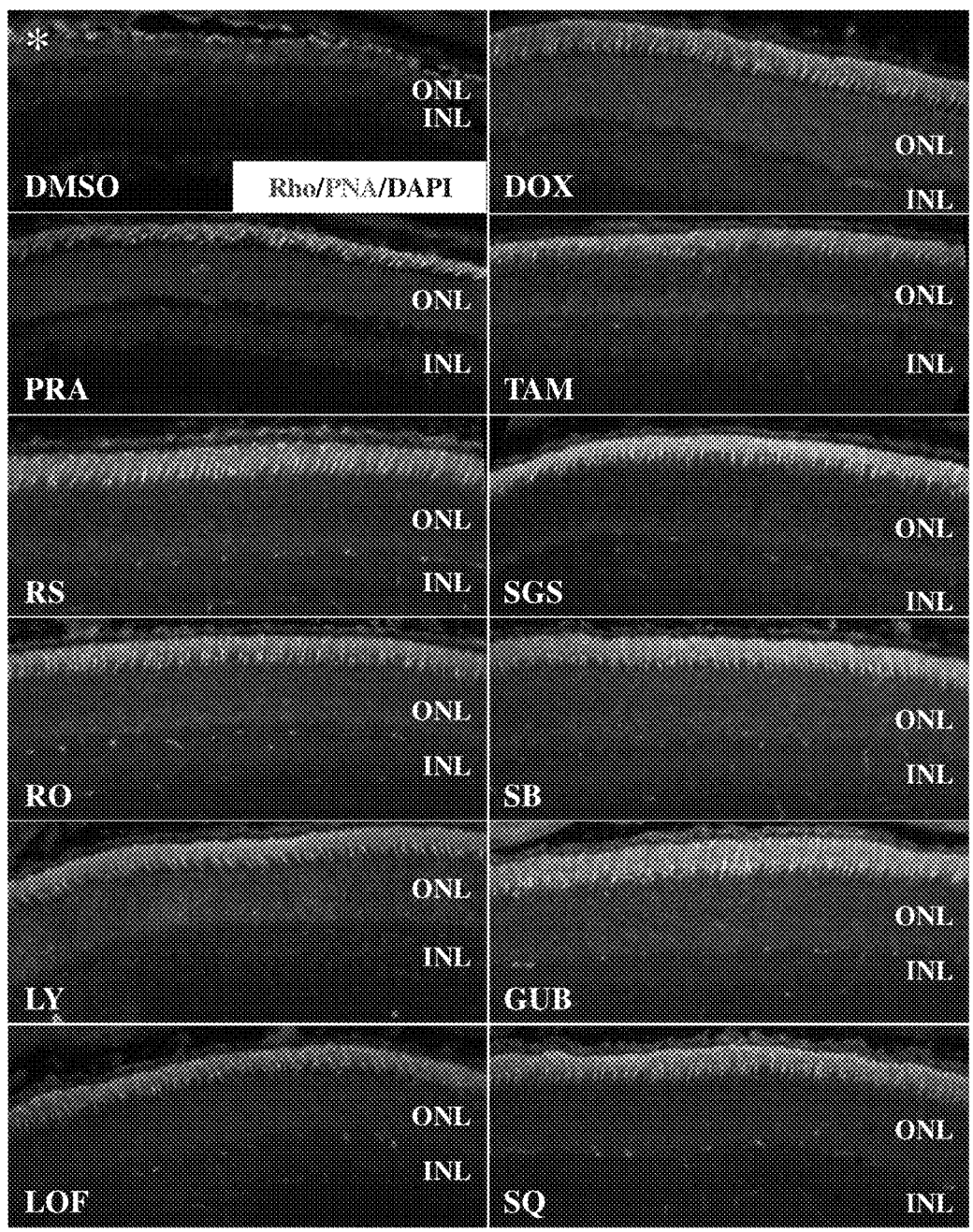
FIG. 23 illustrates retinal immunohistochemical examination validates the therapeutic effects of treatment targeting Gq, Gs, Gi-coupled GPCRs and adenylyl cyclase. Retinal morphological changes after various indicated treatment was further evaluated by photoreceptor immunohistochemical examination (* indicates severely impaired photoreceptor outer segment and inner segment indicated by residual expression of Rhodopsin and peanut agglutinin; ONL, outer nuclear layer; INL inner nuclear layer; Rho: rhodopsin in red, PNA, peanut agglutinin in green and DAPI in blue; 20× objective lens).
Figure 24A:
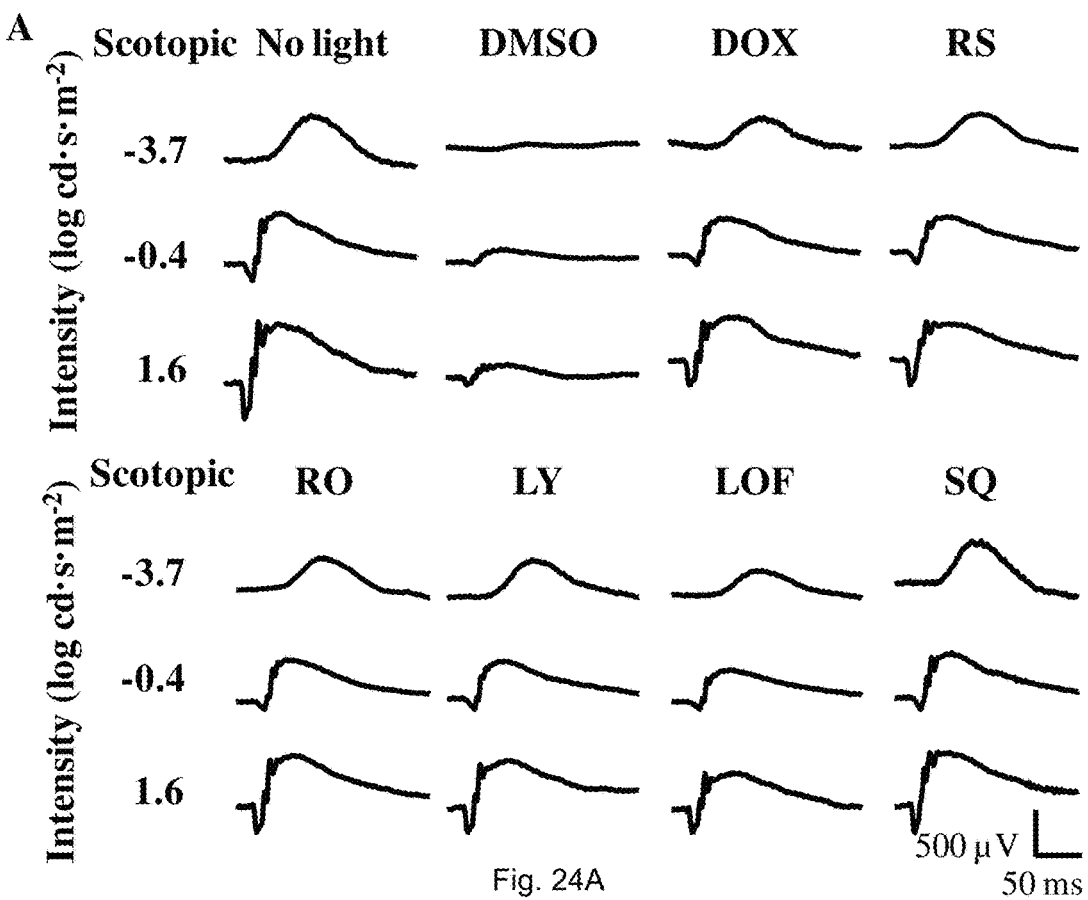
FIGS. 24(A-B) illustrate retinal function is preserved by treatment targeting Gq, Gs, Gi-coupled GPCRs and adenylyl cyclase. ERG was performed to evaluate retinal function in Abca4$^{-/-}$Rdh8$^{-/-}$ mice 2 weeks after they were pretreated with indicated pharmacological agents. Compared to Abca4$^{-/-}$Rdh8$^{-/-}$ mice without being exposed to bright light (No light), Abca4$^{-/-}$Rdh8$^{-/-}$ mice with light exposure at 10,000 lux for 30 min and treated by DMSO vehicle control (DMSO) displayed significantly impaired retinal function as indicated by decreased scotopic a-wave and b-wave amplitude. Compounds exhibiting protective effect against light-induced retinal dysfunction included: DOX, RS, RO, LY, LOF and SQ. A. Representative scotopic a-, b-waves. B. Plotted data of scotopic ERG.
Figure 24B:
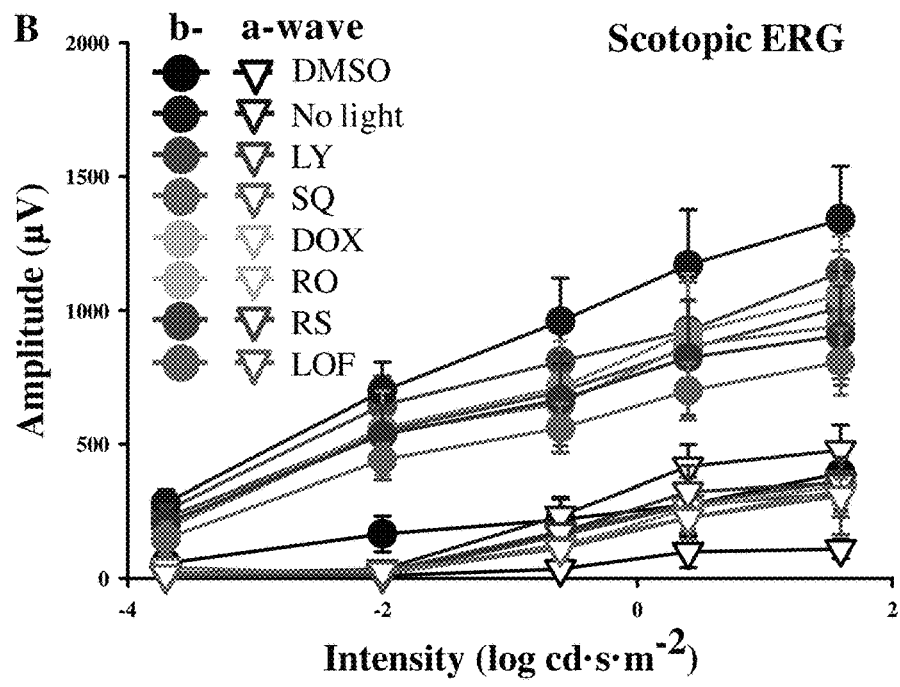

Inhibition of Adenylyl Cyclase Prevents Retinas from Developing Light-Induced Degeneration Our data have demonstrated that multiple antagonists against Gs-coupled GPCRs or agonists at Gi-coupled GPCRs protect retinas against light-induced degeneration. Given that adenylyl cyclase (AC) is the central player mediating the intracellular function of both Gs- and Gi-coupled GPCRs, we further tested the possibility of targeting AC in intervening light-induced retinal degeneration. To address this, AC specific inhibitor SQ 22536 (SQ) was administered to Abca4$^{-/-}$Rdh8$^{-/-}$ mice 30 min before bright light exposure, followed by retinal structural examination by OCT imaging 7 days later. As shown in FIG. 22A, SQ treatment protected retinas from light-induced degeneration in a dose-dependent manner. Further SLO evaluation also showed a dose-dependent effect of SQ on preventing the formation of autofluorescent spot signifying of light-induced photoreceptor damage (FIG. 22B). These data indicate that AC is involved in the pathogenesis of light-induced retinal degeneration and support the notion that AC signaling is a valid target for treating light-induced retinal degeneration. Retinal Morphological Preservation by Pharmacological Intervention Targeting Gq-, Gi-, Gs-Coupled GPCRs and AC Immunohistochemical examination was also performed to evaluate the retinal morphological alterations in detail. Rhodopsin, which labels rod outer segment, peanut agglutinin, which immunohistochemically marks cone cell matrix sheaths in retina, and DAPI, which stains nucleus, were applied to retinal sections collected from Abca4$^{-/-}$Rdh8$^{-/-}$ mice. As shown in FIG. 23, compared to severely damaged photoreceptor structure manifested by light-exposed, Abca4$^{-/-}$Rdh8$^{-/-}$ mice treated with DMSO vehicle, which exhibited residual expression of Rhodopsin and peanut agglutinin and marked decreased thickness of DAPI-stained photoreceptor outer nuclear layer, substantially preserved photoreceptor morphology was evidenced by abundant, well-organized Rhodopsin, peanut agglutinin expression and well-maintained DAPI-stained outer nuclear layer in Abca4$^{-/-}$Rdh8$^{-/-}$ mice treated by pharmacological compounds targeting either Gq- (DOX, PRA and TAM), Gi- (LY, GUB and GUF), Gs- (RS, SGS, RO and LY) coupled GPCRs or AC (SQ).

Protection of Retinal Function by Pharmacological Intervention Targeting Gq-, Gi-, Gs-Coupled GPCRs and AC To further estimate the therapeutic effects of pharmacological treatment that proved to be effective in preserving the retinal morphology, electroretinography was performed 2 weeks after indicated pharmacological pre-treatment and light exposure. As shown in FIG. 23, compared to the mice without light exposure (no light), bright light exposure at 10,000 Lux for 30 min nearly abolished scotopic ERG response in Abca4$^{-/-}$Rdh8$^{-/-}$ mice treated with DMSO vehicle. In sharp to contrast to the ERG response displayed by DMSO-treated mice, substantial preservation of the scotopic ERG response was achieved by treatment targeting multiple GPCRs, including DOX, a compound antagonizing Gq-coupled α1R; RS, a compound antagonizing Gs-coupled 5-HT4 receptor; RO, a compound antagonizing Gs-coupled 5-HT6 receptor; LY, a compound antagonizing 5-HT7 receptor; LOF, a compound activating Gi-coupled α2R and SQ, an inhibitor of AC. Our data indicate that pharmacological treatment targeting these GPCRs exerts protection against light-induced retinal degeneration at functional level as well.

The following Table lists the effectiveness of pharmacological compounds targeting multiple GPCRs evaluated as potential therapeutic candidates to prevent photoreceptor cells from light-induced degeneration as measured by OCT imaging of Abca4$^{-/-}$Rdh8$^{-/-}$ mice administered the agent.

TABLE 1

| Name | Action | Structure | Effect | Dose | Mechanism |
| --- | --- | --- | --- | --- | --- |
| Agomelatine | 5-HT$_{2C}$R antagonist | 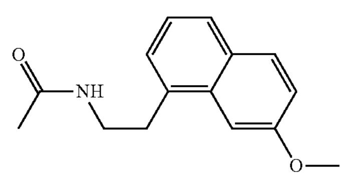 [SMILES: COc1ccc2cccc(CCNC(C)=O)c2c1] | 50% | 25 mg/kg | |
| Nefazodone | 5-HT$_{2A}$R (Gq) antagonist | 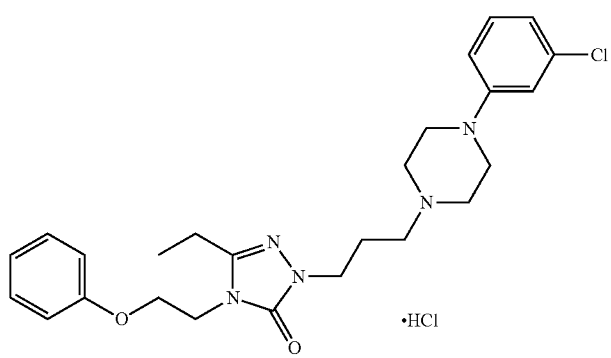 [SMILES: CCc1nn(CCCN2CCN(c3cccc(Cl)c3)CC2)c(=O)n1CCOc1ccccc1 ; Cl] | 100% | 30 mg/kg | PLC |
| Eltoprazine | 5-HT$_{2C}$R antagonist | 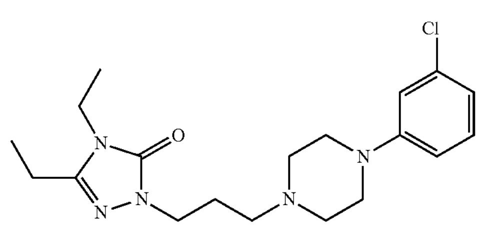 [SMILES: CCc1nn(CCCN2CCN(c3cccc(Cl)c3)CC2)c(=O)n1CC] | 20% | 10 mg/kg | |

TABLE 1-continued

| Name | Action | Structure | Effect | Dose | Mechanism |
|---|---|---|---|---|---|
| Cyproheptadine | 5-HT$_{2B}$R antagonist | 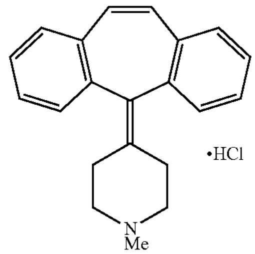 [SMILES: CN1CCC(=C2c3ccccc3C=Cc3ccccc32)CC1 ; Cl] | toxic | 20 mg/kg | |
| Pizotifen | 5-HT$_{2A/C}$R (Gq) antagonist | 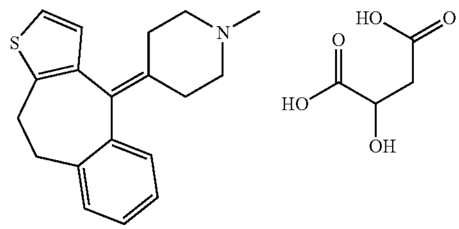 [SMILES: CN1CCC(=C2c3ccccc3CCc3sccc32)CC1 ; O=C(O)CC(O)C(=O)O] | 75% | 10 mg/kg | PLC |
| RS 23579-190 | 5-HT$_{4R}$ (Gs) antagonist | 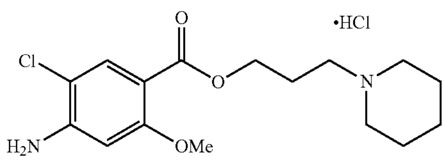 [SMILES: COc1cc(N)c(Cl)cc1C(=O)OCCCN1CCCCC1 ; Cl] | 100% | 20 mg/kg | Adenylyl cyclase |
| GR 125487 | 5-HT$_{4R}$ antagonist | 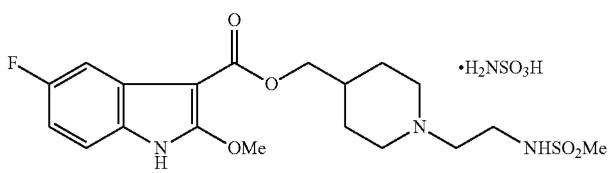 | 0% | 10 mg/kg | |
| RS 39604 | 5-HT$_{4R}$ antagonist | 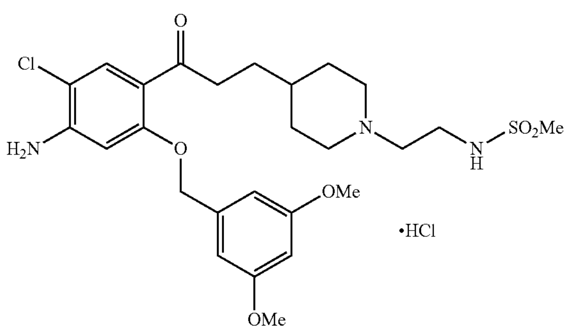 [SMILES: COc1cc(COc2cc(N)c(Cl)cc2C(=O)CCC2CCN(CCNS(C)(=O)=O)CC2)cc(OC)c1 ; Cl] | 0% | 5 mg/kg | |
| SB 203186 | 5-HT$_{4R}$ antagonist | 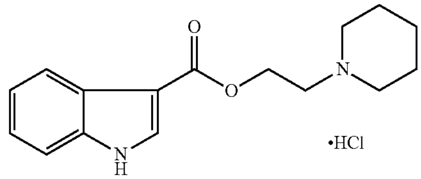 [SMILES: O=C(OCCN1CCCCC1)c1c[nH]c2ccccc12 ; Cl] | 0% | 5 mg/kg | |
| Ro 04-6790 | 5-HT$_{6R}$ (Gs) antagonist | 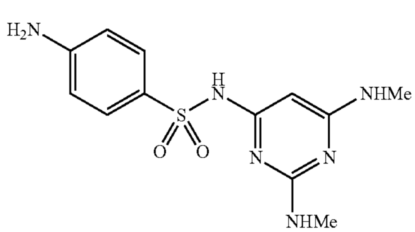 [SMILES: CNc1cc(NS(=O)(=O)c2ccc(N)cc2)nc(NC)n1] | 100% | 30 mg/kg | Adenylyl cyclase |

TABLE 1-continued
| Name | Action | Structure | Effect | Dose | Mechanism |
|---|---|---|---|---|---|
| SB 399885 | 5-HT$_{6R}$ antagonist | 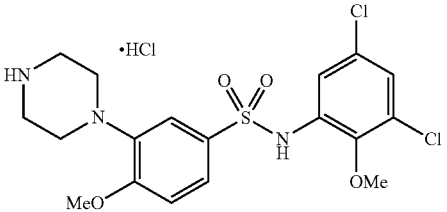 [SMILES: COc1ccc(S(=O)(=O)Nc2cc(Cl)cc(Cl)c2OC)cc1N1CCNCC1 ; Cl] | >25% | 30 mg/kg | |
| SGS 518 oxalate | 5-HT$_{6R}$ (Gs) antagonist | 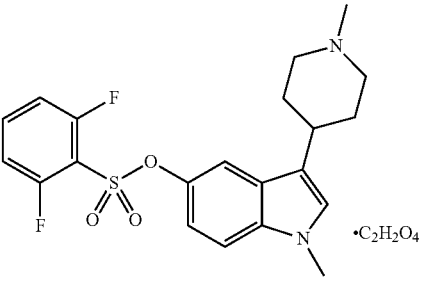 | >75% | 30 mg/kg | Adenylyl cyclase |
| SB 269970 | 5-HT$_{7R}$ (Gs) antagonist | 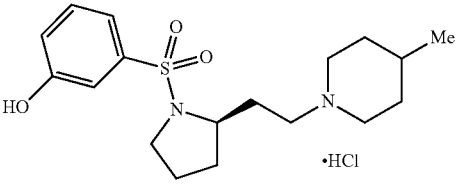 [SMILES: CC1CCN(CC[C@H]2CCCN2S(=O)(=O)c2cccc(O)c2)CC1 ; Cl] | >75% | 30 mg/kg | Adenylyl cyclase |
| LY 215840 | 5-HT$_{7/2R}$ (Gs/Gq) antagonist | 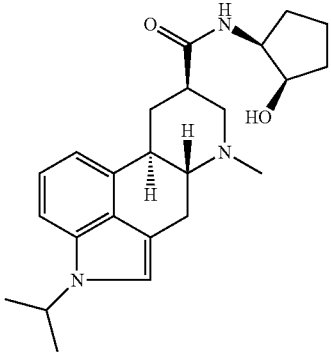 | 100% | 10 mg/kg | Adenylyl cyclase/ PLC |
| Doxazosin | alpha-1 adrenergic receptor (Gq) antagonist | 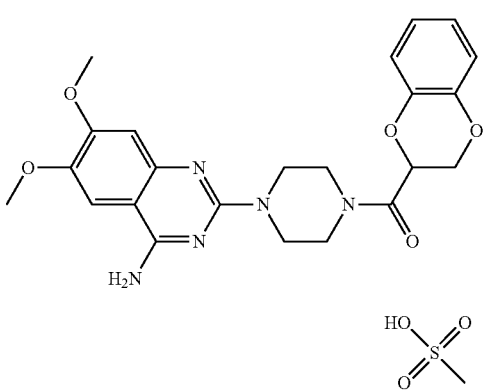 | 100% | 10 mg/kg | PLC |

TABLE 1-continued

| Name | Action | Structure | Effect | Dose | Mechanism |
|---|---|---|---|---|---|
| Prazosin | alpha-1 adrenergic receptor (Gq) antagonist | 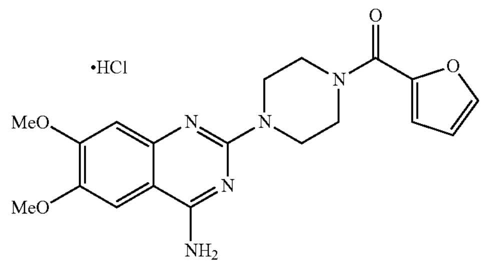 [SMILES: COc1cc2nc(N3CCN(C(=O)c4ccco4)CC3)nc(N)c2cc1OC ; Cl] | 75% | 2 mg/kg | PLC |
| Tamsulosin | alpha-1 adrenergic receptor (Gq) antagonist | 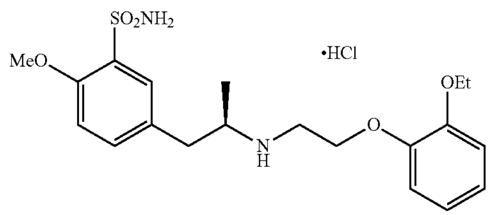 [SMILES: CCOc1ccccc1OCCN[C@H](C)Cc1ccc(OC)c(S(N)(=O)=O)c1 ; Cl] | 75% | 2 mg/kg | PLC |
| Phenoxy-benzamine | alpha-1 adrenergic receptor antagonist | 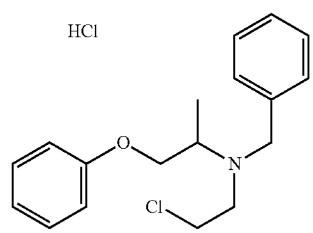 [SMILES: CC(COc1ccccc1)N(CCCl)Cc1ccccc1 ; Cl] | 0% | 25 mg/kg | |
| Phentolamine | alpha-1 adrenergic receptor antagonist | 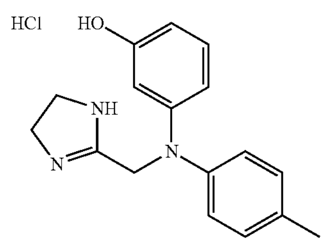 [SMILES: Cc1ccc(N(CC2=NCCN2)c2cccc(O)c2)cc1 ; Cl] | 0% | 5 mg/kg | |
| Guanbenz | alpha-2 adrenergic receptor (Gi) agonist | 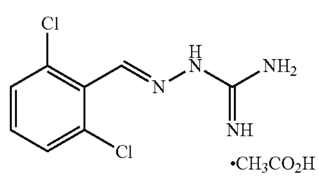 | 100% | 2 mg/kg | Adenylyl cyclase |
| Guanfacine | alpha-2 adrenergic receptor (Gi) agonist | 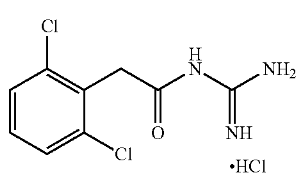 [SMILES: N=C(N)NC(=O)Cc1c(Cl)cccc1Cl ; Cl] | 100% | 2 mg/kg | Adenylyl cyclase |
| Lofexidine | alpha-2 adrenergic receptor (Gi) agonist | 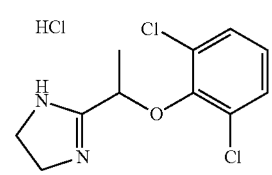 [SMILES: Cl ; CC(Oc1c(Cl)cccc1Cl)C1=NCCN1] | 100% | 2 mg/kg | Adenylyl cyclase |

TABLE 1-continued

| Name | Action | Structure | Effect | Dose | Mechanism |
|---|---|---|---|---|---|
| Fexofenadine | H1 histamine receptor (Gq) antagonist | 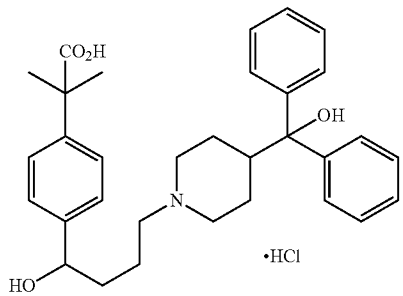 [SMILES: CC(C)(C(=O)O)c1ccc(C(O)CCCN2CCC(C(O)(c3ccccc3)c3ccccc3)CC2)cc1 ; Cl] | 50% | 2 mg/kg | PLC |
| Tolterodine | Muscarinic receptor (Gq) antagonist | 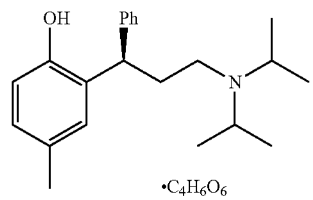 | 50% | 20 mg/kg | PLC |
| ABT-724 | Dopamine D4 receptor agonist | 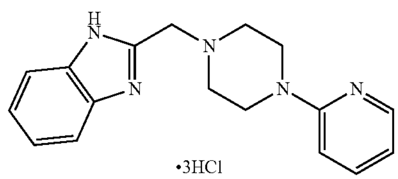 [SMILES: c1ccc(N2CCN(Cc3nc4ccccc4[nH]3)CC2)nc1 ; "·3HCl"] | 0% | 2 mg/kg | |
| PD-168,077 | Dopamine D4 receptor (Gi) agonist | 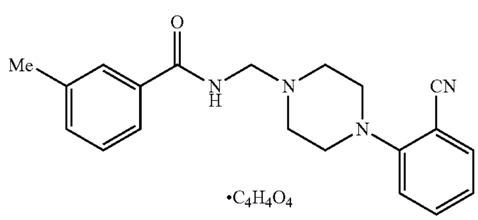 | 60% | 10 mg/kg | Adenylyl cyclase/ PLC |
| Yohimbine | Antagonist at multiple receptors | 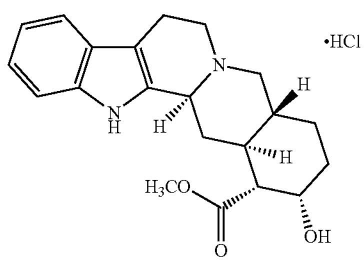 | toxic | 25 mg/kg | |
| Piroxicam | COX-1 inhibitor | 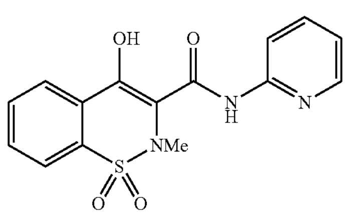 [SMILES: CN1C(C(=O)Nc2ccccn2)=C(O)c2ccccc2S1(=O)=O] | 0% | 2 mg/kg | |

TABLE 1-continued

| Name | Action | Structure | Effect | Dose | Mechanism |
|---|---|---|---|---|---|
| SQ 22536 | Adenylyl cyclase inhibitor | 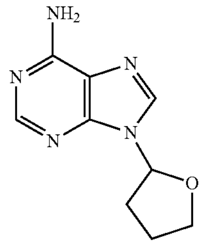 [SMILES: Nc1ncnc2c1ncn2C1CCCO1] | 100% | 0.5 mg/kg | Adenylyl cyclase |

Example 3

We used a systems pharmacology approach with Abca4$^{-/-}$ Rdh8$^{-/-}$ mice that specifically targeted signal transduction by several different GPCRs and their inter-connected mechanisms to identify novel therapeutic strategies for treating blinding retinal disorders such as Stargardt disease and AMD.

Methods

Animals

Abca4$^{-/-}$Abca8$^{-/-}$ mice were generated and genotyped as previously described and mixed genders were used for the present study when they reached 4- to 5-weeks of age. All mice were routinely maintained in a 12 h light ($\leq$10 lux)/12 h dark cyclic environment in the Animal Resource Center at the School of Medicine, CWRU. For bright light exposure experiments, Abca440). Enucleated macaque (*Macaca fascicularis*) eyes in RNAlater (Invitrogen) from 4-year-old animals were obtained from Ricerca Biosciences (Painesville, Ohio, USA). Clinical evaluation and permission of the human patient from whom retinal tissue was obtained were accomplished at the Cleveland Clinic Cole Eye Institute (Cleveland, Ohio) where this research conformed to the tenets of the Declaration of Helsinki. The retina was carefully dissected out from an untreated eye requiring enucleation for a large ocular melanoma and immediately placed in RNALater.

Transcriptome Analyses of the Eye and Retina

Eyes from C57BL/6J (Jackson laboratory) mice at 4-weeks of age were enucleated and immediately processed to isolate total RNA used to prepare cDNA libraries for sequencing with the Illumina platform of RNA-Sequencing instruments. Three biological replicates were made for both whole eye and retinal tissue to generate transcriptome data used to determine fragments per kilobase of gene product per million reads (FPKM) for normalization and differential expression analyses. Clinical evaluations of the human patient from whom retinal tissue was obtained were carried out at the Cleveland Clinic Cole Eye Institute. This research conformed to the tenets of the Declaration of Helsinki. The retina was carefully dissected out of an untreated eye from the patient requiring enucleation for a large ocular melanoma and immediately placed in RNALater (Invitrogen). The experimental sample was obtained from a tumor-free hemiretina. The eye had no signs of inflammation or abnormal neovascularization of the iris or retina.

Eye and retinal tissue libraries were prepared as previously described. Each mouse and human library was run on the Illumina Genome Analyzer IIx (Illumina) in the CWRU Genomics core facility using 36- to 79-single-end read lengths. The processed and raw fastq files from mouse were previously deposited in GEO (accession numbers GSE38359 and GSE29752).

Chemicals

Doxazosin (DOX) was purchased from Selleckchem. Lofexidine was obtained from Santa Cruz. Prazosin (PRA), tamsulosin (TAM), RS 23579-190 (RS), RO 04-6790 (RO), SB 269970 (SB), SGS 518 oxalate (SGS), LY 215840 (LY), guanabenz (GUB), guanfacine (GUF), idazoxan (IDA), and SQ 22536 (SQ) were purchased from TOCRIS Biosciences and all others from Sigma.

Mouse Treatments

All experimental compounds were administered to mice by intraperitoneal injection through a 28 gauge insulin syringe 30 min prior to bright light exposure. Tested compounds and their doses were: DOX, 1 mg/kg body weights (BW), 2 mg/kg BW, 3 mg/kg BW and 10 mg/kg BW, respectively; PRA, 2 mg/kg BW; TAM, 2 mg/kg BW; RS, 20 mg/kg BW; RO, 30 mg/kg BW; SB, 30 mg/kg BW; SGS, 30 mg/kg BW; LY, 10 mg/kg BW; GUB, 0.5 mg/kg BW, 1 mg/kg BW, 1.5 mg/kg and 2 mg/kg BW, respectively; GUF, 2 mg/kg BW; LOF, 2 mg/kg BW; SQ1, 0.083 mg/kg BW; SQ2, 0.125 mg/kg BW; SQ3, 0.25 mg/kg BW; and SQ4, 0.5 mg/kg BW. IDA, 2.5 mg/kg BW and 5 mg/kg BW. All tested compounds were dissolved in DMSO prior to injection except IDA which was dissolved in 0.9% saline.

Spectral Domain-Optical Coherence Tomography (SD-OCT)

Non-invasive ultra-high resolution SD-OCT (Bioptigen) was performed for in vivo imaging of mouse retinas. Mice were anesthetized with an intraperitoneal injection of an anesthetic cocktail consisting of ketamine (6 mg/ml) and xylazine (0.44 mg/ml) diluted with 10 mM sodium phosphate, pH 7.2, and 100 mM NaCl at a dose of 20 µl/g BW. Pupils were dilated with 1% tropicamide prior to SD-OCT imaging. Five frames of OCT images were acquired in the B-mode and averaged for image presentation and analysis. Retinal pathology was subsequently scored according to the criteria indicated below: Grade 0: outer nuclear layer (ONL) was completely disrupted with no visible appearance observed; grade 1: extensive disruption of an ONL spanning the retina 500 µm away from optic nerve head with the ONL thickness less than 0.01 µm; grade 2: extensive disruption of the ONL spanning the retina 500 µm away from optic nerve head with a measured ONL thickness between 0.01 and 0.03 µm; grade 3: reduction in the thickness of the ONL with a measured thickness between 0.03 and 0.05 µm; grade 4: Intact ONL with a measured thickness over 0.05 µm. For evaluation of the impact of Gi and Gq pathways, data points were plotted as the percentage of eyes that developed significant retinal degeneration with an ONL thickness less than 0.035 mm.

Scanning Laser Ophthalmoscopy (SLO) Imaging

SLO (Heidelberg Engineering) was carried out for in vivo whole fundus imaging of mouse retinas. Mice were anesthetized by intraperitoneal injection of the anesthetic cocktail indicated above, followed by pupil dilation with 1% tropicamide prior to SLO imaging under the autofluorescence mode. Numbers of autofluorescent spots were counted and subjected to statistical analyses as described below.

Immunohistochemistry

Retinal immunohistochemistry (IHC) was performed as previously described. Briefly, eyes were enucleated and, after removal of the cornea, lens and vitreous body, eye cups were fixed in 4% paraformaldehyde and processed for cryosectioning. Twelve μm thick cryosections were cut, collected and examined for rhodopsin expression, peanut agglutinin lectin (PNA) for cone sheath and nuclear DAPI staining.

Electroretinograms (ERGs)

ERGs were performed as previously described. Briefly, dark-adapted mice were examined under dim red light transmitted through a Kodak No. 1 Safelight filter (transmittance 560 nm). Pupils were dilated with 1% tropicamide after anesthesia induced by the method described above. Contact lens electrodes were placed on the eyes, and a reference electrode and ground electrode were positioned on the ear and tail, respectively. ERGs were recorded with the universal testing and electrophysiologic system, UTAS E-3000 (LKC Technologies, Inc.).

In Vivo Detection of ROS

In vivo ROS generation was evaluated as previously described. The ROS probe, DHE, at a dose of 20 mg/kg body weight in 25 μl of DMSO, was administered to $Abca4^{-/-}$ $Rdh8^{-/-}$ mice via intraperitoneal injection 1 h prior to light exposure. Eye cups obtained after removing the cornea, lens, and vitreous body from enucleated eye globes 3 h post light illumination were fixed in 4% paraformaldehyde. Cryosections were prepared from fixed eye cups and cut at 12-am thickness for microscopic assessment of ROS fluorescence in the retina with ImageJ software (National Institutes of Health).

Two Photon Microscopy (TPM) Imaging

Ten days after bright light exposure, TMP images were obtained as previously described. Briefly, a Leica TCS SP5 upright confocal microscope (Wetzlar, Germany) equipped with 1.0 NA water immersion objective and tunable laser Vision S, Coherent (Coherent, Santa Clara, Calif.) delivering 75 fs laser pulses at 80 MHz pulse repetition frequency was used. Emission spectra were obtained with a TCS SP5 (Leica) spectrally sensitive detector in the descanned configuration. Only intact, freshly enucleated mouse eyes were used for imaging. Before enucleation, mice were anesthetized by intraperitoneal injection of the anesthetic cocktail indicated above and euthanized in compliance with American Veterinary Medical Association (AVMA) Guidelines on Euthanasia, and approval by the Case Western Reserve University Institutional Animal Care and Use Committee.

Quantification of Selected Drugs in Mouse Tissue

C57BL/6J WT mice at 6 weeks of age (Jackson Laboratory) were treated with DOX, GUB, or SQ at a single dose of 10, 2, and 0.5 mg per kilogram, respectively. The compound was dissolved in 50% DMSO in PBS (137 mM NaCl, 2.7 mM KCl, 0.67 mM Na86, 87). Next, to precipitate excess proteins, 0.3 ml of methanol was added to both the eye homogenate and 0.1 ml of serum. Samples were vortexed for 30 s followed by centrifugation for 15 min at 16,000 g. Clear supernatants were collected and used directly for LC-MS analysis. $_2HPO_4/KH_2PO_4$, pH 7.4) and administered by intraperitoneal injection. Thirty minutes later the mice were anesthetized. Blood samples were collected using the technique of cardiac puncture and subsequently centrifuged (5 min, 16,000 g) to collect serum. Prior to harvesting eyes, mice were intracardially perfused with PBS to minimalize blood contamination. Eye balls were immediately homogenized in 0.1 ml of PBS. The homogenate and serum samples were spiked with 100 pmols of internal standard (IS) (parazosin—2-[4-(2-furoyl)piperazin-1-yl]-6,7-dimethoxyquinazolin-4-amine (Sigma Aldrich) or clenbuterol—(RS)-1-(4-Amino-3,5-dichlorophenyl)-2-(tert-butylamino)ethanol (Sigma Aldrich)) for DOX, GUB or SQ quantification, respectively.

Figure 34:
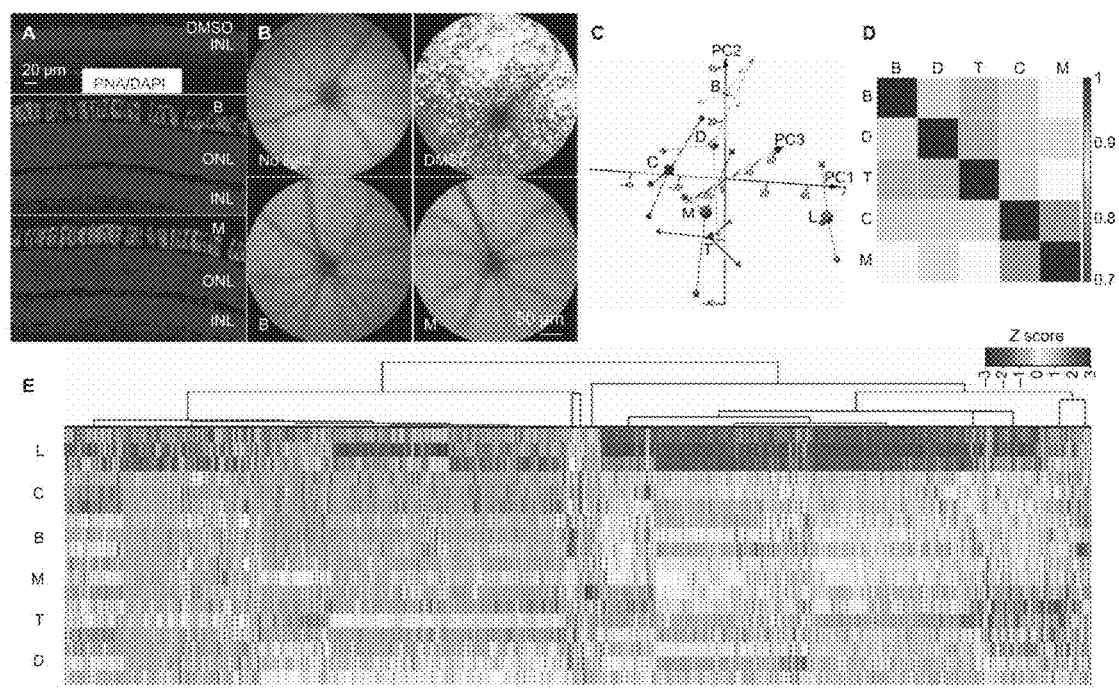
FIGS. 34(A-E) illustrate retina protection conferred by monotherapy (A) Retinal expression of PNA (green) along with DAPI counterstaining (blue) was examined in cryosections collected from light-exposed Abca4$^{-/-}$Rdh8$^{-/-}$ mice pre-treated with DMSO, BRM, or MTP. (B) Autofluorescent spots in the retinas of Abca4$^{-/-}$Rdh8$^{-/-}$ mice imaged after exposure to bright light. Abca4$^{-/-}$Rdh8$^{-/-}$ mice were pre-treated as indicated and exposed to bright light, and then SLO was performed to visualize autofluorescence in retinas of Abca4$^{-/-}$Rdh8$^{-/-}$ mice. (C to E) Total RNA from the indicated experimental groups (n=3 per group) was isolated from Abca4$^{-/-}$Rdh8$^{-/-}$ mice 1 day after light exposure, along with mice unexposed to bright light. Total RNA was then subjected to RNA-seq analysis. (C) Three-dimensional (3D) PCAs of all expressed transcripts are shown for the control mice unexposed to bright light (C), light-exposed, DMSO-pretreated mice (L), and mice pre-treated with either BRM (B), MTP (M), DOX (D), or TAM (T). Small shapes represent individual samples, and large shapes are the centroid representations for each group. (D) Pearson's correlation plots of differentially expressed transcripts from retinas of mice unexposed to bright light and the indicated pretreatment groups. Scale bar indicates correlation co-efficient with identity orange (correlation coefficient, 1). (E) Gene expression clustering of the differentially expressed transcripts is shown for mice with the indicated pretreatments along with clustering from mice unexposed to light and DMSO-pretreated mice exposed to light. Data are shown for the three independent samples in each treatment. Scale bar represents the Z score indicating up-regulation and down-regulation.

Mass spectrometry (MS) based detection and quantification of DOX, GUB, and SQ was performed with a L×Q linear ion trap mass spectrometer (Thermo Scientific) equipped with an electrospray ionization (ESI) interface and coupled to Agilent 1100 HPLC (Agilent Technologies). Separation of drugs and the internal standards was achieved on a reverse phase C18 Phenomenex HPLC column (250× 4.60 mm; 5 μm) by a linear gradient of to 100% acetonitrile in water within 15 min at flow rate of 0.5 ml/min. All solvents contained 0.1% formic acid (v/v). The HPLC effluent was sprayed into the MS via an ESI probe operated in the positive ionization mode. Parameters of ionization and detection were tuned with synthetic standards for the drugs to achieve the highest possible sensitivity. Dox and parazosin (internal standard) were detected by selected reaction monitoring (SRM) using m/z 452.2→344.2 and 384.2→247.1 transitions whereas GUB, SQ and their corresponding IS, clenbuterol, was by fragmentation at m/z 231.1→214.0, 206.1→136.0, and 277.1→259.1, respectively. The elution times for DOX, GUB, and SQ were ~12.8, 12.3, and 10.8 min, respectively. Both internal standards eluted at 12.0 min (FIG. 34). Calibration curves were calculated based on the linear relationship between ratios of SRM ion intensity peak area corresponding to the selected drug and the IS vs. molar ratios of the compounds in the range of 20-500 pmol (FIG. 34H).

Statistical Analyses

Results were collected from at least 4 mice per experimental group. Data are expressed as means±SEM and statistical analyses were performed using a 1-way Students t-test or ANOVA. A p value of ≤0.05 was considered statistically significant.

Results

Expression of GPCRs and GPCR Signaling Genes in Human and Mouse Retina

Expression analysis of retinal GPCRs by immunocytochemistry was unreliable for reasons that include poor specificity and low affinity of antibodies (data not shown) as well as low GPCR expression. Therefore, we turned to quantitative transcriptome analysis of human and mouse retinas without specific cellular localization.

Overall, we found 1766 unique gene products categorized as having GPCR activity by gene ontology in *Mus musculus*. The same mouse transcripts were also recognized in the retinal transcriptome from *Homo sapiens*. Of these 1766, 165 genes displayed expression of at least 1 FPKM (fragment per kilobase exon per million reads mapped), equivalent to 1 transcript per cell, in C57BL/6J mouse eye or retina with 6 genes below the 1 FPKM threshold in mouse eye but above the 1 FPKM threshold in mouse retina (Table 2). Expression of these 165 genes from human retina is also displayed as decreasing FPKM values starting from rhodopsin (Rho), the highest expressed gene in mouse eye. The highest expressed human GPCR was rhodopsin, followed by retinal G protein receptor (RGR) and the cone pigments, Opn1sw and Opn1mw.

A more detailed analysis was carried out of adenylate cyclases (ACs), α1-adrenergic receptors (α1-ARs), α2-ARs and serotonin receptors (5-HTRs) to detect potential pathways that could be affected by a systems pharmacological approach. Reaction quenching molecules, such as arrestins and GPCR kinases were also investigated (Table 3). Expression values for these genes in mouse and human retinas highlighted those pathways that should be most susceptible to pharmacological treatment as well as those targets that would best translate from mouse models to human patients. For example, among isoforms of the α1-ARs and α2-ARs, the human retina expressed α2C-AR at the highest level (Table 3) and among 5-HTRs, 5-HT2AR had the highest expression. Data from real-time PCR analyses corroborated that expression of these genes are readily detected in the mouse retina and/or RPE (unpublished observations).

TABLE 2

| Genes | B6 mouse eye | B6 mouse retina | Human retina |
|---|---|---|---|
| Rho | 6162.01 | 11630.18 | 6896.09 |
| Rgr | 355.74 | 97.66 | 123.98 |
| Opn1sw | 125.13 | 198.54 | 31.69 |
| DRD4 | 93.84 | 241.78 | 139.49 |
| Opn1mw | 62.97 | 95.77 | 172.56 |
| Gprc5b | 29.82 | 12.95 | 22.85 |
| Gpr162 | 29.37 | 73.32 | 46.29 |
| Gpr37 | 28.47 | 41.28 | 66.65 |
| Ednrb | 22.27 | 1.94 | 5.77 |
| Rorb | 21.69 | 23.52 | 24.31 |
| Gpr153 | 20.42 | 37.18 | 15.31 |
| Gabbr1 | 19.78 | 40.24 | 35.38 |
| Rrh | 19.29 | 9.23 | 40.34 |
| Gpr152 | 18.55 | 40.46 | 3.05 |
| Adora1 | 16.20 | 18.26 | 13.55 |
| Lphn1 | 15.98 | 29.73 | 31.85 |
| Tm2d1 | 15.56 | 10.31 | 17.63 |
| Cxcr7 | 14.30 | 3.58 | 2.37 |
| Ppard | 13.68 | 19.37 | 21.61 |
| Agtrap | 13.64 | 17.21 | 8.18 |
| Cd97 | 12.93 | 1.77 | 1.55 |
| Gpr19 | 12.21 | 8.45 | 1.11 |
| Fzd1 | 11.99 | 3.29 | 7.35 |
| Fzd6 | 11.34 | 1.85 | 2.76 |
| Gpr87 | 11.34 | 0.04 | 0.00 |
| Lgr4 | 11.09 | 9.50 | 18.07 |
| Drd2 | 10.82 | 23.10 | 26.33 |
| Smo | 10.75 | 6.35 | 5.91 |
| S1pr1 | 10.66 | 11.21 | 11.78 |
| Bai1 | 10.08 | 27.10 | 10.82 |
| Glp2r | 9.94 | 34.85 | 0.31 |
| Ptger1 | 9.59 | 14.88 | 0.94 |
| Gpr124 | 9.56 | 8.94 | 19.82 |
| F2r | 9.31 | 5.32 | 0.15 |
| Adra2c | 8.96 | 7.17 | 2.38 |
| Gpr146 | 8.91 | 7.49 | 6.17 |
| Vipr2 | 8.79 | 14.33 | 10.69 |
| Fzd5 | 8.69 | 10.01 | 7.73 |
| Gpr110 | 8.59 | 0.08 | 0.02 |
| Adrb1 | 8.43 | 20.18 | 3.84 |
| S1pr3 | 8.42 | 6.95 | 3.56 |
| Gabbr2 | 7.80 | 17.03 | 10.57 |
| Lphn2 | 7.66 | 9.02 | 8.79 |
| Lpar1 | 7.47 | 0.91 | 0.45 |
| P2ry2 | 7.20 | 0.62 | 2.29 |
| Adrb2 | 7.13 | 1.03 | 0.98 |
| Hrh3 | 7.11 | 19.12 | 3.75 |
| Bai2 | 6.81 | 15.34 | 14.64 |
| Gpr143 | 6.80 | 1.25 | 0.80 |
| Celsr2 | 6.53 | 7.26 | 10.80 |
| Fzd7 | 6.34 | 1.88 | 2.51 |
| Drd1a | 6.15 | 9.49 | 8.45 |
| Adora2b | 6.09 | 2.53 | 3.83 |
| Celsr3 | 5.82 | 20.00 | 9.87 |
| Fzd4 | 5.39 | 4.28 | 0.43 |
| Gprc5c | 5.26 | 2.13 | 3.13 |
| Gpr56 | 5.12 | 4.31 | 2.92 |
| Npr3 | 5.10 | 0.72 | 0.44 |
| Tacr3 | 4.95 | 4.63 | 2.36 |
| Grm8 | 4.77 | 6.43 | 2.04 |
| Ramp1 | 4.68 | 1.39 | 5.25 |
| Adra2a | 4.60 | 9.91 | 0.25 |
| Grp85 | 4.56 | 5.72 | 2.70 |
| Lphn3 | 4.22 | 6.49 | 2.90 |
| Htr3a | 4.14 | 2.54 | 0.00 |
| Bai3 | 3.92 | 6.01 | 1.91 |
| Fzd2 | 3.89 | 0.79 | 3.24 |
| Fzd1 | 3.86 | 6.31 | 0.36 |
| Gpr98 | 3.79 | 7.30 | 3.64 |
| Tacr1 | 3.72 | 2.06 | 0.95 |
| Gpr158 | 3.72 | 5.07 | 3.58 |
| Fzd8 | 3.56 | 3.26 | 15.06 |
| Opn4 | 3.35 | 2.94 | 1.11 |
| Tshr | 3.24 | 1.55 | 0.00 |
| S1pr2 | 3.20 | 1.13 | 0.63 |
| Mrgprf | 3.18 | 0.64 | 0.80 |
| Oprl1 | 3.15 | 4.42 | 0.81 |
| F2rl1 | 3.13 | 0.24 | 2.58 |
| S1pr5 | 3.12 | 0.48 | 0.01 |
| Gpr135 | 3.07 | 8.35 | 1.99 |
| Crhr1 | 3.02 | 6.49 | 12.76 |
| Eltd1 | 3.00 | 1.65 | 0.51 |
| Mrgpre | 2.96 | 2.80 | 1.74 |
| Gpr27 | 2.92 | 3.88 | 8.45 |
| Ednra | 2.87 | 0.52 | 0.16 |
| Grm4 | 2.86 | 4.93 | 3.10 |
| Emr1 | 2.60 | 0.22 | 0.03 |
| Opn3 | 2.55 | 1.38 | 2.62 |
| Cnr1 | 2.41 | 2.97 | 0.48 |
| Grm7 | 2.39 | 3.95 | 1.16 |
| Gpr37l1 | 2.39 | 0.96 | 7.73 |
| Grm1 | 2.27 | 3.52 | 4.97 |
| Crhr2 | 2.24 | 1.12 | 4.34 |
| P2ry14 | 2.23 | 0.59 | 0.00 |
| Gpr176 | 2.21 | 3.43 | 4.23 |
| Celsr1 | 2.18 | 0.24 | 0.57 |
| Gpr22 | 2.17 | 1.74 | 0.61 |
| Lgr5 | 2.10 | 4.08 | 0.33 |
| Gpr26 | 2.06 | 3.96 | 0.32 |
| Agrt2 | 2.02 | 0.07 | 0.01 |
| Gpr68 | 2.02 | 1.33 | 0.47 |
| Calcr1 | 2.02 | 0.31 | 0.10 |
| Cckbr | 2.00 | 3.94 | 0.21 |
| Gpr75 | 1.92 | 2.74 | 10.70 |
| P2ry1 | 1.91 | 2.74 | 10.70 |
| Chrm2 | 1.89 | 1.98 | 0.55 |
| Fzd3 | 1.86 | 2.98 | 6.25 |
| Grm5 | 1.83 | 2.19 | 1.57 |
| Adcyap1r1 | 1.81 | 1.50 | 2.86 |
| Htr1b | 1.80 | 3.99 | 0.80 |
| Cx3cr1 | 1.79 | 0.90 | 2.05 |
| Gpr4 | 1.74 | 1.15 | 0.30 |
| P2ry6 | 1.73 | 0.25 | 0.79 |
| Adra1d | 1.72 | 3.83 | 0.08 |
| Tbxa2r | 1.72 | 0.44 | 0.20 |
| Gpr61 | 1.66 | 3.41 | 3.81 |
| Sstr2 | 1.66 | 3.01 | 3.56 |
| Chrm3 | 1.64 | 2.46 | 0.96 |
| Sstr4 | 1.64 | 2.46 | 0.96 |
| Adra1b | 1.60 | 1.62 | 1.12 |
| Cmklr1 | 1.60 | 0.27 | 0.24 |
| Chrm1 | 1.53 | 1.54 | 0.34 |
| Htr1d | 1.49 | 2.58 | 0.00 |
| Cxcr4 | 1.42 | 0.71 | 2.65 |
| Kiss1r | 1.37 | 2.59 | 0.87 |
| C5ar1 | 1.35 | 0.12 | 3.01 |
| Mc1r | 1.32 | 2.05 | 5.65 |
| Ptgfr | 1.32 | 0.06 | 0.12 |
| Fzd9 | 1.30 | 1.86 | 1.39 |

TABLE 2-continued

| Genes | B6 mouse eye | B6 mouse retina | Human retina |
|---|---|---|---|
| Ptgir | 1.20 | 0.38 | 0.17 |
| Hcrtr1 | 1.19 | 2.00 | 0.18 |
| Ccrl2 | 1.16 | 0.27 | 0.07 |
| P2ry12 | 1.16 | 0.54 | 0.34 |
| Gprl2 | 1.15 | 1.94 | 6.01 |
| Gpr173 | 1.13 | 1.77 | 5.26 |
| Gpr88 | 1.11 | 1.78 | 0.91 |
| Chrm4 | 1.10 | 0.78 | 7.70 |
| Galr2 | 1.08 | 0.59 | 0.00 |
| Cysltr1 | 1.07 | 0.02 | 0.12 |
| Lepr | 1.06 | 0.036 | 0.56 |
| Gpr161 | 1.05 | 0.99 | 1.54 |
| Oxtr | 1.02 | 0.72 | 1.60 |
| Gpr64 | 1.01 | 0.17 | 0.26 |
| Gpr157 | 0.95 | 1.05 | 0.61 |
| Drd5 | 0.90 | 1.66 | 2.26 |
| Gpr182 | 0.87 | 1.28 | 0.11 |
| Rxfp3 | 0.76 | 1.09 | 0.00 |
| Nmbr | 0.72 | 1.16 | 0.61 |
| Grik3 | 0.70 | 1.24 | 4.18 |
| Ccr10 | 0.68 | 1.47 | 5.60 |
| Gpr156 | 0.67 | 1.16 | 0.43 |
| Taslr3 | 0.64 | 1.15 | 0.95 |
| Gpr3 | 0.60 | 1.33 | 1.91 |
| Taslr1 | 0.59 | 1.76 | 0.27 |
| Gpr84 | 0.43 | 1.59 | 1.89 |

To better understand GPCR localization in the eye and even the macula, we undertook more in-depth transcriptome studies. We first carried out transcriptome studies of rhodopsin knockout mice, which exhibit no rod pigment expression and fail to form rod photoreceptors, to potentially localize such transcripts to this photoreceptor layer. We also did transcriptome studies with macular tissue isolated from monkeys to learn if these GPCRs localize there and potentially mediate the high resolution vision disrupted in macular diseases such as Stargardt disease. Our results (Table 3) showed that robust expression of Adcyl was present in all eye tissues but it was attenuated in the rhodopsin knockout mouse, indicative of its photoreceptor localization. Adcyl expression was also noticed to be enriched in the monkey macula.

TABLE 3

Expression of adrenergic receptors, serotonin receptors, and adenylate cyclases in the eye and retina of C57BL/6J mice, the eye of photoreceptor degenerated $Rho^{-/-}$ mice, the retina of a human donor eye, and macular tissue from monkey (*Macaca fasicularis*)[4]

| Gene | B6 Mouse Eye | B6 mouse retina | $Rho^{-/-}$ mouse eye | Human Retina | Monkey macula |
|---|---|---|---|---|---|
| *Adenylate Cylases* | | | | | |
| Adcy1 | 17.53 | 37.50 | 9.272 | 68.60 | 81.26 |
| Adcy2 | 14.41 | 21.70 | 22.96 | 5.78 | 11.42 |
| Adcy3 | 5.59 | 5.09 | 1.57 | 5.70 | 21.21 |
| Adcy4 | 1.34 | 0.54 | 2.52 | 1.18 | 0.48 |
| Adcy5 | 7.19 | 11.15 | 11.14 | 8.00 | 12.79 |
| Adcy6 | 17.68 | 49.98 | 11.41 | 9.99 | 7.25 |
| Adcy7 | 4.95 | 0.75 | 0.60 | 1.14 | 2.46 |
| Adcy8 | 2.13 | 3.80 | 2.76 | 3.73 | 8.94 |
| Adcy9 | 3.05 | 3.99 | 3.53 | 4.64 | ND |
| Adcy10 | 0.02 | 0.03 | 0.01 | 0.01 | 0.33 |
| *Adrenergic* | | | | | |
| Adra1a | 0.45 | 0.26 | 0.63 | 0.20 | 1.35 |
| Adra1b | 1.60 | 1.62 | 2.35 | 1.12 | 6.61 |
| Adra1d | 1.72 | 3.83 | 4.26 | 0.08 | 3.97 |
| Adra2a | 4.60 | 9.91 | 6.14 | 0.25 | 0.67 |
| Adra2b | 0.20 | 0.29 | 0.20 | 0.02 | 4.30 |
| Adra2c | 8.96 | 7.17 | 19.28 | 2.38 | 4.30 |
| *Serotonin Receptors* | | | | | |
| Htr1a | 0.17 | 0.28 | 0.13 | 0.15 | 0.16 |
| Htr1b | 1.80 | 3.99 | 1.05 | 0.80 | 8.22 |
| Htr1d | 1.49 | 2.58 | 1.91 | 0.00 | 0.07 |
| Htr1f | 0.03 | 0.04 | 0.03 | 0.44 | 0.06 |
| Htr2a | 0.67 | 0.72 | 0.68 | 1.30 | 0.67 |
| Htr2b | 0.50 | 0.43 | 0.30 | 0.39 | 0.86 |
| Htr2c | 0.56 | 0.73 | 0.52 | 0.02 | 0.27 |
| Htr4 | 0.02 | 0.01 | 0.01 | 0.43 | 0.05 |
| Htr5a | 0.43 | 0.59 | 0.48 | 0.00 | 2.17 |
| Htr6 | 0.19 | 0.19 | 0.36 | 0.29 | 0.00 |
| 0.29Htr7 | 0.31 | 0.31 | 0.1 | 0.01 | 0.59 |
| *Arrestins* | | | | | |
| SAG | 1220.54 | 1805.26 | 301.99 | 3562.22 | 2248.35 |
| Arrb1 | 18.38 | 18.10 | 9.42 | 8.21 | 18.22 |
| Arrb2 | 8.86 | 14.99 | 11.92 | 17.92 | 21.68 |
| Arr3 | 50.73 | 128.48 | 32.62 | 270.16 | 680.86 |
| *GPCR Kinases* | | | | | |
| Grk1 | 111.20 | 236.84 | 14.19 | 175.06 | 88.96 |
| Adrbk1 | 28.70 | 36.88 | 36.15 | 27.29 | 32.71 |

TABLE 3-continued

Expression of adrenergic receptors, serotonin receptors, and adenylate cyclases in the eye and retina of C57BL/6J mice, the eye of photoreceptor degenerated Rho$^{-/-}$ mice, the retina of a human donor eye, and macular tissue from monkey (Macaca fasicularis)[4]

| Gene | B6 Mouse Eye | B6 mouse retina | Rho$^{-/-}$ mouse eye | Human Retina | Monkey macula |
|---|---|---|---|---|---|
| Adrkb2 | 2.83 | 4.68 | 3.52 | 1.30 | 8.84 |
| Grk4 | 0.86 | 0.90 | 0.42 | 5.31 | ND |
| Grk5 | 3.08 | 2.97 | 2.57 | 2.99 | 5.06 |
| Grk6 | 20.26 | 20.31 | 6.95 | 9.69 | 9.02 |
| Grk7 | ND | ND | ND | 8.94 | 20.48 |
| Photoreceptor genes | | | | | |
| Abca4 | 59.00 | 140.14 | 15.85 | 267.71 | 129.68 |
| Opn1sw | 117.79 | 187.21 | 72.95 | 25.42 | 151.31 |
| Rho | 5853.00 | 11081.16 | 39.26 | 6386.12 | 8168.27 |

Contribution of Gi and Gq Pathways to Light-Induced Retinal Pathogenesis in the Abca4$^{-/-}$Rdh8$^{-/-}$ Mouse Model To further elucidate the impact of Gi and Gq GPCR pathways on the pathogenesis of bright light induced degeneration in Abca4$^{-/-}$Rdh8$^{-/-}$ mice, we tested both the additive effects of Gi pathway activation and Gq pathway inhibition and the opposing effects of treatment with both idazoxan (IDA), an α2-AR antagonist, and GUB, an α2-AR agonist. Both GUB (an activator of the Gi pathway) (FIG. 25A) and DOX (an antagonist of the Gq pathway) (FIG. 25B) protected the retinas of Abca4$^{-/-}$Rdh8$^{-/-}$ mice from developing bright light-induced degeneration in a dose-dependent fashion. To further evaluate these positive effects, we first determined the half maximal protective dose of GUB to be 0.3 mg/kg (FIG. 30A) and that of DOX to be 0.4 mg/kg (FIG. 25B). Then we found that treating mice simultaneously with half maximal effective doses of GUB and DOX completely protected retina from bright light-induced degeneration (FIG. 25C) indicating that simultaneous activation of Gi and inhibition of Gq pathways accomplish retinal protection in an additive manner. Additionally, we verified that treating the mice first with α2-AR antagonist, IDA, followed by treating mice with GUB, totally abolished the protective action of a fully effective dosage of the α2-AR agonist, GUB. In distinct contrast to mice treated with GUB alone, retinas of mice pre-treated with IDA and then with GUB were dramatically damaged. Moreover, this damage was more evident with an increased dose of IDA (FIG. 25D). This last result further confirms the positive impact of activating the Gi pathway on retinal protection from bright light-induced degeneration.

Pharmacological Interventions Targeting Gq-, Gi-, Gs-Coupled GPCRs and AC Preserve Retinal Function The effects of pre-treatment with selected compounds affecting Gq-, Gi-, Gs-coupled GPCRs and AC were also examined by scotopic and photopic ERG analyses performed 2 weeks after bright light exposure (FIG. 26). Bright light exposure at 10,000 lux for 30 min nearly abolished the scotopic ERG response in Abca4$^{-/-}$Rdh8$^{-/-}$ mice pre-treated with DMSO vehicle (FIGS. 26, A and B). In marked contrast, substantial preservation of this response was achieved by pre-treatments individually targeting multiple GPCRs. These included DOX, an antagonist of Gq-coupled α1-AR; RS, an antagonist of the Gs-coupled 5-HT4 receptor; RO, an antagonist of the Gs-coupled 5-HT6 receptor; LY, an antagonist of the 5-HT7 receptor; LOF, an agonist of the Gi-coupled α2-AR and SQ, an inhibitor of AC. These data indicate that pharmacological treatment targeting these GPCRs also protects against light-induced retinal degeneration. A complete list of therapeutics is listed in Table 1.

Figure 27:
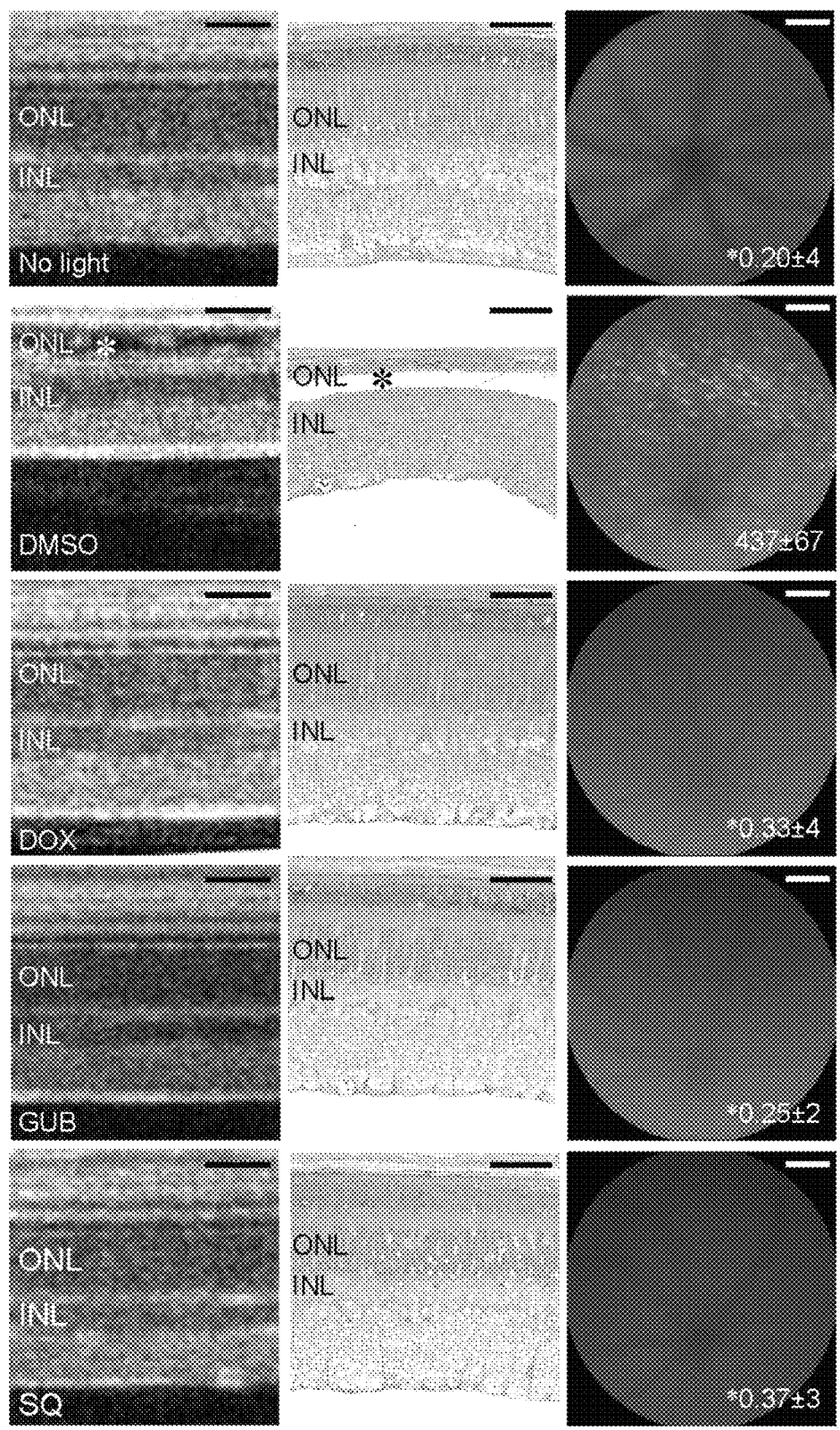
FIG. 27 illustrates Doxazosin (DOX), guanabenz (GUB) and SQ 22536 (SQ) each prevent light-induced retinal degeneration in WT mice. The α1-AR antagonist, DOX; the α2-AR agonist, GUB; or the AC inhibitor, SQ were given to 4-week-old WT (BALB/c) mice by intraperitoneal injection 30 min prior to white light exposure at 10,000 lux for 1 h. BALB/c mice were used to reduce absorption of light by the RPE pigment. Doses of each compound were as follows: DOX; 10 mg/kg; GUB, 2.0 mg/kg; and SQ, 0.5 mg/kg. Effects of these compounds were evaluated by SD-OCT imaging 7 days after light exposure. Representative images of SD-OCT 500 µm away from optic nerve head in the superior retina are shown in the left column. Asterisks indicate damaged photoreceptor structures evident only in DMSO-treated control mice. Retinal cross section images of plastic sections (middle panels) were obtained from areas similar to those used for the OCT images Retinal autofluorescence also was examined by SLO 7 days after light exposure (right panels). Numbers (means±SEM) of bright spots are indicated at the right bottom of SLO images. ONL, outer nuclear layer; INL, inner nuclear layer. Scale bars indicate 50 µm.

Pharmacological Interventions Targeting GPCRs and AC Prevent Light-Induced Degeneration in WT Mice To investigate whether compounds which showed the protective effect against retinal degeneration in Abca4$^{-/-}$Rdh8$^{-/-}$ mice could also prevent retinal degeneration in WT mice, DOX (α1-AR agonist), GUB (α2-AR agonist), and AC inhibitor SQ were further tested for their effect on light-induced retinal degeneration in BALB/c mice. These drugs were administered to 4-week-old BALB/c mice by intraperitoneal injection 30 min prior to white light exposure at 10,000 lux for 1 h. Retinal morphology was assessed 7 days after light exposure by OCT imaging and histological examination. As shown in FIG. 27, severe retinal degeneration was observed in mice treated with DMSO vehicle, whereas retinal morphology of drug-treated mice was maintained and no obvious signs of retinal degeneration being observed. Moreover, SLO examination revealed infiltration of microglia/macrophages into the subretinal space as increased number of autofluorescent spots in DMSO treated and light-exposed mice, which was prevented in mice treated with DOX, GUB or SQ. These results indicate that pharmacological interventions targeting GPCRs and AC also could prevent light-induced degeneration in WT mice.

Figure 28:
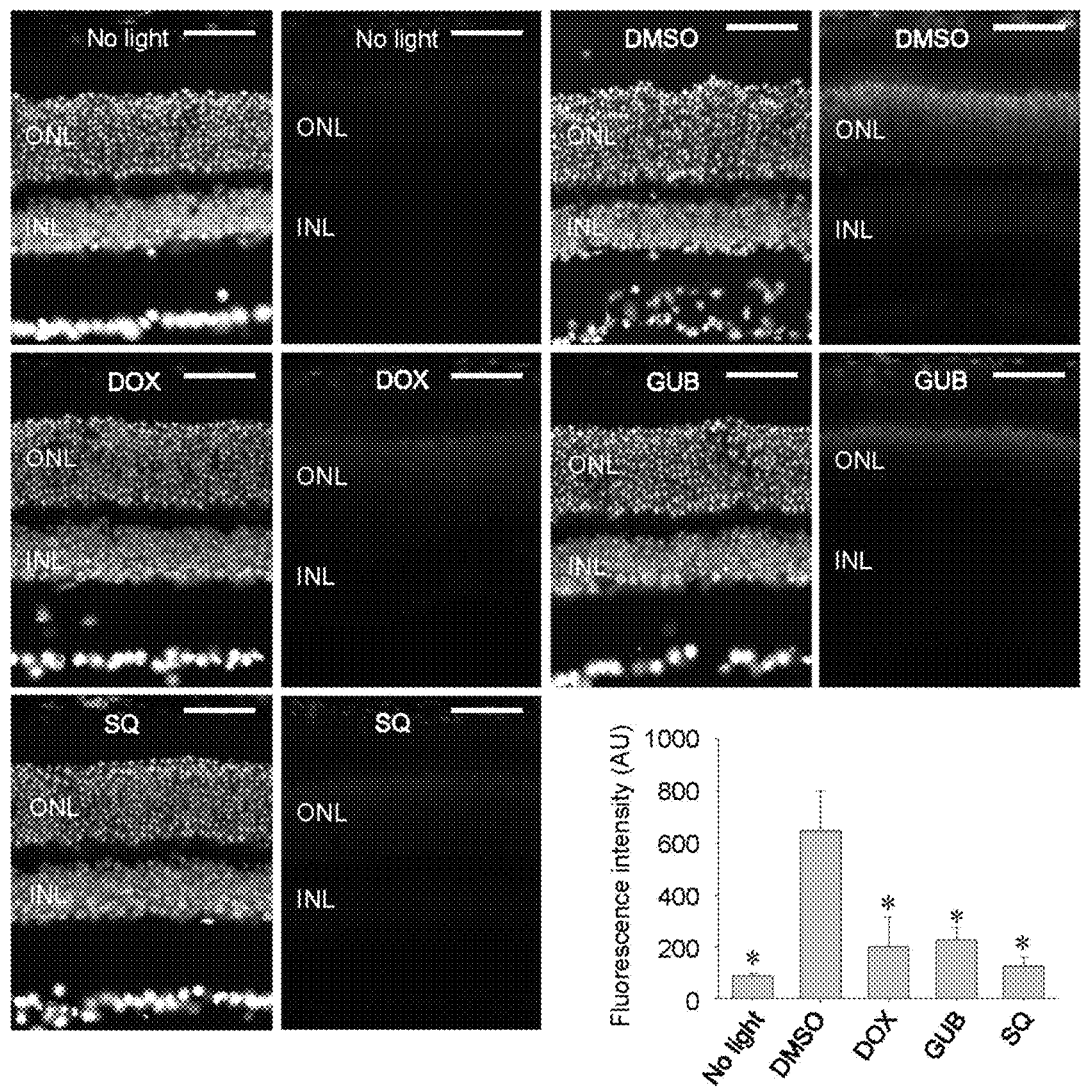
FIG. 28 illustrates ROS generation in photoreceptors of $Abca4^{-/-}Rdh8^{-/-}$ mice after bright light exposure is decreased by either doxazosin (DOX), guanabenz (GUB) or SQ 22536 (SQ) pre-treatment. Dark-adapted pigmented $Abca4^{-/-}Rdh8^{-/-}$ mice at the age of 4-5 weeks were treated with the ROS probe, DHE, 1 h prior to light exposure at 10,000 lux for 30 min. Either vehicle control (DMSO), and DOX, GUB or SQ were also administered by intraperitoneal injection 30 min prior to light exposure. Dose of each compound was as follows: DOX, 10 mg/kg; GUB, 2.0 mg/kg; SQ, 0.5 mg/kg. Dark-adapted $Abca4^{-/-}Rdh8^{-/-}$ mice unexposed to light were included for DHE probe treatment as well (no light). Retinas were harvested 3 h after illumination. ROS signals were obtained with the identical exposure setup under a fluorescence microscope (right panel of each image set). DAPI staining was performed as well to visualize cell nuclei and gross retinal structure (left panel of each image set). Recorded ROS fluorescence intensity in arbitrary units averaged from various areas was further analyzed and summarized for group comparisons (means±SEM). ONL, outer nuclear layer; INL, inner nuclear layer. * $p<0.05$. Scale bars indicate 50 µm.

Pharmacological Interventions Targeting GPCRs and AC Inhibit ROS Generation in Mice after Light Exposure Production of ROS is closely associated with photoreceptor cell death in Abca4$^{-/-}$Rdh8$^{-/-}$ mice. Thus, compounds which showed the protective effect against retinal degeneration in Abca4$^{-/-}$Rdh8$^{-/-}$ mice were also examined for their ability to modulate ROS generation in Abca4$^{-/-}$Rdh8$^{-/-}$ mice after light exposure. Dark-adapted Abca4$^{-/-}$Rdh8$^{-/-}$ mice at the age of 4-5 weeks were intraperitoneally injected with the fluorescent ROS probe, DHE, together with DOX (α1-AR agonist), GUB (α2-AR agonist) or SQ (AC inhibitor) 30 min prior to light exposure at 10,000 lux for 1 h. As shown in FIG. 28, strongest ROS signals were detected in photoreceptor nuclei in DMSO-treated mice among all the mice examined. Pharmacological interventions targeting GPCRs and AC were able to reduce ROS generation in Abca4$^{-/-}$Rdh8$^{-/-}$ mice after light exposure. These results indicate that ROS generation is one of the common downstream pathways potentially mediating the effects of aberrant GPCR/AC signaling in light-induced retinal degeneration in Abca4$^{-/-}$Rdh8$^{-/-}$ mice.

Penetration of DOX, GUB, and SQ into Mouse Eyes

Though drugs administrated into systemic circulation are distributed throughout the body, they also can achieve different concentrations in various organs and tissues depending on rates of vascular perfusion and the drugs' molecular properties, such as their lipid solubility, pKa, and ability to bind to carrier proteins. Moreover, drugs can also be cleared from target organs/tissues at different rates. To investigate whether DOX, GUB, and SQ can penetrate and persist in the eye, we quantified the amounts of these drugs present in the C57BL/6J (WT) whole mouse eye globes within 2 h after drug injection and compared these levels to those in serum. Liquid chromatography-mass spectrometry (LC-MS)-based analyses and quantification revealed the presence of tested compounds at levels in the low picomolar range in eye tissue (Table 4 and FIG. 29). Given that the total volume of a mouse eye is about 0.1 mL, the amounts of examined compounds were comparable with levels found in 0.1 mL of serum samples for GUB and 5 times lower for both DOX and SQ. However, the retinal cell layer with an area of 15.6 mm$^2$ constitutes only a small fraction of the eye that likely absorbs most of these drugs entering from the blood. Thus, considering that prior to harvesting eyes, mice were intracardially perfused with PBS, the amounts of DOX, GUB and SQ confirmed their availability to eye tissue.

TABLE 4

Amount of selected drugs found in the mouse serum and enucleated eyes 30 min after administration of a single dose

| Name | Serum (pmol/100 μl) ± SD | Eye (pmol/eye) ± SD |
|---|---|---|
| DOX | 46.5 ± 12.8 | 11.0 ± 1.7 |
| GUB | 7.0 ± 1.8 | 13.1 ± 4.7 |
| SQ | 19.3 ± 5.5 | 5.6 ± 2.2 |

$^A$Doxazosin (DOX), guanabenz (GUB), and SQ 22536 (SQ) were detected and quantified in tissues of C57BL/J WT mice by LC-MS. All three drugs were found to penetrate and persist in the eye, with GUB reaching higher concentration in the eye than in the serum.

Pharmacological Intervention Targeting Gq- and Gi-Coupled GPCRs Prevents Formation of Large Fluorescent Deposits in the RPE.

The above results demonstrate a protective effect on photoreceptor morphology and function by pre-treatment with pharmacological compounds targeting Gq-, Gi-, Gs-coupled GPCRs. To investigate their impact on the RPE, we treated 4 to 5-week-old albino Abca4$^{-/-}$Rdh8$^{-/-}$ mice with GUF, GUB, DOX, PRA or TAM, 30 min before bright light exposure. Changes in RPE morphology were assessed on freshly enucleated mouse eyes by TPM performed 10 days after treatment. Mice exposed to bright light but not pre-treated with the above compounds accumulated large long-wavelength evoked fluorescent deposits in the RPE which otherwise appeared structurally unaffected. Representative TPM images comparing the RPE from mice treated with PRA, GUB and vehicle are shown in FIG. 30A. Spectra of these granules, shown in FIG. 30B, displayed broad maxima at 590 to 625 nm indicative of pyridinium bisretinoid, A2E and related retinoids. These data indicate that treatment with compounds targeting Gq- and Gi-coupled GPCRs can prevent the RPE from accumulating potentially toxic long-wavelength fluorescent deposits.

Our results indicate that GPCR pathways provide distinct activation and inhibitory actions that can control photoreceptor cell survival. Thus, activation of the Gq pathway, accomplished by the α1AR among others, can lead to photoreceptor cell death through the phospholipase C-mediated signaling pathway. Photoreceptor death can also result from aberrant functioning of Gs and Gi pathways that modulate the formation of cAMP. Gs, affected by the action of the 5-HT4, 6 and 7 receptors, activates this pathway whereas Gi, mediated by the α2AR, inhibits it. Therefore, the degenerative photoreceptor phenotypes in pathological states could be abrogated by pharmacological inhibition of either Gq or Gs pathways or activation of the Gi pathway.

It is also worth noting that rhodopsin could be a central player in light-induced retinal degeneration, and that reduced amounts of rhodopsin protect the retina from light-induced degeneration. Therefore we examined the potential impact of the AC inhibitor SQ on chromophore regeneration given that AC is the central player in our newly identified GPCR signaling implicated in light-induced retinopathy (FIG. 1). When the effect of SQ treatment on ERG responses and 11-cis-retinal levels after bleaching was evaluated, no significant changes were observed, indicating that the protection against retinal degeneration conferred by SQ treatment was unlikely due to inhibition of visual pigment regeneration. Therefore, the possibility of an acute effect of pharmacological compounds on phototransduction could be ruled out.

Together, experimental results described here and in the previous examples identify a series of intrinsically linked events, including the participation of GPCRs, PLC/IP3/Ca2+ signaling, and NADPH oxidase-mediated ROS production, which collectively are responsible for the pathogenesis of retinal dystrophy in Abca4$^{-/-}$Rdh8$^{-/-}$ mice, a model for rod/cone degeneration resembling features of human Stargardt disease. Our findings show that atRAL toxicity in bright light-induced retinal degeneration could be mediated through a signaling cascade implicating GPCRs, PLC/IP3/Ca2+ signaling, and NADPH oxidase. Here we report that, in addition to Gq signaling, inhibition of the cAMP pathway also has a protective effect against retinal degeneration. Our results demonstrate that GPCR pathways provide distinct activation and inhibitory actions that could control photoreceptor cell survival. Thus, activation of the Gq pathway, accomplished by the α1-AR among others, can lead to photoreceptor cell death through the phospholipase C-mediated signaling pathway. Photoreceptor death can also result from aberrant functioning of Gs and Gi pathways that modulate the formation of cAMP. Gs, affected by the action of the 5-HT4, 6 and 7 receptors, activates this pathway whereas Gi, mediated by the α2-AR, inhibits it.

As presented here, the degenerative photoreceptor phenotypes was reversed by pharmacological inhibition of either Gq or Gs pathways or activation of the Gi pathway (FIG. 1). These proof-of-concept studies demonstrate interactions between interconnected and diverse pathways involved in the pathogenesis of retinal degeneration induced by strong light.

Example 4

Figure 31:
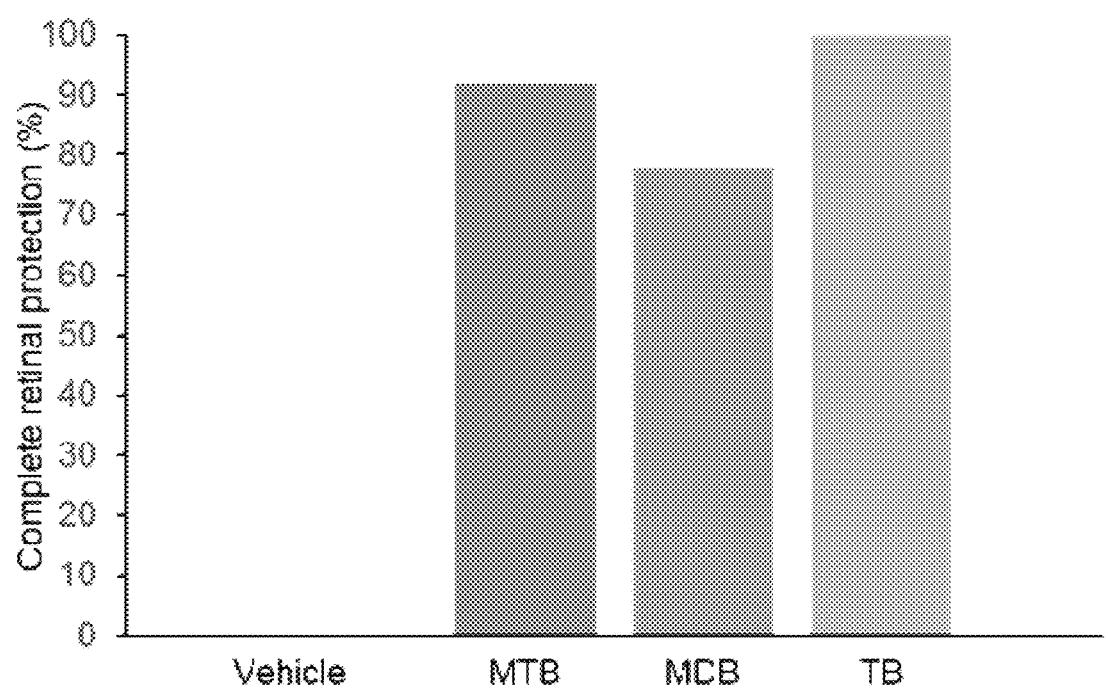
FIG. 31 illustrates combinatorial treatment protected against bright light-induced retinal degeneration in $Abca4^{-/-}Rdh8^{-/-}$ mice.

The expression of GPCRs in the mouse and human retinas was analyzed by RNA-sequencing. Based on the expression level and the presence in both mouse and human retinas, twenty GPCRs were selected for further evaluation of potential targeting in retinal degeneration. The selection of the ligands targeting these receptors were based on the mechanisms implying different contribution of Gi, Gs, and Gq protein-coupled receptors in light-induced retinal degeneration revealed by our previous studies. Briefly, increased functionality of Gs or Gq-coupled receptors and decreased activity of Gi-coupled receptors are mechanistically implicated in the pathogenesis of light-induced retinopathy. Thus antagonist at selected Gs-coupled receptor or Gq-coupled receptor or agonist at selected Gi-coupled receptor was administered to bright light-exposed Abca4$^{-/-}$Rdh8$^{-/-}$ mouse, a model manifesting remarkable susceptibility to light-induced retinal degeneration, and the effects on retinal protection was evaluated. Abca4$^{-/-}$ Rdh8$^{-/-}$ mice were exposed to bright light at the intensity of 10,000 Lux for 30 min and severe retinal degeneration characterized by nearly complete ablation of photoreceptors was revealed by morphological and functional assessment of retinas including optical coherence tomography (OCT), scanning laser ophthalmoscope, gross histology and electroretinogram (ERG), respectively. As summarized in Table 5, compared to that from the vehicle-treated mice which conferred no retinal protection, treatment of agonists targeting dopamine D2 receptor, dopamine D4 receptor, metabotropic glutamate receptor 4 showed complete morphological and functional retinal protection in bright light-exposed Abca4$^{-/-}$Rdh8$^{-/-}$ mice. Moreover, antagonists at Gs-coupled corticotropin releasing hormone receptor 1, dopamine receptor 1, β1 adrenergic receptor and β2 adrenergic receptor exhibited significant retinal protection in bright light-exposed Abca4$^{-/-}$Rdh8$^{-/-}$ mice as revealed by morphological and functional assays. Antagonists at Gq-coupled receptors also protected the retinas against bright light-induced degeneration in Abca4$^{-/-}$Rdh8$^{-/-}$ mice, which included metabotropic glutamate receptor 1, tachykinin receptor 1 and prostaglandin E receptor 1. Treatment of antagonists at adenosine A2b receptor, a receptor associated with both Gs and Gq-mediated signaling, also resulted in significant morphological and functional protection in bright light-exposed Abca4$^{-/-}$Rdh8$^{-/-}$ mice. Based on these results and that from our previous studies, four FDA-approved drugs exhibiting optimal treatment response in the mice were further examined for combinatorial treatment regimen, which include Metoprolol, Doxazosin, Tamsulosin and Bromocriptine. Each drug component of the combination was first examined to decide on the dose that was subtherapeutic (no protection or less than 20% complete protection) in bright light-exposed Abca4$^{-/-}$Rdh8$^{-/-}$ mice. Retinal protection from combined treatment was then evaluated with each drug component given at subtherapeutic dose. As shown in the FIG. 31, in distinct contrast to severe retinal degeneration observed in vehicle-treated, bright light-exposed Abca4$^{-/-}$Rdh8$^{-/-}$ mice, combined treatment of Metoprolol, Tamsulosin and Bromocriptine (MTB) led to complete retinal protection in 91.7% of mice. Moreover, Metoprolol, Doxazosin and Bromocriptine combination (MDB) resulted in complete retinal protection in 77.8% of mice exposed to bright light. Additionally, combined treatment of Bromocriptine and Tamsulosin (TB) given at subtherapeutic but higher doses than that adopted in MTB and MDB combinations, could provide significant retinal protection in bright light-exposed Abca4$^{-/-}$Rdh8$^{-/-}$ mice.

TABLE 5

GPCR modulating compounds effective at protecting against light-induced retinopathy in Abca4$^{-/-}$Rdh8$^{-/-}$ mice

| Agent | Major action(s) | G protein | Trade name(s) | Indication(s) |
|---|---|---|---|---|
| SCH 23390 hydrochloride | Dopamine receptor D1 and 5 antagonist | Gs | | |
| Rotigotine hydrochloride | Dopamine receptor D2 and 3 agonist | Gi | Neupro | Parkinson's disease, restless legs syndrome |
| 2-Bromo-α-ergocryptine methanesulfonate salt | Dopamine receptor D2 and 3 agonist | Gi | Parlodel | hyperprolactinemia, hypogonadism, acromegaly, Parkinson's disease; type 2 diabetes |
| Sumanirole maleate* | Dopamine receptor D2 agonist | Gi | | |
| B-HT 920 | Dopamine receptor D2, α2 adrenergic receptor agonist | Gi | Talipexole | |
| Ro 10-5824 dihydrochloride | Dopamine receptor D4 agonist | Gi | | |
| YM 202074 | mGluR1 receptor antagonist | Gq | | |
| Cinnabarinic acid | mGluR4 receptor agonist | Gi | | |
| Metoprolol tartrate | ADRB1 antagonist | Gs | Lopressor | angina, hypertension, heart attack |
| ICI 118,551 hydrochloride | ADRB2 antagonist | Gs | | |
| GS 6201 | Adenosine $A_{2B}$ receptor antagonist | Gs | | |
| PSB 1115 | Adenosine $A_{2B}$ receptor antagonist | Gs | | |
| SC 19220 | EP1 prostanoid receptor antagonist | Gq | | |
| CP 154526 | CRF1 antagonist | Gs | | |
| L-733060 | Tachykinin NK1 receptor antagonist | Gq | | |

TABLE 5-continued

GPCR modulating compounds effective at protecting against light-induced retinopathy in Abca4$^{-/-}$Rdh8$^{-/-}$ mice

| Agent | Major action(s) | G protein | Trade name(s) | Indication(s) |
|---|---|---|---|---|
| CP 96345 | Tachykinin NK1 receptor antagonist | Gq | | |

TABLE 6

Targeting GPCRs using FDA-approved drugs to protect against light-induced retinopathy

| GPCR(s) | Ligand | G protein signaling | Drug(s) | Indication(s) |
|---|---|---|---|---|
| Dopamine receptor D2 and 3 | agonist | Gi | Parlodel; Cycloset | hyperprolactinemia, hypogonadism, acromegaly, Parkinson's disease; type 2 diabetes |
| 5-HT2R | antagonist | Gq | Serzone | depression |
| ADRA1 | antagonist | Gq | Cardura | hypertension, benign prostatic hyperplasia |
| ADRA1 | antagonist | Gq | Minipress | hypertension |
| ADRA1 | antagonist | Gq | Flomax | benign prostatic hyperplasia |
| ADRA2 | agonist | Gi | Wytensin | hypertension |
| ADRA2 | agonist | Gi | Intuniv, Tenex | attention deficit hyperactivity disorder, hypertension |
| ADRB1 | antagonist | Gs | Lopressor | angina, hypertension, heart attack |

TABLE 7

Targeting G protein signaling using FDA-approved drugs to protect against light-induced retinopathy

| G protein signaling | GPCR(s) | Ligand | Drug(s) | Indication(s) |
|---|---|---|---|---|
| Gi | Dopamine receptor D2 and 3 | agonist | Parlodel; Cycloset | hyperprolactinemia, hypogonadism, acromegaly, Parkinson's disease; type 2 diabetes |
| Gq | 5-HT2R | antagonist | Serzone | depression |
| Gq | ADRA1 | antagonist | Cardura | hypertension, benign prostatic hyperplasia |
| Gq | ADRA1 | antagonist | Minipress | hypertension |
| Gq | ADRA1 | antagonist | Flomax | benign prostatic hyperplasia |
| Gi | ADRA2 | agonist | Wytensin | hypertension |
| Gi | ADRA2 | agonist | Intuniv, Tenex | attention deficit hyperactivity disorder, hypertension |
| Gs | ADRB1 | antagonist | Lopressor | angina, hypertension, heart attack |

TABLE 8

GPCR modulating compounds effective at protecting against light-induced retinopathy

| Agent | Major action(s) | G protein | Trade name(s) | Indication(s) |
|---|---|---|---|---|
| SCH 23390 hydrochloride | Dopamine receptor D1 and 5 antagonist | Gs | | |
| Rotigotine hydrochloride | Dopamine receptor D2 and 3 agonist | Gi | Neupro | Parkinson's disease, restless legs syndrome |
| 2-Bromo-α-ergocryptine methanesulfonate salt | Dopamine receptor D2 and 3 agonist | Gi | Parlodel; Cycloset | hyperprolactinemia, hypogonadism, acromegaly, Parkinson's disease; type 2 diabetes |
| Sumanirole maleate* | Dopamine receptor D2 agonist | Gi | | |
| B-HT 920 | Dopamine receptor D2, α2 adrenergic receptor agonist | Gi | | |
| Ro 10-5824 dihydrochloride | Dopamine receptor D4 agonist | Gi | | |
| YM 202074 | mGluR1 receptor antagonist | Gq | | |
| Cinnabarinic acid | mGluR4 receptor agonist | Gi | | |
| Metoprolol tartrate | ADRB1 antagonist | Gs | Lopressor | angina, hypertension, heart attack |
| ICI 118,551 hydrochloride | ADRB2 antagonist | Gs | | |

TABLE 8-continued

GPCR modulating compounds effective at protecting against light-induced retinopathy

| Agent | Major action(s) | G protein | Trade name(s) | Indication(s) |
|---|---|---|---|---|
| GS 6201 | Adenosine $A_{2B}$ receptor antagonist | Gs | | |
| PSB 1115 | Adenosine $A_{2B}$ receptor antagonist | Gs | | |
| SC 19220 | EP1 prostanoid receptor antagonist | Gq | | |
| CP 154526 | CRF1 anatgonist | Gs | | |
| Ketanserin | 5HT2A receptor antagonist | Gq | Sufrexal[1] | hypertension |
| Ritanserin | 5HT2 receptor antagonist | Gq | | |
| Nefazodone | 5HT2A receptor antagonist | Gq | Serzone | depression |
| Pizotifen | 5HT2 receptor antagonist | Gq | Sandomigran[2] | migraine |
| RS 23579-190 | 5HT4 receptor antagonist | Gs | | |
| Ro 04-6790 | 5HT6 receptor antagonist | Gs | | |
| SGS 518 oxalate | 5HT6 receptor antagonist | Gs | | |
| SB 269970 | 5HT7 receptor antagonist | Gs | | |
| LY 215840 | 5HT2 and 7 receptor antagonist | Gq/Gs | | |
| Doxazosin | ADRA1 antagonist | Gq | Cardura | hypertension, benign prostatic hyperplasia |
| Prazosin | ADRA1 antagonist | Gq | Minipress | hypertension |
| Tamsulosin | ADRA1 antagonist | Gq | Flomax | Benign prostatic hyperplasia |
| Guanabenz | ADRA2 agonist | Gi | Wytensin | hypertension |
| Guanfacine | ADRA2 agonist | Gi | Tenex, Intuniv | hypertension; ADHD |
| Lofexidine | ADRA2 agonist | Gi | Britlofex[3] | Hypertension; opioid withdrawal symptom |
| 4-DAMP | M3 cholinergic receptor | Gq | | |

TABLE 9

Available drugs targeting the GPCRs that are implicated in light-induced retinopathy

| GPCR | G protein | Ligand | Drug(s) |
|---|---|---|---|
| Dopamine receptor D1 and 5 | Gs | Antagonist | |
| Dopamine receptor D2 | Gi | Agonist | Bromocriptine, Cabergoline, Rotigotine |
| Dopamine receptor D4 | Gi | Agonist | Apomorphine |
| mGluR1 receptor | Gq | Antagonist | |
| mGluR4 receptor | Gi | Agonist | |
| ADRB1 | Gs | Antagonist | Metoprolol, Atenolol, Acebutolol, Bisoprolol, Esmolol, Betaxolol, Celiprolol, Nebivolol |
| ADRB2 | Gs | Antagonist | |
| ADRA1 | Gq | Antagonist | Prazosin, Doxazosin, Tamsulosin, Terozosin, Alfuzosin, Silodosin, Trimazosin |
| ADRA2 | Gi | Agonist | Clonidine, Brimonidine, Guanfacine, Guanabenz, Methydopa, Tizanidine |
| Adenosine $A_{2B}$ receptor | Gs | Antagonist | |
| EP1 prostanoid receptor | Gq | Antagonist | |
| CRF1 | Gs | Antagonist | |
| 5HT2 receptor | Gq | Antagonist | Ketanserin[2], Clozapine, Cyproheptadine, Nefazodone |
| 5HT4 receptor | Gs | Antagonist | |

TABLE 9-continued

Available drugs targeting the GPCRs that are implicated in light-induced retinopathy

| GPCR | G protein | Ligand | Drug(s) |
|---|---|---|---|
| 5HT6 receptor | Gs | Antagonist | |
| 5HT7 receptor | Gs | Antagonist | |
| M3 cholinergic receptor | Gq | Antagonist | Darifenacin, Solifenasin |

TABLE 10

Further drug search for targeting GPCRs in light-induced retinopathy

| GPCR | G protein | Ligand | Effective research compound(s) |
|---|---|---|---|
| Dopamine receptor D1 | Gs | antagonist | SCH 23390 hydrochloride |
| Dopamine receptor D4 | Gi | agonist | Ro 10-5824 dihydrochloride |
| mGluR1 receptor | Gq | antagonist | YM 202074 |
| mGluR4 receptor | Gi | agonist | Cinnabarinic acid |
| ADRB2 | Gs | antagonist | ICI 118,551 hydrochloride |
| Adenosine $A_{2B}$ receptor | Gs | antagonist | GS 6201, PSB 1115 |
| EP1 prostanoid receptor | Gq | antagonist | SC 19220 |
| CRF1 | Gs | antagonist | CP 154526 |
| 5HT4 receptor | Gs | antagonist | RS 23579-190 |
| 5HT6 receptor | Gs | antagonist | Ro 04-6790, SGS 518 oxalate |
| 5HT7 receptor | Gs | antagonist | SB 269970 |

TABLE 11

The expression of GPCRs in the eye, retina and RPE revealed by RNA-seq

| Gene | Annotation | Mouse Eye | Mouse Retina | $Rho^{-/-}$ | Cultured RPE | Human Retina | Agonist | Antagonist |
|---|---|---|---|---|---|---|---|---|
| Rho | Rhodopsin | 6162.04 | 11630.18 | 39.26 | 0.31 | 6896.09 | | |
| Tulp1 | Tubby like protein 1(TUBL1), RP14, LCA15 | 261.30 | 605.59 | 84.05 | 0.04 | 463.97 | | |
| Opn1mw | opsin 1 (cone pigment), | 62.97 | 95.77 | 63.07 | 0.01 | 172.56 | | |
| Drd4 (Gi) | dopamine receptor D4 | 93.84 | 241.78 | 39.61 | 0.03 | 139.49 | A 412997 dihydrochloride, Ro 10-5824 dihydrochloride | |
| Rgr | retinal G protein coupled receptor | 355.74 | 97.66 | 231.52 | 4.52 | 123.98 | | |
| Gpr37 | | 28.47 | 41.28 | 44.37 | 0.03 | 66.65 | | |
| Tub | Tubby bipartite transcription factor | 36.49 | 92.32 | 13.72 | 0.11 | 51.72 | | |
| Gpr162 | | 29.37 | 73.32 | 60.92 | 1.03 | 46.29 | | |
| Rrh | RPE-derived rhodopsin homolog, peropsin | 19.29 | 9.23 | 16.13 | 1.85 | 40.34 | | |
| Gabbr1 (Gi) | GABAB receptor | 19.78 | 40.24 | 21.90 | 9.08 | 35.38 | Acamprosate calcium, (R)-Baclofen, SKF 97541, Rac BHFF (postive modeulator) | |
| Gpr160 | | 4.04 | 0.00 | 2.08 | 0.10 | 34.50 | | |
| Lphn1 | Latrophilin 1 | 15.98 | 29.73 | 23.23 | 9.55 | 31.85 | | |
| Opn1sw | opsin 1 (cone pigment), short wave sensitive, blue cone photo- | 125.13 | 198.54 | 72.95 | 0.07 | 31.69 | | |

TABLE 11-continued

The expression of GPCRs in the eye, retina and RPE revealed by RNA-seq

| Gene | Annotation | Mouse Eye | Mouse Retina | Rho$^{-/-}$ | Cultured RPE | Human Retina | Agonist | Antagonist |
|---|---|---|---|---|---|---|---|---|
| Grm6 (Gi) | receptor pigment metabotropic glutamate receptor 6 | 6.17 | 0.00 | 37.81 | 0.00 | 28.74 | | |
| Drd2 (Gi) | dopamine receptor D2 | 10.82 | 23.10 | 16.95 | 0.05 | 26.33 | B HT-920, Rotigotine hydrochloride, Sumanirole maleate | |
| Rorb | RAR related ophan receptor B | 21.69 | 23.52 | 2.56 | 0.18 | 24.31 | | |
| Gprc5b | G Protein-Coupled Receptor, Class C, Group 5, Member B | 29.82 | 12.95 | 21.76 | 26.62 | 22.85 | | |
| Ppard | peroxisome proliferator-activated receptor delta | 13.68 | 19.37 | 13.97 | 11.99 | 21.61 | | |
| Darc | Duffy Blood Group, Atypical Chemokine Receptor 1 | 28.91 | 64.45 | 43.65 | 0.04 | 19.95 | | |
| Gpr124 | | 9.56 | 8.94 | 18.11 | 7.27 | 19.82 | | |
| Lgr4 | leucine-rich repeat containing G protein-coupled receptor 4 | 11.09 | 9.50 | 9.15 | 12.33 | 18.07 | | |
| Tm2d1 | TM2 Domain Containing 1, Beta-Amyloid-Binding Protein 2 | 15.56 | 10.31 | 5.99 | 22.28 | 17.63 | | |
| Gpr153 | | 20.42 | 37.18 | 39.11 | 12.35 | 15.31 | | |
| Fzd8 | | 3.56 | 3.26 | 6.62 | 5.23 | 15.06 | | |
| Bai2 | brain angiogenesis inhibitor 2 | 6.81 | 15.34 | 5.30 | 0.29 | 14.64 | | |
| Adora1 (Gi) | adenosine receptor a1 | 16.20 | 18.26 | 9.08 | 4.78 | 13.55 | (±)-5'-Chloro-5'-deoxy-ENBA | |
| Crhr1 (Gs) | Corticotropin Releasing Hormone Receptor 1, CRF1 | 3.02 | 6.49 | 5.31 | 0.34 | 12.76 | | Antalarmin hydrochloride, CP 154526, NBI 35965 hydrochloride |
| S1pr1 (Gi) | Sphingosine-1-Phosphate Receptor 1 | 10.66 | 11.21 | 13.67 | 5.99 | 11.78 | SEW 2871 | |
| Bai1 | brain agngiogenesis inhibitor 1 | 10.08 | 27.10 | 19.84 | 0.02 | 10.82 | | |
| Celsr2 | Cadherin, EGF LAG Seven-Pass G-Type Receptor 21 | 6.53 | 7.26 | 3.80 | 4.39 | 10.80 | | |
| Vipr2 | Vasoactive Intestinal Peptide Receptor 2 | 8.79 | 14.33 | 10.01 | 3.73 | 10.69 | | |
| Gabbr2 | GABAB rece 2 | 7.80 | 17.03 | 12.88 | 0.02 | 10.57 | | |

TABLE 11-continued

The expression of GPCRs in the eye, retina and RPE revealed by RNA-seq

| Gene | Annotation | Mouse Eye | Mouse Retina | Rho$^{-/-}$ | Cultured RPE | Human Retina | Agonist | Antagonist |
|---|---|---|---|---|---|---|---|---|
| Celsr3 | Cadherin, EGF LAG Seven-Pass G-Type Receptor 3 | 5.82 | 20.00 | 3.97 | 0.25 | 9.87 | | |
| Lphn2 | Latrophilin 2 | 7.66 | 9.02 | 9.64 | 1.92 | 8.79 | | |
| Gpr27 | | 2.92 | 3.88 | 6.98 | 0.01 | 8.45 | | |
| Drd1a (Gs) | dopamine receptor D1a | 6.15 | 9.49 | 5.89 | 0.00 | 8.45 | | SCH 23390 hydrochloride |
| Agtrap | angiotensin II receptor associated protein | 13.64 | 17.21 | 13.37 | 12.46 | 8.18 | | |
| Gpr3711 | | 2.39 | 0.96 | 5.26 | 0.01 | 7.73 | | |
| Fzd5 | | 8.69 | 10.01 | 6.17 | 11.39 | 7.73 | | |
| Crcp | Calcitonin Gene-Related Peptide-Receptor Component Protein 1 | 21.88 | 19.55 | 22.41 | 14.84 | 7.49 | | |
| Fzd1 | | 11.99 | 3.29 | 21.52 | 13.32 | 7.35 | | |
| Gpr146 | | 8.91 | 7.49 | 8.44 | 7.06 | 6.17 | | |
| Smo (Gi) | Smoothed | 10.75 | 6.35 | 18.14 | 15.85 | 5.91 | Purmorph-amine | |
| Ednrb (Gq) | endothelin receptor type B | 22.27 | 1.94 | 8.43 | 5.02 | 5.77 | | BQ 788 sodium salt |
| Ramp1 | | 4.68 | 1.39 | 7.28 | 0.38 | 5.25 | | |
| Igf2r | | 3.64 | 3.51 | 4.11 | 68.57 | 5.02 | | |
| Grm1 (Gq) | | 2.27 | 3.52 | 0.97 | 0.00 | 4.97 | | bay36-7620, 3-MATIDA, YM 202074, MPEP (antagonizes at GRM5) |
| Crhr2 | Corticotropin Releasing Hormone Receptor 2, CRF2 | 2.24 | 1.12 | 3.72 | 0.92 | 4.34 | | |
| Gpr176 | | 2.21 | 3.43 | 2.86 | 15.55 | 4.23 | | |
| Adrb1 (Gs) | | 8.43 | 20.18 | 12.26 | 0.08 | 3.84 | | Metoprolol-tartrate, |
| Adora2b (Gs) | adenosine receptor a2b | 6.09 | 2.53 | 9.02 | 6.24 | 3.83 | | GS 6201, MRS 1754, PSB 1115 |
| Hrh3 (Gi) | histamine receptor H3 | 7.11 | 19.12 | 17.53 | 0.01 | 3.75 | (R)-(-)-α-Methyl-histamine dihydro-bromide, Methimepipdi-hydro-bromide | |
| Gpr98 | | 3.79 | 7.30 | 1.10 | 0.52 | 3.64 | | |
| Gpr158 | | 3.72 | 5.07 | 4.12 | 0.00 | 3.58 | | |
| S1pr3 | | 8.42 | 6.95 | 17.44 | 1.30 | 3.56 | | |
| Fzd2 | | 3.89 | 0.79 | 7.18 | 4.71 | 3.24 | | |
| Gprc5c | G Protein-Coupled Receptor, Family C, Group 5, Member C | 5.26 | 2.13 | 4.48 | 1.71 | 3.13 | | |
| Grm4 (Gi) | | 2.86 | 4.93 | 6.27 | 0.35 | 3.10 | Cinnabarinic acid, VU 0155041 sodium salt | |
| Gpr152 | | 18.55 | 40.46 | 4.75 | 0.06 | 3.05 | | |
| Lnpep | Leucyl/Cystinyl Amino-peptidase | 5.08 | 6.16 | 3.88 | 11.46 | 3.05 | | |

TABLE 11-continued

The expression of GPCRs in the eye, retina and RPE revealed by RNA-seq

| Gene | Annotation | Mouse Eye | Mouse Retina | Rho$^{-/-}$ | Cultured RPE | Human Retina | Agonist | Antagonist |
|---|---|---|---|---|---|---|---|---|
| Gpr56 | | 5.12 | 4.31 | 4.42 | 0.69 | 2.92 | | |
| Lphn3 | latrophilin 3 | 4.22 | 6.49 | 5.37 | 3.74 | 2.90 | | |
| Fzd6 | | 11.34 | 1.85 | 4.67 | 43.38 | 2.76 | | |
| Gpr85 | | 4.56 | 5.72 | 4.29 | 0.44 | 2.70 | | |
| Opn3 | opsin 3 | 2.55 | 1.38 | 2.09 | 1.85 | 2.62 | | |
| | F2rl1 | 3.13 | 0.24 | 4.32 | 14.18 | 2.58 | | |
| Fzd7 | | 6.34 | 1.88 | 10.35 | 37.17 | 2.51 | | |
| Adra2c (Gi) | | 8.96 | 7.17 | 19.28 | 0.03 | 2.38 | | |
| Cxcr7 | | 14.30 | 3.58 | 15.89 | 16.73 | 2.37 | | |
| Tacr3 (Gq) | tachykinin receptor 3 | 4.95 | 4.63 | 5.27 | 0.00 | 2.36 | | |
| P2ry2 | | 7.20 | 0.62 | 14.65 | 3.00 | 2.29 | | |
| Grm8 (Gi) | | 4.77 | 6.43 | 2.87 | 0.13 | 2.04 | (RS)-PPG | |
| Gpr135 | | 3.07 | 8.35 | 4.70 | 0.20 | 1.99 | | |
| Bai3 | | 3.92 | 6.01 | 3.21 | 0.01 | 1.91 | | |
| Mrgpre | MAS-related GPR, member E | 2.96 | 2.80 | 5.44 | 2.43 | 1.74 | | |
| Cd97 | | 12.93 | 1.77 | 2.52 | 39.37 | 1.55 | | |
| Grm7 (Gi) | | 2.39 | 3.95 | 3.04 | 0.10 | 1.16 | AMN 082 dihydro-chloride | |
| Opn4 | opsin 4 | 3.35 | 2.94 | 2.53 | 0.24 | 1.11 | | |
| Gpr19 | | 12.21 | 8.45 | 1.24 | 1.47 | 1.11 | | |
| Adrb2 (Gs) | | 7.13 | 1.03 | 12.54 | 0.50 | 0.98 | | ICI 118,551 hydrochloride |
| Tacr1 (Gq) | tachykinin receptor 1, neurokinin 1 receptor (NK1R), substance P receptor (SPR) | 3.72 | 2.06 | 5.08 | 0.32 | 0.95 | | CP 96345, L-733,060 |
| Ptger1 (Gq) | Prostaglandin E Receptor 1 (Subtype EP1) | 9.59 | 14.88 | 16.95 | 9.61 | 0.94 | | SC 51322, SC 51089, SC19220 |
| Oprl1 | Opiate Receptor-Like 1 | 3.15 | 4.42 | 3.73 | 0.06 | 0.81 | | |
| Gpr143 | | 6.80 | 1.25 | 8.05 | 1.28 | 0.80 | | |
| Mrgprf | MAS-related GPR, member F | 3.18 | 0.64 | 5.93 | 0.46 | 0.80 | | |
| S1pr2 (Gs, Gq) | sphingosine-1-phosphate receptor 2 | 3.20 | 1.13 | 5.47 | 5.11 | 0.63 | | JTE 013 |

Example 5

In this example, we show that combination therapy derived from a systems pharmacology approach could achieve a protective effect against retinal degeneration without significant adverse consequences. The results demonstrate that exposure to bright light caused a complex cellular impairment in the mouse retina, disrupting neighboring bipolar and horizontal cells as well as inducing photoreceptor cell degeneration. Combination therapeutic regimens consisting of FDA-approved drugs targeting different GPCRs but used for other primary indications protected these retinas against light-induced loss of photoreceptor cells. Bipolar and horizontal cells also were protected, even when the individual drugs were given at their own subtherapeutic doses. Finally, transcriptome analysis provided molecular evidence supporting the protective effects of these combination therapies.

Methods

Animals

Male and female Abca4$^{-/-}$Rdh8$^{-/-}$ and BALB/cJ mice (The Jackson Laboratory) at 4 to 6 weeks of age were used for the current study. Mice were genotyped by well-established methods. Only Rd8 mutation-free mice with the Leu variation at amino acid 450 of RPE65 were used. Abca4$^{-/-}$Rdh8$^{-/-}$ mice were maintained with either pigmented 129Sv/Ev or C57BL/6 mixed backgrounds, and their siblings were used for most experiments. Either pigmented C57BL/6J or albino C57BL/6J (C57BL/6J-Tyrc-2J/J) mice from The Jackson Laboratory and their littermates were used as wild-type controls. BALB/c mice were obtained from The Jackson Laboratory. All mice were housed and maintained in a 12-hour light (≤10 lux)/12-hour dark cyclic environment in the Animal Resource Center at the School of Medicine, Case Western Reserve University (CWRU). Bright light-induced retinal damage was generated by exposing Abca4$^{-/-}$Rdh8$^{-/-}$ mice or dark-adapted BALB/c mice to white light delivered at 10,000 lux (150-W spiral lamp, Commercial Electric) for 30 min. Abca4$^{-/-}$Rdh8$^{-/-}$ mouse pupils were dilated with 1% tropicamide before light exposure, whereas tropicamide was not needed for BALB/c mice. All animal handling procedures and experimental protocols were approved by the Institutional Animal Care and Use Committee at CWRU and conformed to recommendations of both the American Veterinary Medical Association (AVMA) Panel on Euthanasia and the Association for Research in Vision and Ophthalmology.

Chemicals

2-Bromo-α-ergocryptine methanesulfonate salt (BRM) was purchased from Sigma-Aldrich. Aprepitant was obtained from Selleck. All the other compounds tested were purchased from Tocris Biosciences, including SCH 23390 hydrochloride, rotigotine hydrochloride, sumanirole maleate, B-HT 920, Ro 10-5824 dihydrochloride, YM 202074, cinnabarinic acid, MTP, ICI 118,551 hydrochloride, GS 6201, PSB 1115, SC 19220, CP 154526, L-733060, CP 96345, TAM, DOX, A 412997 dihydrochloride, AMN 082 dihydrochloride, SKF 97541, Rac BHFF, SEW 2871, purmorphamine, (R)-(−)-α-methylhistamine dihydrobromide, methimepip dihydrobromide, VU 0155041 sodium salt, antalarmin hydrochloride, NBI 35965 hydrochloride, BQ 788 sodium salt, BAY36-7620, 3-MATIDA, MPEP hydrochloride, MRS 1754, SC 51322, SC 19220, and JTE 013.

Complementary DNA Constructs for GPCR Signaling Assays

Dopamine D1, dopamine D4, and α1A-adrenergic receptors were purchased from cDNA Resource Center (Bloomsburg University, Bloomsburg, Pa.). Plasmid encoding the Flag-tagged, long isoform of the D2 dopamine receptor was a gift from A. Kovoor (University of Rhode Island). pCMV5 plasmids encoding GαoA were gifts from H. Itoh (Nara Institute of Science and Technology, Japan). Plasmids encoding Venus 156-239-Gβ1 and Venus 1-155-Gγ2 were gifts from N. Lambert (Georgia Regents University). Plasmids encoding RGS9-2, Gβ5S, R7BP, and masGRK3ct-Nluc were previously described.

BRET Assay for G Protein Activation in Live Cells

BRET experiments were performed as previously reported with slight modifications. Briefly, 293T/17 cells were grown in Dulbecco's modified Eagle's medium supplemented with 10% fetal bovine serum, minimum Eagle's medium nonessential amino acids, 1 mM sodium pyruvate, and antibiotics [penicillin (100 U/ml) and streptomycin (100 μg/ml)] at 37° C. in a humidified incubator containing 5% $CO^2$. Cells were transfected with Lipofectamine LTX transfection reagents. BRET measurements were performed using a microplate reader (POLARstar Omega, BMG Labtech) equipped with two emission photomultiplier tubes. All measurements were performed at room temperature. The BRET signal is determined by calculating the ratio of the light emitted by Gβ1γ2-Venus (535 nm) over the light emitted by masGRK3ct-Nluc (475 nm). The average baseline value recorded before agonist stimulation was subtracted from BRET signal values, and the resulting difference (ΔBRET ratio) was obtained.

Mouse Treatments

All indicated treatments were administered by intraperitoneal injection 30 min before bright light exposure. Compounds and their tested doses were as follows: SCH 23390 hydrochloride, 5 and 10 mg/kg bw; rotigotine hydrochloride, 5 mg/kg bw; BRM, 0.1, 0.25, 1, 2.5, and 10 mg/kg bw; sumanirole maleate, 10 mg/kg bw; B-HT 920, 10 mg/kg bw; Ro 10-5824 dihydrochloride, 50 mg/kg bw; YM 202074, 20 mg/kg bw; cinnabarinic acid, 10 mg/kg bw; MTP, 1, 2.5, and 10 mg/kg bw; ICI 118,551 hydrochloride, 10 mg/kg bw; GS 6201, 50 mg/kg bw; PSB 1115, 50 mg/kg bw; SC 19220, 10 mg/kg bw; CP 154526, 10 mg/kg bw; L-733060, 10 mg/kg bw; CP 96345, 25 mg/kg bw; TAM, 0.05, 0.5, and 2.5 mg/kg bw; DOX, 1, 2.5, and 10 mg/kg bw; A 412997 dihydrochloride, 10 mg/kg bw; AMN 082 dihydrochloride, 12.5 mg/kg bw; SKF 97541, 5 and 10 mg/kg bw; SEW 2871, 10 and 50 mg/kg bw; purmorphamine, 20 mg/kg bw; (R)-(−)-t-methylhistamine dihydrobromide, 10 mg/kg bw; methimepip dihydrobromide, 50 mg/kg bw; VU 0155041 sodium salt, 10 mg/kg bw; antalarmin hydrochloride, 10 mg/kg bw; NBI 35965 hydrochloride, 20 mg/kg bw; BQ 788 sodium salt, 1 mg/kg bw; BAY36-7620, 10 and 25 mg/kg bw; 3-MATIDA, 10 mg/kg bw; MPEP hydrochloride, 20 mg/kg bw; MRS 1754, 50 mg/kg bw; SC 51089, 20 mg/kg bw; and JTE 013, 5 mg/kg bw. All compounds were dissolved in DMSO and delivered in a total volume of 50 μl per injection.

Spectral Domain OCT

Ultrahigh-resolution spectral domain OCT (Bioptigen) was performed for in vivo imaging of mouse retinas as previously described. Briefly, mice were injected with an anesthetic cocktail consisting of ketamine (6 mg/ml) and xylazine (0.44 mg/ml) at a dose of 10 μl/g bw, and pupils were dilated with 1% tropicamide before spectral domain OCT imaging. Five frames of OCT images were acquired in the B-mode and then averaged. For quantitative measurements addressing early changes in the illuminated retinas and assessing the retinal protection of tested compounds, thicknesses of the ONL or those of the outer segment and inner segment layers were measured 0.45 mm away from the ONH in the temporal retina, where the most severe damage was found in bright light-exposed Abca4$^{-/-}$Rdh8$^{-/-}$ mice.

Complete protection was defined by those retinas with intact structures similar to those of mice without exposure to bright light and with ONL thicknesses of ≥50 μm at the measured sites. No protection was defined by retinas exhibiting morphology similar to that of light-exposed and vehicle-treated mice, but with an ONL thickness of ≤20 μm at the measured sites. Partial protection defined retinas manifesting a reduction in the thickness of the ONL between 20 and 50 μm measured at these sites. For OCT measurements performed in BALB/cJ mice, the thickness of the ONL was measured at 0.15, 0.25, 0.35, and 0.45 mm away from the ONH in both the superior and the inferior retina.

SLO Imaging

SLO (Heidelberg Engineering) was carried out for whole fundus imaging of mouse retinas in vivo. Mice were anesthetized, and their pupils were dilated as described above. SLO images were then acquired in the autofluorescence mode.

Histology

For examination of gross retinal histology, mouse eyes were enucleated and then fixed in 4% paraformaldehyde and 0.5% glutaraldehyde before paraffin sectioning. Paraffin sections (5 μm thick) were stained by H&E. Eye cups were fixed in 2% glutaraldehyde and 4% paraformaldehyde and then processed for Epon embedding. Sections (1 μm thick) were stained with toluidine blue for histological examination. Light microscopy (Leica) was performed to observe the H&E- or toluidine blue-stained sections. Electron microscopic examination was used for some Epon-embedded sections as previously described.

Immunohistochemistry

Eye cups were fixed in 4% paraformaldehyde and processed for cryosectioning. Sections (12 μm thick) were then used for immunohistochemical processing. Primary antibodies used for immunohistochemistry included rabbit anti-synaptophysin antibody (Abcam), rabbit anti-calbindin D antibody (Abcam), mouse anti-PKCα antibody (Abcam), rabbit anti-GFAP antibody (Dako), and fluorescein isothiocyanate-conjugated anti-PNA antibody (Sigma).

Secondary antibodies included Alexa Fluor 488-conjugated goat anti-rabbit immunoglobulin G (IgG) or Alexa Fluor 488-conjugated goat anti-mouse IgG.

Electroretinograms

ERGs were obtained as previously described. Briefly, dark-adapted mice were anesthetized, and their pupils were dilated as described in previous sections. Contact lens electrodes, a reference electrode, and a ground electrode were positioned on both corneas, ear, and tail, respectively. ERGs were then recorded with a UTAS-E 3000 (LKC Technologies Inc.).

TPM Imaging

TPM imaging was performed as previously published. Briefly, a Leica TCS SP5 confocal MP system equipped with a tunable Vision-S laser (Coherent) delivering 75-fs pulses at an 80-MHz pulse repetition frequency was used for TPM imaging. Before eye enucleation, mice were anesthetized by intraperitoneal injection of an anesthetic mixture containing ketamine (6 mg/ml) and xylazine (0.44 mg/ml) at a dose of 10 μl/g bw and then euthanized in compliance with the *AVMA Guidelines for the Euthanasia of Animals* and approval by the CWRU Institutional Animal Care and Use Committee. Images of the retina and RPE in the enucleated, intact mouse eyes were obtained with a 20× magnification, 1.0 numerical aperture water immersion objective. Laser light power at the sample was maintained at 5 to 10 mW. TPM 3D reconstructions of raw retinal images were analyzed offline with a Leica LAS AF 3.0.0.

Strand-Specific RNA-Seq

Transcriptome analyses of the human retina were carried out as previously described. Total RNA from mouse retinas was isolated with TRIzol (Invitrogen) following the manufacturer's protocol. The quality of isolated RNA was assessed with a Bioanalyzer RNA 6000 Nano assay (Agilent Technologies). Strand-specific mRNA sequencing libraries were constructed from 100 ng of total RNA with the TruSeq Stranded mRNA Library Prep Kit (Illumina), and 125-base paired-end sequence reads were generated on the HiSeq 2500 platform (Illumina). Base calls were generated with RTAv1.18.64 software, and sequencing reads passing Illumina's chastity filter were used for further analysis. Illumina adapter trimming was performed with Trimmomatic v0.33. Quality control of trimmed Fastq files was achieved with FastQC v0.11.2 software (www.bioinformatics.babraham.ac.uk/projects/fastqc/). Transcript quantitation was accomplished with eXpress v1.5.1 streaming pass filter reads aligned to Ensembl v78 transcriptome annotation using Bowtie2 v2.2.6 as previously described. BAM files were generated by aligning to the GRCm38.p3/Ensembl v78 assembly and annotation with TopHat2 v2.1.0 as previously noted. This study also used the high-performance computational capabilities of the Biowulf Linux cluster at the National Institutes of Health (http://hpc.nih.gov).

RNA-Seq Differential Gene Expression Analysis

Single and combined pretreatment differential expression studies were performed separately. Initially, analyses involved filtering out low- and/or non-expressing transcripts and retaining transcripts expressing ≥1.0 FPKM (from eXpress output) in all replicates of any group.

Effective counts from the eXpress output of transcripts that passed FPKM filtering were TMM (trimmed mean of M values)-normalized with edgeR v3.10.2. Differential expression analyses comparing all drug treatments for light damage were performed with limma v3.24.15. Briefly, a generalized linear model was set up with untreated light damage as a reference, dispersion estimation was performed with the voom function, and appropriate contrast statistics were used with the eBayes function. Transcripts featuring greater than a twofold change and a false discovery rate (FDR) of less than 0.05 in any comparison were considered to be differentially expressed and thus were used for further analysis.

Secondary Analyses

All secondary analyses were performed in the R statistical environment (www.r-project.org). PCAs were accomplished with normalized log 2 FPKM values and visualized with the pca3d v0.8 package. Pearson's correlation analyses were performed with normalized log 2 FPKM values of differentially expressed transcripts. Expression clustering of differentially expressed transcripts was done with affinity propagation that used the "corSimMat" function in apcluster v1.4.1 after data Z score standardization. Gene Ontology (GO) analysis involved the functional annotation clustering method of DAVID v6.7 (60, 61) with GOTERM_BP_5 as implemented in RDAVIDWebService. To reduce redundancy normally associated with GO analyses, we selected only clusters having an enriched term<0.01 FDR, and a representative of each cluster was then selected by choosing the most significant end-of-branch term. Biological pathways associated with experimental groups under comparison, for example, retinal expression profiles from DMSO-treated, light-exposed mice compared to mice unexposed to bright light, were obtained by GSEA. Gene sets with a normalized enrichment score of >0.5 and a nominal P value of <0.05 were considered as significantly enriched.

Statistical Analyses

Results were collected from at least five mice from each experimental group unless otherwise specifically indicated. Data are means±SEM, and statistical analyses were performed with either Student's t test or ANOVA. P<0.05 was considered statistically significant.

Results

Figure 32:
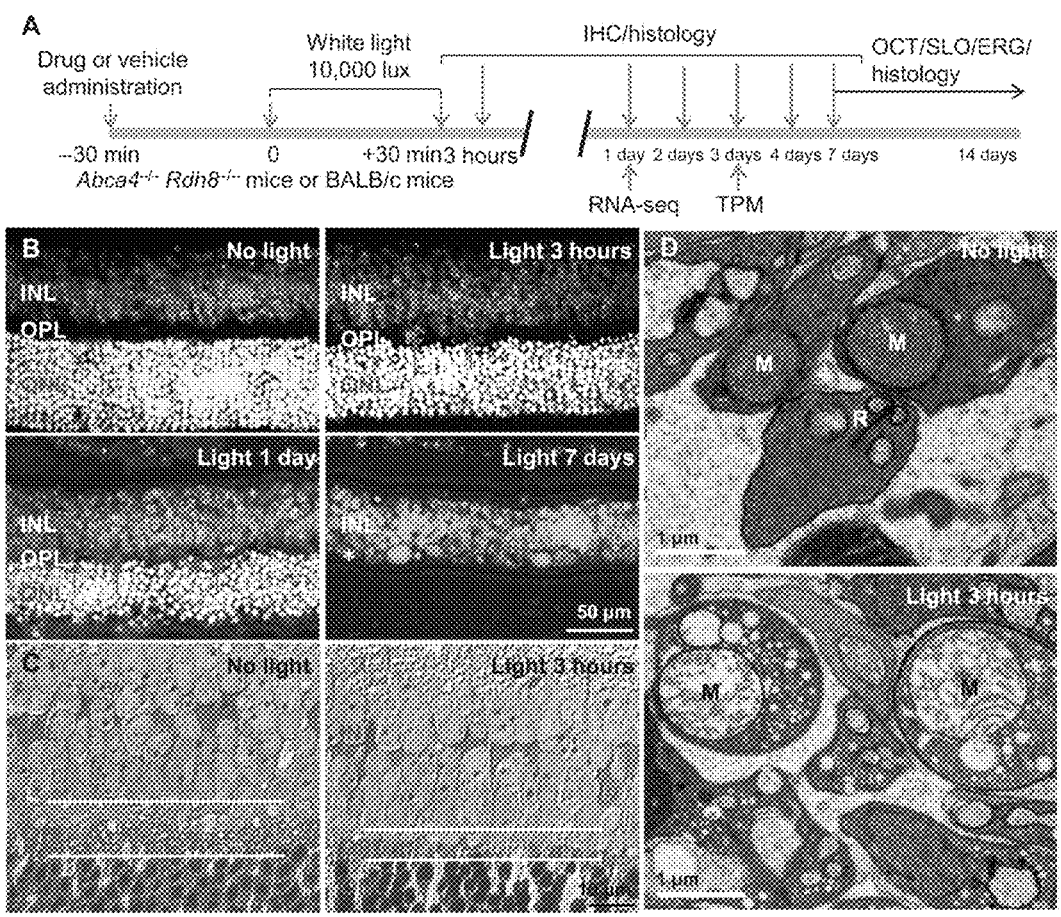
FIGS. 32(A-D) illustrate disruption of the OPL and damage of photoreceptor synaptic terminals in bright light-exposed retinas of $Abca4^{-/-}Rdh8^{-/-}$ mice (A) Schematic of the experimental protocol. Four- to 6-week-old male and female pigmented $Abca4^{-/-}Rdh8^{-/-}$ mice or BALB/c mice were exposed to bright light at 10,000 lux for 30 min, followed by the procedures as indicated. IHC, immunohistochemistry; OCT, optical coherence tomography; SLO, scanning laser ophthalmoscopy; ERG, electroretinogram; TPM, two-photon microscopy; RNA-seq, RNA sequencing. (B) After 4',6-diamidino-2-phenylindole (DAPI) staining, retinal cryosections from Abca4$^{-/-}$Rdh8$^{-/-}$ mice were observed under a fluorescence microscope. Retinas were collected from Abca4$^{-/-}$Rdh8$^{-/-}$ mice at the time points indicated including 3 hours, 1 day, and 7 days after light exposure. Red arrows mark areas showing the thinning of the OPL. (C) Toluidine blue-stained retinal sections from Abca4$^{-/-}$Rdh8$^{-/-}$ mice unexposed to bright light or at 3 hours after light exposure. White lines outline the OPL. (D) Electron microscopy of retinal sections from Abca4$^{-/-}$Rdh8$^{-/-}$ mice unexposed to bright light or at 3 hours after light exposure. M, mitochondrion; R, synaptic ribbon in photoreceptor synaptic terminal. Red arrows, cytoplasmic vacuolation.

Bright Light Exposure Impairs OPL and Photoreceptor Terminal Morphology in Abca4$^{-/-}$Rdh8$^{-/-}$ Mice Abca4$^{-/-}$Rdh8$^{-/-}$ mice lack adenosine triphosphate-binding cassette, subfamily A (ABC 1), member 4 (Abca4) and retinol dehydrogenase 8 (Rdh8), and exhibit increased susceptibility to light-induced photoreceptor degeneration. In addition to the loss of photoreceptors induced by exposure to bright light at 10,000 lux for 30 min (FIGS. 32A and B), histological examination of the retinas revealed thinning of the OPL that accompanied the onset of photoreceptor cell loss. The OPL is a network of synapses of photoreceptors, bipolar cells, and horizontal cells. We observed sporadic thinning of the OPL in retinas 3 hours after light exposure and detected uniform thinning 1 day later (FIG. 32B). Most photoreceptor cells had disappeared 7 days after light exposure, and the distinct demarcation between the inner nuclear layer (INL), which represents packed bipolar, horizontal, and amacrine cells, and the outer nuclear layer (ONL), which represents photoreceptors, was no longer apparent. Histological examination at higher resolution consistently demonstrated narrowing of the OPL 3 hours after light exposure (FIG. 32C). Transmission electron microscopy revealed damaged mitochondria, cytoplasmic vacuolization, and the loss of synaptic ribbons in photoreceptor synaptic terminals, which are major cellular constituents of the OPL, 3 hours after light exposure when only sporadic photoreceptor cell death had begun (FIG. 32D and FIG. 40A). These results indicated that light exposure caused rapid impairment of photoreceptor synaptic terminals and disruption of OPL morphology.

Figure 33:
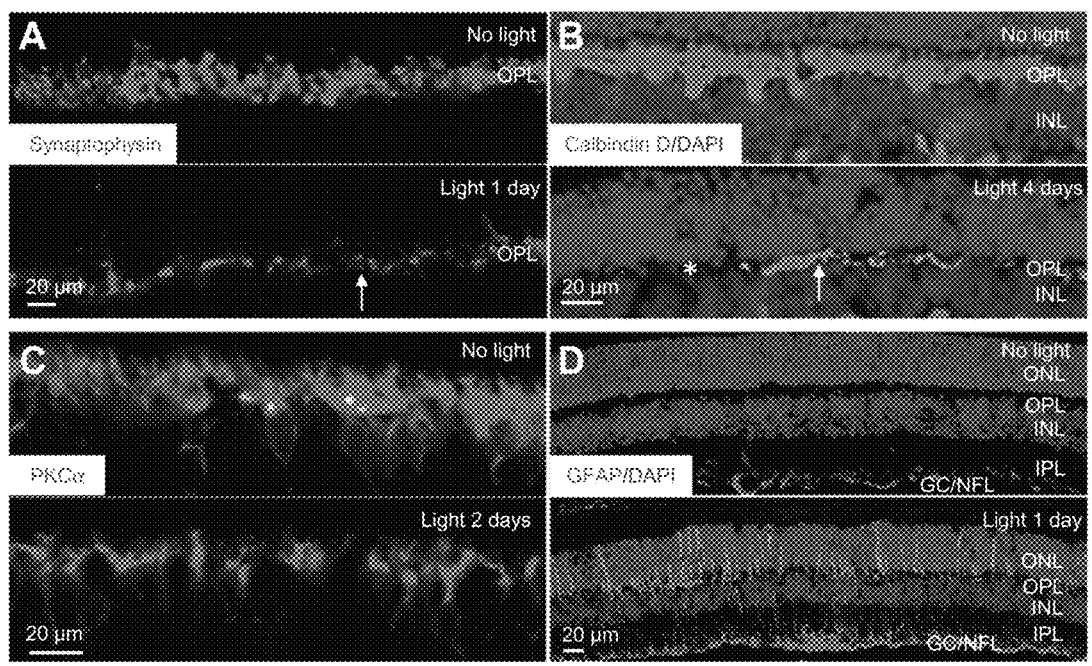
FIGS. 33(A-D) illustrate impaired photoreceptor synaptic terminals, horizontal cell morphology, bipolar cell dendrites, and retinal gliosis in bright light-exposed Abca4$^{-/-}$Rdh8$^{-/-}$ mice Retinal cryosections were obtained from Abca4$^{-/-}$Rdh8$^{-/-}$ mice either unexposed to bright light or after exposure to light at the indicated days. (A to D) Abundance of synaptophysin, calbindin D, PKCα (protein kinase Cα), and GFAP (glial fibrillary acidic protein) (all of which are green) was then revealed by immunohistochemistry and observed by fluorescence microscopy. DAPI counterstaining (blue) was performed to visualize the retinal structure in (B) and (D). IPL, inner plexiform layer; GC, ganglion cell; NFL, nerve fiber layer. White arrows in (A) and (B) indicate representative areas with diminished synaptophysin or calbindin D. Asterisks in (B) identify areas where calbindin D immunoreactivity was barely detected.

To evaluate other changes in the OPL after exposure to bright light, we performed immunohistochemistry. We used antibodies recognizing the synaptic vesicle protein synaptophysin to label rod and cone terminals. We observed a broad distribution of synaptophysin in the OPL of mice that had not been exposed to bright light, and this staining was disrupted 1 day after exposure to bright light (FIG. 33A).

Abca4$^{-/-}$Rdh8$^{-/-}$ mice bred into an albino background that lack pigmentation in the retina and choroid also exhibited susceptibility to bright light-induced retinal damage (FIG. 40). Similar to the pigmented Abca4$^{-/-}$Rdh8$^{-/-}$ mice, light induced a reduction in synaptophysin labeling in the retinas of the albino mice (FIG. 40B). These results confirmed that bright light exposure damaged photoreceptor synaptic terminals in mouse retinas.

Secondary Neurons are Impaired in Light-Exposed Abca4$^{-/-}$Rdh8$^{-/-}$ Mice

In addition to photoreceptor cell synaptic terminals, the OPL consists of horizontal cell projections and bipolar cell dendrites, which represent secondary neurons. We used calbindin D as a marker to assess any changes in horizontal cells in response to bright light and PKCα to assess light-induced changes in bipolar cells. Calbindin D staining was reduced in the retinas of light-exposed Abca4$^{-/-}$Rdh8$^{-/-}$ mice such that, by 4 days after exposure to bright light, calbindin D immunoreactivity was no longer present in the central retina and only residual staining was detected in the peripheral retina (FIG. 33B). These results indicated a light-induced loss of horizontal cell projections. We observed similar changes in calbindin D staining in albino Abca4$^{-/-}$Rdh8$^{-/-}$ mice after exposure to bright light; however, these mice had diminished retinal calbindin D abundance by 2 days after bright light exposure (FIG. 40C). The reduction in PKCα staining (FIG. 33C) indicated that bipolar cell dendrites were compromised 2 days after exposure to bright light in the retinas of Abca4$^{-/-}$Rdh8$^{-/-}$ mice.

In response to retinal injury, Müller cells undergo reactive gliosis characterized by enhanced transcription and ensuing protein abundance of GFAP, an intermediate filament protein that is present in Müller cells but normally only in those Müller cells in the retinal layers containing GCs and the NFL. We detected GFAP throughout the IPL (which is the retinal layer composed of bipolar cell axons, amacrine cell dendrites, and GC branches), the INL, and the ONL starting 1 day after exposure to bright light (FIG. 33D).

Figure 42:
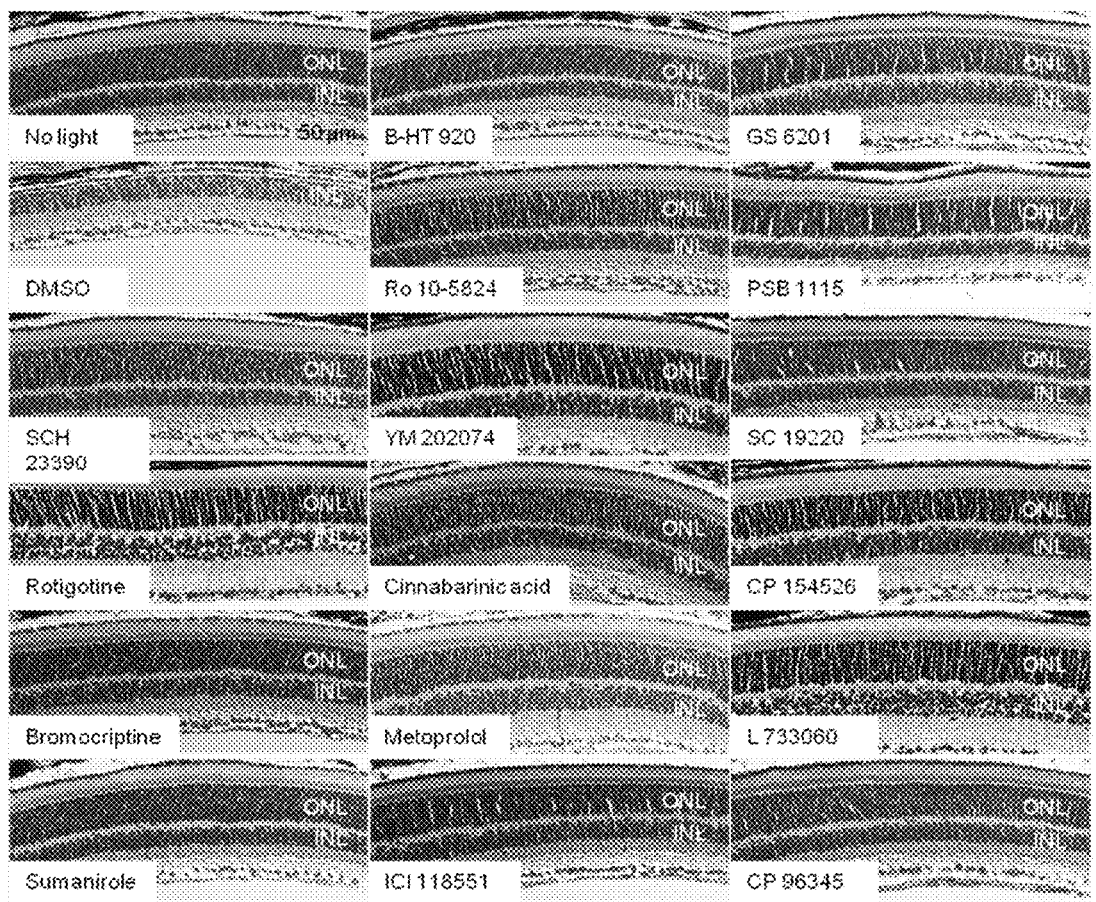
FIG. 42 illustrates variable preservation of retinal morphology by pharmacological pretreatments targeting different GPCRs in bright light-exposed Abca4$^{-/-}$Rdh8$^{-/-}$ mice. H&E staining of paraffin sections of eyes from Abca4$^{-/-}$Rdh8$^{-/-}$ mice was performed either without light exposure, or 14 days after bright light exposure and pretreatment with either DMSO or the indicated compounds listed in Table 7. ONL: outer nuclear layer; INL: inner nuclear layer. Scale bar: 50 µm.
Figure 43:
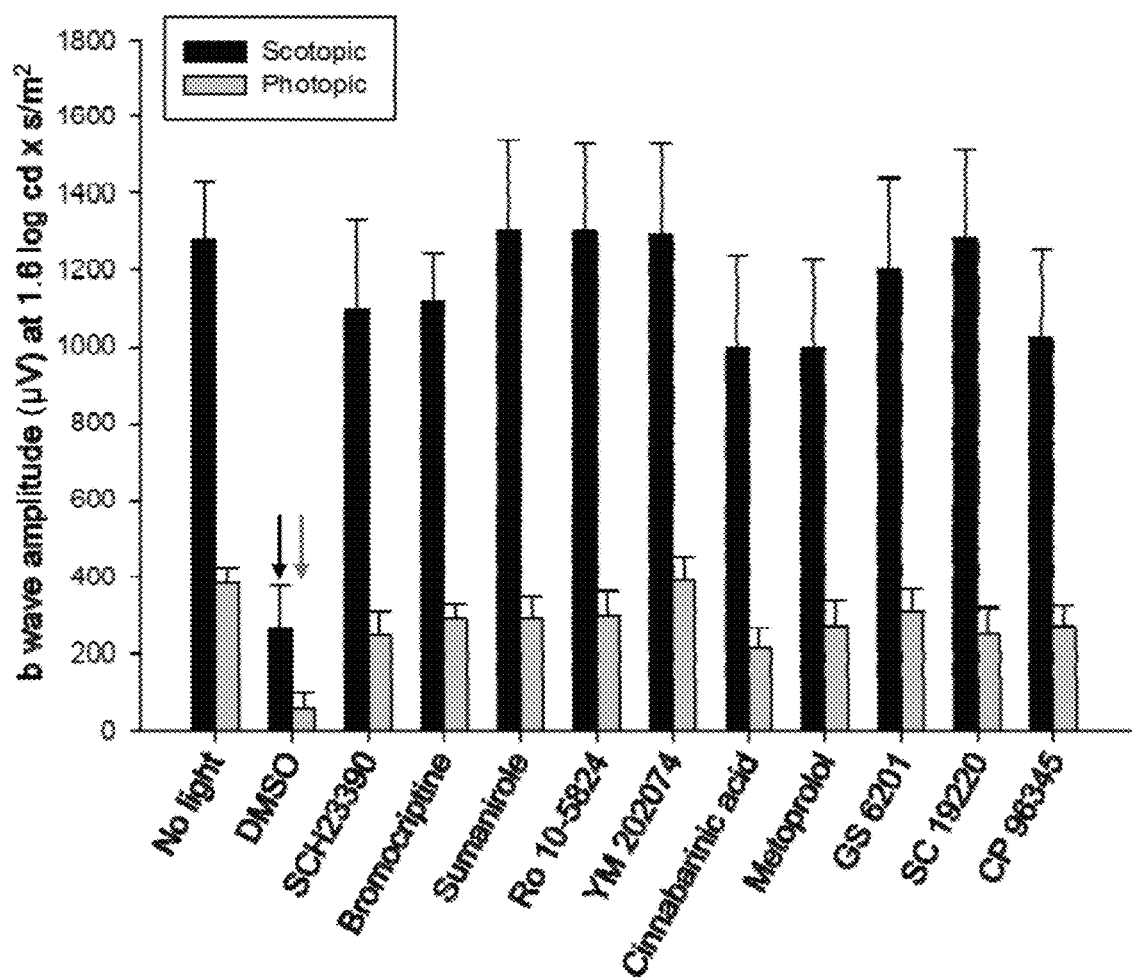
FIG. 43 illustrates pharmacological pretreatment affecting various GPCRs preserves retinal function in bright light-exposed Abca4$^{-/-}$Rdh8$^{-/-}$ mice. ERG analyses of retinal function were performed in Abca4$^{-/-}$Rdh8$^{-/-}$ mice either unexposed to bright light, or with light exposure and pretreatment with either DMSO or the indicated compounds listed in Table 7. Black and grey arrows highlight the decreased scotopic and photopic b wave amplitudes, respectively, in light-exposed, DMSO-treated mice. ERG was performed 10 days after bright light exposure.

Diverse GPCR-Modulating Compounds Preserve Retinal Morphology and Function in Abca4$^{-/-}$Rdh8$^{-/-}$ Mice Exposed to Bright Light The pathogenesis of light-induced retinopathy in Abca4$^{-/-}$Rdh8$^{-/-}$ mice involves changes in the activities of GPCRs that are coupled to Gq, Gs, or Gi. In particular, those activating Gq or Gs contribute to retinopathy, and those activating Gi protect photoreceptor cells from light-induced death. Therefore, we evaluated the effect of pharmacological compounds that either antagonize Gq/11- or Gs-coupled receptors or stimulate activated Gi/o-coupled receptors on bright light-induced retinopathy in Abca4$^{-/-}$Rdh8$^{-/-}$ mice. To identify appropriate pharmacological compounds, we predicted the abundance of specific GPCRs from their transcript abundance in mouse and human retinas (Table 12). Sixteen compounds with activity on 11 of the 20 GPCRs with abundant transcripts in the retinas produced complete protection against bright light-induced photoreceptor degeneration (Table 13). When administered by intraperitoneal injection to Abca4$^{-/-}$Rdh8$^{-/-}$ mice, these 16 drugs preserved retinal morphology, as revealed by OCT imaging (FIG. 41) and H&E (hematoxylin and eosin) staining (FIG. 42), after the exposure of the mice to bright light. Furthermore, administration of any of these 16 drugs individually preserved retinal function, as assessed by ERG recordings (FIG. 43). These results provided evidence that pharmacologically targeting GPCRs protects photoreceptor cells under light conditions that induced retinal degeneration.

TABLE 12

Expression of GPCR genes encoding potential therapeutic targets for retinal degeneration in the Abca4$^{-/-}$ Rdh8$^{-/-}$ mouse model of bright light-induced retinopathy. FPKM, normalized fragments per kilobase of exon per million mapped reads

| Gene* | Mouse retina | Human retina | Receptor | G protein | Ago | Antag |
|---|---|---|---|---|---|---|
| Drd4 | 241.78 | 139.49 | Dopamine receptor | Gi | + | |
| Gabbr | 40.24 | 35.38 | γ-Aminobutyric acid | Gi | + | |
| Drd2 | 23.1 | 26.33 | Dopamine receptor | Gi | + | |
| Adora | 18.26 | 13.55 | Adenosine A1 | Gi | + | |
| Crhr1 | 6.49 | 12.76 | Corticotropin- | Gs | | + |
| S1pr1 | 11.21 | 11.78 | Sphingosine-1- | Gi | + | |
| Drd1a | 9.49 | 8.45 | Dopamine receptor | Gs | | + |
| Smo | 6.35 | 5.91 | Smoothened | Gi | + | |
| Ednrb | 1.94 | 5.77 | Endothelin receptor | Gq | | + |
| Grm1 | 3.52 | 4.97 | Metabotropic | Gq | | + |
| Adrb1 | 20.18 | 3.84 | β1-Adrenergic | Gs | | + |
| Adora | 2.53 | 3.83 | Adenosine A2B | Gs and Gq | | + |
| Hrh3 | 19.12 | 3.75 | Histamine receptor H3 | Gi | + | |
| Grm4 | 4.93 | 3.1 | Metabotropic | Gi | + | |
| Grm8 | 6.43 | 2.04 | Metabotropic | Gi | + | |
| Grm7 | 3.95 | 1.16 | Metabotropic | Gi | + | |
| Adra1 | 0.45 | 0.20 | α1A-Adrenergic | Gq | | |
| Adra1 | 1.60 | 1.12 | α1B-Adrenergic | Gq | | |
| Adra1 | 1.72 | 1.08 | α1D-Adrenergic | Gq | | |
| Adrb2 | 1.03 | 0.98 | β2-Adrenergic | Gs | | + |
| Tacr1 | 2.06 | 0.95 | Tachykinin receptor 1 | Gq | | + |

TABLE 12-continued

Expression of GPCR genes encoding potential therapeutic targets for retinal degeneration in the Abca4$^{-/-}$ Rdh8$^{-/-}$ mouse model of bright light-induced retinopathy. FPKM, normalized fragments per kilobase of exon per million mapped reads

| Gene* | Mouse retina | Human retina | Receptor | G protein | Ago | Antag |
|---|---|---|---|---|---|---|
| Ptger1 | 14.88 | 0.94 | Prostaglandin E | Gq | | + |
| S1pr2 | 1.13 | 0.63 | Sphingosine-1- | Gq, Gs, and | | |

*Genes in bold, italicized font encode receptors targeted by the drugs displaying efficacy in this study.
†Data from previous study.

Morphological protection was assessed as morphological preservation of the retina by OCT imaging 7 days after exposure to bright light. Complete protection represented the retinas with intact ONL morphology similar to those of mice unexposed to bright light, with ONL thicknesses of ≥50 μm at 0.45 mm away from the optic nerve head (ONH) in the temporal retina. Functional protection was assessed by ERG analyses of retinal function in Abca4$^{-/-}$Rdh8$^{-/-}$ mice 10 days after bright light exposure. Protection data were collected from at least five mice from each experimental group unless otherwise specifically indicated. ERG data are means±SD, and statistical analyses were performed with either Student's t test or analysis of variance (ANOVA). P<0.05 was considered statistically significant.

TABLE 13

Summary of GPCR-modulating compounds that conferred retinal morphological and functional protection in bright light-exposed Abca4$^{-/-}$/Rdh8$^{-/-}$ mice

| Agent | Major action(s) | G protein |
|---|---|---|
| SCH 23390 hydrochloride | Dopamine receptor D1 and D5 | G$_s$ |
| Rotigotine hydrochloride | Dopamine receptor D2 and D3 | G$_i$ |
| 2-Bromo-α-ergocryptine | Dopamine receptor D2 and D3 | G$_i$ |
| Sumanirole maleate | Dopamine receptor D2 agonist | G$_i$ |
| B-HT 920 | Dopamine receptor D2, α$_2$ | G$_i$ |
| Ro 10-5824 dihydrochloride | Dopamine receptor D4 agonist | G$_i$ |
| YM 202074 | mGluR1 receptor antagonist | G$_q$ |
| Cinnabarinic acid | mGluR4 receptor agonist | G$_i$ |
| Doxazosin* | Adrenergic receptor α$_1$ antagonist | G$_q$ |
| Tamsulosin* | Adrenergic receptor α$_1$ antagonist | G$_q$ |
| MTP tartrate | Adrenergic receptor β$_1$ antagonist | G$_s$ |
| ICI 118,551 hydrochloride | Adrenergic receptor β$_1$ antagonist | G$_s$ |
| GS 6201 | Adenosine A$_{2B}$ receptor | G$_s$ |
| PSB 1115 | Adenosine A$_{2B}$ receptor | G$_s$ |
| SC 19220 | EP1 prostanoid receptor | G$_q$ |
| CP 154526 | Corticotropin-releasing factor 1 | G$_s$ |
| L-733060 | Tachykinin NK1 receptor | G$_q$ |
| CP 96345 | Tachykinin NK1 receptor | G$_q$ |

*Compounds identified from previous study.

Bromocriptine or Metoprolol Protects the Retinas of Abca4$^{-/-}$Rdh8$^{-/-}$ Mice Against Bright Light-Induced Degeneration Among the 16 compounds that protected retinas of Abca4$^{-/-}$Rdh8$^{-/-}$ mice against exposure to bright light, we selected the 2 with FDA-approved counterparts—the synthetic ergot derivative bromocriptine (BRM) and the β1 receptor antagonist metoprolol (MTP)—for further evaluation in the light-exposed Abca4$^{-/-}$Rdh8$^{-/-}$ mouse model. We administered either BRM or MTP by intraperitoneal injection before light exposure at doses of 2.5 or 10 mg/kg body weight (bw), respectively. As the controls for these experiments, we used light-exposed mice injected with dimethyl sulfoxide (DMSO), the solvent used for the drugs. DMSO administered intraperitoneally does not cause retinal degeneration. We assessed retinal morphology, including photoreceptor protection, by labeling the cone cell sheath with peanut agglutinin (PNA) 7 days after light exposure. A labeling revealed that the ONL was severely disrupted in retinas of light-exposed, DMSO-treated Abca4$^{-/-}$Rdh8$^{-/-}$ mice such that PNA labeling was barely detected in photoreceptor cells (FIG. 34A). However, pretreatment with either BRM or MTP resulted in the preservation of the ONL and photoreceptor cells detected by PNA staining. SLO imaging also revealed many autofluorescent spots in the retinas of light-exposed Abca4$^{-/-}$Rdh8$^{-/-}$ mice, an indication of light damage, whereas the retinas of BRM- or MTP-treated mice lacked these autofluorescent spots (FIG. 34B) and were similar to the retinas of mice that had not been exposed to bright light.

Figure 44A:
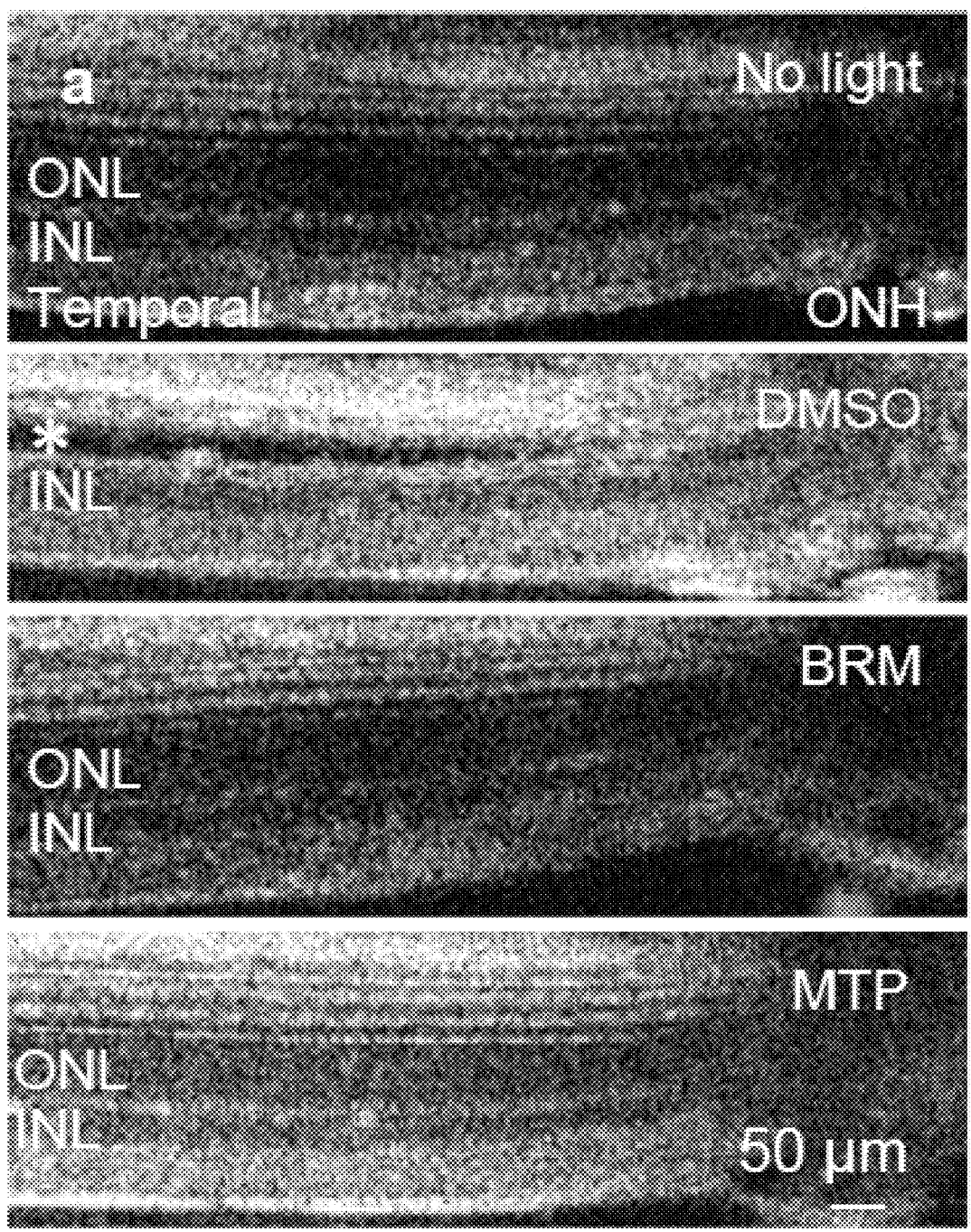
FIGS. 44(A-C) illustrate BRM or MTP pretreatment protects retinas of BALB/c mice from bright light-induced degeneration. A. BALB/c mice were pretreated as indicated, and exposed to bright light. OCT imaging was performed 7 d later to examine retinal structures either unexposed to bright light, exposed to bright light and pretreated with DMSO, exposed to bright light and pretreated with BRM at 2.5 mg/kg bw (BRM), or exposed to bright light and pretreated with MTP at 10 mg/kg bw (MTP). B. ONL thickness was measured in OCT images 0.45 mm away from the ONH in the temporal retina. * Compared to No light, P<0.05; # Compared to DMSO, P<0.05. ONH: optic nerve head; ONL: outer nuclear layer; INL: inner nuclear layer. Asterisk indicates reduced ONL thickness. C. Retinal expression of PNA (green) along with DAPI counterstaining (blue) was examined in cryosections collected from light-exposed BALB/c mice pretreated with either DMSO, BRM or MTP. Scale bar; 20 µm.
Figure 44B:
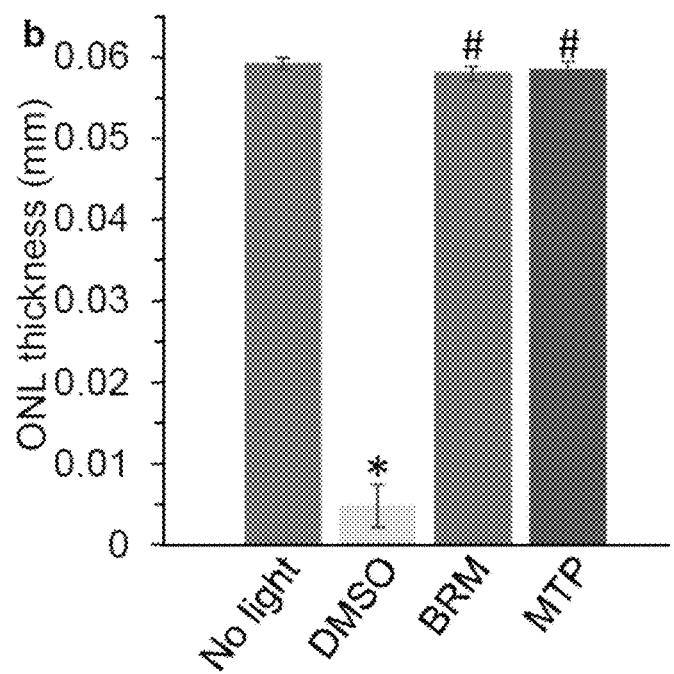
Figure 44C:
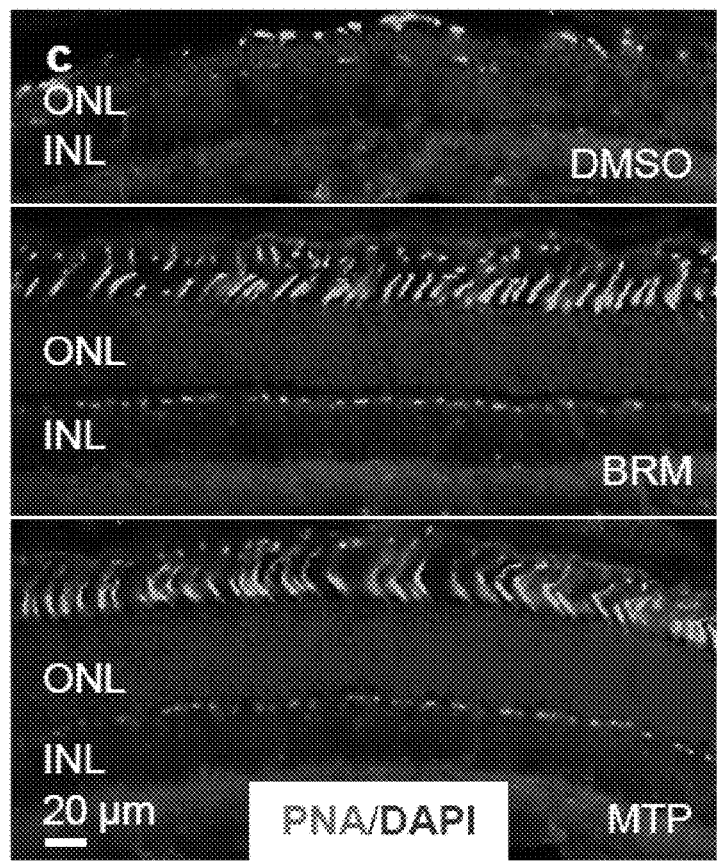

Light-exposed BALB/c mice served as an additional model. We subjected these mice to the same pretreatment with either BRM or MTP and performed OCT imaging 7 days after light exposure. The ONL was severely disrupted in the retinas of light-exposed, DMSO-treated BALB/c mice (FIGS. 44A and B), and pretreatment with either BRM or MTP preserved the ONL (FIGS. 44A and B). Moreover, we detected only residual PNA staining in the outer retina of light-exposed, DMSO-treated BALB/c mice (FIG. 44C), in contrast to the nearly normal pattern of PNA staining observed in both BRM- and MTP-treated mice. Thus, BRM or MTP protected cone photoreceptor cells from light-induced damage based on morphological assessment. These results validated the retinal protection conferred by either BRM or MTP in two different models of light-induced retinal degeneration.

Figure 45A:
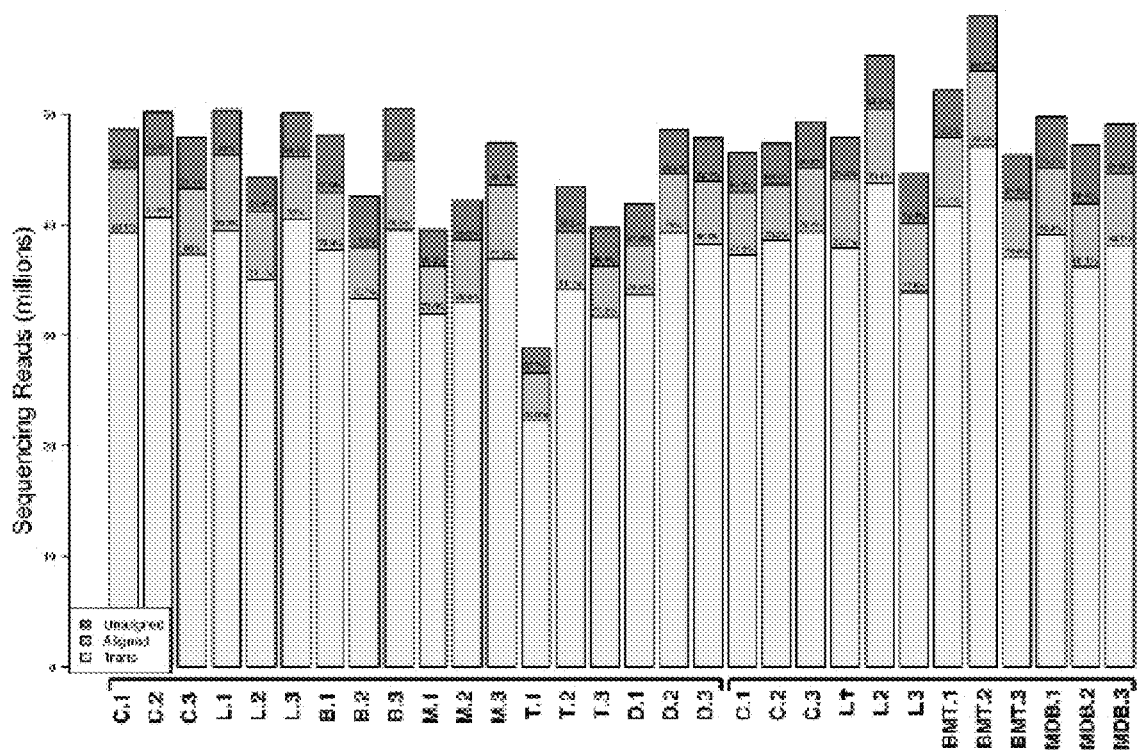
FIGS. 45(A-E) illustrates transcriptome analysis of the retina. Sequencing depth and alignment statistics for the RNA-seq experiment performed for retinal samples collected from Abca4$^{-/-}$Rdh8$^{-/-}$ mice unexposed to bright light (C), light-exposed mice pretreated with DMSO vehicle control (L), or BRM (B), MTP (M), TAM (T), DOX (D), BMT (B+M+T) and MDB (B+M+D). Doses used for retinal transcriptome analyses of the mice receiving mono treatment were: 1 mg/kg bw for BRM, 10 mg/kg bw for MTP, 2.5 mg/kg bw for TAM and 10 mg/kg bw for DOX. Doses for combined treatment with B+M+T were 0.1 mg/kg bw for BRM, 1 mg/kg bw for MTP and 0.05 mg/kg bw for TAM. Doses for combined treatment with B+M+D were 0.1 mg/kg bw for BRM, 1 mg/kg bw for MTP and 1 mg/kg bw for DOX. A. Trans indicates the number of reads mapping to the known gene annotation. Aligned are the amounts of intronic and intergenic reads mapping to the genome. Unaligned are the number of reads not successfully aligned. Shown also are the normalized count values and distribution after normalization of the mono pretreatments (B) and combination pretreatments (C), respectively. D, E. Clustering of the fold change values is evident from the differential expression analysis of the mono pretreatments (D) and combination pretreatments (E).
Figures 45D, 45E:
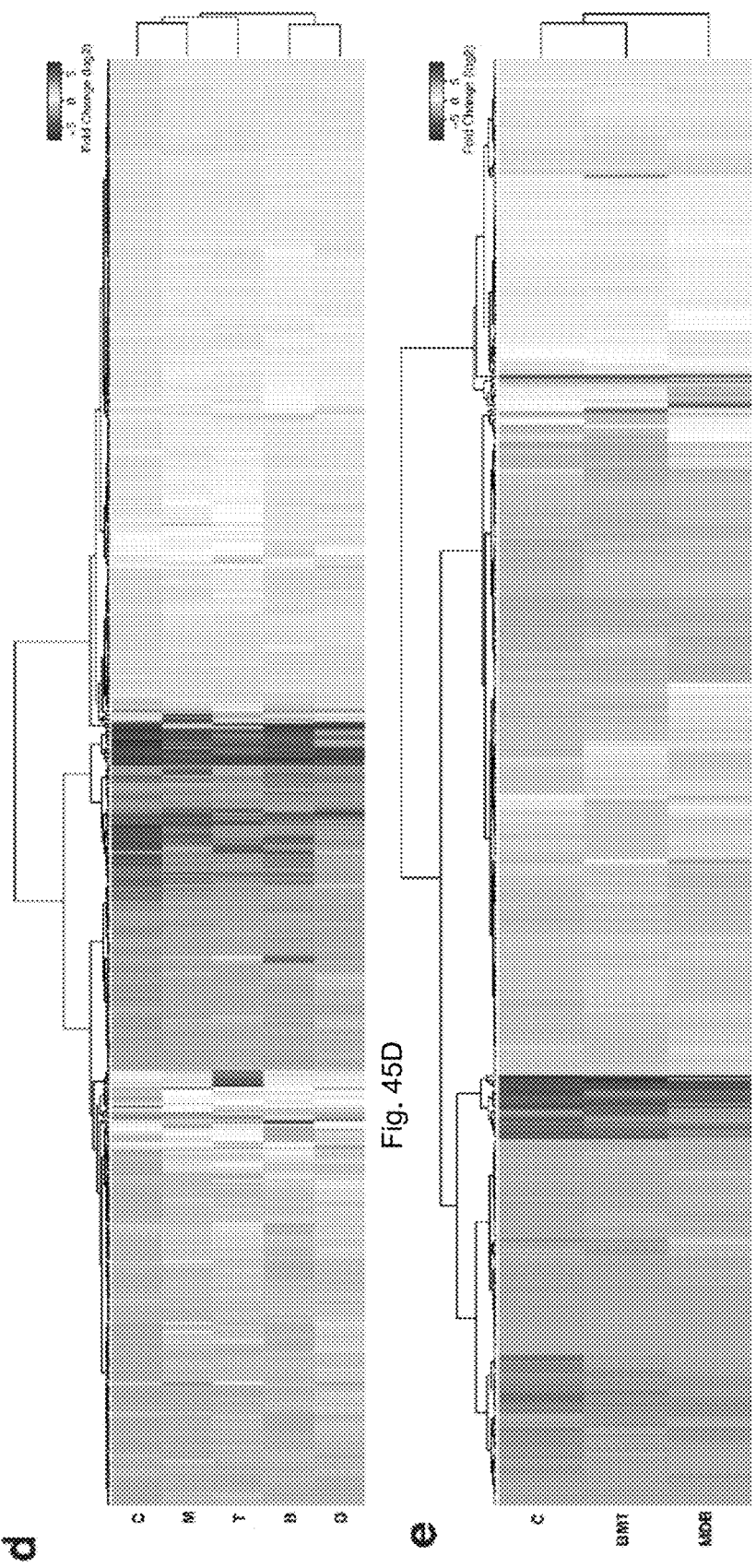

To examine the impact of these drug regimens at the molecular level, we used global transcriptome analysis by RNA-seq. Retinas were collected from mice that had not been exposed to bright light and 1 day after exposure to light coupled with pretreatment with DMSO or individual drugs, including BRM, MTP, TAM (tamsulosin), and DOX (doxazosin). TAM and DOX are ADRA1 antagonists identified in a previous study as photoreceptor-protective agents against light-induced degeneration. Retinal RNA samples from three mice (six eyes) for each condition were sequenced to a mean depth of 46.9±5.4 million paired-end reads with a genomic alignment percentage of 91.4±1.0 and transcriptomic alignment percentage of 79.2±1.4 (FIG. 45A). After normalization, read depths and count distributions were examined for outliers (FIG. 45B). The data set included 18,483 expressed transcripts after eliminating transcripts with very low expression (<1 FPKM).

Principal components analysis (PCA) performed on the normalized FPKM values from the entire expressed data set revealed good biological replication (FIG. 34C). Each condition resulted in a different pattern within the principal component space, indicating differential gene expression profiles associated with normal retinas, light-exposed retinas, and light-exposed retinas from mice receiving the different treatments. Data from the retinas from the DMSO-pretreated and light-exposed animals, the control animals that were not exposed to light, as well as the BRM-pretreated and light-exposed animals were the most consistent across the individual mice. Data from the DOX-, MTP-, or TAM-pretreated and light-exposed animals were more variable. However, retinas of control mice that had not been exposed to bright light and DMSO-pretreated and light-exposed mice had the largest separation in gene expression along principal component 1 (PC 1) (FIG. 34C), consistent with retinal damage producing large changes in global gene expression. Pearson's correlation was performed using the expression values from the differentially expressed genes and showed that pretreatment with individual drug regimens produced shifts in global gene expression toward that exhibited by mice that had not been exposed to bright light (correlation coefficient>0.8) (FIG. 34D). These findings suggested that, although the different pharmacological agents produced variable differential gene expression profiles in light-exposed retinas, overall each tended to shift the gene expression pattern to one similar to the pattern in control undamaged retina, indicating protective effects against light-induced retinal damage (FIG. 34D). MTP produced a gene expression pattern most similar to the undamaged control (not light exposed) (FIG. 34D), indicating that MTP conferred the most protection. Cluster analysis of the 622 differentially expressed transcripts that were significantly stimulated or repressed by bright light exposure showed that the profiles from the retinas from the drug-treated and light-exposed mice showed some individual variation within their respective groups but were overall more similar to the retinas of the control mice than to the damaged retinas from the DMSO-treated and light-exposed mice (FIG. 34E and FIG. 45C).

Figure 35:
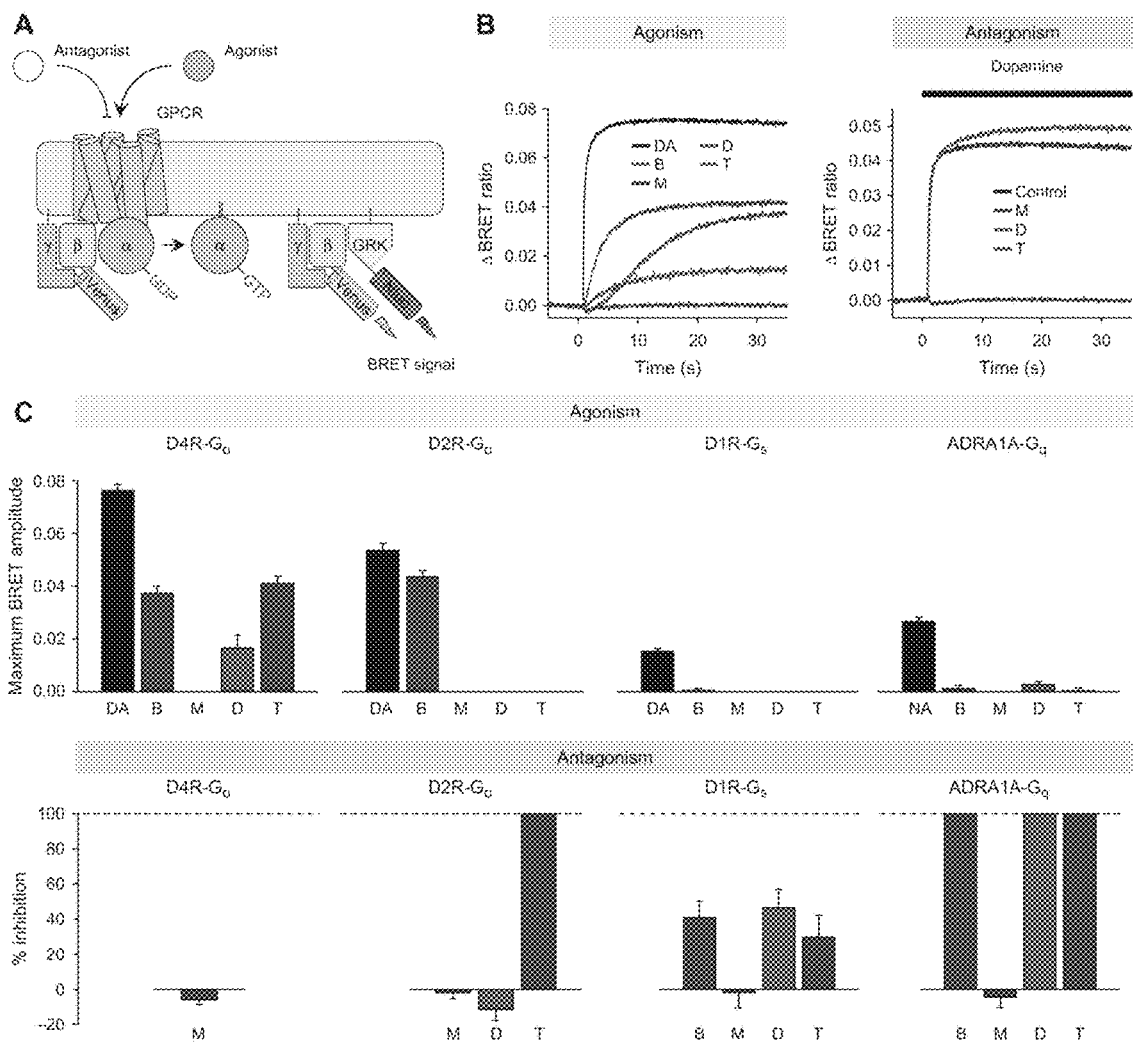
FIGS. 35(A-C) illustrate characterizing the activity of BRM, MTP, DOX, and TAM on dopamine and adrenaline receptors (A) Schematic representation of the BRET assay used to evaluate actions of drugs on selected GPCRs. Activation of a GPCR by agonist leads to the dissociation of inactive heterotrimeric G proteins into active GTP-bound Gα and Venus-Gβγ subunits. The free Venus-Gβγ then interacts with the Gβγ-effector mimetic masGRK3ct-Nluc to produce the BRET signal. GDP, guanosine diphosphate; GRK, G protein-coupled receptor kinase; Nluc, nanoluciferase. (B) Left: Representative BRET signal traces recorded upon activation of D4R with indicated drugs in cells expressing Gαo and Venus-Gβγ, illustrating the agonism assay. Right: Representative traces of D2R responses to 1 µM dopamine in the absence (control) or presence of indicated drugs, illustrating antagonism assay. Note that, in the antagonism assay shown, the black trace overlaps with the red trace and therefore is not visible. (C) Top: Quantification of agonistic activity of ligands on D2R, D4R, D1R, and ADRA1A. D2R-G$_O$, D4R-G$_O$, D1R-G$_s$, and ADRA1A-Gq signaling were reconstituted in HEK293T/17 cells by transient transfection separately. Maximum amplitudes induced by dopamine (DA; 100 µM), noradrenaline (NA; 100 µM), BRM (25 µM), MTP (100 µM), DOX (50 µM), and TAM (100 µM) were plotted as bar graphs. Bottom: Quantification of antagonistic activity of ligands. To examine the antagonistic activity, cells were preincubated with each of the ligands, and then 1 µM dopamine for dopamine receptors or 1 µM noradrenaline for the adrenaline receptor was applied. In these experiments, only ligands that did not show any agonistic effect were examined for each receptor-G protein combination. The activity is plotted as percent inhibition. Data are means±SD. Results are representative of two independent experiments each performed with 12 replicates.

G Protein Activation Assays Reveal a Mechanistic Basis for Retinal-Protective Adrenergic and Dopaminergic Ligands To assess how BRM, MTP, DOX, and TAM influence GPCR signaling to exert a protective effect against retinal degeneration, we analyzed their ability to activate G proteins. We used a real-time kinetic assay in which G protein activation by GPCRs is quantified by monitoring changes in the bioluminescence resonance energy transfer (BRET) signal between Venus-tagged Gβγ and its luciferase-tagged reporter in living cells (FIG. 35A). The ability of ligands to increase in the BRET signal indicated agonistic activity [FIGS. 35B (left) and C (top)]. Conversely, the antagonistic activities were ascertained by the ability of ligand pretreatment to inhibit BRET signal induction by the physiological agonist dopamine or noradrenaline [FIGS. 35B (right) and C (bottom)]. Because the four synthetic drugs are adrenergic and dopaminergic ligands (Table 13), we focused on dopamine D2, D4, D1, and ADRA1 as representative Gi/o-, Gs-, and Gq-coupled receptors, which are encoded by genes that were prominently expressed in Abca4$^{-/-}$Rdh8$^{-/-}$ mouse retina (Table 12). The β1-adrenergic receptor ADRB1 is the target of MTP. We excluded ADRB1 from the group of receptors tested because, with the exception of BRM, which is a weak antagonist, it lacks high-affinity interactions with the test compounds. All possible ligand-GPCR pairs were examined.

Representative BRET data are shown in FIG. 35B, and quantification of the activity analysis is shown in FIG. 35C. As predicted from reported studies, BRM activated D4R and D2R, as well as inhibited ADRA1A. However, BRM had no significant agonistic effect on D1R and, instead, exhibited partial antagonism at this receptor. As expected, DOX was a full antagonist for ADRA1A, but DOX also exhibited a partial agonistic effect on D4R and had a partial antagonistic effect on D1R. The ADRA1 antagonist TAM demonstrated complex activity on the four receptors. In addition to ADRA1A, TAM exhibited antagonistic activity on D2R and acted as a partial antagonist toward D1R. TAM also had a partial agonistic effect on D4R. We observed no agonistic or antagonistic effects of MTP on any of the four GPCRs tested, likely consistent with the lack of unexpected pharmacology beyond its selective antagonism at Gs-coupled β-adrenergic receptors.

Although BRM and TAM had opposite effects on D2R, our data showed that both of these ligands activated D4R and inhibited D1R and ADRA1A. Because we detected almost 10-fold higher expression of transcripts for D4R than D2R and the transcript analysis suggested that D4R is the most abundant GPCR in the retina among those examined (Table 12), we predict that D4R is a predominant source of protective Gi/o signaling in the mouse retina. Thus, we hypothesized that, in the retina, these drugs would activate protective Gi/o signaling through D4R and inhibit adverse effects of Gs and Gq signaling by antagonizing D1R and ADRA1A receptors.

Figure 46:
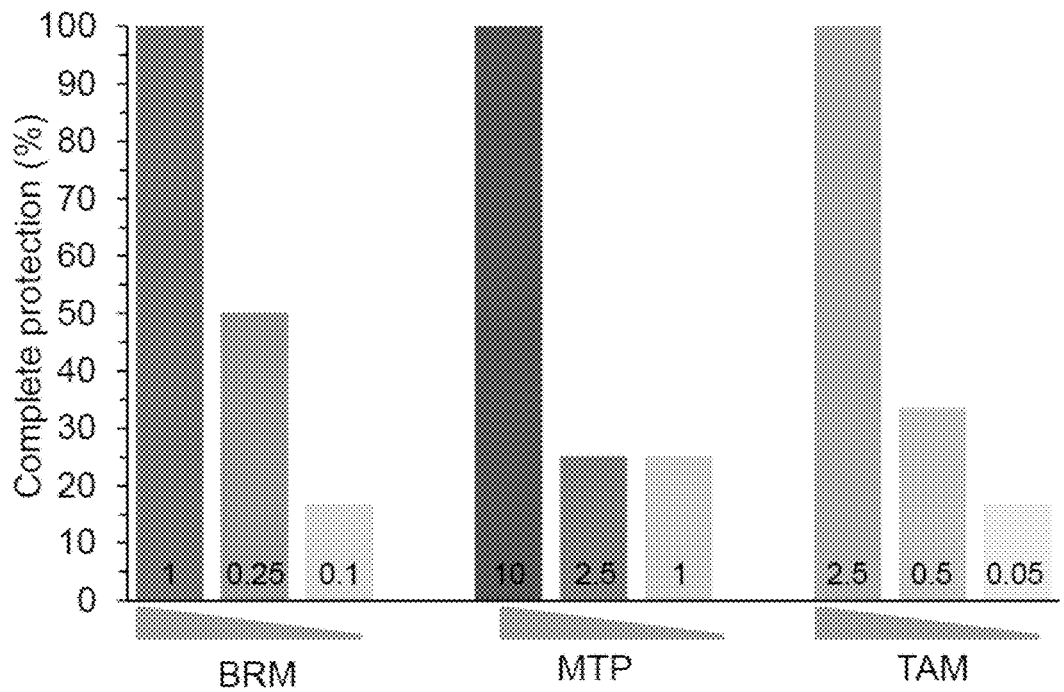
FIG. 46 illustrates dose-dependent protection of retinal morphology in Abca4$^{-/-}$Rdh8$^{-/-}$ mice by BRM, MTP and TAM pretreatment. Abca4–/–Rdh8–/– mice pretreated with different doses of BRM, MTP, and TAM were exposed to bright light. OCT imaging was performed 7 d after lightexposure. The percentage of complete retinal protection is summarized for each treatment delivered at the dose indicated.
Figure 47:
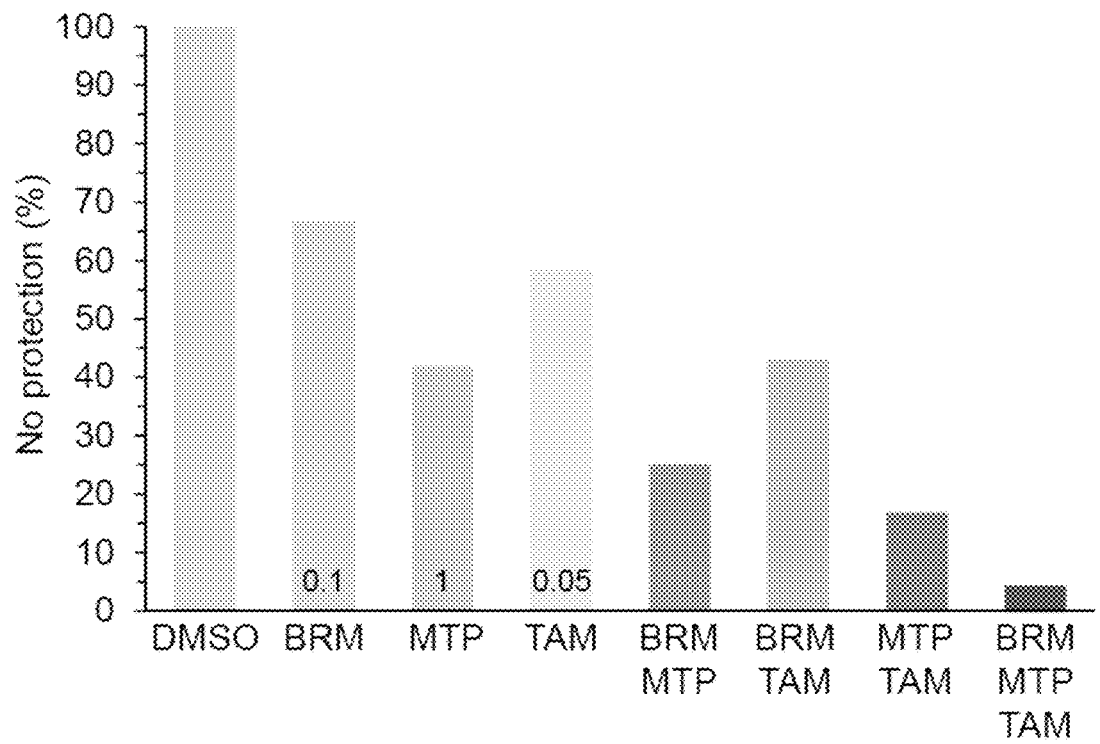
FIG. 47 illustrates combined pretreatments improve retinal morphological protection against bright light-exposure in Abca4$^{-/-}$Rdh8$^{-/-}$ mice. Either BRM, MTP, or TAM was administered individually at a sub-effective dose to Abca4$^{-/-}$Rdh8$^{-/-}$ mice or in a combined pretreatment consisting of two or three of these compounds, each at its sub-effective dose. This was followed by exposure to bright light and OCT imaging performed 7 d later. Percentages of mice manifesting no protection of retinal structures were calculated for each condition. Doses for either mono or combined pretreatments were 0.1 mg/kg bw, 1 mg/kg bw, and 0.05 mg/kg bw for BRM, MTP and TAM, respectively.
Figure 48A:
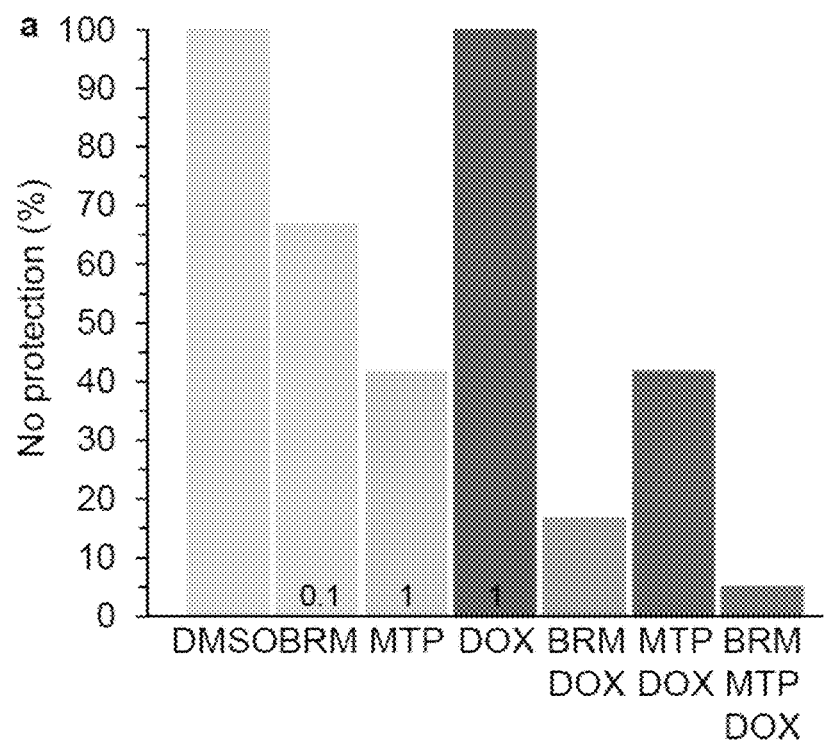
FIGS. 48(A-B) illustrate combined treatments with sub-effective doses of individual drugs exhibit improved retinal morphological protection in bright light-exposed Abca4$^{-/-}$Rdh8$^{-/-}$ mice. BRM, MTP, or DOX was individually administered at a sub-effective dose or together with one or two other compounds, each delivered at a sub-effective dose, to Abca4$^{-/-}$Rdh8$^{-/-}$ mice prior to bright light exposure. OCT imaging was performed 7 d after light exposure. The percentage of mice manifesting either (A) no protection or (B) complete protection of retinal structure is summarized for each treatment. Doses in all conditions were 0.1 mg/kg bw, 1 mg/kg bw, and 1 mg/kg bw for BRM, MTP and DOX, respectively.
Figure 48B:
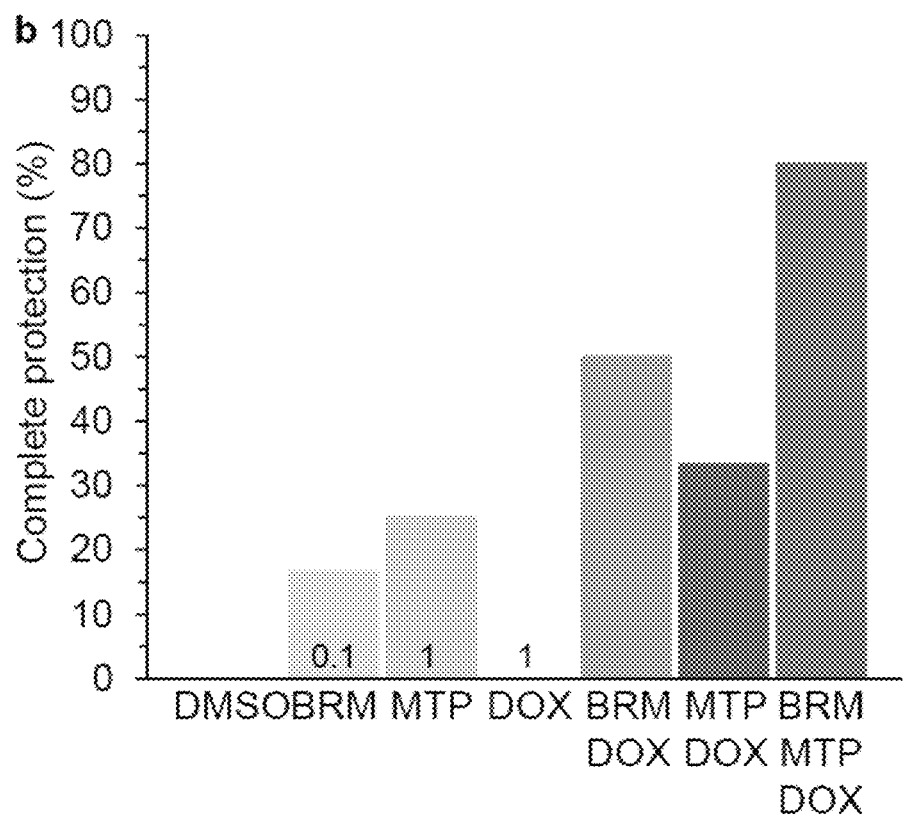

Combined Pretreatments Improve Protection of Abca4−/− Rdh8−/− Mouse Retina Against Bright Light-Induced Degeneration The complex effects of BRM, DOX, and TAM on GPCR signaling observed in the BRET-based signaling assays led us to hypothesize that combinations of retinal-protective drugs at individual subeffective doses could achieve synergistic effects by concurrent modulation of distinct pathways and that these synergistic effects might provide better preservation of retinal integrity. Although MTP was not a ligand for any of the four GPCRs tested in the functional assay, we included MTP, because it exhibited remarkable protection against light-induced retinal degeneration. To test this concept, we compared the protective effect of each of the FDA-approved drugs BRM, MTP, and TAM individually with their protective effect at lower doses in combination. We performed OCT imaging to determine the percentage of mice showing complete protection of retinal structure, as defined by indistinguishable ONL morphology from that of mice unexposed to light. Each drug individually conferred dose-dependent retinal protection in light-exposed Abca4$^{-/-}$ Rdh8$^{-/-}$ mice (FIG. 46). Complete retinal protection occurred when BRM, MTP, and TAM were administered individually at doses of 1, 10, and 2.5 mg/kg bw, respectively, but this was reduced to only 17, 25, and 17% of light-exposed Abca4$^{-/-}$Rdh8$^{-/-}$ mice when each drug was given individually at the lower doses of 0.1, 1, and 0.05 mg/kg bw, respectively (Table 14). We then used these subeffective doses to evaluate retinal protection conferred by combined regimens with these drugs in light-exposed Abca4$^{-/-}$Rdh8$^{-/-}$ mice. Subeffective doses of the combination of all three drugs (BRM, MTP, and TAM) produced complete retinal protection in 88% of light-exposed mice, whereas complete protection was observed in fewer light-exposed Abca4$^{-/-}$Rdh8$^{-/-}$ mice pretreated with subeffective combinations of either BRM+MTP, BRM+TAM, or MTP+TAM (Table 14). Conversely, the percentage of light-exposed Abca4$^{-/-}$Rdh8$^{-/-}$ mice showing no retinal protection was reduced with the combination treatments compared with the individual treatments at subeffective doses (Table 14). When the combination of BRM, MTP, and TAM was administered at subeffective doses, only 4% of light-exposed Abca4$^{-/-}$Rdh8$^{-/-}$ mice exhibited no retinal protection (FIG. 47 and Table 14). Similar results were observed when DOX, an ADRA1 antagonist that was previously shown to protect retina against light-induced degeneration, was used in combination with BRM and MTP (FIG. 48 and Table 14). Therefore, improved retinal protection could be attained by combined pretreatment with suboptimal doses of individual drugs with different mechanisms of action involving separate GPCRs.

Either BRM, MTP, or TAM was administered individually at a subeffective dose to Abca4$^{-/-}$Rdh8$^{-/-}$ mice or in a combined pretreatment consisting of two or three of these compounds, each at its subeffective dose. Doses for either single or combined pretreatments were 0.1, 1, and 0.05 mg/kg bw for BRM, MTP, and TAM, respectively. Protection was assessed as morphological preservation of the retina by OCT imaging 7 days after exposure to bright light. Complete protection represented the retinas with intact ONL morphology similar to those of mice unexposed to bright light, with ONL thicknesses of ≥50 μm at 0.45 mm away from the ONH in the temporal retina. No protection represented retinas exhibiting morphology similar to that of light-exposed and vehicle-treated mice, with ONL thickness of ≤20 μm at 0.45 mm away from the ONH in the temporal retina. Partial protection defined retinas manifesting a reduction in the thickness of the ONL between 20 and 50 μm measured 0.45 mm away from the ONH in the temporal retina. This was followed by exposure to bright light and OCT imaging performed 7 days later. Percentages of mice manifesting no protection of retinal structures were calculated for each condition.

TABLE 14

Retinal protection conferred by individual and combination therapies targeting GPCRs

| Drug | Percent of mice with | Percent of mice with |
|---|---|---|
| BRM | 16.7 | 66.7 |
| MTP | 25 | 41.7 |
| TAM | 16.7 | 58.3 |
| DOX | 0 | 100 |
| BRM + MTP | 33.3 | 25 |
| BRM + TAM | 42.86 | 42.86 |
| MTP + TAM | 41.7 | 16.7 |
| BRM + MTP | 87.5 | 4.17 |
| BRM + DOX | 50 | 16.7 |
| MTP + DOX | 33.3 | 41.7 |
| BRM + MTP | 80 | 5 |

Figure 36:
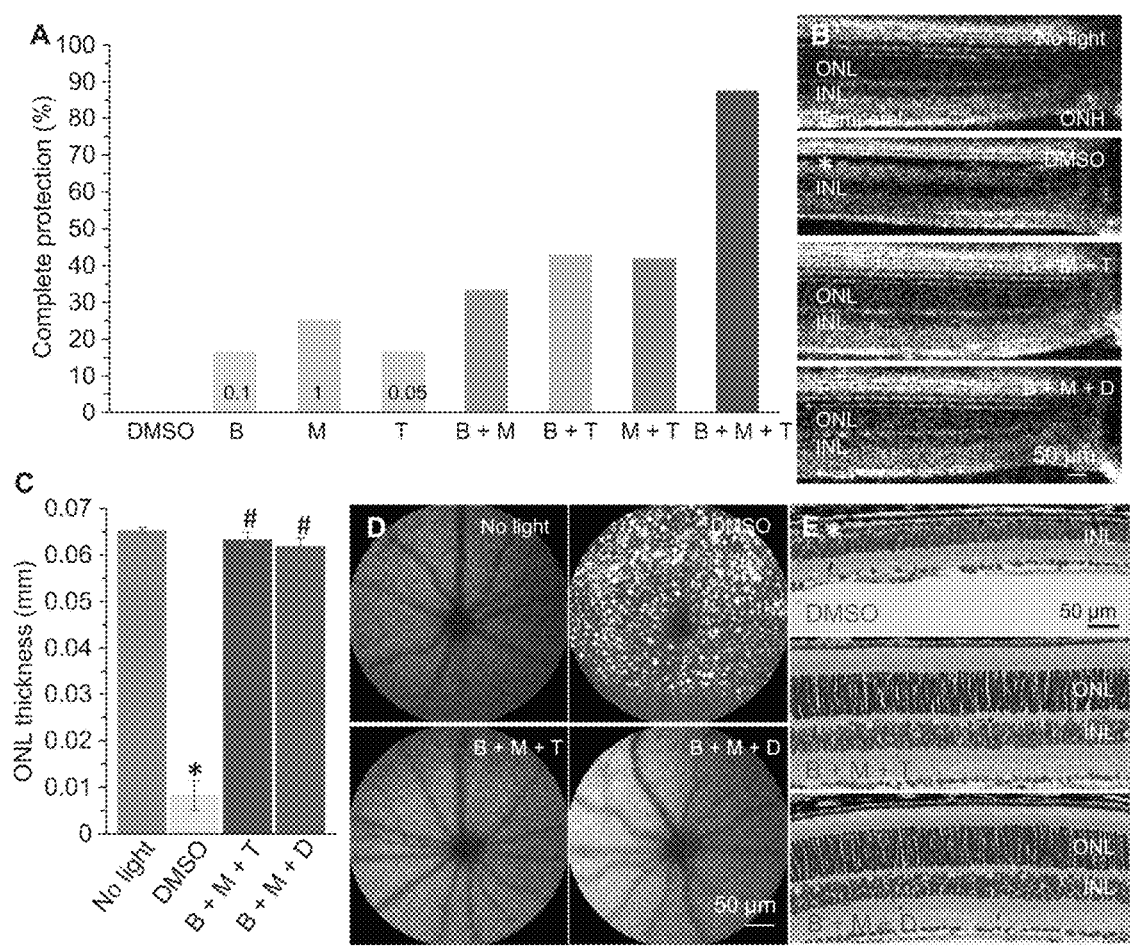
FIGS. 36(A-E) illustrate combination pretreatments improve retinal morphological protection against bright light exposure in Abca4$^{-/-}$Rdh8$^{-/-}$ mice (A) BRM, MTP, or TAM was administered either individually at the indicated subeffective dose (in mg/kg bw) to Abca4$^{-/-}$Rdh8$^{-/-}$ mice or as a combined pretreatment as indicated, each at its subeffective dose. The mice were then exposed to bright light, and OCT imaging was performed 7 days later. Percentages of mice manifesting complete protection of retinal structures were calculated for each condition. For individual drug treatment, combination treatment with BRM and MTP, and combination treatment with MTP and TAM, n=12 mice per group. For combination of BRM and TAM, n=21 per group. For combination of BRM, MTP, and TAM, n=24 per group. (B) Retinal OCT images of Abca4$^{-/-}$Rdh8$^{-/-}$ mice either unexposed to bright light or exposed to bright light after pretreatment with DMSO or the indicated drug combinations at the subeffective doses for each. Images were obtained 7 days after light exposure. Asterisk indicates impaired ONL structure. (C) The thickness of the ONL was determined from OCT images at 0.45 mm away from the ONH in the region of the retinas in the direction of the temples from five mice 7 days after light exposure. *P<0.05, compared to no light; #P<0.05, compared to DMSO (independent samples t test). (D) SLO was performed to image autofluorescent spots in the retinas of Abca4$^{-/-}$Rdh8$^{-/-}$ mice unexposed to bright light or exposed to light after the indicated pretreatment. SLO imaging was performed 9 days after light exposure. (E) Gross morphology of retinas was examined after H&E staining of paraffin sections collected from light-exposed Abca4$^{-/-}$Rdh8$^{-/-}$ mice pretreated as indicated. Retinal tissue was obtained 10 days after light exposure. Asterisk indicates severely diminished ONL. All morphological analyses in (B) to (E) were performed with at least five mice.

OCT imaging revealed preservation of retinal structures in mice pretreated with combinations of BRM, MTP, and TAM, or BRM, MTP, and DOX with each drug at an individual subeffective dose (FIG. 36A to C). This was in distinct contrast to the damaged photoreceptor structures noted in light-exposed, DMSO-treated Abca4$^{-/-}$Rdh8$^{-/-}$ mice. SLO imaging revealed that either of these combination treatments prevented retinas from developing retinal autofluorescence associated with damage induced by exposure to bright light (FIG. 36D). Examination of retinal gross histology further confirmed the structural protection conferred by these combined pretreatments (FIG. 36E).

Figure 37:
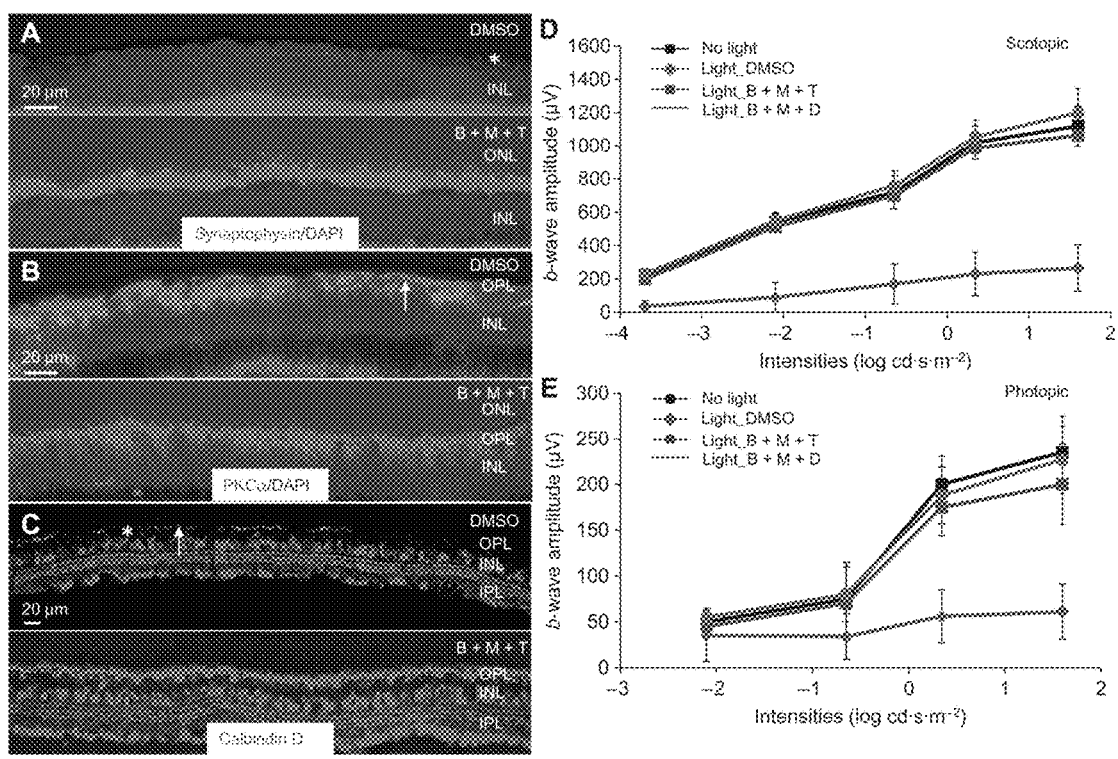
FIGS. 37(A-E) illustrate combination pretreatment preserves OPL morphology and retinal function in light-exposed Abca4$^{-/-}$Rdh8$^{-/-}$ mice Seven days after bright light exposure, cryosections were prepared from the eye cups of light-exposed Abca4$^{-/-}$Rdh8$^{-/-}$ mice pretreated with DMSO or a combination of BRM (0.1 mg/kg bw), MTP (1 mg/kg bw), and TAM (0.05 mg/kg bw) (B+M+T). (A to C) The abundance of synaptophysin, PKCα, and calbindin D was examined by immunohistochemistry. DAPI counterstaining was performed in (A) and (B) to visualize the retinal structure. Asterisk indicates a representative area showing diminished ONL and residual staining for synaptophysin (A) or the absence of calbindin D immunoreactivity (C). (D and E) Scotopic and photopic b-wave amplitudes were analyzed after ERG recordings were performed in Abca4$^{-/-}$Rdh8$^{-/-}$ mice either unexposed to bright light or exposed to bright light and pretreated with either DMSO, a combination of BRM (0.1 mg/kg bw), MTP (1 mg/kg bw), and TAM (0.05 mg/kg) (B+M+T), or a combination of BRM (0.1 mg/kg bw), MTP (1 mg/kg bw), and DOX (1 mg/kg) (B+M+D). Data are means±SD from five mice.

Combined Pretreatments Protect Against Bright Light-Induced Damage to Retinal Morphology and Function in Abca4$^{-/-}$Rdh8$^{-/-}$ and BALB/c Mice Protective effects of combined pretreatments against light-induced photoreceptor degeneration in Abca4$^{-/-}$Rdh8$^{-/-}$ mice were further examined by staining for the synaptic vesicle protein synaptophysin. Abundant and well-organized staining of synaptophysin in photoreceptor synaptic terminals was evident in light-exposed Abca4$^{-/-}$Rdh8$^{-/-}$ mice pretreated with BRM, MTP, and TAM (FIG. 37A). This was in contrast with the diminished residual amount of synaptophysin detected in the outer retina of light-exposed, DMSO-treated mice (FIG. 37A). Similarly, PKCα staining indicated that bipolar and horizontal cell morphologies were maintained in retinas of light-exposed mice pretreated with the combination regimen. Uniform arbor-shaped bipolar cell dendrites were preserved in light-exposed Abca4$^{-/-}$Rdh8$^{-/-}$ mice pretreated with a combination of BRM, MTP, and TAM, each at a suboptimal individual dose (FIG. 37B). In addition, the combination treatment prevented the disintegrated horizontal cell morphology detected with calbindin D staining in light-exposed, DMSO-treated Abca4$^{-/-}$ Rdh8$^{-/-}$ mice (FIG. 37C). Our results therefore provide evidence that combined pretreatment protected mouse retinas against light-induced damage to photoreceptor, bipolar, and horizontal cells.

Functional assessments of the retina by ERG revealed that both scotopic and photopic b-wave amplitudes were decreased in mice exposed to bright light and pretreated with DMSO, indicating impaired retinal function (FIGS. 37D and E). Both scotopic and photopic b-wave amplitudes in the Abca4$^{-/-}$Rdh8$^{-/-}$ mice not exposed to bright light were similar to those in the Abca4$^{-/-}$Rdh8$^{-/-}$ mice exposed to bright light but pretreated with subeffective dose combinations of BRM, MTP, and TAM, or BRM, MTP, and DOX. These results indicated that combined pretreatments preserved retinal function in Abca4$^{-/-}$Rdh8$^{-/-}$ mice exposed to bright light.

Figure 49C:
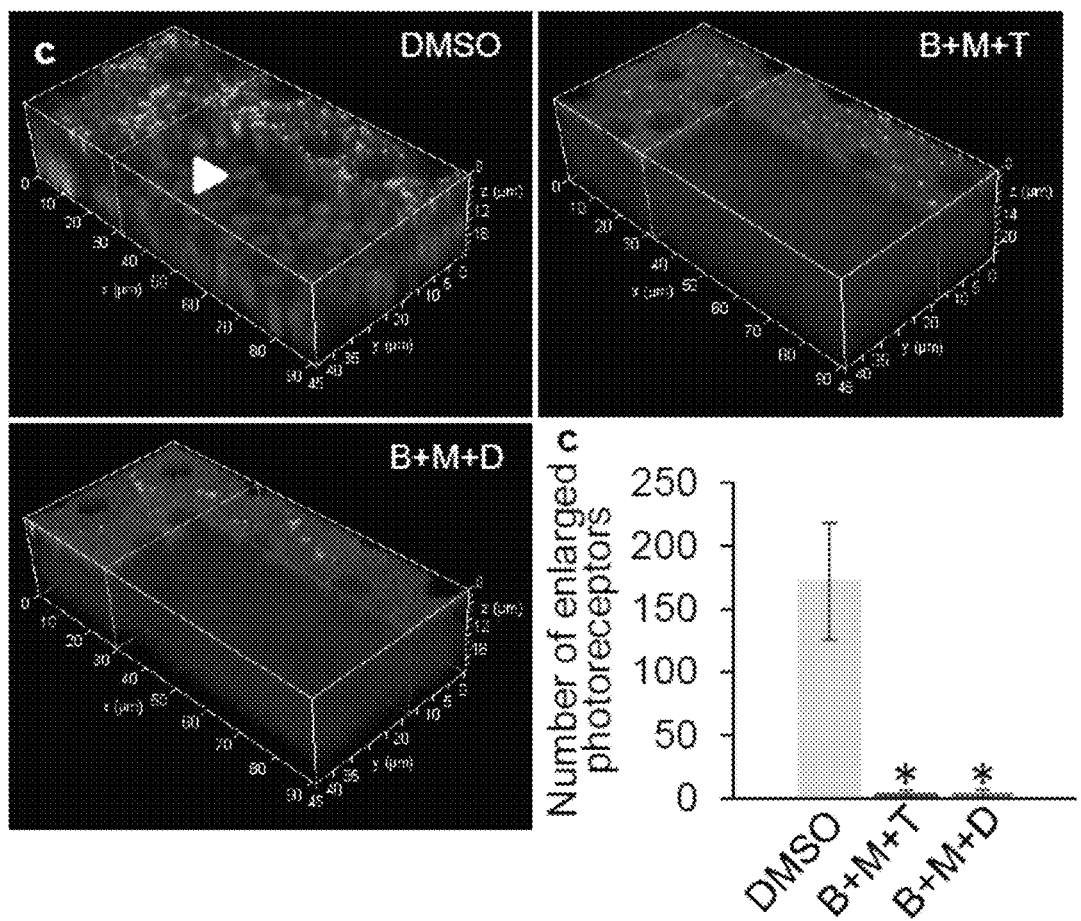
FIGS. 49(A-D) illustrate combined pretreatments protect retinas of BALB/c mice from bright light-induced photoreceptor degeneration. BALB/c mice were exposed to bright light after pretreatment with DMSO, a combination of either BRM (0.1 mg/kg bw), MTP (1 mg/kg bw) and TAM (0.05 mg/kg bw) (B+M+T) or a combination of BRM (0.1 mg/kg bw), MTP (1 mg/kg bw) and DOX (1 mg/kg bw) (B+M+D). A. OCT imaging of BALB/c mice was performed 7 days following exposure to bright light. Thicknesses of the ONL were measured from the OCT images. ONH: optic nerve head. ONL: outer nuclear layer; INL: inner nuclear layer. B. Cryosections were prepared from mice unexposed to bright light or BALB/c mice 2 weeks after bright light exposure. Retinal GFAP staining (green) was then determined by IHC with DAPI counterstaining (blue). ONL: outer nuclear layer; INL: inner nuclear layer; IPL: inner plexiform layer; GC: ganglion cell; NFL: nerve fiber layer. Scale bar: 20 μm. C. TPM imaging was performed 3 days after light exposure to examine the changes in photoreceptors; enlarged photoreceptors were quantified. White arrowhead indicates an enlarged photoreceptor cell. # Compared to DMSO, P<0.05. D. ERG examinations were performed 10 days after light exposure and the changes in scotopic b wave amplitudes were analyzed after ERG recordings.
Figure 49D:
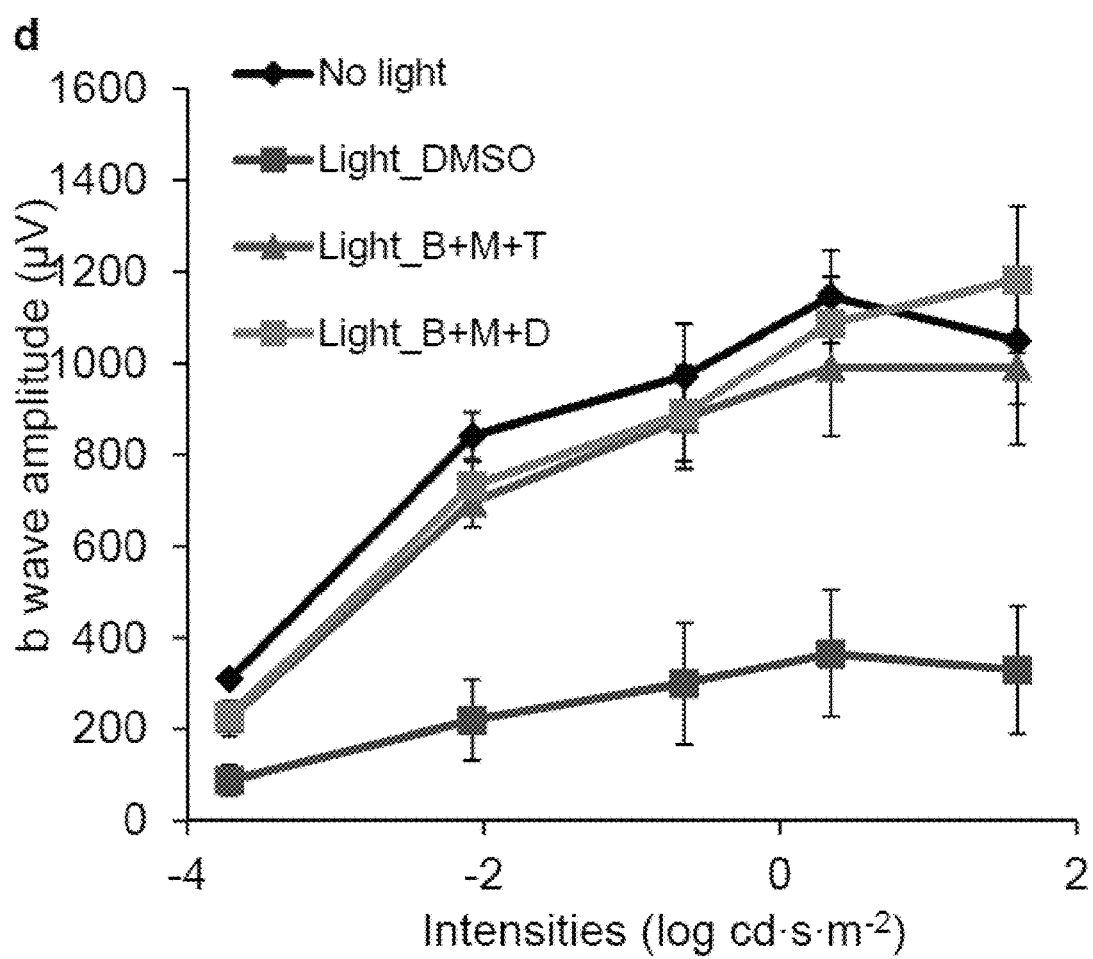

To confirm the retinal protection of combined treatments, we also examined the effects of the combined GPCR modulators in light-exposed BALB/c mice, a wild-type mouse strain that is susceptible to bright light-induced retinal degeneration and accessible to TPM because of its albino features (FIG. 49). OCT imaging of these mice demonstrated full protection of the thickness of the ONL (FIG. 49A). Staining anti-GFAP antibody indicated that activation of the Müller cells was diminished (FIG. 49B). Enlargement of photoreceptor cells is an early manifestation of light-induced retinal degeneration. Thus, we performed TPM imaging, which revealed that the combined pretreatments significantly diminished the number of enlarged photoreceptor outer segments compared to the number observed in DMSO-pretreated, light-exposed BALB/c mice (FIG. 49C). In concordance with the morphological findings, ERG analyses revealed the preservation of retinal function after either combined pretreatment regimen in light-exposed BALB/c mice. Whereas light exposure resulted in decreased scotopic b-wave amplitudes in DMSO-treated BALB/c mice, retinal function was preserved with combinations of BRM, MTP, and TAM, or BRM, MTP, and DOX, each at suboptimal doses (FIG. 49D).

Figure 38:
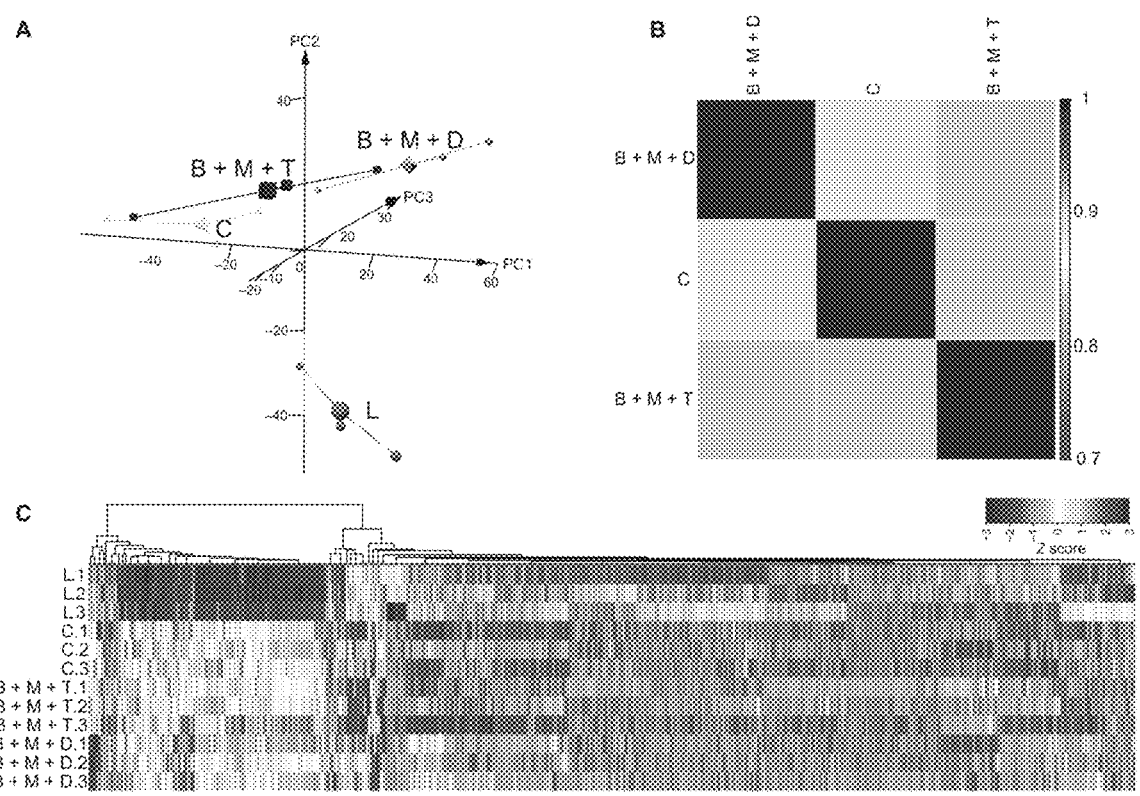
FIGS. 38(A-C) illustrate RNA-seq analysis of retinal gene expression in Abca4$^{-/-}$Rdh8$^{-/-}$ mice pretreated with drug combinations total RNA from the indicated experimental groups (n=3 per group) was isolated from Abca4$^{-/-}$Rdh8$^{-/-}$ mice 1 day after light exposure, along with mice unexposed to bright light. Total RNA was then subjected to RNA-seq analysis. (A) 3D PCAs of all expressed transcripts are shown for the control mice unexposed to bright light (C), light-exposed, DMSO-pretreated mice (L), and mice pretreated with combinations of either BRM, MTP, and TAM (B+M+T) or BRM, MTP, and DOX (B+M+D). (B) Pearson's correlation plots of the differentially expressed transcripts from retinas of mice unexposed to bright light or subjected to combination therapy before light exposure. Scale bar represents correlation coefficient. (C) Gene expression clustering of differentially expressed transcripts is shown for mice with the indicated combined pre-treatments along with clustering from mice unexposed to light and DMSO-pretreated mice exposed to light. Scale bar represents the Z score indicating up-regulation and down-regulation.

Transcriptomic Analysis Shows that Combination Pretreatments Preserve an Undamaged Retina Gene Expression Profile As a molecular indication of protection, we evaluated the effect of the combined pretreatments with BRM, MTP, and TAM, or BRM, MTP, and DOX on global retinal gene expression (FIG. 45A). Read depths and count distributions were examined for outliers after normalization (FIG. 45C). The data set included 17,982 expressed transcripts after eliminating transcripts with very low expression (<1 FPKM). Good biological replication was revealed by PCA of the transcriptome data (FIG. 38A). The largest separation in gene expression along PCI was observed between retinas from mice that had not been exposed to bright light and light-exposed mice pretreated with DMSO. Both combined treatments clustered closer to mice that had not been exposed to bright light (FIG. 38A). Pearson's coefficient analysis showed that pretreatment with either combination shifted global gene expression toward that exhibited by mice that had not been exposed to bright light (correlation coefficient>0.8) (FIG. 38B). Cluster analysis of the 521 differentially expressed transcripts demonstrated a gene signature consistent with protection from light damage by either regimen, although the BRM, MTP, and TAM regimen produced a pattern that was more similar to the undamaged control than did the BRM, MTP, and DOX regimen (FIG. 38C and FIG. 45C).

Although single drugs acting on different GPCRs provided morphological protection of the retina when administered at high doses, the resulting transcriptome profiles differed among them (FIGS. 34D and E). Gene set enrichment analysis (GSEA) of pathways associated with each therapeutic demonstrated that 44 gene sets were significantly up-regulated in light-exposed, DMSO-treated mice as compared to mice unexposed to bright light. BRM, MTP, TAM, and DOX pretreatment resulted in significant down-regulation of 29, 36, 32, and 28, respectively, of the gene sets associated with bright light exposure. Among pathways up-regulated by bright light exposure, those implicated in the pathogenesis of light-induced retinal degeneration genes in these pathways were down-regulated by each individual therapeutic agent (Table 15). Six pathways were down-regulated in retinas from DMSO-treated, light-exposed mice compared to retinas from mice that had not been exposed to bright light, and pretreatment with either BRM, MTP, TAM, or DOX prevented several of these changes in gene expression. These results provided further evidence supporting the retinal protection conferred by each of these compounds.

with a combination of drugs, each administered at an individual subeffective dose, engendered a more normal landscape of mRNAs in the retina (FIGS. 38B and C). As revealed by GSEA of an independent experiment, exposure to bright light resulted in significant up-regulation of 45 gene sets. Most (37 and 31) of these gene sets were significantly down-regulated by combined pretreatment with BRM, MTP, and TAM, or BRM, MTP, and DOX, respectively. These sets included genes expected to be involved in pathways that would contribute to retinal degeneration (Table 15). In addition, the bright light-induced down-regulation of gene set related to phototransduction involved in physiological signaling of light stimuli at normal light levels was prevented by pretreatment with the combination of BRM, MTP, and TAM, or BRM, MTP, and DOX. Moreover, when genes for each relevant signaling pathway were examined, for example, those affecting apoptosis and phototransduction, each treatment exhibited a similar impact on gene expression within the same set of genes.

Notably, when the retinal transcriptomes from different single and combined pretreatments were compared to those of mice that had not been exposed to bright light, a down-regulated phototransduction gene set was detected for most of the treatments except for the combination of BRM, MTP, and TAM. Moreover, when considering retinal expression of apoptosis and p53 signaling pathway genes, only mice pretreated with combined BRM, MTP, and TAM were statistically indistinguishable from mice that had not been exposed to bright light. These results suggest that combined pretreatment with BRM, MTP, and TAM was most effective at maintaining phototransduction, apoptosis, and p53 signaling pathways at their normal physiological levels.

We used a systems pharmacology approach to evaluate combinations of FDA-approved drugs that achieve protection in mouse models of bright light-induced retinal degeneration. The drugs were administered by intraperitoneal

TABLE 15

Effect of single and combination therapies on gene sets associated with retinal degeneration pathways

| PATHWAYS | Experiment 1: Change in light-exposed retinas NES (P)* | BRM NES (P †) | MTP NES (P †) | TAM NES (P †) | DOX NES (P †) | (P)* | BRM + MTP + TAM NES (P †) | BRM + MTP + DOX NES (P †) |
|---|---|---|---|---|---|---|---|---|
| APOPTOSIS | 1.83 (0) | 1.75 (0.001 | 1.61 (0.005 | 1.60 (0.011 | 1.75 (0.001 | 1.88 (0) | 1.81 | 1.89 (0) |
| P53 | 2.29 (0) | 2.06 | 2.04 | 1.98 | 2.18 | 1.71 | 1.98 | 1.69 |
| CYTOKINE-RECEPTOR INTERACTIO | 2.50 (0) | 2.31 | 2.30 | 2.29 | 2.42 | 2.18 (0) | 2.13 | 2.04 (0) |
| CHEMOKINE SIGNALING | 1.62 (0.0042) | 1.67 (0.001 | 1.44 (0.02) | 1.39 (0.019 | 1.41 (0.018 | 1.71 (0) | 1.57 (0.010 | 1.67 (0.0014 |
| TOLL-LIKE SIGNALING | 2.14 (0) | 2.20 | 2.05 | 1.83 | 1.99 | 2.10 (0) | 2.10 | 2.21 (0) |

* Comparison of the transcriptomes from vehicle-treated and light-exposed retinas against those from the mice unexposed to bright light.
† Comparison of the transcriptomes from vehicle-treated and light-exposed retinas against those from the mice treated by indicated drug(s).

GSEA identified pathways associated with retinal degeneration in retinas from light-exposed mice. NES, normalized enrichment score.

Figure 39:
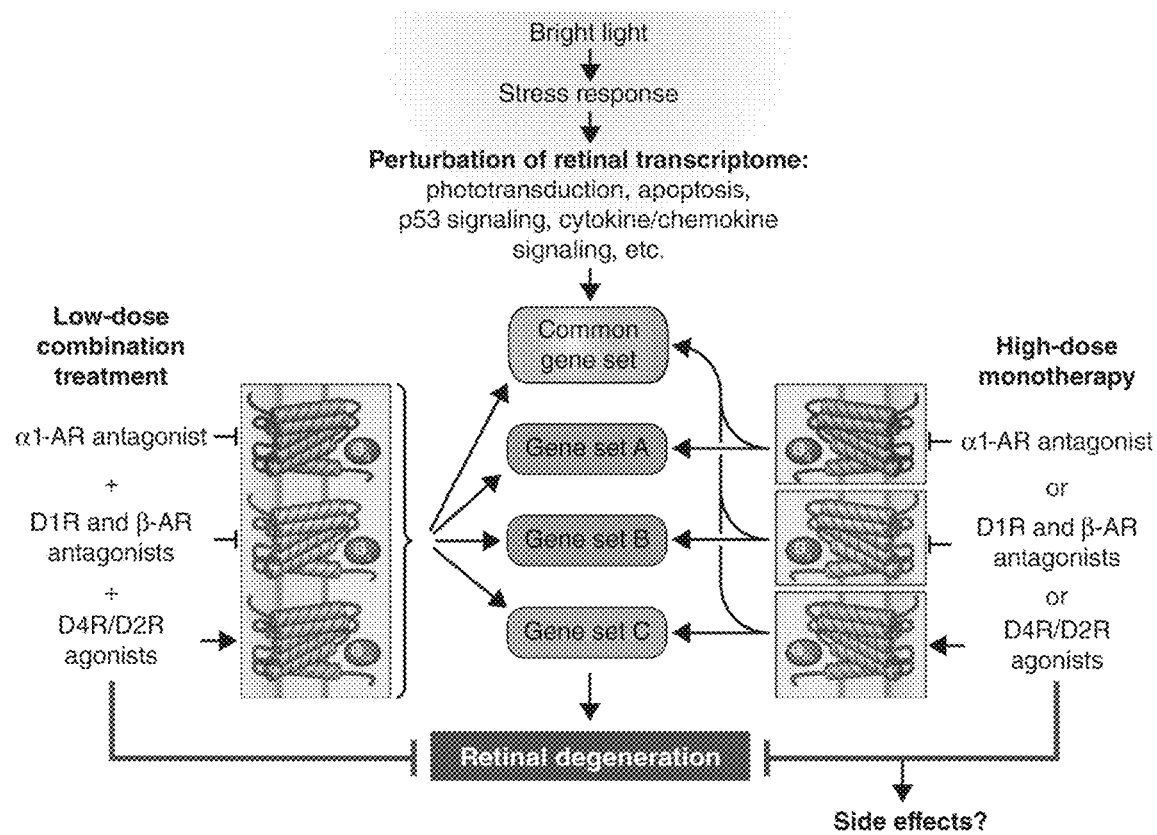
FIG. 39 illustrates pharmacological treatments protect against bright light-induced alterations in the retinal transcriptome and retinal degeneration. Bright light exposure causes retinal degeneration that is associated with perturbation of retinal transcriptome homeostasis manifested as dysregulation of multiple gene sets, including but not limited to down-regulation of the phototransduction pathway and up-regulation of the apoptosis pathway, p53 signaling, cytokine-cytokine receptor interactions, and chemokine signaling. Pretreatment with individual drugs that act as antagonists at Gs-coupled GPCRs, agonists at Gi-coupled GPCRs, or antagonists at Gq-coupled GPCRs results in retinal protection. We found that, when each drug is delivered at lower subeffective doses, combinations of these drugs acting synergistically upon different GPCRs protected retinas from bright light-induced degeneration. The retinal protection by different treatment modalities, namely, monotherapy at high doses or combined treatments consisting of subeffective doses of drugs, not only prevents light-induced changes in common gene sets but also affects gene sets specific to each treatment. Combined treatment results in improved preservation of the retinal transcriptome compared to that conferred by monotherapy and may also offer the benefit of reduced side effects because of lower doses required for effectiveness.

Although individually the therapeutic GPCR-targeting agents partially prevented the abnormal transcriptome profile in these models of photoreceptor degeneration, treatment injection, but other delivery systems should be considered in the future. We identified BRM and MTP as GPCR-targeting drugs that protected the retina against phototoxicity, similar to DOX and TAM, as we have shown in a previous study. BRET-based GPCR signaling assays demonstrated that combination treatment with these drugs is generally expected to promote signaling through Gi/o-coupled dopamine D4R and D2R, as well as attenuate D1R-mediated Gs and ADRA1-mediated Gq signaling, in addition to the known stimulatory effects on β1-adrenergic receptors, which are Gs-coupled. Consistent with a coordinated effect of these compounds on GPCR signaling, we observed that administration of combined treatments consisting of BRM, MTP, and TAM, or BRM, MTP, and DOX with each component dosed at an individual subeffective level resulted in morphological and functional protection of photoreceptor cells. In addition, bipolar and horizontal cells were also preserved by these combined treatments. Transcriptome analyses demonstrated that combination treatments also exhibited an enhanced capability to preserve a genome-wide gene expression pattern in the retina similar to that of un-damaged retinas compared to the patterns resulting from individual component therapeutics (FIG. 39).

Complex diseases are not easily managed and are typically confounded by aging. For example, multiple distinct cellular pathways have been associated with AMD and should be targeted for successful treatment. Monotherapies typically have partial effects even at high doses. Polypharmacology that takes advantage of diverse and unrelated targets may effectively deal with the initial problem but at the risk of multiple unwanted side effects. This risk could be acceptable for treating terminal diseases or chronic infections (for example, cancer or HIV), but for diseases such as blindness, polypharmacology is probably not the best solution. Systems pharmacology differs from polypharmacology in that it modifies several pathways that culminate in a common response, whether mediated by enzymes, second messengers, or channels. An advantageous solution is the modulation of pharmacologically accessible GPCRs, because their overlapping downstream pathways can elicit synergistic effects. Therefore, suboptimal doses of different GPCR modulators can be used in concert to achieve an enhanced desired effect. Low doses of combined GPCR-targeted drugs can also prevent massive internalization of their receptors and enable prolonged therapy. For chronic diseases, where prophylaxis would be most beneficial, systems pharmacology could play a major role. As examples of neuronal diseases, rod and cone retinopathies such as Stargardt disease, AMD, or RP could benefit greatly from systems pharmacology approaches focused on long-term preservation of cone function.

Biological insights derived from transcriptome analyses and gene regulatory networks associated with the pharmacological actions of drugs can provide an important reference for future clinical evaluation of different treatment regimens. Moreover, in addition to gaining insights into retinal protective changes at the transcriptome level, we can also infer possible off-target effects of drugs and drug interactions. These advantages should make transcriptome analyses another standard approach in the evaluation of drug therapy.

In summary, we present a systems pharmacology approach to treat mouse models of human retinopathies that cause the death of rod and cone photoreceptor cells. We demonstrated that the therapies identified by systems pharmacology preserve photoreceptor cells and other neuronal cells in the retina, as well as the overall structure, function, and transcriptional integrity of the retina. Moreover, we showed that, at the molecular level, the combined effect of our systems pharmacology-based treatments is to activate Gi/o signaling through D2R and D4R, as well as to inhibit adverse effects of Gs and Gq signaling by antagonistic effects on D1R and ADRA1A receptors, respectively.

The GSEA analyses of the transcriptomic data suggested a link between the GPCR signaling and the JAK (Janus kinase)/STAT (signal transducer and activator of transcription) pathway, a pathway implicated in retinal degeneration. The GSEA data are also consistent with the evidence linking adrenergic receptor signaling and the JAK/STAT pathway. In cultured human vascular smooth muscle cells, the α1 agonist phenylephrine induces tyrosine phosphorylation of JAK2 and STAT1, indicating activation of this pathway. This stimulation occurs through an interaction of the α1B-adrenergic receptor with JAK2 and STAT1.

Because GPCRs are pharmacologically accessible targets, the application of systems pharmacology could benefit the treatment of other complex diseases. For example, in another visual impairment disorder, RPE65 (retinal pigment epithelium 65)-related (type 2) Leber congenital amaurosis, gene transfer can rescue the direct enzymatic defect that initiates the disease, but it does not prevent the ensuing pathology, indicating that (i) multiple therapeutic approaches could be needed to inhibit the progression of this chronic disease, and (ii) methods are needed to determine whether a chosen therapy normalizes signaling within the targeted cells. From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of treating an ocular disorder associated with light induced retinal degeneration, aberrant all-trans-retinal clearance, or reactive oxygen species generation in the retina of a subject, comprising:
administering to the subject individually subtherapeutic amounts of two or more agents, wherein the two or more agents comprise an agent that inhibits and/or blocks the activation of Gs- or Gq-protein coupled receptors or Gs- or Gq-signaling cascade in ocular cells of the subject, and an agent that activates Gi-protein coupled receptors, wherein the activation of Gs- or Gq-protein coupled receptors or Gs- or Gq-signaling cascade is induced or triggered by light induced all-trans-retinal generation.

2. The method of claim 1, wherein the two or more agents are selected from the group consisting of Gs or Gq coupled serotonin receptor antagonists, Dopamine receptor D1 antagonists, Dopamine receptor D5 antagonists, β1 adrenergic receptor antagonists, β2 adrenergic receptor antagonists, Adenosine $A_{2B}$ receptor antagonists, corticotropin releasing hormone receptor 1 antagonists, metabotropic glutamate receptor 1 antagonists, tachykinin receptor 1 antagonists, prostaglandin E receptor 1 antagonists, dopamine receptor D2 agonists, dopamine receptor D3 agonists, dopamine receptor D4 agonists, metabotropic glutamate receptor 4 agonists, alpha-2 adrenergic receptor agonists, adenylyl cyclase inhibitors, M3 receptor antagonists, and PLC inhibitors.

3. The method of claim 1, wherein the agents comprise at least two of a Gi-coupled dopamine D2 receptor agonist, a Gs-coupled β1 adrenergic receptor antagonist, or a Gq-coupled α1 adrenergic receptor blocker.

4. The method of claim 1, wherein the agents comprise at least two of bromocriptine, metoprolol, tamsulosin, or doxazosin.

5. The method of claim 1, wherein the agents comprise bromocriptine, metoprolol, and tamsulosin.

6. The method of claim 1, wherein the agents comprise bromocriptine, metoprolol, and doxazosin.

7. The method of claim 1, the agents being delivered to the subject by at least one of topical administration, systemic administration, intravitreal injection, and intraocular delivery.

8. The method of claim 1, the agents being provided in an ocular preparation for sustained delivery.

9. The method of claim 1, the ocular disorder comprising at least one of macular degeneration, geographic atrophy (GA), Stargardt disease, retinitis pigmentosa, and diabetic retinopathy.

10. A method of treating geographic atrophy (GA), Stargardt disease, macular degeneration, retinitis pigmentosa, or diabetic retinopathy in a subject, the method comprising:
   administering to the subject individually subtherapeutic amounts of two or more agents, wherein the two or more agents comprise an agent that inhibits and/or blocks the activation of Gs- or Gq-protein coupled receptors or Gs- or Gq-signaling cascade in ocular cells of the subject, and an agent that activates Gi-protein coupled receptors, wherein the activation of Gs- or Gq-protein coupled receptors or Gs- or Gq-signaling cascade is induced or triggered by light induced all-trans-retinal generation.

11. The method of claim 10, wherein the two or more agents are selected from the group consisting of Gs or Gq coupled serotonin receptor antagonists, Dopamine receptor D1 antagonists, Dopamine receptor D5 antagonists, $\beta 1$ adrenergic receptor antagonists, $\alpha 2$ adrenergic receptor antagonists, Adenosine A2B receptor antagonists, corticotropin releasing hormone receptor 1 antagonists, metabotropic glutamate receptor 1 antagonists, tachykinin receptor 1 antagonists, prostaglandin E receptor 1 antagonists, dopamine receptor D2 agonists, dopamine receptor D3 agonists, dopamine receptor D4 agonists, metabotropic glutamate receptor 4 agonists, alpha-2 adrenergic receptor agonists, adenylyl cyclase inhibitors, M3 receptor antagonists, and PLC inhibitors.

12. The method of claim 10, wherein agents comprise at least two of a Gi-coupled dopamine D2 receptor agonist, a Gs-coupled $\beta 1$ adrenergic receptor antagonist, or a Gq-coupled $\alpha 1$ adrenergic receptor blocker.

13. The method of claim 10, wherein the agents comprise at least two of bromocriptine, metoprolol, tamsulosin, or doxazosin.

14. The method of claim 10, wherein the agents comprise bromocriptine, metoprolol, and tamsulosin.

15. The method of claim 10, wherein the agents comprise bromocriptine, metoprolol, and doxazosin.

16. The method of claim 10, the agents being delivered to the subject by at least one of topical administration, systemic administration, intravitreal injection, and intraocular delivery.

17. The method of claim 10, the agents being provided in an ocular preparation for sustained delivery.

* * * * *